United States Patent
Myers et al.

(10) Patent No.: US 10,669,261 B2
(45) Date of Patent: Jun. 2, 2020

(54) HETEROARYLHYDROXYPYRIMIDINONES AS AGONISTS OF THE APJ RECEPTOR

(71) Applicant: BRISTOL-MYERS SQUIBB COMPANY, Princeton, NJ (US)

(72) Inventors: Michael C. Myers, Newtown, PA (US); R. Michael Lawrence, Yardley, PA (US); Donna M. Bilder, Lambertville, NJ (US); Wei Meng, Pennington, NJ (US); Zulan Pi, Pennington, NJ (US); Robert Paul Brigance, Levittown, PA (US); Heather Finlay, Skillman, NJ (US)

(73) Assignee: Bristl-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/061,365

(22) PCT Filed: Dec. 15, 2016

(86) PCT No.: PCT/US2016/066750
§ 371 (c)(1),
(2) Date: Jun. 12, 2018

(87) PCT Pub. No.: WO2017/106396
PCT Pub. Date: Jun. 22, 2017

(65) Prior Publication Data
US 2018/0362508 A1    Dec. 20, 2018

Related U.S. Application Data

(60) Provisional application No. 62/267,997, filed on Dec. 16, 2015.

(51) Int. Cl.
| | | |
|---|---|---|
| A61K 31/506 | (2006.01) |
| A61K 31/513 | (2006.01) |
| C07D 403/04 | (2006.01) |
| C07D 413/04 | (2006.01) |
| C07D 413/14 | (2006.01) |
| C07D 417/04 | (2006.01) |
| C07D 417/14 | (2006.01) |
| A61P 9/04 | (2006.01) |
| A61P 9/10 | (2006.01) |
| A61P 9/12 | (2006.01) |
| A61P 9/00 | (2006.01) |

(52) U.S. Cl.
CPC ......... *C07D 403/04* (2013.01); *C07D 413/04* (2013.01); *C07D 413/14* (2013.01); *C07D 417/14* (2013.01)

(58) Field of Classification Search
CPC .. A61K 31/506; A61K 31/513; C07D 403/04; C07D 413/04; C07D 413/14; C07D 417/04; C07D 417/14; A61P 9/04; A61P 9/10; A61P 9/12; A61P 9/00

USPC .......................... 514/269; 544/319, 298, 333
See application file for complete search history.

(56) References Cited

U.S. PATENT DOCUMENTS

| | | |
|---|---|---|
| 6,174,998 B1 | 1/2001 | Muhlegger et al. |
| 6,310,069 B1 | 10/2001 | Lohray et al. |
| 6,369,067 B1 | 4/2002 | Gurram et al. |
| 2007/0167621 A1 | 7/2007 | Durley |
| 2013/0029232 A1 | 1/2013 | Zheng et al. |

FOREIGN PATENT DOCUMENTS

| | | |
|---|---|---|
| DE | 10 2012 006 896 A1 | 10/2013 |
| GB | 2 263 639 A | 8/1999 |
| IN | 2001MA00568 A | 3/2005 |
| JP | 08311041 A | 11/1996 |
| JP | 2006036708 A | 3/2006 |
| KR | 201531023 B1 | 6/2015 |
| KR | 2015090605 A | 8/2015 |
| WO | 2001/60805 A1 | 8/2001 |
| WO | 2002/06242 A2 | 1/2002 |
| WO | 2002/081454 A1 | 10/2002 |
| WO | 2003/094839 A2 | 11/2003 |
| WO | 2003/099211 A2 | 12/2003 |
| WO | 2004/094408 A1 | 11/2004 |
| WO | 2005/026148 A1 | 3/2005 |
| WO | 2005/041888 A2 | 5/2005 |
| WO | 2005/060654 A2 | 7/2005 |
| WO | 2006/128563 A1 | 12/2006 |
| WO | 2007/037543 A1 | 4/2007 |
| WO | 2007/064797 A2 | 6/2007 |
| WO | 2007/124397 A2 | 11/2007 |
| WO | 2008/052861 A2 | 5/2008 |
| WO | 2008/052863 A2 | 5/2008 |
| WO | 2008/103277 A2 | 8/2008 |
| WO | 2009/152902 A2 | 12/2009 |
| WO | 2010/000396 A1 | 1/2010 |
| WO | 2010/072696 A2 | 7/2010 |
| WO | 2010/132999 A1 | 11/2010 |

(Continued)

*Primary Examiner* — Matthew P Coughlin
*Assistant Examiner* — Sagar Patel
(74) *Attorney, Agent, or Firm* — Hong Liu

(57) ABSTRACT

The present invention provides compounds of Formula (I): wherein all variables are as defined in the specification, and compositions comprising any of such novel compounds. These compounds are APJ agonists which may be used as medicaments, in particular for treating cardiovascular disorders.

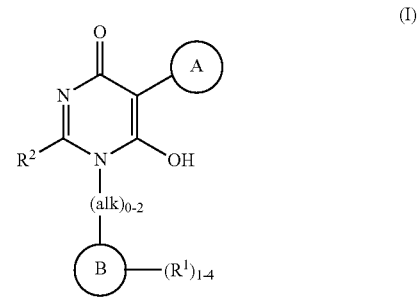

17 Claims, No Drawings

(56) References Cited

FOREIGN PATENT DOCUMENTS

| | | | |
|---|---|---|---|
| WO | 2012/020742 | A1 | 2/2012 |
| WO | 2012/163489 | A1 | 12/2012 |
| WO | 2012/163490 | A1 | 12/2012 |
| WO | 2013/184755 | A2 | 12/2013 |
| WO | 2014/056844 | A1 | 4/2014 |
| WO | 2014/067603 | A1 | 5/2014 |
| WO | 2014/078778 | A2 | 5/2014 |
| WO | 2014/207100 | A1 | 12/2014 |
| WO | 2015/049034 | A1 | 4/2015 |
| WO | 2015/079028 | A1 | 6/2015 |
| WO | 2015/184011 | A2 | 12/2015 |
| WO | 2016/074757 | A1 | 5/2016 |
| WO | 2016/196771 | A1 | 12/2016 |
| WO | WO-2016196771 A1 * | 12/2016 | ........... C07D 498/04 |
| WO | 2017/066402 | A1 | 4/2017 |
| WO | 2017/096130 | A1 | 6/2017 |
| WO | 2017/165640 | A1 | 9/2017 |
| WO | 2017/218617 | A1 | 12/2017 |
| WO | 2017/218633 | A1 | 12/2017 |
| WO | 2018/071622 | A1 | 4/2018 |

* cited by examiner

HETEROARYLHYDROXYPYRIMIDINONES AS AGONISTS OF THE APJ RECEPTOR

CROSS REFERENCE TO RELATED APPLICATIONS

This application is a 371 application of PCT/US2016/066750, filed Dec. 15, 2016, which is entitled to priority pursuant to 35 U.S.C. § 119(e) to U.S. provisional patent application No. 62/267,997, filed Dec. 16, 2015, which is incorporated herein in its entirety.

FIELD OF THE INVENTION

The present invention provides substituted heteroarylhydroxypyrimidinones, and their analogues thereof, which are APJ agonists, compositions containing them, and methods of using them, for example, for the treatment or prophylaxis of heart failure, atherosclerosis, ischemic heart disease and related conditions.

BACKGROUND OF THE INVENTION

Heart failure (HF) and related complications constitute major health burden in developed countries with an estimated prevalence of 5,700,000 in the United States alone (Roger, V. L. et al., *Circulation*, 125(1):e2-e220 (2012)). Despite considerable advances in recent two decades, the prognosis remains very poor, with survival rates of only ~50% within 5-years of diagnosis (Roger, V. L. et al., *JAMA*, 292(3):344-350 (2004)). In addition to poor survival, the impaired quality of life and recurrent hospitalizations constitute clear unmet medical need for development of novel treatment options.

HF is a clinical syndrome characterized by the inability of the heart to deliver sufficient supply of blood and oxygen to meet the metabolic demands of organs in the body. Main symptoms associated with HF include shortness of breath due to pulmonary edema, fatigue, reduced tolerance to exercise and lower extremity edemas. The etiology of HF is highly complex with multiple associated risk factors and potential causes.

Among the leading causes of HF are coronary artery disease and cardiac ischemia, acute myocardial infarction, intrinsic cardiomyopathies and chronic uncontrolled hypertension. HF can develop either acutely (functional impairment post myocardial infarction) or as a chronic condition, characterized by long-term maladaptive cardiac tissue remodeling, hypertrophy and cardiac dysfunction (for example due to uncontrolled long-term hypertension). According to the diagnostic criteria and type of ventricular dysfunction, HF is classified to two major groups, HF with "reduced ejection fraction" (HFrEF) or HF with "preserved ejection fraction" (HFpEF). Both types are associated with similar signs and symptoms, but differ in the type of ventricular functional impairment (Borlaug, B. A. et al., *Eur. Heart J.*, 32(6):670-679 (2011)).

APJ receptor (APLNR) and its endogenous peptidic ligand apelin have been implicated as important modulators of cardiovascular function and candidates for therapeutic intervention in HF (for review see Japp, A. G. et al., *Biochem. Pharmacol.*, 75(10):1882-1892 (2008)).

Accumulated evidence from preclinical disease models and human heart failure patients have implicated apelin and APJ agonism as beneficial in the setting of HF. Mice lacking Apelin or APJ gene have impaired myocyte contractility (Charo, D. N. et al., *Am. J. Physiol. Heart Circ. Physiol.*, 297(5):H1904-H1913 (2009)). Apelin knockout (KO) mice develop progressive cardiac dysfunction with aging and are more susceptible to HF in the model of trans-aortic constriction (TAC) (Kuba, K. et al., *Circ. Res.*, 101(4):e32-42 (2007)). The functional impairment in chronic HF is a result of prolonged demand on the heart and is associated with maladaptive cardiac remodeling, manifested by the cardiac hypertrophy, increased inflammation and interstitial fibrosis which eventually lead to decrease in cardiac performance.

Acute administration of apelin increases cardiac output in rodents under normal conditions and also in models of heart failure (Berry, M. F., *Circulation*, 110(11 Suppl. 1):II187-II193 (2004)). Increased cardiac output is a result of direct augmentation of cardiac contractility and reduced peripheral vascular resistance in the arterial and venous beds (Ashley, E. A., *Cardiovasc. Res.*, 65(1):73-82 (2005)). Reduction in the vascular resistance leads to lower pre-load and after-load on the heart and thus lesser work load (Cheng, X. et al., *Eur. J. Pharmacol.*, 470(3): 171-175 (2003)). Similar to rodent studies, acute infusion of apelin to healthy human subjects and patients with heart failure produces similar hemodynamic responses with increased cardiac output and increased vasodilatory response in peripheral and coronary arteries (Japp, A. G. et al., *Circulation*, 121(16):1818-1827 (2010)).

The mechanisms underlying inotropic action of apelin are not well understood, but appear to be distinct from clinically used $\beta_1$-adrenergic agonists (dobutamine) due to lack of increase in heart rate. The vasodilatory action of apelin is primarily mediated via endothelial nitric oxide synthase pathways (Tatemoto, K., *Regul. Pept.*, 99(2-3):87-92 (2001)). Apelin is induced under hypoxic conditions, promotes angiogenesis and has been shown to limit the infarct size in ischemia-reperfusion models (Simpkin, J. C., *Basic Res. Cardiol.*, 102(6):518-528 (2007)).

In addition to aforementioned studies evaluating acute administration of apelin, several studies have clearly demonstrated beneficial effects of prolonged administration of apelin in a number of chronic rodent models of HF, including the angiotensin II model, TAC model and rat Dahl salt-sensitive model (Siddiquee, K. et al., *J. Hypertens.*, 29(4):724-731 (2011); Scimia, M. C. et al., *Nature*, 488 (7411):394-398 (2012); Koguchi, W. et al., *Circ. J.*, 76(1): 137-144 (2012)). In these studies, prolonged apelin infusion reduced cardiac hypertrophy and cardiac fibrosis, and was associated with improvement in cardiac performance.

Genetic evidence is also emerging that polymorphisms in the APJ gene are associated with slower progression of HF (Sarzani, R. et al., *J. Card. Fail.*, 13(7):521-529 (2007)). Importantly, while expression of APJ and apelin can be reduced or vary considerably with HF progression, the cardiovascular hemodynamic effects of apelin are sustained in patients with developed HF and receiving standard of care therapy (Japp, A. G. et al., *Circulation*, 121(16):1818-1827 (2010)).

In summary, there is a significant amount of evidence to indicate that APJ receptor agonism plays a cardioprotective role in HF and would be of potential benefit to HF patients. Apelin's very short half life in circulation limits its therapeutic utility, and consequently, there is a need for APJ receptor agonists with improved pharmacokinetic and signaling profile while maintaining or enhancing the beneficial effects of endogenous APJ agonist apelin.

SUMMARY OF THE INVENTION

The present invention provides substituted heteroarylhydroxypyrimidinones, and their analogues thereof, which are useful as APJ agonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with APJ, such as heart failure, coronary artery disease, cardiomyopathy, diabetes and related conditions including but not limited to acute coronary syndrome, myocardial ischemia, hypertension, pulmonary hypertension, coronary vasospasm, cerebral vasospasm, ischemia/reperfusion injury, angina, renal disease, metabolic syndrome and insulin resistance.

The compounds of the invention may be used in therapy.

The compounds of the invention may be used for the manufacture of a medicament for the treatment and/or prophylaxis of multiple diseases or disorders associated with APJ.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

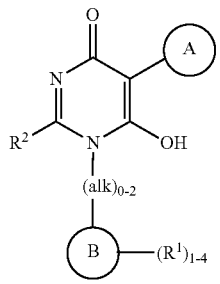

(I)

or a stereoisomer, an enantiomer, a diastereoisomer, a tautomer, a pharmaceutically acceptable salt, or a solvate thereof, wherein:
alk is $C_{1-6}$ alkyl substituted with 1-5 $R^7$;
ring A is independently selected from

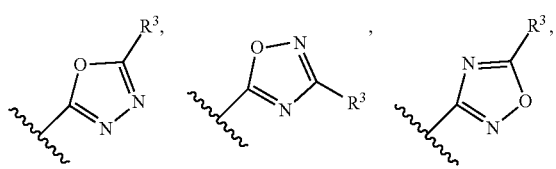

-continued ring B is independently selected from $C_{3-6}$ cycloalkyl, $C_{3-6}$ cycloalkenyl, aryl, bicyclic carbocyclyl, and 6-membered heteroaryl;

$R^1$ is independently selected from H, halogen, $NO_2$, —$(CH_2)_nOR^b$, —$(CH_2)_nS(O)_pR_c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_nOC(=O)NR^aR^a$, —$(CH_2)_nC(=O)OR^b$, —$(CH_2)_nS(O)_pNR^aR^a$, —$(CH_2)_nNR^aS(O)_pNR^aR^a$, —$(CH_2)_nNR^aS(O)_pR^c$, $C_{1-4}$ alkyl substituted with 0-3 $R^e$, —$(CH_2)_n$—$C_{3-6}$ carbocyclyl substituted with 0-3 $R^e$, and —$(CH_2)_n$-heterocyclyl substituted with 0-3 $R^e$;

$R^2$ is independently selected from $C_{1-5}$ alkyl substituted with 0-3 $R^e$; $C_{2-5}$ alkenyl substituted with 0-3 $R^e$, aryl substituted with 0-3 $R^e$, heterocyclyl substituted with 0-3 $R^e$, and $C_{3-6}$ cycloalkyl substituted with 0-3 $R^e$; provided when $R^2$ is $C_{1-5}$ alkyl, the carbon atom and the groups attached thereto except the one attached to the pyrimidine ring may be replaced by O, N, and S;

$R^3$ is independently selected from
(1) —$(CR^4R^4)_rC(=O)OC_{1-4}$ alkyl substituted with 0-5 $R^e$,
(2) —$(CR^4R^4)_rNR^aR^a$,
(3) —$(CR^4R^4)_rC(=O)NR^aR^a$,
(4) —$(CR^4R^4)_rNR^aC(=O)C_{1-4}$alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$, and
(8) —$(CR^4R^4)_rNR^aC(=O)(CR^4R^4)_nR^5$;

$R^4$ is, independently at each occurrence, selected from H, halogen. $NR^aR^a$. $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently at each occurrence, selected from —$(CH_2)_n$—$C_{3-10}$ carbocycle and —$(CH_2)_n$-heterocycle, each substituted with 0-3 $R^6$;

$R^6$ is independently selected from H, halogen, =O, —$(CH_2)_nOR^b$, —$(CH_2)_nS(O)_pR_c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_n$ $OC(=O)NR^aR^a$, —$(CH_2)_nC(=O)OR^b$, —$(CH_2)_nS(O)_pNR^aR^a$, —$(CH_2)_n$ $NR^aS(O)_pNR^aR^a$, —$(CH_2)_nNR^aS(O)_pR^c$, $C_{1-5}$ alkyl substituted with 0-3 R$^e$, —(CH$_2$)$_n$—C$_{3-6}$ carbocyclyl substituted with 0-3 R$^e$, and —(CH$_2$)$_n$-heterocyclyl substituted with 0-3 R$^e$;

R$^7$ is independently selected from H, C$_{1-5}$ alkyl substituted with 0-3 R$^e$, —(CH$_2$)$_n$—C$_{3-6}$ carbocyclyl substituted with 0-3 R$^e$, and —(CH$_2$)$_n$-heterocyclyl substituted with 0-3 R$^e$;

R$^a$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^c$, at each occurrence, is independently selected from C$_{1-6}$ alkyl substituted with 0-5 R$^e$, C$_{2-6}$alkenyl substituted with 0-5 R$^e$, C$_{2-6}$alkynyl substituted with 0-5 R$^e$, C$_{3-6}$carbocyclyl, and heterocyclyl;

R$^d$, at each occurrence, is independently selected from H and C$_{1-4}$alkyl substituted with 0-5 R$^e$;

R$^e$, at each occurrence, is independently selected from C$_{1-6}$ alkyl substituted with 0-5 R$^f$, C$_{2-6}$ alkenyl, C$_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$_f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR$^f$, OC(=O)NR$^f$R$^f$ and —(CH$_2$)$_n$NR$^f$R$^f$;

R$^f$, at each occurrence, is independently selected from H, F, Cl, Br, CN, OH, C$_{1-5}$alkyl (optionally substituted with halogen and OH), C$_{3-6}$ cycloalkyl, and phenyl, or R$^f$ and R$^f$ together with the nitrogen atom to which they are both attached form a heterocyclic ring optionally substituted with C$_{1-4}$alkyl;

n is independently selected from zero, 1, 2, and 3;
r is independently selected from 1 and 2; and
p, at each occurrence, is independently selected from zero, 1, and 2.

In a second aspect, the present disclosure provides a compound of Formula (II):

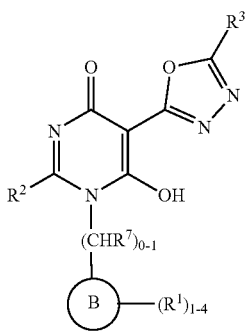

(II)

or a stereoisomer, an enantiomer, a diastereoisomer, a tautomer, a pharmaceutically acceptable salt, or a solvate thereof, within the scope of the first aspect, wherein:
ring B is independently selected from

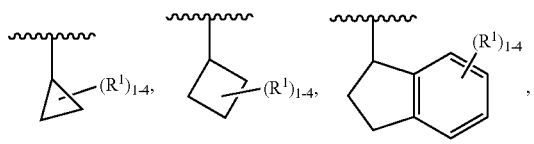

-continued

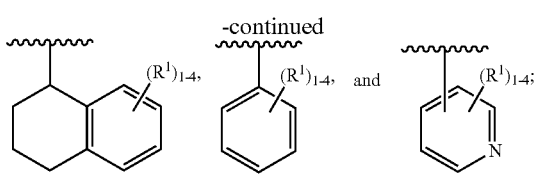

R$^1$ is independently selected from H, F, Cl, Br, NO$_2$, —(CH$_2$)$_n$OR$^b$, —(CH$_2$)$_n$C(=O)R$^b$, —(CH$_2$)$_n$NR$^a$R$^a$, —(CH$_2$)$_n$CN, —(CH$_2$)$_n$C(=O)NR$^a$R$^a$, —(CH$_2$)$_n$NR$^a$C (=O)R$^b$, C$_{1-4}$ alkyl substituted with 0-3 R$^e$ and C$_{3-6}$ cycloalkyl substituted with 0-3 R$^e$;

R$^2$ is independently selected from C$_{1-5}$ alkyl substituted with 0-3 R$^e$; C$_{2-5}$ alkenyl, aryl substituted with 0-3 R$^e$, heterocyclyl substituted with 0-3 R$^e$, and C$_{3-6}$ cycloalkyl; provided when R$^2$ is C$_{1-5}$ alkyl, the carbon atom and the groups attached thereto except the one attached to the pyrimidine ring may be replaced by O, N, and S;

R$^3$ is independently selected from
(1) —(CR$^4$R$^4$)$_r$C(=O)OC$_{1-4}$ alkyl substituted with 0-5 R$^e$,
(2) —(CR$^4$R$^4$)$_r$NR$^a$R$^a$,
(3) —(CR$^4$R$^4$)$_r$C(=O)NR$^a$R$^a$,
(4) —(CR$^4$R$^4$)$_r$NR$^a$C(=O)C$_{1-4}$alkyl substituted with 0-5 R$^e$,
(5) —(CR$^4$R$^4$)$_r$NR$^B$C(=O)(CR$^4$R$^4$)$_n$OC$_{1-4}$alkyl substituted with 0-5 R$^e$,
(6) —(CR$^4$R$^4$)$_r$—R$^5$,
(7) —(CR$^4$R$^4$)$_r$ OR$^5$, and
(8) —(CR$^4$R$^4$)$_r$NR$^a$C(=O)(CR$^4$R$^4$)$_n$R$^5$;

R$^4$ is, independently at each occurrence, selected from H, F, Cl, NR$^a$R$^a$, OC$_{1-4}$ alkyl, and C$_{1-4}$ alkyl; or R$^4$ and R$^4$ together with the carbon atom to which they are both attached form C$_{3-6}$ cycloalkyl substituted with 0-5 R$^e$;

R$^5$ is independently at each occurrence, selected from —(CH$_2$)$_n$-aryl, —(CH$_2$)$_n$—C$_{3-6}$ cycloalkyl and —(CH$_2$)$_n$-heterocycle, each substituted with 0-3 R$^6$;

R$^6$ is independently selected from H, F, Cl, Br, —OR$^b$, =O, —(CH$_2$)$_n$C(=O)R$^b$, —(CH$_2$)$_n$C(=O)OR$^b$, —(CH$_2$)$_f$NR$^a$R$^a$, CN, —(CH$_2$)$_n$C(=O)NR$^a$R$^a$, C$_{1-4}$ alkyl substituted with 0-3 R$^e$, —(CH$_2$)$_n$—C$_{3-6}$ carbocyclyl substituted with 0-3 R$^e$, and —(CH$_2$)$_n$-heterocyclyl substituted with 0-3 R$^e$;

R$^a$, at each occurrence, is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

R$^b$, at each occurrence, is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^e$, at each occurrence, is independently selected from C$_{1-6}$ alkyl substituted with 0-5 R$^f$, C$_{2-6}$ alkenyl, C$_{2-6}$ alkynyl, —(CH$_2$)$_n$—C$_{3-6}$ cycloalkyl, —(CH$_2$)$_n$—C$_{1-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$_f$, S(O)$_p$R$^f$, C(=O)NR$^f$R$^f$, NR$^f$C(=O)R$^f$, S(O)$_p$NR$^f$R$^f$, NR$^f$S(O)$_p$R$_f$, NR$^f$C(=O) OR$^f$, OC(=O)NR$^f$R$^f$ and —(CH$_2$)$_n$NR$^f$R$^f$;

R$^f$, at each occurrence, is independently selected from H, F, Cl, Br, CN, OH, C$_{1-5}$alkyl (optionally substituted with halogen and OH), C$_{3-6}$ cycloalkyl, and phenyl;

n is independently selected from zero, 1, 2, and 3;
r is independently selected from 1 and 2; and
p, at each occurrence, is independently selected from zero, 1, and 2.

In a third aspect, the present disclosure provides a compound of Formula (III):

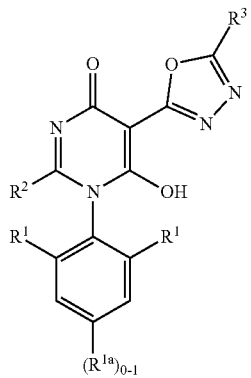

(III)

or a stereoisomer, an enantiomer, a diastereoisomer, a tautomer, a pharmaceutically acceptable salt, or a solvate thereof, within the scope of the first or second aspect, wherein:

$R^1$ is independently selected from H, F, Cl, Br, $OR^b$, CN, $C_{1-4}$ alkyl, and $C_{3-6}$cycloalkyl;

$R^{1a}$ is independently selected from F, Cl, and $C_{1-2}$ alkyl;

$R^2$ is independently selected from $C_{1-5}$ alkyl optionally substituted with halogen and $C_{3-6}$cycloalkyl, $C_{2-5}$ alkenyl, phenyl substituted with 0-3 $R^e$, 6-membered heteroaryl substituted with 0-3 $R^e$, $C_{3-6}$ cycloalkyl, $-(CH_2)_{1-4}OC_{1-3}$alkyl, and $-(CH_2)_{1-3}$O-cycloalkyl;

$R^3$ is independently selected from
(1) $-(CR^4R^4)_rC(=O)OC_{1-4}$ alkyl substituted with 0-5 $R^e$,
(2) $-(CR^4R^4)_rNR^aR^a$,
(3) $-(CR^4R^4)_rC(=O)NR^aR^a$,
(4) $-(CR^4R^4)_rNR^aC(=O)C_{1-4}$alkyl substituted with 0-5 $R^e$,
(5) $-(CR^4R^4)_rNR^aC(=O)(CR^4R^4)_nOC_{1-4}$alkyl substituted with 0-5 $R^e$,
(6) $-(CR^4R^4)_r-R^5$,
(7) $-(CR^4R^4)_r-OR^5$, and
(8) $-(CR^4R^4)_rNR^aC(=O)(CR^4R^4)_nR^5$;

$R^4$ is, independently at each occurrence, selected from H, F, Cl, $NR^aR^a$, $OC_4$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently at each occurrence, selected from $-(CH_2)_n$-aryl, $-(CH_2)_n-C_{3-6}$ cycloalkyl and $-(CH_2)_n$-heterocycle, each substituted with 0-3 $R^6$;

$R^6$ is independently selected from H, F, Cl, Br, $-OR^b$, $=O$, $-(CH_2)_nC(=O)R^b$, $-(CH_2)_nC(=O)OR^b$, $-(CH_2)_nNR^aR^a$, CN, $-(CH_2)_nC(=O)NR^aR^a$, $C_{1-4}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$, $R^a$, at each occurrence, is independently selected from H, $C_{1-6}$ alkyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$:

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, $=O$, $CO_2H$;

r is independently selected from 1 and 2; and n is independently selected from zero, 1, 2, and 3.

In a fourth aspect, the present disclosure provides a compound of Formula (III), or a stereoisomer, an enantiomer, a diastereoisomer, a tautomer, a pharmaceutically acceptable salt, or a solvate thereof, within the scope of any of the first, second and third aspects, wherein:

$R^1$ is independently selected from F, Cl, Br, OH, $OC_{1-4}$ alkyl $OC_{3-6}$cycloalkyl, CN, $C_{1-4}$ alkyl, and $C_{3-6}$cycloalkyl:

$R^2$ is independently selected from $-CH_2CH_2CH_2CH_3$, $-CH_2CH_2CH(CH_3)_2$, $CH_2CH_2CH_2CF_3$, $-CH_2$-cyclopropyl, $-CH_2CH_2$-cyclopropyl, $CH_2CH_2CH=CH_2$, phenyl (optionally substituted with F), pyridyl (optionally substituted with $C_{1-2}$alkyl), $C_{3-5}$ cycloalkyl, $CH_2O(CH_2)_{1-3}CH_3$, $CH_2OCH(CH_3)_2$, and $CH_2O$-cyclopropyl;

$R^3$ is independently selected from
(1) $-CR^4R^4-R^5$ and
(2) $-CR^4R^4-NR^aC(=O)(CR^4R^4)_nR^5$;

$R^4$ is, independently at each occurrence, selected from H, F, Cl, $N(CH_3)_2$, $OCH_3$, and $CH_3$; or $R^4$ and $R^4$ together with the carbon atom to which they are both attached form cyclopropyl;

$R^5$ is independently at each occurrence, selected from

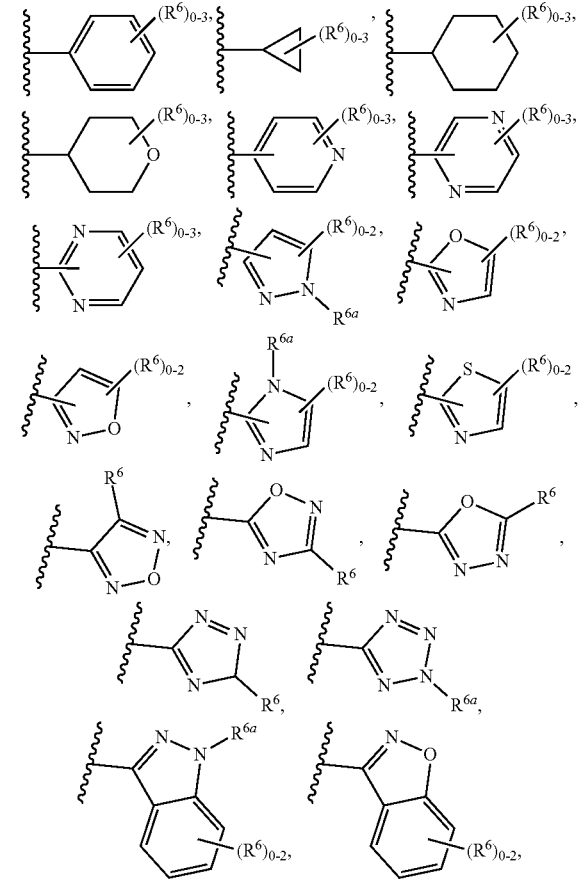

-continued

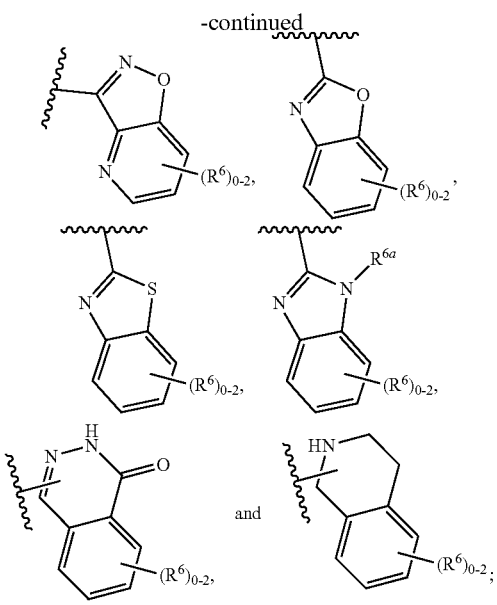

R[6] is independently selected from H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R[e], and —(CH$_2$)$_n$-heterocyclyl substituted with 0-3 R[e];

R[6a] is independently selected from H, CH$_3$, aryl substituted with 0-3 R[e], and heterocyclyl substituted with 0-3 R[e];

R[a], at each occurrence, is independently selected from H, C$_{1-6}$ alkyl substituted with 0-5 R[e], —(CH$_2$)$_n$—C$_{3-10}$carbocyclyl substituted with 0-5 R[e], and —(CH$_2$)$_n$-heterocyclyl substituted with 0-5 R[e];

R[e], at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

In a fifth aspect, the present disclosure provides a compound of Formula (III), or a stereoisomer, an enantiomer, a diastereoisomer, a tautomer, a pharmaceutically acceptable salt, or a solvate thereof, within the scope of any of the first, second, third, and fourth aspects, wherein:

R[1] is independently selected from F, Cl, Br, OH, OCH$_3$, OCD$_3$, OCH$_2$CH$_3$, OCH(CH$_3$)$_2$, O-cyclopropyl, CN, and cyclopropyl;

R[2] is independently selected from —CH$_2$CH$_2$CH$_2$CH, —CH$_2$CH$_2$CH(CH$_3$)$_2$, CH$_2$CH$_2$CH$_2$CF$_3$, —CH$_2$-cyclopropyl, —CH$_2$CH$_2$-cyclopropyl, CH$_2$CH$_2$CH=CH$_2$, phenyl (optionally substituted with F), pyridyl (optionally substituted with C$_{1-2}$alkyl), cyclopentyl, CH$_2$O(CH$_2$)$_{1-3}$CH$_3$, CH$_2$OCH(CH$_3$)$_2$, and CH$_2$O-cyclopropyl;

R[3] is independently selected from
(1) —CH$_2$—R[5] and
(2) —CH$_2$—NR[a]C(=O)R[5];

R[4] is, independently at each occurrence, selected from H, F, Cl, N(CH$_3$)$_2$, OCH$_3$, and CH$_3$; or R[4] and R[4] together with the carbon atom to which they are both attached form cyclopropyl;

R[5] is independently at each occurrence, selected from

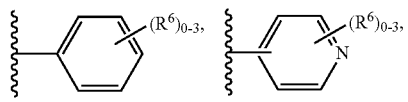

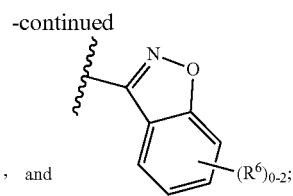

R[6] is independently selected from H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R[e], and —(CH$_2$)$_n$-heterocyclyl substituted with 0-3 R[e];

R[a], at each occurrence, is independently selected from H, C$_{1-6}$ alkyl substituted with 0-5 R[e], —(CH$_2$)$_n$—C$_{3-10}$carbocyclyl substituted with 0-5 R[e], and —(CH$_2$)$_n$-heterocyclyl substituted with 0-5 R[e];

R[e], at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

In a sixth aspect, the present disclosure provides a compound of Formula (III), or a stereoisomer, an enantiomer, a diastereoisomer, a tautomer, a pharmaceutically acceptable salt, or a solvate thereof, within the scope of any of the first, second and third aspects, wherein:

R[1] is independently selected from F, Cl, Br, OH, OC$_{1-4}$ alkyl. OC$_{3-6}$cycloalkyl, CN, C$_{1-4}$ alkyl, and C$_{3-6}$cycloalkyl:

R[2] is independently selected from —CH$_2$CH$_2$CH$_2$CH$_3$, —CH$_2$CH$_2$CH(CH$_3$)$_2$, CH$_2$CH$_2$CH$_2$CF$_3$, —CH$_2$-cyclopropyl. —CH$_2$CH$_2$-cyclopropyl, CH$_2$CH$_2$CH=CH$_2$, phenyl (optionally substituted with F), pyridyl (optionally substituted with C$_{1-2}$alkyl), C$_{3-5}$ cycloalkyl, CH$_2$O (CH$_2$)$_{1-3}$CH$_3$, CH$_2$OCH(CH$_3$)$_2$, and CH$_2$O-cyclopropyl;

R[3] is independently selected from
(1) —(CR[4]R[4])$_r$NR[a]R[a], and
(2) —(CR[4]R[4])$_r$C(=O)NR[a]R[a];

R[4] is, independently at each occurrence, selected from H, F, Cl, N(CH$_3$)$_2$, OCH$_3$, and CH$_3$; or R[4] and R[4] together with the carbon atom to which they are both attached form C$_{3-6}$ cycloalkyl substituted with 0-5 R[e];

R[a] and R[a] together with the nitrogen atom to which they are both attached form a heterocyclic ring selected from

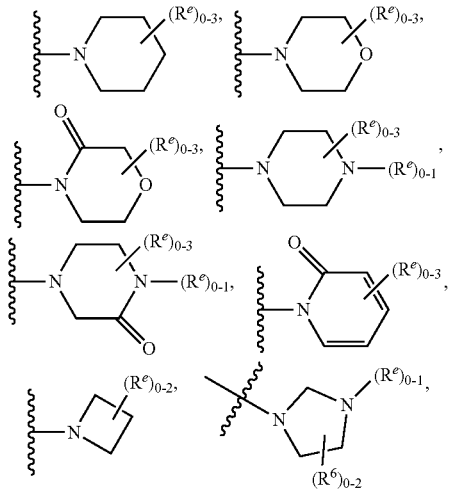

11
-continued

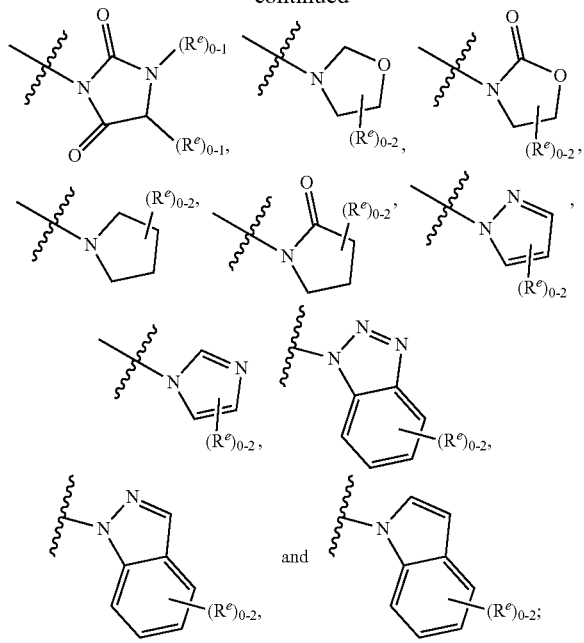

$R^e$, at each occurrence, is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, =O, $CO_2H$;

r is independently selected from 1 and 2; and n is independently selected from zero, 1, 2, and 3.

In a seventh aspect, the present disclosure provides a compound of Formula (III), or a stereoisomer, an enantiomer, a diastereoisomer, a tautomer, a pharmaceutically acceptable salt, or a solvate thereof, within the scope of the sixth aspect, wherein:

$R^1$ is independently selected from F, Cl, Br, OH, $OCH_3$, $OCD_3$, $OCH_2CH_3$, $OCH(CH_3)_2$, O-cyclopropyl, CN, and cyclopropyl;

$R^2$ is independently selected from $-CH_2CH_2CH_2CH_3$, $-CH_2CH_2CH(CH_3)_2$, $CH_2CH_2CH_2CF_3$, $-CH_2$-cyclopropyl, $-CH_2CH_2$-cyclopropyl, $CH_2CH_2CH=CH_2$, phenyl (optionally substituted with F), pyridyl (optionally substituted with $C_{1-2}$alkyl), cyclopentyl, $CH_2O(CH_2)_{1-3}CH_3$, $CH_2OCH(CH_3)_2$, and $CH_2O$-cyclopropyl;

$R^3$ is independently selected from
(1) $-CH_2-NR^aR^a$, and
(2) $-CH_2-C(=O)NR^aR^a$;

$R^4$ is, independently at each occurrence, selected from H, F, Cl, $N(CH_3)_2$, $OCH_3$, and $CH_3$; or $R^4$ and $R^4$ together with the carbon atom to which they are both attached form $C_{1-6}$ cycloalkyl substituted with 0-5 $R^e$;

$R^a$ and $R^a$ together with the nitrogen atom to which they are both attached form a heterocyclic ring selected from

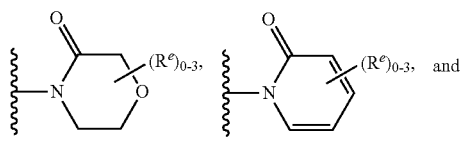

12
-continued

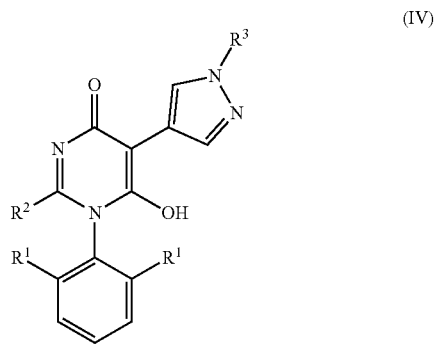

$R^e$, at each occurrence, is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)$-heteroaryl, F, Cl, Br, CN, $NO_2$, =O, $CO_2H$; and n is independently selected from zero, 1, 2, and 3.

In an eighth aspect, the present invention provides a compound of Formula (IV):

(IV)

[Structure of Formula IV]

or a stereoisomer, an enantiomer, a diastereoisomer, a tautomer, a pharmaceutically acceptable salt, or a solvate thereof, within the scope of the first aspect, wherein:

$R^1$ is independently selected from F, Cl, Br, $OR^b$, CN, $C_{1-4}$ alkyl, and $C_{3-6}$cycloalkyl;

$R^2$ is independently selected from $C_{1-5}$ alkyl optionally substituted with halogen and $C_{3-6}$ cycloalkyl, $C_{2-5}$ alkenyl, phenyl substituted with 0-3 $R^e$, 6-membered heteroaryl substituted with 0-3 $R^e$, $C_{3-6}$ cycloalkyl, $CH_2OC_{1-3}$alkyl, and $CH_2O$-cycloalkyl;

$R^3$ is independently selected from
(1) $-CH-R^5$,
(2) $-CH_2-OR^5$, and
(3) $-CH_2-NR^aC(=O)R^5$:

$R^4$ is, independently at each occurrence, selected from H, F, Cl, $NR^aR^a$, $OC_{1-4}$ alkyl, and $C_{1-4}$ alkyl;

$R^5$ is independently at each occurrence, selected from aryl, $C_{3-6}$ cycloalkyl and heterocycle, each substituted with 0-3 $R^6$;

$R^6$ is independently selected from H, F, Cl, Br, $-OR^b$, =O, $-(CH_2)_nC(=O)R^b$, $-(CH_2)_nC(=O)OR^b$, $-(CH_2)_nNR^aR^a$, CN, $-(CH_2)_nC(=O)NR^aR^a$, $C_{1-4}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

$R^a$, at each occurrence, is independently selected from H, $C_{1-6}$ alkyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$:

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —(CH$_2$)$_n$—C$_{3-10}$carbocyclyl substituted with 0-5 R$^e$, and —(CH$_2$)$_n$-heterocyclyl substituted with 0-5 R$^e$;

R$^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO, =O, CO$_2$H; and n is independently selected from zero, 1, 2, and 3.

In a ninth aspect, the present invention provides a compound of Formula (V):

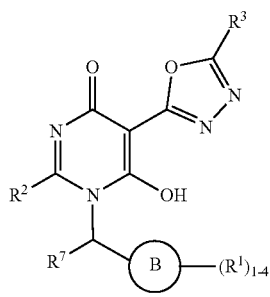

(V)

or a stereoisomer, an enantiomer, a diastereoisomer, a tautomer, a pharmaceutically acceptable salt, or a solvate thereof, within the scope of the first or second aspect, wherein:

ring B is independently selected from

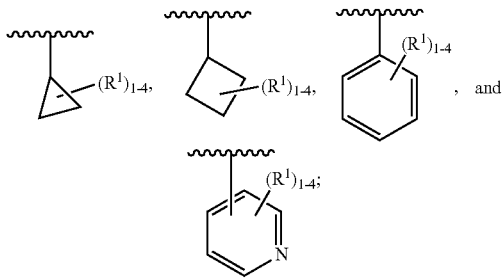

R$^1$ is independently selected from H, F, Cl, Br, OC$_{1-4}$ alkyl, CN, and C$_{1-4}$ alkyl;

R$^2$ is independently selected from —CH$_2$CH$_2$CH$_2$CH$_3$, —CH$_2$CH$_2$CH(CH$_3$)$_2$, CH$_2$CH$_2$CH$_2$CF$_3$, —CH$_2$-cyclopropyl, —CH$_2$CH$_2$-cyclopropyl, CH$_2$CH$_2$CH=CH$_2$, phenyl (optionally substituted with F), pyridyl (optionally substituted with C$_{1-2}$alkyl), C$_{3-5}$ cycloalkyl, CH$_2$O(CH$_2$)$_{1-3}$CH$_3$, CH$_2$OCH(CH$_3$)$_2$, and CH$_2$O-cyclopropyl;

R$^3$ is independently selected from
(1) —CH$_2$R$^5$ and
(2) —CH$_2$OR$^5$;

R$^5$ is independently at each occurrence, selected from

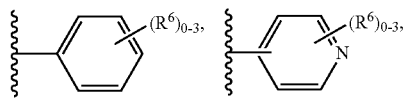

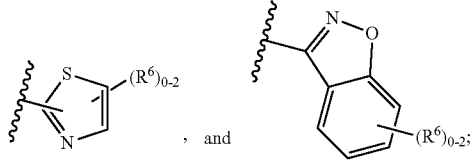

, and

R$^6$ is independently selected from H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)$_n$-heterocyclyl substituted with 0-3 R$^e$;

R$^7$ is independently selected from CH$_3$, CH$_2$CH$_3$, CH$_2$CH$_2$CH$_3$, CH(CH$_3$)$_2$, and CH$_2$OCH$_3$;

R$^e$, at each occurrence, is independently selected from C$_{1-6}$ alkyl substituted with 0-5 R$_f$, C$_{2-6}$ alkylene, —(CH$_2$)$_r$—C$_{3-6}$ cycloalkyl, —(CH$_2$)$_n$—C$_{4-6}$ heterocyclyl, —(CH$_2$)$_n$-aryl. —(CH$_2$)$_n$-heteroaryl, F, Cl, Br, CN, NO$_2$, =O, and CO$_2$H;

n is independently selected from zero, 1, 2, and 3.

In a tenth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the tenth aspect.

In another aspect, the present invention provides a compound selected from the following list:
5-(5-(benzo[d]isoxazol-3-ylmethyl)-1,3,4-oxadiazol-2-yl)-2-butyl-1-(2,6-dimethoxyphenyl)-6-hydroxypyrimidin-4 (1H)-one (1),
2-butyl-5-{5-[(4-chlorophenyl)methyl]-1,3,4-oxadiazol-2-yl}-1-(2,6-dimethoxyphenyl)-6-hydroxy-1,4-dihydropyrimidin-4-one (2),
5-[5-(1,2-benzoxazol-3-ylmethyl)-1,3,4-oxadiazol-2-yl]-2-(but-3-en-1-yl)-1-(2,6-dimethoxyphenyl)-6-hydroxy-1,4-dihydropyrimidin-4-one (3),
5-[5-(1,2-benzoxazol-3-ylmethyl)-1,34-oxadiazol-2-yl]-2-butyl-1-(2,6-diethylphenyl)-6-hydroxy-1,4-dihydropyrimidin-4-one (4),
2-butyl-1-(2,6-dimethoxyphenyl)-6-hydroxy-5-{5-[(2-methyl-1,3-thiazol-4-yl)methyl]-1,3,4-oxadiazol-2-yl}-1, 4-dihydropyrimidin-4-one (5),
2-butyl-1-(2,6-dimethoxyphenyl)-6-hydroxy-5-{5-[(2-oxo-1,2-dihydropyridin-1-yl)methyl]-1,3,4-oxadiazol-2-yl}-1,4-dihydropyrimidin-4-one (6),
1-(2,6-dimethoxyphenyl)-6-hydroxy-2-(3-methylbutyl)-5-{5-[(2-oxopyrrolidin-1-yl)methyl]-1,3,4-oxadiazol-2-yl}-1,4-dihydropyrimidin-4-one (7),
2-butyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one (8),
2-butyl-1-(2,6-dimethoxyphenyl)-6-hydroxy-5-(5-{[3-(pyridin-2-yl)-1,2,4-oxadiazol-5-yl]methyl}-1,3,4-oxadiazol-2-yl)-1,4-dihydropyrimidin-4-one (9),
1-(2,6-dimethoxyphenyl)-6-hydroxy-2-(3-methylbutyl)-5-{5-[(2-oxo-1,2-dihydropyridin-1-yl)methyl]-1,3,4-oxadiazol-2-yl}-1,4-dihydropyrimidin-4-one (10),
2-(but-3-en-1-yl)-1-(2,6-dimethoxyphenyl)-6-hydroxy-5-(5-{[3-(pyridin-2-yl)-1,2,4-oxadiazol-5-yl]methyl}-1,3, 4-oxadiazol-2-yl)-1,4-dihydropyrimidin-4-one (11),
5-[5-(1,2-benzoxazol-3-ylmethyl)-1,3,4-oxadiazol-2-yl]-1-(2,6-dimethoxyphenyl)-6-hydroxy-2-(4,4,4-trifluorobutyl)-1,4-dihydropyrimidin-4-one (12), 5-[5-(1,2-benzoxazol-3-ylmethyl)-1,3,4-oxadiazol-2-yl]-2-butyl-6-hydroxy-1-(2-methoxy-6-methylphenyl)-1,4-dihydropyrimidin-4-one (13), 2-(but-3-en-1-yl)-5-{5-[(4-chlorophenyl)methyl]-1,3,4-oxadiazol-2-yl}-1-(2,6-dimethoxyphenyl)-6-hydroxy-1,4-dihydropyrimidin-4-one (14), 5-[5-(1,2-benzoxazol-3-ylmethyl)-1,3,4-oxadiazol-2-yl]-2-butyl-1-(2,6-dibromophenyl)-6-hydroxy-1,4-dihydropyrimidin-4-one (15), 4-({5-[1-(2,6-dimethoxyphenyl)-6-hydroxy-2-(3-methylbutyl)-4-oxo-1,4-dihydropyrimidin-5-yl]-1,3,4-oxadiazol-2-yl}methyl)morpholin-3-one (16), 5-[5-(1,2-benzoxazol-3-ylmethyl)-1,3,4-oxadiazol-2-yl]-2-(but-3-en-1-yl)-6-hydroxy-1-(2-methoxy-6-methylphenyl)-1,4-dihydropyrimidin-4-one (17), 5-[5-(1,2-benzoxazol-3-ylmethyl)-1,3,4-oxadiazol-2-yl]-2-butyl-1-(4,6-dimethoxypyrimidin-5-yl)-6-hydroxy-1,4-dihydropyrimidin-4-one (18), 5-[5-(1,2-benzoxazol-3-ylmethyl)-1,3,4-oxadiazol-2-yl]-2-butyl-1-(2,6-dichlorophenyl)-6-hydroxy-1,4-dihydropyrimidin-4-one (19), 5-[5-(1,2-benzoxazol-3-ylmethyl)-1,3,4-oxadiazol-2-yl]-2-(cyclopropylmethyl)-1-(2,6-dimethoxyphenyl)-6-hydroxy-1,4-dihydropyrimidin-4-one (20), 5-{5-[(4-chlorophenyl)methyl]-1,3,4-oxadiazol-2-yl}-2-(cyclopropylmethyl)-1-(2,6-dimethoxyphenyl)-6-hydroxy-1,4-dihydropyrimidin-4-one (21), 2-(cyclopropylmethyl)-1-(2,6-dimethoxyphenyl)-6-hydroxy-5-(5-{[3-(pyridin-2-yl)-1,2,4-oxadiazol-5-yl]methyl}-1,3,4-oxadiazol-2-yl)-1,4-dihydropyrimidin-4-one (22), 5-(5-(Benzo[d]isoxazol-3-ylmethyl)-1,3,4-oxadiazol-2-yl)-2-butyl-1-(2,6-diethoxyphenyl)-6-hydroxypyrimidin-4(1H)-one (23), 5-[5-(1,2-benzoxazol-3-ylmethyl)-1,3,4-oxadiazol-2-yl]-1-[2,6-bis(propan-2-yloxy)phenyl]-2-butyl-6-hydroxy-1,4-dihydropyrimidin-4-one (24), 2-butyl-1-(2,6-diethoxyphenyl)-6-hydroxy-5-{5-[(2-methyl-1,3-thiazol-4-yl)methyl]-1,3,4-oxadiazol-2-yl}-1,4-dihydropyrimidin-4-one (25), 2-butyl-5-{5-[(4-chlorophenyl)methyl]-1,3,4-oxadiazol-2-yl}-1-(2,6-diethoxyphenyl)-6-hydroxy-1,4-dihydropyrimidin-4-one (26), 5-(Benzo[d]isoxazol-3-ylmethyl)-1,3,4-oxadiazol-2-yl)-2-butyl-1-(2,6-dicyclopropylphenyl)-6-hydroxypyrimidin-4(1H)-one Example 27a. 2,6-Dicyclopropylaniline (27)

2-(5-(5-(Benzo[d]isoxazol-3-ylmethyl)-1,3,4-oxadiazol-2-yl)-2-butyl-6-hydroxy-4-oxopyrimidin-1(4H)-yl)isophthalonitrile (28)

2-butyl-5-(5-(4-chlorobenzyl)-1,3,4-oxadiazol-2-yl)-1-(2,6-dicyclopropoxyphenyl)-6-hydroxypyrimidin-4(1H)-one (29), 5-[5-(1,2-benzoxazol-3-ylmethyl)-1,3,4-oxadiazol-2-yl]-2-butyl-1-(2,6-dicyclopropoxyphenyl)-6-hydroxy-1,4-dihydropyrimidin-4-one (30), 5-(1-benzyl-1H-pyrazol-4-yl)-2-butyl-3-(2,6-dimethoxyphenyl)-6-hydroxypyrimidin-4(3H)-one (31), 2-butyl-5-{1-[(4-chlorophenyl)methyl]-1H-pyrazol-4-yl}-3-(2,6-dimethoxyphenyl)-6-hydroxy-3,4-dihydropyrimidin-4-one (32), 5-(5-(benzo[d]isoxazol-3-ylmethyl)-1,3,4-oxadiazol-2-yl)-1-(2,6-dimethoxyphenyl)-6-hydroxy-2-(ethoxymethyl)pyrimidin-4(1H)-one (33), 5-[5-(1,2-benzoxazol-3-ylmethyl)-1,3,4-oxadiazol-2-yl]-1-(2,6-dimethoxyphenyl)-6-hydroxy-2-[(propan-2-yloxy)methyl]-1,4-dihydropyrimidin-4-one (34), 5-[5-(1,2-benzoxazol-3-ylmethyl)-1,3,4-oxadiazol-2-yl]-1-(2,6-diethylphenyl)-2-(ethoxymethyl)-6-hydroxy-1,4-dihydropyrimidin-4-one (35), 5-{5-[(4-chlorophenyl)methyl]-1,3,4-oxadiazol-2-yl}-1-(2,6-dimethoxyphenyl)-6-hydroxy-2-[(propan-2-yloxy)methyl]-1,4-dihydropyrimidin-4-one (36), 5-{5-[(4-chlorophenyl)methyl]-1,3,4-oxadiazol-2-yl}-1-(2,6-diethylphenyl)-2-(ethoxymethyl)-6-hydroxy-1,4-dihydropyrimidin-4-one (37), 5-{5-[(4-chloro-3-fluorophenyl)methyl]-1,3,4-oxadiazol-2-yl}-1-(2,6-dimethoxyphenyl)-2-(ethoxymethyl)-6-hydroxy-1,4-dihydropyrimidin-4-one (38), 1-(2,6-dimethoxyphenyl)-2-(ethoxymethyl)-6-hydroxy-5-{5-[(2-phenyl-1,3-thiazol-4-yl)methyl]-1,3,4-oxadiazol-2-yl}-1,4-dihydropyrimidin-4-one (39), 5-{5-[(4-chlorophenyl)methyl]-1,3,4-oxadiazol-2-yl}-1-(2,6-dimethoxyphenyl)-2-(ethoxymethyl)-6-hydroxy-1,4-dihydropyrimidin-4-one (40), 5-[5-(1,2-benzoxazol-3-ylmethyl)-1,3,4-oxadiazol-2-yl]-1-(2,6-dicyclopropylphenyl)-6-hydroxy-2-[(propan-2-yloxy)methyl]-1,4-dihydropyrimidin-4-one (41), 5-(5-(benzo[d]isoxazol-3-ylmethyl)-1,3,4-oxadiazol-2-yl)-2-(2-cyclopropylethyl)-1-(2,6-dimethoxyphenyl)-6-hydroxypyrimidin-4(1H)-one (42), 2-(2-cyclopropylethyl)-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one (43), 2-(cyclopropylethyl)-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one (44), 5-{5-[(4-chlorophenyl)methyl]-1,3,4-oxadiazol-2-yl}-2-(2-cyclopropylethyl)-1-(2,6-dimethoxyphenyl)-6-hydroxy-1,4-dihydropyrimidin-4-one (45), 2-(2-cyclopropylethyl)-1-(2,6-dimethoxyphenyl)-6-hydroxy-5-{5-[(2-oxo-1,2-dihydropyridin-1-yl)methyl]-1,3,4-oxadiazol-2-yl}-1,4-dihydropyrimidin-4-one (46), 4-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)morpholin-3-one (47), 5-(5-(Benzo[d]isoxazol-3-ylmethyl)-1,3,4-oxadiazol-2-yl)-2-butyl-1-(2,6-di($^2$H$_3$)methoxyphenyl)-6-hydroxypyrimidin-4(1H)-one (48), 1-[2,6-bis($^2$H$_3$)methoxyphenyl]-2-butyl-5-{5-[(4-chlorophenyl)methyl]-1,3,4-oxadiazol-2-yl}-6-hydroxy-1,4-dihydropyrimidin-4-one (49), 5-[5-(1,2-benzoxazol-3-ylmethyl)-1,3,4-oxadiazol-2-yl]-1-[2,6-bis($^2$H$_3$)methoxyphenyl]-2-(ethoxymethyl)-6-hydroxy-1,4-dihydropyrimidin-4-one (50), 1-[2,6-bis($^2$H$_3$)methoxyphenyl]-5-{5-[(4-chlorophenyl)methyl]-1,3,4-oxadiazol-2-yl}-2-(ethoxymethyl)-6-hydroxy-1,4-dihydropyrimidin-4-one (51), 2-(5-(2-(2-Cyclopropylethyl)-1-(2,6-dimethoxyphenyl)-6-hydroxy-4-oxo-1,4-dihydropyrimidin-5-yl)-1,3,4-oxadiazol-2-yl)-N,N-diethylacetamide (52), N-((5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)methyl)-N-methylpicolinamide (53), N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)-N-methylpyridine-2-carboxamide (54), 3-chloro-N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)benzamide (55), N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)pyridine-3-carboxamide (56), N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)benzamide (57), N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)pyridine-2-carboxamide (58), 5-{5-[(5-chloropyridin-2-yl)methyl]-1,3,4-oxadiazol-2-yl}-2-(2-cyclopropylethyl)-1-(2,6-dimethoxyphenyl)-6-hydroxy-1,4-dihydropyrimidin-4-one (59), 5-{5-[(4-chloro-2-fluorophenyl)methyl]-1,3,4-oxadiazol-2-yl}-1-(2,6-dimethoxyphenyl)-6-hydroxy-2-[(propan-2-yloxy)methyl]-1,4-dihydropyrimidin-4-one (60), 2-(2-cyclopropylethyl)-1-(2,6-dimethoxyphenyl)-5-{5-[(5-fluoropyridin-2-yl)methyl]-1,3,4-oxadiazol-2-yl}-6-hydroxy-1,4-dihydropyrimidin-4-one (61), 2-cyclopentyl-1-(2,6-dimethoxyphenyl)-6-hydroxy-5-{5-[(2-oxo-1,2-dihydropyridin-1-yl)methyl]-1,3,4-oxadiazol-2-yl}-1,4-dihydropyrimidin-4-one (62), 5-{5-[(6-chloropyridin-3-yl)methyl]-1,3,4-oxadiazol-2-yl}-2-cyclopentyl-1-(2,6-dimethoxyphenyl)-6-hydroxy-1,4-dihydropyrimidin-4-one (63), 2-cyclopentyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one (64), 2-cyclopentyl-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one (65), 5-{5-[(5-chloropyridin-2-yl)methyl]-1,3,4-oxadiazol-2-yl}-2-cyclopentyl-1-(2,6-dimethoxyphenyl)-6-hydroxy-1,4-hydropyrimidin-4-one (66), 2-cyclopentyl-1-(2,6-dimethoxyphenyl)-5-{5-[(5-fluoropyridin-2-yl)methyl]-1,3,4-oxadiazol-2-yl}-6-hydroxy-1,4-dihydropyrimidin-4-one (67), 2-cyclopentyl-1-(2,6-dimethoxyphenyl)-6-hydroxy-5-{5-[(6-methylpyridin-3-yl)methyl]-1,3,4-oxadiazol-2-yl}-1,4-dihydropyrimidin-4-one (68), 5-{5-[(5-chloro-3-fluoropyridin-2-yl)methyl]-1,3,4-oxadiazol-2-yl}-2 cyclopentyl-1-(2,6-dimethoxyphenyl)-6-hydroxy-1,4-dihydropyrimidin-4-one (69), 5-{5-[(5-chloropyridin-2-yl)methyl]-1,3,4-oxadiazol-2-yl}-2-cyclobutyl-1-(2,6-dimethoxyphenyl)-6-hydroxy-1,4-dihydropyrimidin-4-one (70), 5-{5-[(5-chloro-3-fluoropyridin-2-yl)methyl]-1,3,4-oxadiazol-2-yl}-2-cyclobutyl-1-(2,6-dimethoxyphenyl)-6-hydroxy-1,4-dihydropyrimidin-4-one (71), 2-cyclobutyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one (72), 2-cyclobutyl-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one (73), (S)-5-(5-(Benzo[d]isoxazol-3-ylmethyl)-1,3,4-oxadiazol-2-yl)-2-butyl-6-hydroxy-3-(1-phenylpropyl)pyrimidin-4(3H)-one (74), 5-{5-[(1,2-benzoxazol-3-yl)methyl]-1,3,4-oxadiazol-2-yl}-2-butyl-6-hydroxy-3-[(1S)-1-phenylethyl]-3,4-dihydropyrimidin-4-one (75), 2-butyl-6-hydroxy-5-{5-[(2-methyl-1,3-thiazol-4-yl)methyl]-1,3,4-oxadiazol-2-yl}-3-[(1S)-1-phenylethyl]-3,4-dihydropyrimidin-4-one (76), 2-butyl-5-{5-[(4-chlorophenyl)methyl]-1,3,4-oxadiazol-2-yl}-3-[(1S)-1-cyclopropylethyl]-6-hydroxy-3,4-dihydropyrimidin-4-one (77), 5-{5-[(1,2-benzoxazol-3-yl)methyl]-1,3,4-oxadiazol-2-yl}-2-butyl-6-hydroxy-3-[(1R)-1-(2-methoxyphenyl)ethyl]-3,4-dihydropyrimidin-4-one (78), 2-butyl-6-hydroxy-3-[(1R)-1-(2-methoxyphenyl)ethyl]-5-{5-[(2-methyl-1,3-thiazol-4-yl)methyl]-1,3,4-oxadiazol-2-yl}-3,4-dihydropyrimidin-4-one (79), 2-butyl-3-[(1R)-1-cyclopropylethyl]-6-hydroxy-5-{5-[(2-methyl-1,3-thiazol-4-yl)methyl]-1,3,4-oxadiazol-2-yl}-3,4-dihydropyrimidin-4-one (80), 2-butyl-5-{5-[(4-chlorophenyl)methyl]-1,3,4-oxadiazol-2-yl}-6-hydroxy-3-[(1R)-1-(2-methoxyphenyl)ethyl]-3,4-dihydropyrimidin-4-one (81), 2-butyl-6-hydroxy-5-{5-[(2-methyl-1,3-thiazol-4-yl)methyl]-1,3,4-oxadiazol-2-yl}-3-[(1R)-1-phenylethyl]-3,4-dihydropyrimidin-4-one (82), 2-butyl-5-{5-[(4-chlorophenyl)methyl]-1,3,4-oxadiazol-2-yl}-6-hydroxy-3-[(1R)-1-phenylethyl]-3,4-dihydropyrimidin-4-one (83), 2-butyl-5-{5-[(4-chlorophenyl)methyl]-1,3,4-oxadiazol-2-yl}-6-hydroxy-3-[(1S)-1-phenylpropyl]-3,4-dihydropyrimidin-4-one (84), 2-butyl-6-hydroxy-5-{5-[(2-methyl-1,3-thiazol-4-yl)methyl]-1,3,4-oxadiazol-2-yl}-3-[(1S)-1-phenylpropyl]-3,4-dihydropyrimidin-4-one (85), 5-{5-[(1,2-benzoxazol-3-yl)methyl]-1,3,4-oxadiazol-2-yl}-2-butyl-6-hydroxy-3-[(1R)-1-phenylethyl]-3,4-dihydropyrimidin-4-one (86), 5-{5-[(1,2-benzoxazol-3-yl)methyl]-1,3,4-oxadiazol-2-yl}-2-butyl-6-hydroxy-3-[(1R)-1-phenylpropyl]-3,4-dihydropyrimidin-4-one (87), 2-butyl-6-hydroxy-5-{5-[(2-methyl-1,3-thiazol-4-yl)methyl]-1,3,4-oxadiazol-2-yl})-3-[(1R)-1-phenylpropyl]-3,4-dihydropyrimidin-4-one (88), 2-butyl-5-{5-[(4-chlorophenyl)methyl]-1,3,4-oxadiazol-2-yl}-6-hydroxy-3-[(1R)-1-phenylpropyl]-3,4-dihydropyrimidin-4-one (89), 5-{5-[(1,2-benzoxazol-3-yl)methyl]-1,3,4-oxadiazol-2-yl}-2-butyl-6-hydroxy-3-[(1S)-2-methoxy-1-phenylethyl]-3,4-dihydropyrimidin-4-one (90), 5-{5-[(1,2-benzoxazol-3-yl)methyl]-1,3,4-oxadiazol-2-yl}-2-butyl-6-hydroxy-3-[(1R)-2-methoxy-1-phenylethyl]-3,4-dihydropyrimidin-4-one (91), 5-{5-[(1,2-benzoxazol-3-yl)methyl]-1,3,4-oxadiazol-2-yl}-2-butyl-6-hydroxy-3-[(1S)-1,2,3,4-tetrahydronaphthalen-1-yl]-3,4-dihydropyrimidin-4-one (92), 2-butyl-6-hydroxy-3-[(1S)-2-methoxy-1-phenylethyl]-5-{5-[(2-methyl-1,3-thiazol-4-yl)methyl]-1,3,4-oxadiazol-2-yl}-3,4-dihydropyrimidin-4-one (93), 2-butyl-6-hydroxy-3-[(1R)-2-methoxy-1-phenylethyl]-5-{5-[(2-methyl-1,3-thiazol-4-yl)methyl]-1,3,4-oxadiazol-2-yl}-3,4-dihydropyrimidin-4-one (94), 2-butyl-3-[(1S)-1-(4-fluorophenyl)ethyl]-6-hydroxy-5-{5-[(2-methyl-1,3-thiazol-4-yl)methyl]-1,3,4-oxadiazol-2-yl}-3,4-dihydropyrimidin-4-one (95), 5-{5-[(1,2-benzoxazol-3-yl)methyl]-1,3,4-oxadiazol-2-yl}-2-butyl-3-[(1S)-2,3-dihydro-1H-inden-1-yl]-6-hydroxy-3,4-dihydropyrimidin-4-one (96), 2-butyl-3-[(1S)-2,3-dihydro-1H-inden-1-yl]-6-hydroxy-5-{5-[(2-methyl-1,3-thiazol-4-yl)methyl]-1,3,4-oxadiazol-2-yl}-3,4-dihydropyrimidin-4-one (97), 2-butyl-5-{5-[(5-chloropyridin-2-yl)methyl]-1,3,4-oxadiazol-2-yl}-3-[(1S)-1-(4-fluorophenyl)ethyl]-6-hydroxy-3,4-dihydropyrimidin-4-one (98), 2-butyl-5-{(5-[(5-chloropyridin-2-yl)methyl]-1,3,4-oxadiazol-2-yl}-6-hydroxy-3-[(1S)-2-methoxy-1-phenylethyl]-3,4-dihydropyrimidin-4-one (99), 2-butyl-5-{5-[(5-chloropyridin-2-yl)methyl]-1,3,4-oxadiazol-2-yl}-6-hydroxy-3-[(1S)-1,2,3,4-tetrahydronaphthalen-1-yl]-3,4-dihydropyrimidin-4-one (100), 2-butyl-5-{5-[(5-chloropyridin-2-yl)methyl]-1,3,4-oxadiazol-2-yl}-6-hydroxy-3-[(1R)-2-methoxy-1-phenylethyl]-3,4-dihydropyrimidin-4-one (101), 5-{5-[(1,2-benzoxazol-3-yl)methyl]-1,3,4-oxadiazol-2-yl}-2-butyl-6-hydroxy-3-[(1S)-1-(4-methoxyphenyl)ethyl]-3,4-dihydropyrimidin-4-one (102), 3-[(1S)-1-(5-{5-[(1,2-benzoxazol-3-yl)methyl]-1,3,4-oxadiazol-2-yl}-2-butyl-4-hydroxy-6-oxo-1,6-dihydropyrimidin-1-yl)ethyl]benzonitrile (103), 3-[(1S)-1-(2-butyl-4-hydroxy-5-{5-[(2-methyl-1,3-thiazol-4-yl)methyl]-1,3,4-oxadiazol-2-yl}-6-oxo-1,6-dihydropyrimidin-1-yl)ethyl]benzonitrile (104), 2-butyl-5-{5-[(5-chloropyridin-2-yl)methyl]-1,3,4-oxadiazol-2-yl}-6-hydroxy-3-[(1S)-1-phenylbutyl]-3,4-dihydropyrimidin-4-one (105), 2-butyl-6-hydroxy-5-{5-[(2-methyl-1,3-thiazol-4-yl)methyl]-1,3,4-oxadiazol-2-yl}-3-[(1S)-1-phenylbutyl]-3,4-dihydropyrimidin-4-one (106), 5-{5-[(1,2-benzoxazol-3-yl)methyl]-1,3,4-oxadiazol-2-yl}-2-butyl-6-hydroxy-3-[(1S)-1-phenylbutyl]-3,4-dihydropyrimidin-4-one (107), 3-[(1S)-1-(2-butyl-5-{5-[(5-chloropyridin-2-yl)methyl]-1,3,4-oxadiazol-2-yl}-4-hydroxy-6-oxo-1,6-dihydropyrimidin-1-yl)ethyl]benzonitrile (108), 2-butyl-5-{5-[(5-chloropyridin-2-yl)methyl]-1,3,4-oxadiazol-2-yl}-6-hydroxy-3-[1-(pyridin-4-yl)ethyl]-3,4-dihydropyrimidin-4-one (109), 5-{5-[(1,2-benzoxazol-3-yl)methyl]-1,3,4-oxadiazol-2-yl}-2-butyl-6-hydroxy-3-[1-(pyridin-4-yl)ethyl]-3,4-dihydropyrimidin-4-one (110), 2-butyl-5-{(5-[(5-chloropyridin-2-yl)methyl]-1,3,4-oxadiazol-2-yl}-6-hydroxy-3-[1-(pyridin-yl)ethyl]-3,4-dihydropyrimidin-4-one (111), 2-butyl-6-hydroxy-5-{5-[(2-methyl-1,3-thiazol-4-yl)methyl]-1,3,4-oxadiazol-2-yl}-3-(2-methyl-1-phenylpropyl)-3,4-dihydropyrimidin-4-one (112), 2-butyl-5-{5-[(5-chloropyridin-2-yl)methyl]-1,3,4-oxadiazol-2-yl}-6-hydroxy-3-(2-methyl-1-phenylpropyl)-3,4-dihydropyrimidin-4-one (113), 5-{5-[(1,2-benzoxazol-3-yl)methyl]-1,3,4-oxadiazol-2-yl}-2-butyl-6-hydroxy-3-[(1S)-1-(3-methoxyphenyl)ethyl]-3,4-dihydropyrimidin-4-one (114).

5-{5-[(1,2-benzoxazol-3-yl)methyl]-1,3,4-oxadiazol-2-yl}-2-butyl-6-hydroxy-3-(2-methyl-1-phenylpropyl)-3,4-dihydropyrimidin-4-one (115), 2-butyl-5-{5-[(5-chloropyridin-2-yl)methyl]-1,3,4-oxadiazol-2-yl}-6-hydroxy-3-[(1S)-1-(3-methoxyphenyl)ethyl]-3,4-dihydropyrimidin-4-one (116), 5-{5-[(1,2-benzoxazol-3-yl)methyl]-1,3,4-oxadiazol-2-yl}-2-butyl-3-[(1R)-2,3-dihydro-1H-inden-1-yl]-6-hydroxy-3,4-dihydropyrimidin-4-one (117), 2-butyl-5-{5-[(5-chloropyridin-2-yl)methyl]-1,3,4-oxadiazol-2-yl}-6-hydroxy-3-[(1S)-1-phenylpropyl]-3,4-dihydropyrimidin-4-one (118), 2-butyl-5-{5-[(5-chloropyridin-2-yl)methyl]-1,3,4-oxadiazol-2-yl}-6-hydroxy-3-[(1S)-1-phenylethyl]-3,4-dihydropyrimidin-4-one (119), 2-butyl-5-{5-[(5-chloropyridin-2-yl)methyl]-1,3,4-oxadiazol-2-yl}-6-hydroxy-3-[(1R)-1-phenylethyl]-3,4-dihydropyrimidin-4-one (120), 5-{5-[(1,2-benzoxazol-3-yl)methyl]-1,3,4-oxadiazol-2-yl}-2-butyl-6-hydroxy-3-[1-(pyridin-3-yl)ethyl]-3,4-dihydropyrimidin-4-one (121), 2-butyl-5-({5-[(5-chloropyridin-2-yl)methyl]-1,3,4-oxadiazol-2-yl}-3-[(1R)-2,3-dihydro-1H-inden-1-yl]-6-hydroxy-3,4-dihydropyrimidin-4-one (122), 2-butyl-5-{5-[(5-chloropyridin-2-yl)methyl]-1,3,4-oxadiazol-2-yl}-6-hydroxy-3-[1-(pyridin-3-yl)ethyl]-3,4-dihydropyrimidin-4-one (123), and 2-butyl-6-hydroxy-5-{5-[(2-methyl-1,3-thiazol-4-yl)methyl]-1,3,4-oxadiazol-2-yl}-3-[1-(pyridin-3-yl)ethyl]-3,4-dihydropyrimidin-4-one (124).

In another aspect, the present invention provides compounds of Formula (I), or stereoisomers, enantiomers, diastereomers, tautomers, pharmaceutically acceptable salts, solvates, or prodrugs thereof, wherein:

alk is $C_{1-6}$ alkyl substituted with 1-5 $R^7$;

ring A is 5- to 6-membered heteroaryl;

ring B is independently selected from $C_{3-6}$ cycloalkyl, $C_{3-6}$ cycloalkenyl, aryl, bicyclic carbocyclyl, and 6-membered heteroaryl;

$R^1$ is independently selected from H, halogen, $NO_2$, $-(CH_2)_nOR^b$, $(CH_2)_nS(O)_pR_c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_nOC(=O)NR^aR^a$, $-(CH_2)_nC(=O)OR^b$, $-(CH_2)_nS(O)_pNR^aR^a$, $-(CH_2)_nNR^aS(O)_pNR^aR^a$, $-(CH_2)_nNR^aS(O)_pR^c$, $C_{1-4}$ alkyl substituted with 0-3 $R^e$, $-(CH_2)_n-C_{3-6}$ carbocyclyl substituted with 0-3 $R^e$, and $-(CH_2)_n$-heterocyclyl substituted with 0-3 $R^e$;

$R^2$ is independently selected from $C_{1-5}$ alkyl substituted with 0-3 $R^e$; $C_{2-5}$ alkenyl substituted with 0-3 $R^e$, aryl substituted with 0-3 $R^e$, heterocyclyl substituted with 0-3 $R^e$, and $C_{3-6}$ cycloalkyl substituted with 0-3 $R^e$; provided when $R^2$ is $C_{1-5}$ alkyl, the carbon atom and the groups attached thereto except the one attached to the pyrimidine ring may be replaced by O, N, and S;

$R^3$ is independently selected from (1) $-(CR^4R^4)_rC(=O)OC_{1-4}$ alkyl substituted with 0-5 $R^e$, (2) $-(CR^4R^4)_rNR^8R^8$, (3) $-(CR^4R^4)_rC(=O)NR^8R^8$, (4) $-(CR^4R^4)_rNR^aC(=O)C_{1-4}$ alkyl substituted with 0-5 $R^e$, (5) $-(CR^4R^4)_rNR^aC(=O)(CR^4R^4)_nOC_{1-4}$ alkyl substituted with 0-5 $R^e$, (6) $-(CR^4R^4)_r-R^5$, (7) $-(CR^4R^4)_r-OR^5$, and (8) $-(CR^4R^4)_rNR^aC(=O)(CR^4R^4)_nR^5$;

$R^4$ is, independently at each occurrence, selected from H, halogen, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently at each occurrence, selected from $-(CH_2)_n-C_{3-10}$ carbocycle and $-(CH_2)_n$-heterocycle comprising carbon atoms and 1-3 heteroatoms selected from N, $NR^{6a}$, O, and S, each substituted with 0-5 $R^6$;

$R^6$ is independently selected from H, halogen, $=O$, $-(CH_2)_nOR^b$, $(CH_2)_nS(O)_pR_c$, $-(CH_2)_nC(=O)R^b$, $-(CH_2)_nNR^aR^a$, $-(CH_2)_nCN$, $-(CH_2)_nC(=O)NR^aR^a$, $-(CH_2)_nNR^aC(=O)R^b$, $-(CH_2)_nNR^aC(=O)NR^aR^a$, $-(CH_2)_nNR^aC(=O)OR^b$, $-(CH_2)_n OC(=O)NR^aR^a$, $-(CH_2)_nC(=O)OR^b$, $-(CH_2)_zS(O)_pNR^aR^a$, $-(CH_2)_n NR^aS(O)_pNR^aR^a$. $-(CH_2)_nNR^aS(O)_pR^c$, $C_{1-5}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

$R^{6a}$ is independently selected from H, $-S(O)_pR_c$, $-C(=O)R^b$, $-C(=O)NR^aR^a$, $-C(=O)OR^b$, $-S(O)_pNR^aR^a$, $C_{1-5}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

R⁷ is independently selected from H, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^8$ and $R^8$ together with the nitrogen atom to which they are both attached form a heterocyclic ring comprising carbon atoms and 0-3 additional heteroatoms selected from N, $NR^{6a}$, O, and S, and substituted with 0-5 $R^6$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$-alkenyl substituted with 0-5 $R^e$, $C_{2-6}$alkynyl substituted with 0-5 $R^e$, $C_{3-6}$-carbocyclyl, and heterocyclyl;

$R^d$, at each occurrence, is independently selected from H and $C_{1-4}$alkyl substituted with 0-5 $R^e$;

$R^e$, at each occurrence, is independently selected from $C_{1-6}$ alkyl (optionally substituted with halogen, OH, and CN), $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, NO, =O, $CO_2H$, —$(CH_2)_nOR^f$, $S(O)_pR^f$, $C(=O)NR^fR^f$, $NR^fC(=O)R^f$, $S(O)_pNR^fR^f$, $NR^f$-$S(O)_pR^f$, $NR^fC(=O)OR^f$, $OC(=O)NR^fR^f$ and —$(CH_2)_n$ $NR^fR^f$;

$R^f$, at each occurrence, is independently selected from H, $C_{1-5}$alkyl (optionally substituted with halogen and OH), $C_{3-6}$ cycloalkyl, and phenyl, or $R^f$ and $R^f$ together with the nitrogen atom to which they are both attached form a heterocyclic ring optionally substituted with $C_{1-4}$alkyl;

n is independently selected from zero, 1, 2, and 3;

r is independently selected from 1 and 2; and p, at each occurrence, is independently selected from zero, 1, and 2.

In another aspect, the present invention provides compounds of Formula (I), or stereoisomers, enantiomers, diastereomers, tautomers, pharmaceutically acceptable salts, solvates, or prodrugs thereof, wherein:

alk is $C_{1-6}$ alkyl substituted with 1-5 $R^7$;

ring A is independently selected from

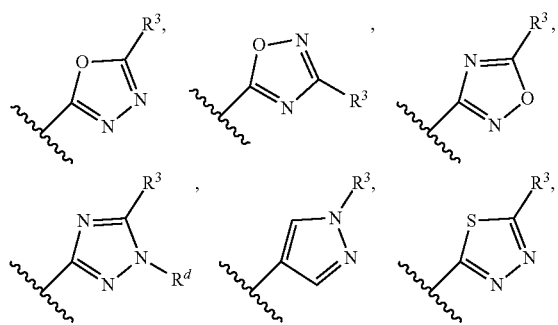

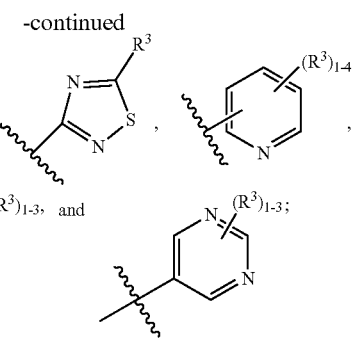

ring B is independently selected from $C_{3-6}$ cycloalkyl, $C_{3-6}$ cycloalkenyl, aryl, bicyclic carbocyclyl, and 6-membered heteroaryl;

$R^1$ is independently selected from H, halogen, NO, —$(CH_2)_nOR^b$, $(CH_2)_nS(O)_pR_c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_n$ $OC(=O)NR^aR^a$, —$(CH_2)_nC(=O)OR^b$, —$(CH_2)_fS(O)_pNR^aR^a$, —$(CH_2)_f$ $NR^aS(O)_pNR^aR^a$, —$(CH_2)_nNR^aS(O)_pR^c$, $C_{1-4}$ alkyl substituted with 0-3 $R^e$, —$(CH_2)_n$—$C_{3-6}$ carbocyclyl substituted with 0-3 $R^e$, and —$(CH_2)_n$-heterocyclyl substituted with 0-3 $R^e$;

$R^2$ is independently selected from $C_{1-5}$ alkyl substituted with 0-3 $R^e$; $C_{2-5}$ alkenyl substituted with 0-3 $R^e$, aryl substituted with 0-3 $R^e$, heterocyclyl substituted with 0-3 $R^e$, and $C_{3-6}$ cycloalkyl substituted with 0-3 $R^e$; provided when $R^2$ is $C_{1-5}$ alkyl, the carbon atom and the groups attached thereto except the one attached to the pyrimidine ring may be replaced by O, N, and S:

$R^3$ is independently selected from
(1) —$(CR^4R^4)_rC(=O)OC_{1-4}$ alkyl substituted with 0-5 $R^e$,
(2) —$(CR^4R^4)_rNR^8R^8$,
(3) —$(CR^4R^4)_rC(=O)NR^8R^8$,
(4) —$(CR^4R^4)_rNR^BC(=O)C_{1-4}$ alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$, and
(8) —$(CR^4R^4)_rNR^aC(=O)(CR^4R^4)_nR^5$;

$R^4$ is, independently at each occurrence, selected from H, halogen, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently at each occurrence, selected from —$(CH_2)_n$—$C_{3-10}$ carbocycle and —$(CH_2)_n$-heterocycle comprising carbon atoms and 1-3 heteroatoms selected from N, $NR^{6a}$, O, and S, each substituted with 0-5 $R^6$;

$R^6$ is independently selected from H, halogen, =O, —$(CH_2)_nOR^b$, $(CH_2)_nS(O)_pR_c$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, —$(CH_2)_nNR^aC(=O)NR^aR^a$, —$(CH_2)_nNR^aC(=O)OR^b$, —$(CH_2)_n$ $OC(=O)NR^aR^a$, —$(CH_2)_nC(=O)OR^b$, —$(CH_2)_fS(O)_pNR^aR^a$, —$(CH_2)_n$ $NR^aS(O)_pNR^aR^a$, —$(CH_2)_nNR^aS(O)_pR^c$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$:

$R^{6a}$ is independently selected from H, —$S(O)_pR_c$, —$C(=O)$ $R^b$, —$C(=O)NR^aR^a$, —$C(=O)OR^b$, —$S(O)_pNR^aR^a$, $C_{1-5}$ alkyl substituted with 0-3 $R^e$, $(CH_2)_n$—$C_{34}$ carbocyclyl substituted with 0-3 $R^e$, and —$(CH_2)_n$-heterocyclyl substituted with 0-3 $R^e$;

$R^7$ is independently selected from H, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^8$ and $R^8$ together with the nitrogen atom to which they are both attached form a heterocyclic ring comprising carbon atoms and 0-3 additional heteroatoms selected from N, $NR^{6a}$, O, and S, and substituted with 0-5 $R^6$;

$R^a$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^c$, at each occurrence, is independently selected from $C_{1-6}$ alkyl substituted with 0-5 $R^e$, $C_{2-6}$alkenyl substituted with 0-5 $R^e$, $C_{2-6}$alkynyl substituted with 0-5 $R^e$, $C_{3-6}$carbocyclyl, and heterocyclyl;

$R^d$, at each occurrence, is independently selected from H and $C_{1-4}$alkyl substituted with 0-5 $R^e$;

$R^e$, at each occurrence, is independently selected from $C_{1-6}$ alkyl (optionally substituted with halogen, OH, and CN), $C_{2-6}$ alkenyl, $C_{2-6}$ alkynyl, —$(CH_2)_n$—$C_{3-6}$ cycloalkyl, —$(CH_2)_n$—$C_4$ heterocyclyl, —$(CH_2)_n$-aryl, —$(CH_2)_n$-heteroaryl, F, Cl, Br, CN, $NO_2$, =O, $CO_2H$, —$(CH_2)_n$$OR_f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and —$(CH_2)_nNR^fR^f$;

$R^f$, at each occurrence, is independently selected from H, $C_{1-5}$alkyl (optionally substituted with halogen and OH), $C_{3-6}$ cycloalkyl, and phenyl, or $R^f$ and $R^f$ together with the nitrogen atom to which they are both attached form a heterocyclic ring optionally substituted with $C_{1-4}$alkyl:

n is independently selected from zero, 1, 2, and 3;

r is independently selected from 1 and 2; and p, at each occurrence, is independently selected from zero, 1, and 2.

In another aspect, the present invention provides compounds of Formula (II), or stereoisomers, enantiomers, diastereomers, tautomers, pharmaceutically acceptable salts, solvates, or prodrugs thereof, wherein:

ring B is independently selected from

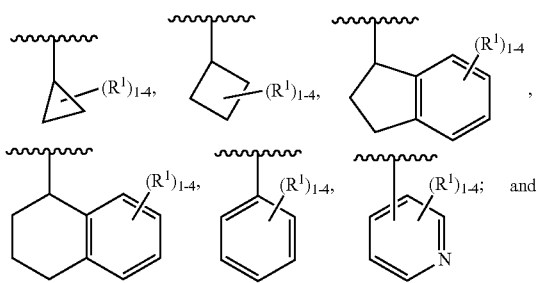

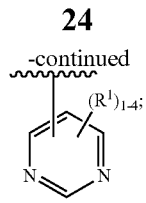

$R^1$ is independently selected from H, F, Cl, Br, $NO_2$, —$(CH_2)_nOR^b$, —$(CH_2)_nC(=O)R^b$, —$(CH_2)_nNR^aR^a$, —$(CH_2)_nCN$, —$(CH_2)_nC(=O)NR^aR^a$, —$(CH_2)_nNR^aC(=O)R^b$, $C_{1-4}$ alkyl substituted with 0-3 R and $C_{3-6}$ cycloalkyl substituted with 0-3 $R^e$;

$R^2$ is independently selected from $C_{1-5}$ alkyl substituted with 0-3 $R^e$; $C_{2-5}$ alkenyl, aryl substituted with 0-3 $R^e$, heterocyclyl substituted with 0-3 $R^e$, and $C_{3-6}$ cycloalkyl; provided when $R^2$ is $C_{1-5}$ alkyl, the carbon atom and the groups attached thereto except the one attached to the pyrimidine ring may be replaced by O, N, and S;

$R^3$ is independently selected from
(1) —$(CR^4R^4)_rC(=O)OC_{1-4}$ alkyl substituted with 0-5 $R^e$,
(2) —$(CR^4R^4)_rNR^8R^8$,
(3) —$(CR^4R^4)_rC(=O)NR^8R^8$,
(4) —$(CR^4R^4)_rNR^aC(=O)C_{1-4}$alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$, and
(8) —$(CR^4R^4)_rNR^aC(O)(CR^4R^4)_nR^5$;

$R^4$ is, independently at each occurrence, selected from H, F, Cl, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently at each occurrence, selected from —$(CH_2)_n$-aryl, —$(CH_2)_n$—$C_{3-6}$ cycloalkyl and —$(CH_2)_n$-heterocycle comprising carbon atoms and 1-3 heteroatoms selected from N, $NR^{6a}$, O, and S, each substituted with 0-3 $R^6$;

$R^6$ is independently selected from H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^{6a}$ is independently selected from H, —$S(O)_pR_c$, —$C(=O)R^b$, —$C(=O)NR^aR^a$, —$C(=O)OR^b$, —$S(O)_pNR^aR^a$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^8$ and $R^8$ together with the nitrogen atom to which they are both attached form a heterocyclic ring comprising carbon atoms and 0-3 additional heteroatoms selected from N, $NR^{6a}$, O, and S, and substituted with 0-5 $R^6$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with halogen, OH, and CN), $C_{2-6}$ alkenyl, $C_2$, alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_n$ $OR_f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and —$(CH_2)_nNR^fR^f$;

$R^f$, at each occurrence, is independently selected from H, $C_{1-5}$alkyl (optionally substituted with halogen and OH), $C_{3-6}$ cycloalkyl, and phenyl;

n is independently selected from zero, 1, 2, and 3;

r is independently selected from 1 and 2; and p, at each occurrence, is independently selected from zero, 1, and 2.

In another aspect, the present invention provides compounds of Formula (III), or stereoisomers, enantiomers, diastereomers, tautomers, pharmaceutically acceptable salts, solvates, or prodrugs thereof, wherein:

$R^1$ is independently selected from H, F, Cl, Br, $OR^b$, CN, $C_{1-4}$ alkyl, and $C_{3-6}$cycloalkyl;

$R^{1a}$ is independently selected from F, Cl, and $C_{1-2}$ alkyl;

$R^2$ is independently selected from $C_{1-5}$ alkyl optionally substituted with halogen and $C_{3-6}$cycloalkyl, $C_{2-5}$ alkenyl, phenyl substituted with 0-3 $R^e$, 6-membered heteroaryl substituted with 0-3 $R^e$, $C_{3-6}$ cycloalkyl, —$(CH_2)_{1-4}OC_{1-3}$alkyl, and —$(CH_2)_{1-3}$O-cycloalkyl;

$R^3$ is independently selected from (1) —$(CR^4R^4)_rC(=O)OC_{1-4}$ alkyl substituted with 0-5 $R^e$, (2) —$(CR^4R^4)_rNR^8R^8$, (3) —$(CR^4R^4)_rC(=O)NR^8R^8$, (4) —$(CR^4R^4)_rNR^aC(=O)C_{1-4}$alkyl substituted with 0-5 $R^e$, (5) —$(CR^4R^4)_rNR^aC(=O)(CR^4R^4)_nOC_{1-4}$alkyl substituted with 0-5 $R^e$, (6) —$(CR^4R^4)_1$—$R^5$, (7) —$(CR^4R^4)_r$—$OR^5$, and (8) —$(CR^4R^4)_rNR^aC(=O)(CR^4R^4)_nR^5$;

$R^4$ is, independently at each occurrence, selected from H, F, Cl, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently at each occurrence, selected from —$(CH_2)_n$-aryl, —$(CH_2)_n$—$C_{3-6}$ cycloalkyl and —$(CH_2)_n$-heterocycle comprising carbon atoms and 1-3 heteroatoms selected from N, $NR^{6a}$, O, and S, each substituted with 0-3 $R^6$;

$R^6$ is independently selected from H, F, Cl, Br, —$OR^b$, =O, —$(CH_2)_nC(=O)R^b$, —$(CH_2)_nC(=O)OR^b$, —$(CH_2)_n$$NR^aR^a$. CN, —$(CH_2)_nC(=O)NR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^{6a}$ is independently selected from H, —$S(O)_pR_c$, —$C(=O)$ $R^b$, —$C(=O)NR^aR^a$, —$C(=O)OR^b$, —$S(O)_pNR^aR^a$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^8$ and $R^8$ together with the nitrogen atom to which they are both attached form a heterocyclic ring comprising carbon atoms and 0-3 additional heteroatoms selected from N, $NR^{6a}$, O, and S, and substituted with 0-5 $R^6$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, NO, =O, $CO_2H$;

r is independently selected from 1 and 2; and n is independently selected from zero, 1, 2, and 3.

In another aspect, the present invention provides compounds of Formula (III), or stereoisomers, enantiomers, diastereomers, tautomers, pharmaceutically acceptable salts, solvates, or prodrugs thereof, wherein:

$R^1$ is independently selected from F, Cl, Br, OH, $OC_{1-4}$ alkyl, $OC_{3-6}$cycloalkyl, CN, $C_{1-4}$ alkyl, and $C_{3-6}$cycloalkyl;

$R^2$ is independently selected from —$CH_2CH_2CH_2CH_3$, —$CH_2CH_2CH(CH_3)_2$, $CH_2CH'CH_2CF_3$, —$CH_2$-cyclopropyl, —$CH_2CH_2$-cyclopropyl, $CH_2CH_2CH=CH_2$, phenyl (optionally substituted with F), pyridyl (optionally substituted with $C_{1-2}$alkyl), $C_{3-5}$ cycloalkyl, $CH_2O$ $(CH_2)_{1-3}CH_3$, $CH_2OCH(CH_3)_2$, and $CH_2O$-cyclopropyl;

$R^3$ is independently selected from (1) —$CR^4R^4$—$R^5$ and (2) —$CR^4R^4$—$NR^aC(=O)(CR^4R^4)_nR^5$;

$R^4$ is, independently at each occurrence, selected from H, F, Cl, $N(CH_3)_2$, $OCH_3$, and $CH_3$; or $R^4$ and $R^4$ together with the carbon atom to which they are both attached form cyclopropyl;

$R^5$ is independently at each occurrence, selected from

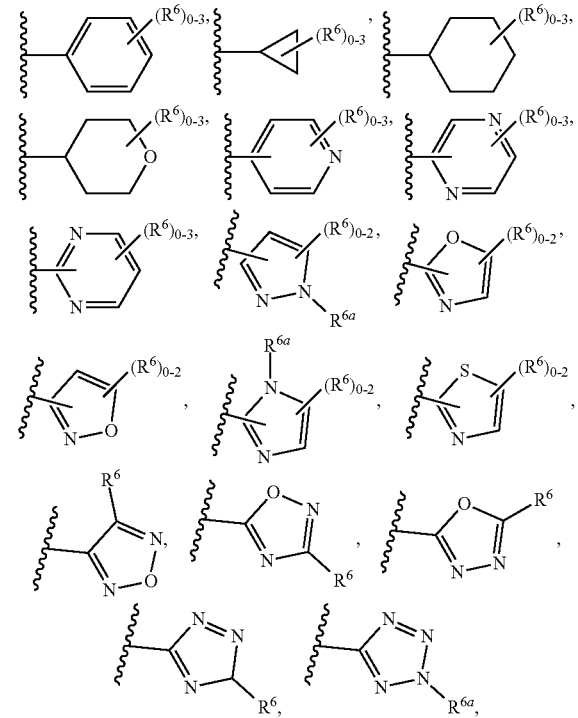

-continued

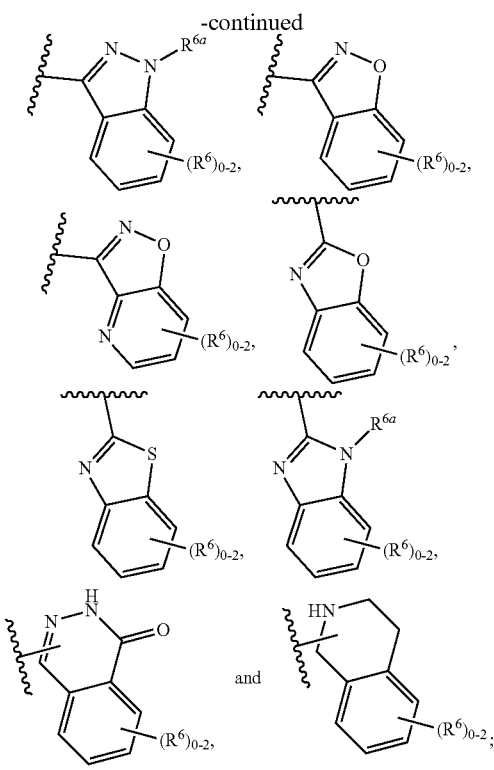

R⁶ is independently selected from H, F, Cl, Br, —OCH₃, —OCF₃, =O, CN, CH₃, CF₃—(CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ;

R⁶ᵃ is independently selected from H, CH₃, aryl substituted with 0-3 Rᵉ, and heterocyclyl substituted with 0-3 Rᵉ;

Rᵃ, at each occurrence, is independently selected from H, C₁₋₆ alkyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ;

Rᵉ, at each occurrence, is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H; and n is independently selected from zero, 1, 2, and 3.

In another aspect the present invention provides compounds of Formula (III), or stereoisomers, enantiomers, diastereomers, tautomers, pharmaceutically acceptable salts, solvates, or prodrugs thereof, wherein:

R¹ is independently selected from F, Cl, Br, OH, OCH₃, OCD₃, OCH₂CH₃, OCH(CH₃)₂, O-cyclopropyl, CN, and cyclopropyl;

R² is independently selected from —CH₂CH₂CH₂CH₃, —CH₂CH₂CH(CH₃)₂, CH₂CH₂CH₂CF₃, —CH₂-cyclopropyl, —CH₂CH₂-cyclopropyl, CH₂CH₂CH=CH₂, phenyl (optionally substituted with F), pyridyl (optionally substituted with C₁₋₂alkyl), cyclobutyl, cyclopentyl, CH₂O(CH₂)₁₋₃CH₃, CH₂OCH(CH₃)₂, and CH₂O-cyclopropyl;

R³ is independently selected from
(1) —CH₂—R⁵ and
(2) —CH₂—NRᵃC(=O)R⁵;

R⁵ is independently at each occurrence, selected from

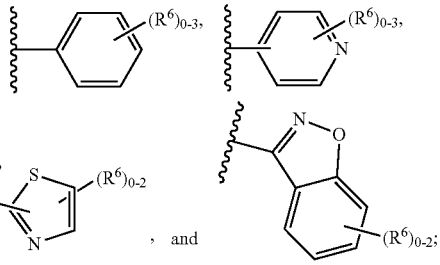

R⁶ is independently selected from H, F, Cl, Br, —OCH₃, —OCF₃, CN, CH₃, CF₃—(CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ;

Rᵃ, at each occurrence, is independently selected from H, C₁₋₆ alkyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ;

Rᵉ, at each occurrence, is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H; and n is independently selected from zero, 1, 2, and 3.

In another aspect, the present invention provides compounds of Formula (IIIa):

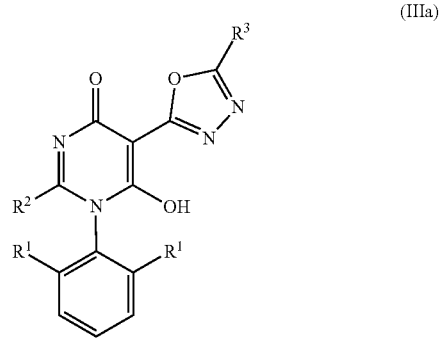

(IIIa)

or stereoisomers, enantiomers, diastereomers, tautomers, pharmaceutically acceptable salts, solvates, or prodrugs thereof, wherein:

R¹ is independently selected from OCH₃ and OCD₃;

R² is independently selected from —CH₂CH₂CH₂CH, —CH₂CH₂CH(CH₃)₂, CH₂CH₂CH₂CF₃, —CH₂-cyclopropyl, —CH₂CH₂-cyclopropyl, cyclobutyl., cyclopentyl, CH₂O(CH₂)₁₋₃CH₃, and CH₂OCH(CH₃)₂:

R³ is independently selected from
(1) —CH₂—R⁵ and
(2) —CH₂—NHC(=O)R⁵;

R⁵ is independently at each occurrence, selected from

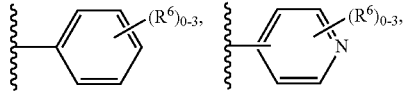

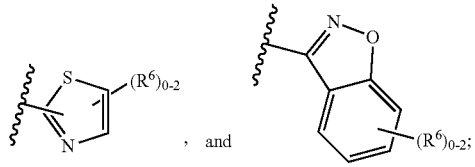

and $R^6$ is independently selected from H, F, Cl, Br, —OCH$_3$, —OCF$_3$, CN, CH$_3$, and CF$_3$.

In another aspect, the present invention provides compounds of Formula (III), or stereoisomers, enantiomers, diastereomers, tautomers, pharmaceutically acceptable salts, solvates, or prodrugs thereof, wherein:

$R^1$ is independently selected from F, Cl, Br, OH, OC$_{1-4}$ alkyl, OC$_{3-6}$cycloalkyl, CN, C$_{1-4}$ alkyl, and C$_{3-6}$cycloalkyl;

$R^2$ is independently selected from —CH$_2$CH$_2$CH$_2$CH$_3$, —CH$_2$CH$_2$CH(CH$_3$)$_2$, CH$_2$CH$_2$CH$_2$CF$_3$, —CH$_2$-cyclopropyl, —CH$_2$CH$_2$-cyclopropyl, CH$_2$CH$_2$CH=CH$_2$, phenyl (optionally substituted with F), pyridyl (optionally substituted with C$_{1-2}$alkyl), C$_{3-5}$ cycloalkyl, CH$_2$O (CH$_2$)$_{1-3}$CH$_3$, CH$_2$OCH(CH$_3$)$_2$, and CH$_2$O-cyclopropyl;

$R^3$ is independently selected from
(1) —(CR$^4$R$^4$)$_r$NR$^8$R$^8$ and
(2) —(CR$^4$R$^4$)$_r$C(=O)NR$^8$R$^8$;

$R^4$ is, independently at each occurrence, selected from H, F, Cl, N(CH$_3$)$_2$, OCH$_3$, and CH$_3$; or $R^4$ and $R^4$ together with the carbon atom to which they are both attached form C$_{3-6}$ cycloalkyl substituted with 0-5 R$^e$;

$R^6$ is independently selected from H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)-heterocyclyl substituted with 0-3 R$^e$;

$R^{6a}$ is independently selected from H, CH$_3$, aryl substituted with 0-3 R$^e$, and heterocyclyl substituted with 0-3 R$^e$;

$R^8$ and $R^8$ together with the nitrogen atom to which they are both attached form a heterocyclic ring selected from

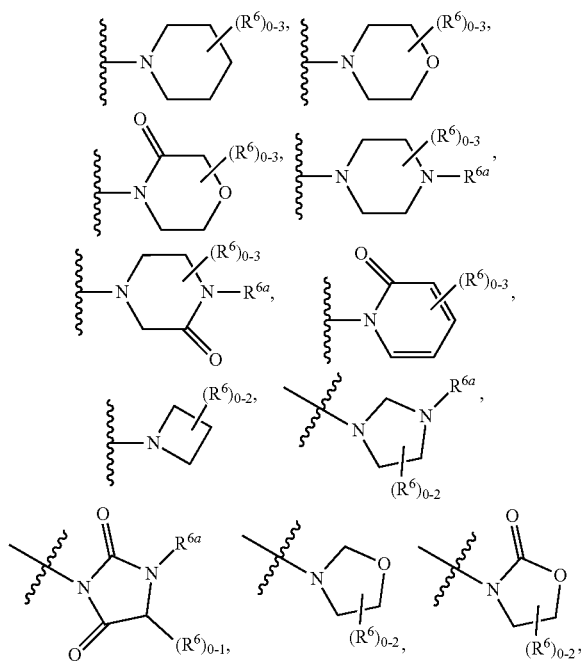

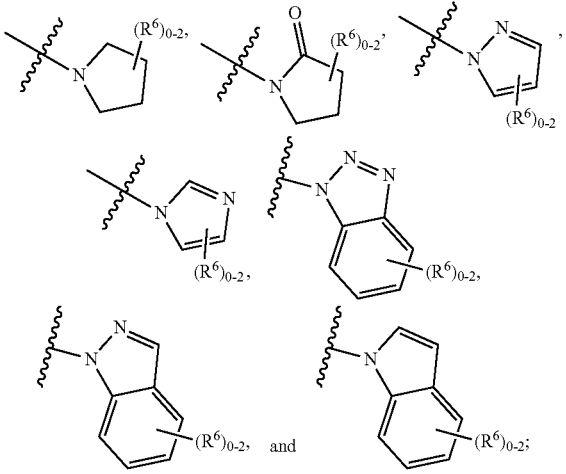

$R^e$, at each occurrence, is independently selected from C$_{1-6}$ alkyl (optionally substituted with F and Cl), OH, OCH$_3$, OCF$_3$, —(CH$_2$)$_n$—C$_{1-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H;

r is independently selected from 1 and 2; and
n is independently selected from zero, 1, 2, and 3.

In another aspect, the present invention provides compounds of Formula (III), or stereoisomers, enantiomers, diastereomers, tautomers, pharmaceutically acceptable salts, solvates, or prodrugs thereof, wherein:

$R^1$ is independently selected from OCH$_3$ and OCD$_3$;

$R^2$ is independently selected from —CH$_2$CH$_2$CH$_2$CH$_3$, —CH$_2$CH$_2$CH(CH$_3$)$_2$, CH$_2$CH$_2$CH$_2$CF$_3$, —CH$_2$-cyclopropyl, —CH$_2$CH$_2$-cyclopropyl, CH$_2$CH$_2$CH=CH$_2$, phenyl (optionally substituted with F), pyridyl (optionally substituted with C$_{1-2}$alkyl), cyclopentyl, CH$_2$O(CH$_2$)$_{1-3}$CH$_3$, CH$_2$OCH(CH$_3$)$_2$, and CH$_2$O-cyclopropyl;

$R^3$ is independently selected from
(1) —CH$_2$—NR$^8$R$^8$ and
(2) —CH$_2$—C(=O)NR$^8$R$^8$;

$R^6$ is independently selected from H, F, Cl, Br, —OCH$_3$, —OCF$_3$, =O, CN, CH$_3$, CF$_3$—(CH$_2$)$_n$-aryl, —(CH$_2$)$_n$—C$_{3-6}$ cycloalkyl substituted with 0-3 R$^e$, and —(CH$_2$)-heterocyclyl substituted with 0-3 R$^e$;

$R^8$ and $R^8$ together with the nitrogen atom to which they are both attached form a heterocyclic ring selected from

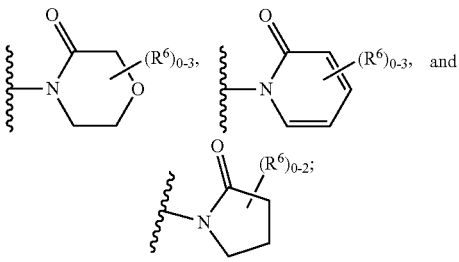

$R^e$, at each occurrence, is independently selected from C$_{1-6}$ alkyl (optionally substituted with F and Cl), OH, OCH$_3$, OCF$_3$, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H; and n is independently selected from zero, 1, 2, and 3.

In another aspect, the present invention provides compounds of Formula (V), or stereoisomers, enantiomers, diastereomers, tautomers, pharmaceutically acceptable salts, solvates, or prodrugs thereof, wherein:
ring B is independently selected from

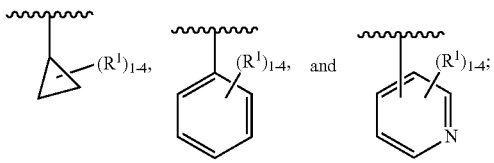

R$^1$ is independently selected from H, F, Cl, Br, OC$_{1-4}$ alkyl, CN, and C$_{1-4}$ alkyl;
R$^2$ is independently selected from —CH$_2$CH$_2$CH$_2$CH$_3$, —CH$_2$CH$_2$CH(CH$_3$)$_2$, CH$_2$CH$_2$CH$_2$CF$_3$, —CH$_2$CH$_2$CH=CH$_2$, CH$_2$O(CH$_2$)$_{1-3}$CH$_3$, and CH$_2$OCH(CH$_3$)$_2$;
R$^3$ is independently selected from
  (1) —CH$_2$R$^5$ and
  (2) —CH$_2$OR$^5$;
R$^5$ is independently at each occurrence, selected from

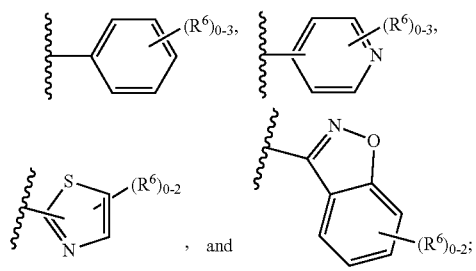

R$^6$ is independently selected from H, F, Cl, Br, —OCH$_3$, —OCF$_3$, =O, CN, CH$_3$, and CF$_3$;
R$^7$ is independently selected from CH, CH$_2$CH$_3$, CH$_2$CH$_2$CH$_3$, CH(CH$_3$)$_2$, and CH$_2$OCH$_3$; and;
n is independently selected from zero, 1, 2, and 3.

In another aspect, the present invention provides compounds of Formula (VI):

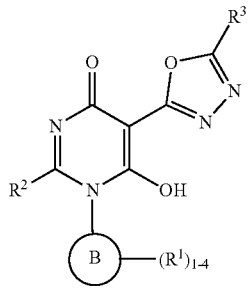

(VI)

or stereoisomers, enantiomers, diastereomers, tautomers, pharmaceutically acceptable salts, solvates, or prodrugs thereof, wherein:
ring B is independently selected from

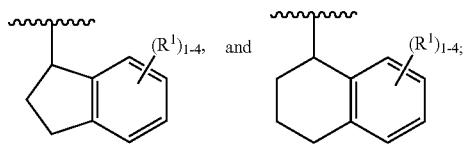

R$^1$ is independently selected from H, F, Cl, Br, OC$_{1-4}$ alkyl, CN, and C$_{1-4}$ alkyl;

R$^2$ is independently selected from —CH$_2$CH$_2$CH$_2$CH$_3$, —CH$_2$CH$_2$CH(CH$_3$)$_2$, CH$_2$CH$_2$CH$_2$CF$_3$, —CH$_2$-cyclopropyl, —CH$_2$CH$_2$-cyclopropyl, cyclobutyl, cyclopentyl, CH$_2$O(CH$_2$)$_{1-3}$CH$_3$, and CH$_2$OCH(CH$_3$)$_2$;
R$^3$ is independently selected from
  (1) —CH$_2$—R$^5$ and
  (2) —CH$_2$—NHC(=O)R$^5$;
R$^5$ is independently at each occurrence, selected from

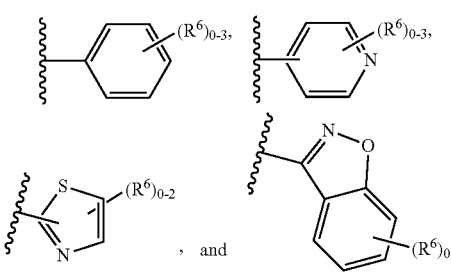

and
R$^6$ is independently selected from H, F, Cl, Br, —OCH$_3$, —OCF$_3$, CN, CH$_3$, and CF$_3$.

In one non-limiting embodiment, ring A is

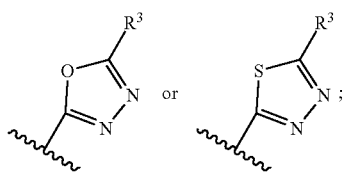

ring B is

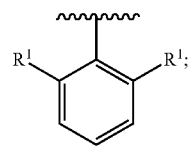

R$^1$ is OC$_{1-4}$ alkyl; R$^2$ is independently selected from: C$_{1-5}$ alkyl substituted with 0-3 R$^e$; C$_{2-5}$ alkenyl, and C$_{1-6}$ cycloalkyl; provided when R$^2$ is C$_{1-5}$ alkyl, the carbon atom except the one attached directly to the pyrimidine ring may be replaced by O, N, and S; R$^3$ is CH$_2$—R$^5$; R$^5$ is aryl, C$_{3-6}$ cycloalkyl and heteroaryl, each substituted with 0-3 R$^6$; R$^6$ is independently selected from: H, F, Cl, Br, —OR$^b$, =O, —(CH$_2$)$_n$C(=O)R$^b$, —(CH$_2$)$_n$C(=O)OR$^b$, —(CH$_2$)$_n$NR$^a$R$^a$, CN, —(CH$_2$)$_n$C(=O)NR$^a$R$^a$, —S(O)$_2$NH$_2$, C$_{1-4}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$; R$^8$ is independently selected from H, C$_{1-6}$ alkyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R and R$^a$ together with the nitrogen atom to which they are both attached form a heterocyclic ring substituted with 0-5 R$^e$; R$^b$ is independently selected from H, C$_{1-6}$ alkyl substituted with 0-5 R$^e$, C$_{2-6}$ alkenyl substituted with 0-5 R$^e$, C$_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; R$^e$ is independently selected from C$_{1-6}$ alkyl (optionally substituted with F and Cl), OH, OCH₃, OCF₃, —(CH₂)ₙ—C₃₋₆ cycloalkyl, —(CH₂)ₙ—C₄₋₆heterocyclyl, —(CH₂)ₙ-aryl, —(CH₂)ₙ-heteroaryl, F, Cl, Br, CN, NO₂, =O, CO₂H; n is independently selected from zero, 1, 2, and 3.

In another non-limiting embodiment, ring A is

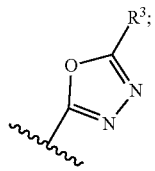

ring B is

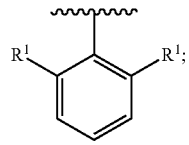

R¹ is OC₁₋₄ alkyl; R² is independently selected from C₁₋₅ alkyl substituted with 0-3 Rᵉ; and C₁₋₆ cycloalkyl; provided when R² is C₁₋₅ alkyl, the carbon atom except the one attached directly to the pyrimidine ring may be replaced by O; R³ is CH₂—R⁵; R⁵ is aryl, C₃₋₆ cycloalkyl and heteroaryl, each substituted with 0-3 R⁶; R⁶ is independently selected from: H, F, Cl, Br, —OR^b, =O, —(CH₂)ₙC(=O)R^b, —(CH₂)ₙC(=O)OR^b, —(CH₂)ₙNRᵃRᵃ, CN, —(CH₂)ₙC(=O)NRᵃRᵃ, —S(O)₂NH₂, C₁₋₄ alkyl substituted with 0-3 Rᵉ, (CH₂)ₙ—C₃₋₆ carbocyclyl substituted with 0-3 Rᵉ, and —(CH₂)ₙ-heterocyclyl substituted with 0-3 Rᵉ; Rᵉ is independently selected from H, C₁₋₆ alkyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ; or Rᵃ and Rᵃ together with the nitrogen atom to which they are both attached form a heterocyclic ring substituted with 0-5 Rᵉ; R^b is independently selected from H, C₁₋₆ alkyl substituted with 0-5 Rᵉ, C₂₋₆ alkenyl substituted with 0-5 Rᵉ, C₂₋₆ alkynyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ; Rᵉ is independently selected from C₁₋₆ alkyl (optionally substituted with F and Cl), OH, OCH-3, OCF₃, —(CH₂)ₙ—C₃₋₆ cycloalkyl, —(CH₂)ₙ—C₄₋₆heterocyclyl, —(CH₂)ₙ-aryl, —(CH₂)ₙ-heteroaryl, F, Cl, Br, CN, NO₂, =O, CO₂H; n is independently selected from zero, 1, 2, and 3.

In another non-limiting embodiment, ring A is

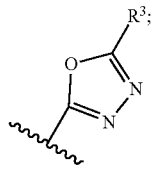

ring B is

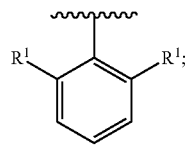

R¹ is OC₁₋₄ alkyl; R² is independently selected from: C₁₋₄ alkyl substituted with 0-3 Rᵉ; C₂₋₄ alkenyl, C₁₋₆ cycloalkyl, and CH₂O(CH₂)₁₋₃CH₃; R³ is CH₂—R⁵; R⁵ is aryl or heteroaryl selected from

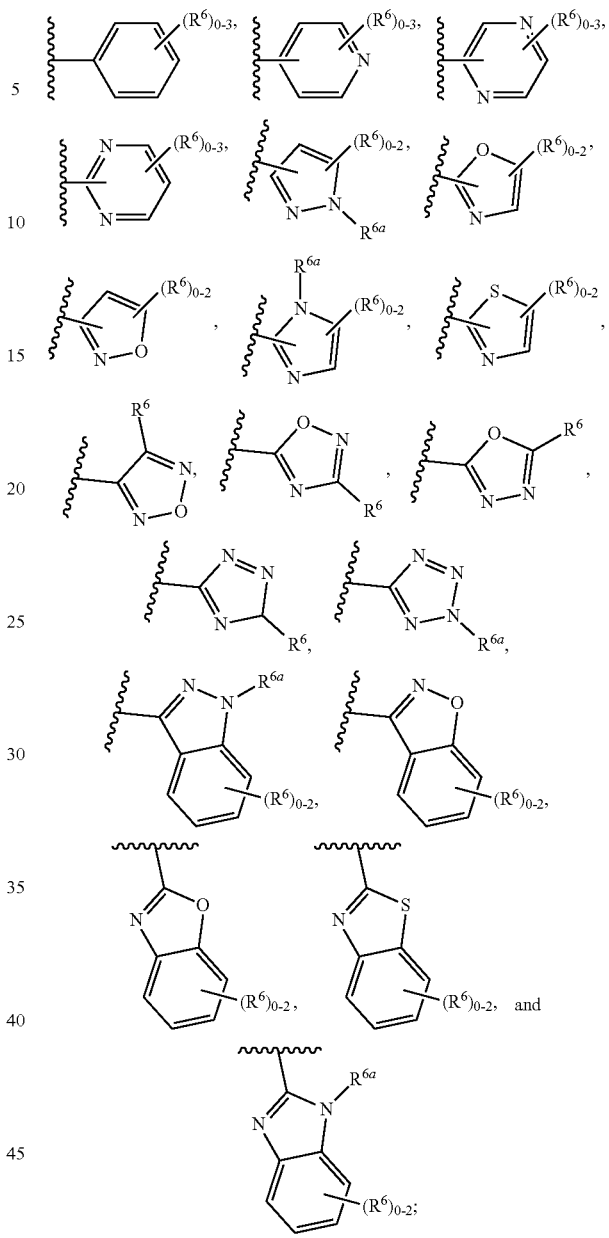

R⁶ is independently selected from: H, F, Cl, Br, —OCH₃, —OCF₃, =O, CN, CH₃, CF₃—(CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ; R⁶ is independently selected from: H, CH₃, Rᵉ is independently selected from C₁₋₆ alkyl (optionally substituted with F and Cl), OH, OCH₃, OCF₃, F, Cl, Br, CN, NO₂; n is independently selected from zero, 1, 2, and 3.

In another non-limiting embodiment, ring A is

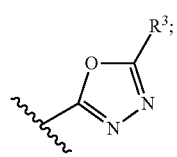

ring B is

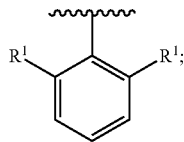

$R^1$ is $OC_{1-4}$ alkyl; $R^2$ is independently selected from: $C_{1-4}$ alkyl substituted with 0-3 $R^e$; $C_{2-5}$ alkenyl, $C_{1-6}$ cycloalkyl, and $CH_2O(CH_2)_{1-3}CH_3$; $R^3$ is $CH_2$—$R^5$; $R^5$ is aryl or heteroaryl selected from

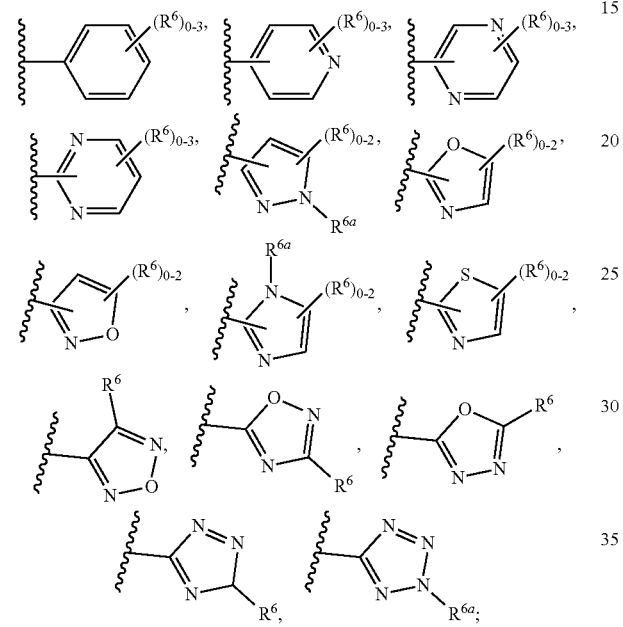

$R^6$ is independently selected from: H, F, Cl, Br, —$OCH_3$, —$OCF_3$, =O, CN, $CH_3$, $CF_3$—$(CH_2)_n$-aryl, —$(CH_2)_n$—$C_{3-6}$ cycloalkyl substituted with 0-3 $R^e$, and —$(CH_2)_n$-heterocyclyl substituted with 0-3 $R^e$; $R^{6a}$ is independently selected from: H, $CH_3$, $R^e$ is independently selected from $C_{1-6}$ alkyl (optionally substituted with F and Cl), OH, $OCH_3$, $OCF_3$, F, Cl, Br, CN, $NO_2$; n is independently selected from zero, 1, 2, and 3.

In another non-limiting embodiment, ring A is

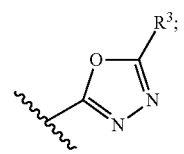

ring B is

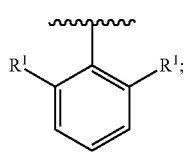

$R^1$ is $OC_{1-4}$ alkyl; $R^2$ is $C_{1-4}$ alkyl or $CH_2O(CH_2)_{1-3}CH_3$; $R^3$ is $CH_2$—$R^5$; $R^5$ is aryl or heteroaryl selected from

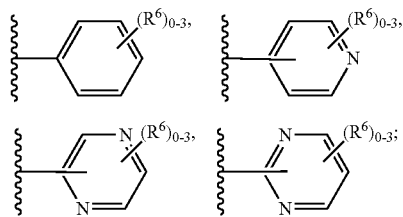

$R^6$ is independently selected from: H, F, Cl, Br, —$OCH_3$, —$OCF_3$, CN, $CH_3$, and $CF_3$.

In another non-limiting embodiment, ring A is

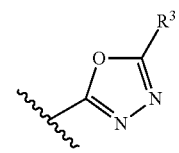

ring B is

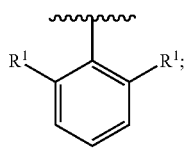

$R^1$ is independently selected from Et and OMe; $R^2$ is independently selected from —$CH_2CH_2CH_2CH_3$, —$CH_2CH_2CH(CH_3)_2$, —$CH_2OCH(CH_3)_2$, —$CH_2OC_{3-6}$ cycloalkyl, —$CH_2CH_2C_{3-6}$ cycloalkyl, $C_{3-6}$ cycloalkyl,

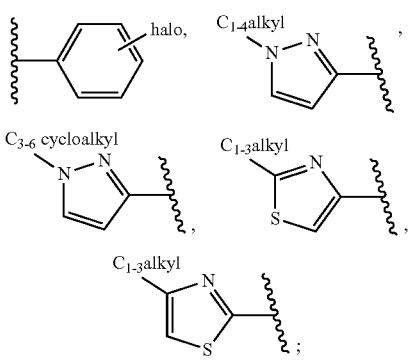

$R^3$ is —$(CH_2)_{0-1}NR^8R^8$, wherein $R^8$ and $R^8$ together with the nitrogen atom to which they are both attached form a heterocyclic ring selected from

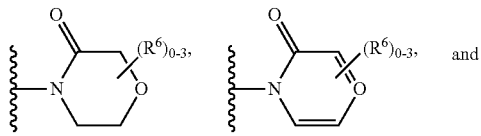

-continued

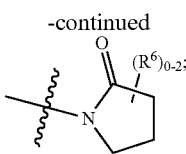

R⁶ is independently selected from H, F, Cl, Br, —OCH₃, —OCF₃, =O, CN, CH₃, CF₃—(CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ; Rᵉ, at each occurrence, is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H.

In another non-limiting embodiment ring A is

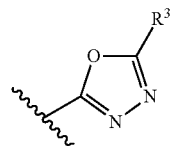

ring B is

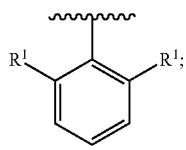

R¹ is independently selected from Et and OMe; R² is independently selected from —CH₂CH₂CH₂CH₃, —CH₂CH₂CH(CH₃)₂, —CH₂OCH(CH₃)₂, —CH₂OC₃₋₆ cycloalkyl, —CH₂CH₂C₃₋₆ cycloalkyl, C₃₋₆ cycloalkyl,

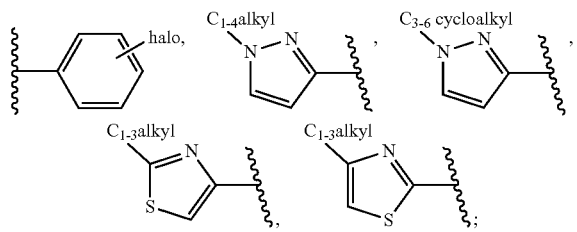

R³ is —(CH₂)₀₋₁C(=O)NR⁸R⁸, wherein R⁸ and R⁸ together with the nitrogen atom to which they are both attached form a heterocyclic ring selected from

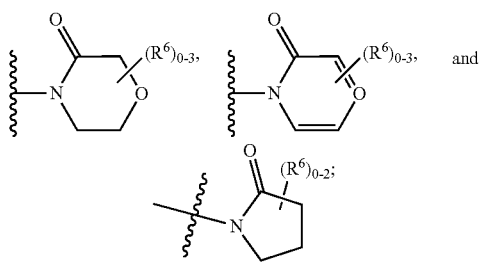

R⁶ is independently selected from H, F, Cl, Br, —OCH₃, —OCF₃, =O, CN, CH₃, CF₃—(CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ; Rᵉ, at each occurrence, is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, and CO₂H.

In another non-limiting embodiment of formula (V), ring B is independently selected from

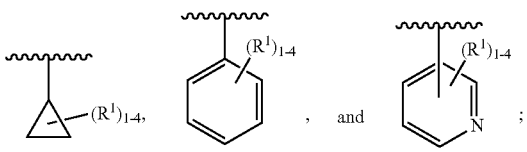

R¹ is independently selected from H, F, Cl, Br, OC₁₋₄ alkyl, CN, and C₁₋₄ alkyl, R² is independently selected from —CH₂CH₂CH₂CH₃; R³ is —CH₂R⁵; R⁵ is independently at each occurrence, selected from

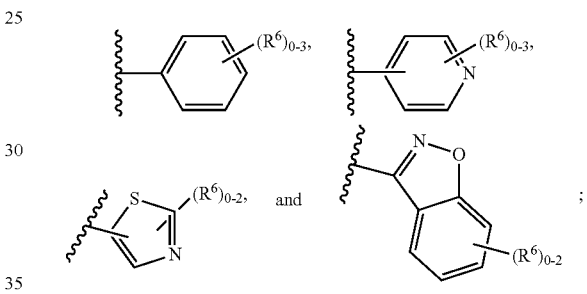

R⁶ is independently selected from H, F, Cl, Br, —OCH₃, —OCF₃, =O, CN, CH, and CF₃:

R⁷ is independently selected from CH₃, CH₂CH₃, CH₂CH₂CH₃, CH(CH₃)₂, and CH₂OCH₃.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of formula I, or an enantiomer, diastereomer, or a pharmaceutically-acceptable salt, and a pharmaceutically acceptable carrier therefore.

In another embodiment, the compounds of the present invention have EC₅₀ values ≤10 μM, using the APJ hcAMP assay disclosed herein, preferably, EC₅₀ values ≤5 μM, more preferably, EC₅₀ values ≤1 μM, even more preferably, EC₅₀ values ≤0.5 μM, even more preferably, EC₅₀ values ≤0.1 μM, even more preferably, EC₅₀ values ≤0.01 μM.

In another aspect, the present invention provides compounds selected from any subset list of compounds exemplified in the present application.

In another aspect, the present invention provides compounds selected from the subset in which the APJ hcAMP EC₅₀ potency range is A.

In another aspect, the present invention provides compounds selected from the subset in which the APJ hcAMP EC$_{50}$ potency range is B.

In another aspect, the present invention provides compounds selected from the subset in which the APJ hcAMP EC$_{50}$ potency range is C.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

The present invention provides a pharmaceutical composition further comprising additional therapeutic agent(s). In a preferred embodiment, the present invention provides pharmaceutical composition, wherein the additional therapeutic agent is, for example, angiotensin converting enzyme (ACE) inhibitor, R-adrenergic receptor blocker, angiotensin II receptor blocker, diuretic, aldosterone antagonist and digitalis compound.

In another embodiment, the present invention provides a method for the treatment and/or prophylaxis of multiple diseases or disorders associated with APJ or apelin activity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the APJ and apelin that can be prevented, modulated, or treated according to the present invention include, but are not limited to heart failure such as acute decompensated heart failure (ADHF), atrial fibrillation, coronary artery disease, peripheral vascular disease, atherosclerosis, diabetes, metabolic syndrome, hypertension, pulmonary hypertension, cerebrovascular disorders and the sequelae thereof, cardiovascular disorders, angina, ischemia, stroke, myocardial infarction, acute coronary syndrome, reperfusion injury, angioplastic restenosis, vascular complications of diabetes and obesity.

In another embodiment, the present invention provides a method for the treatment and/or prophylaxis of heart failure, coronary artery disease, peripheral vascular disease, atherosclerosis, diabetes, metabolic syndrome, hypertension, pulmonary hypertension, atrial fibrillation, angina, ischemia, stroke, myocardial infarction, acute coronary syndrome, reperfusion injury, angioplastic restenosis, vascular complications of diabetes, obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of heart failure such as ADHF, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes and obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of pulmonary hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of acute coronary syndrome and cardiac ischemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides compounds according to the present invention for use as a medicament.

In another embodiment, the present invention provides a compound of the present invention for use in therapy for the treatment and/or prophylaxis of multiple diseases or disorders associated with APJ and apelin.

In another embodiment, the present invention also provides the use of a compound of the present invention for the manufacture of a medicament for the treatment and/or prophylaxis of multiple diseases or disorders associated with APJ and apelin.

In another embodiment, the present invention provides a method for the treatment and/or prophylaxis of multiple diseases or disorders associated with APJ and apelin, comprising administering to a patient in need thereof a therapeutically effective amount of a first and second therapeutic agent, wherein the first therapeutic agent is a compound of the present invention. Preferably, the second therapeutic agent, for example selected inotropic agent such as i-adrenergic agonist (for example dobutamine).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with APJ and apelin.

Where desired, the compound of the present invention may be used in combination with one or more other types of cardiovascular agents and/or one or more other types of therapeutic agents which may be administered orally in the same dosage form, in a separate oral dosage form or by injection. The other type of cardiovascular agents that may be optionally employed in combination with the APJ agonist of the present invention may be one, two, three or more cardiovascular agents administered orally in the same dosage form, in a separate oral dosage form, or by injection to produce an additional pharmacological benefit.

The compounds of the present invention may be employed in combination with additional therapeutic agent(s) selected from one or more, preferably one to three, of the following therapeutic agents: anti-hypertensive agents, ACE inhibitors, mineralocorticoid receptor antagonists, angiotensin receptor blockers, calcium channel blockers, 3-adrenergic receptor blockers, diuretics, vasorelaxation agents such as nitrates, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating heart failure: ACE inhibitors, β-blockers, diuretics, mineralocorticoid receptor antagonists, renin inhibitors, calcium channel blockers, angiotensin II receptor antagonists, nitrates, digitalis compounds, inotropic agents.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin).

As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, John Wiley & Sons, Inc., New York (2007). "$C_{6-10}$ (aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quatemized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolvl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pynrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered hetcrocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R''NH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis,* 4th Edition, *Wiley* (2007) and *The Peptides: Analysis, Synthesis, Biology*, Vol. 3. Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and 1-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press. London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*. Elsevier (1985), and Widder. K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth. C. G., ed., *The Practice of Medicinal Chemistry*, 3rd Edition, Academic Press, San Diego. Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "2H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius. "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere. "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Wuts, P. G. M. et al., *Protecting Groups in Organic Synthesis*, 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press. New York, N.Y. (1991): Smith, M. B. et al., *March's Advanced Organic Chemistry: Reactions, Mechanisms, and Structure*. 6th Edition, Wiley & Sons, New York, N.Y. (2007), Katritzky, A. R. et al, eds., *Comprehensive Organic Functional Groups Transformations II*, 2nd Edition. Elsevier Science Inc., Tarrytown, N.Y. (2004): Larock, R. C., *Comprehensive Organic Transformations*, VCH Publishers. Inc., New York, N.Y. (1999), and references therein.

Scheme 1

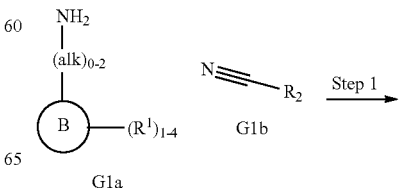

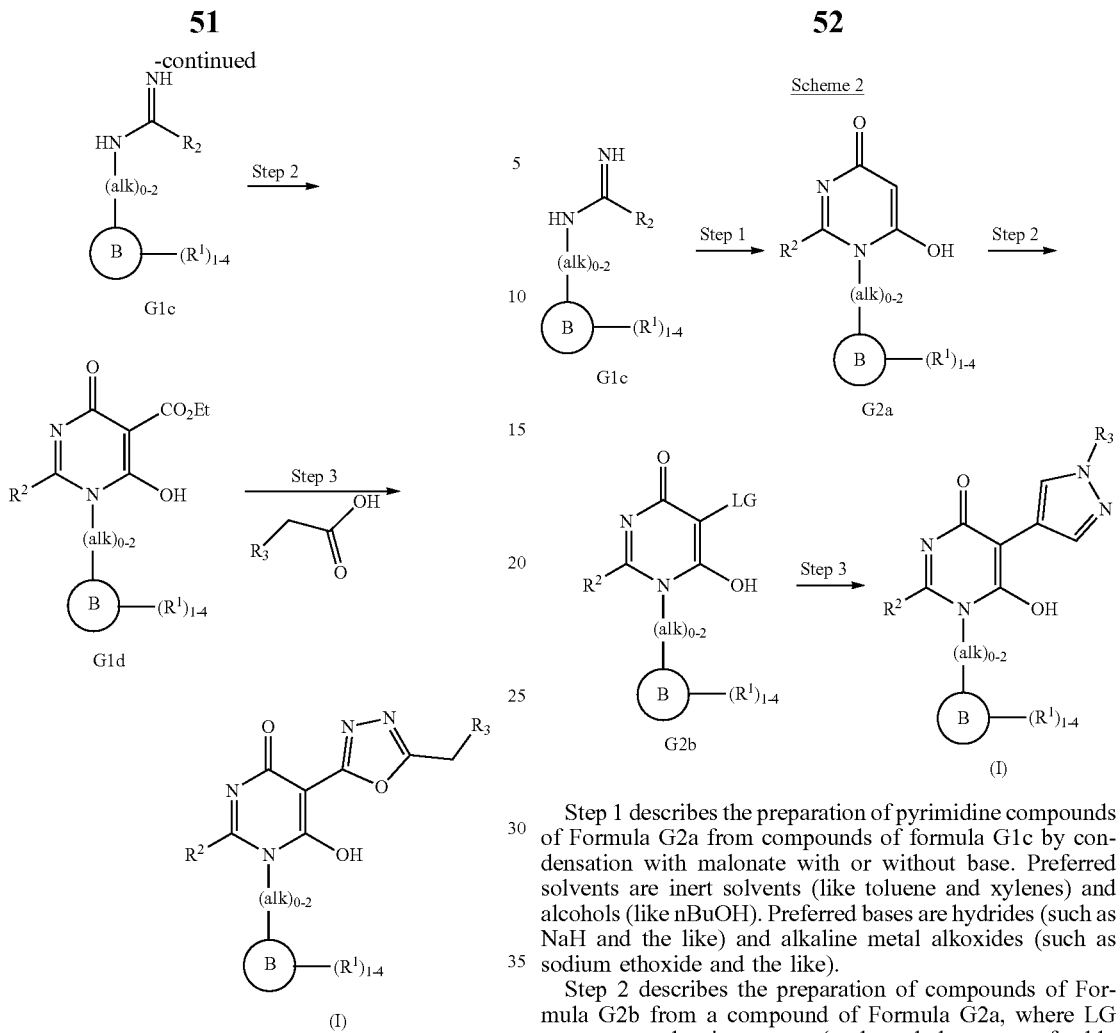

Step 1 describes the preparation of compounds of Formula G1c from a compound of Formula G1a, by acylating with a nitrile of Formula G1b in the presence of a Lewis acid (like $AlMe_3$). Preferred solvents are aprotic solvents (such as toluene and the like).

Step 2 describes the preparation of pyrimidine compounds of Formula G1d from compounds of formula G1c by condensation with triethyl methanetricarboxylate with or without base. Preferred solvents are aprotic solvents (like toluene and xylenes). Preferred bases are tertiary amines (such as TEA, DIEA and the like) and alkaline metal alkoxides (such as sodium ethoxide and the like).

Step 3 describes the preparation of compounds of Formula (I) by conversion of the ester of compounds of Formula G1d to a heterocycle Ⓐ. The conversion of compounds of Formula G1d to compounds of Formula (I) can be performed in one step or in several steps, depending on the heterocycle Ⓐ. The ester of Formula G1d can be condensed with an N'-hydroxy imidamide to give a 1,2,4-oxadiazole in a single step. Alternatively in a two step process the ester of Formula G1d can by condensed with hydrazine in the presence of alcohol solvents (such as methanol and the like) to form a hydrazide, then the hydrazide condensed with an acid in the presence of a dehydrating reagents (such as $T_3P®$, EDC and the like) and an inert solvent (such as dioxane, EtOAc and the like) to give a 1,3,4-oxadiazole.

Step 1 describes the preparation of pyrimidine compounds of Formula G2a from compounds of formula G1c by condensation with malonate with or without base. Preferred solvents are inert solvents (like toluene and xylenes) and alcohols (like nBuOH). Preferred bases are hydrides (such as NaH and the like) and alkaline metal alkoxides (such as sodium ethoxide and the like).

Step 2 describes the preparation of compounds of Formula G2b from a compound of Formula G2a, where LG represents a leaving group (such as halogens, preferably bromine). Preferred reagents for incorporating the leaving group are sources of bromine (such as elemental bromine and NBS and the like). Preferred solvents are halogenated solvents (such as DCM and the like).

Step 3 describes the preparation of compounds of Formula (I) by coupling boronic acids or esters with a compound of Formula G2b under Suzuki conditions in the presence of a transition metal catalyst and base. Preferred catalysts are ($Pd(OAc)_2$, $Pd(dppf)Cl_2$, $2^{nd}$ Gen. Xphos and the like). Preferred bases include alkaline metal-carbonates, -bicarbonates, (such as sodium carbonate, sodium bicarbonate, cesium carbonate and the like). Preferred solvents are ethers (such as tetrahydrofuran, dioxane and the like) and water.

Scheme 3

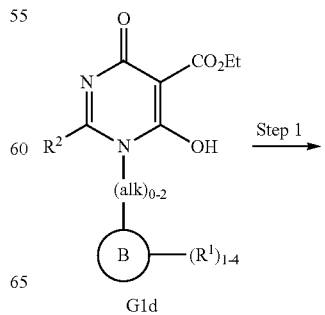

Step 1

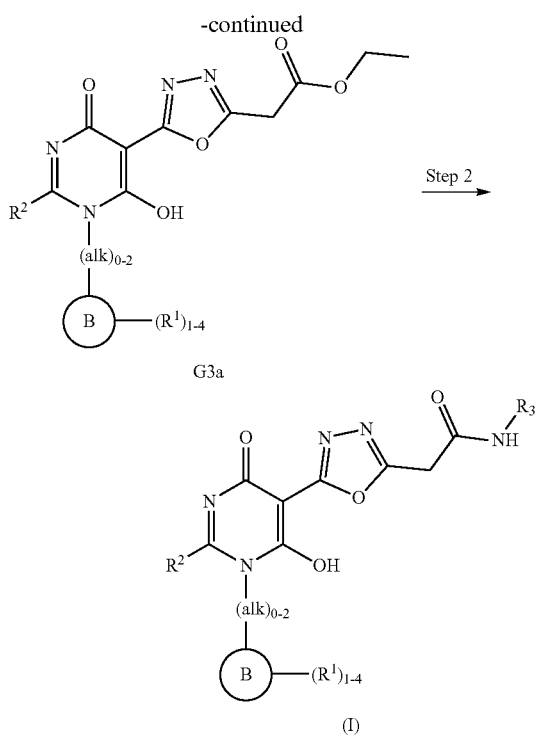

Step 1 describes the preparation of compounds of Formula G3a by conversion of the ester of compounds of Formula G1d to a heterocycle (A) substituted with an ethylacetate group, G3a.

Step 2 describes the preparation of amide compounds of Formula (I) from compounds of formula G3a by first hydrolyzing the ester followed by amide coupling in the presence of coupling reagents (like EDC, HOBt and the like). The process can be performed stepwise. Preferred solvents for the first step of the two step process are alcohol solvents (such as MeOH and the like), ethers (such as tetrahydrofuran) and water. Preferred bases for the first step of the two step process are hydroxides (such as lithium hydroxide and sodium hydroxide and the like). Preferred solvents for the second step are polar aprotic solvents (such as DMF and the like). Preferred bases for the second step are tertiary amines (such as TEA, DIEA and the like)

IV. Biology

APJ receptor was discovered in 1993 as an orphan G protein-coupled receptor (GPCR) and was subsequently found to recognize apelin peptide as its endogenous ligand. It belongs to class A of GPCRs and has a classical 7-transmembrane domain structure, exhibiting greatest sequence homology to angiotensin ATI receptor (for review see Pitkin, S. L. et al., *Pharmacol. Rev.*, 62(3):331-342 (2010)). APJ is expressed in wide variety of peripheral tissues and the CNS, and has relatively high expression in placenta, myocardium, vascular endothelial cells, smooth muscle cells as well as cardiac myocytes (Kleinz, J. M. et al., *Pharmacol. Ther.*, 107(2): 198-211(2005)). Apelin peptide was originally identified in bovine stomach extract and remains to date the only known endogenous ligand and agonist of APJ receptor (Tatemoto, K. et al., *Biochem. Biophys. Res. Commun.*, 255:471-476 (1998)). Tissue expression of apelin gene mirrors closely the APJ expression pattern and has been postulated to act in an autocrine or paracrine manner, often exemplified by reference to "apelin-APJ system". Apelin gene encodes 77 amino acid precursor peptide that is cleaved to form mature secreted peptide undergoing further proteolytic cleavage forming shorter C-terminal fragments. Apelin-36, -17 and -13 represent the major active forms with the pyroglutamated form of apelin-13 being the most stable and the most abundant form present in the cardiac tissue (Maguire, J. J. et al., *Hypertension*, 54(3):598-604 (2009)). Apelin has very short half life in circulation, estimated to be less than 5 minutes (Japp, A. G. et al., *Circulation*, 121(16): 1818-1827 (2010)).

Activation of APJ receptor is known to inhibit forskolin-stimulated cyclic AMP (cAMP) levels in pertussis toxin-sensitive manner, indicating coupling to the Gi proteins. The binding affinity of apelin and the $EC_{50}$ values in the cAMP assay are reported to be in the sub-nanomolar range (for review see Pitkin, S. L. et al., *Pharmacol. Rev.*, 62(3):331-342(2010)). In addition to cAMP inhibition, APJ receptor activation also leads to β-arrestin recruitment, receptor internalization and activation of extracellular-regulated kinases (ERKs) (for review see Kleinz, J. M. et al., *Pharmacol. Ther.*, 107(2):198-211 (2005)). Which of these signaling mechanisms contribute to modulation of downstream physiological effects of apelin is not clear at present. APJ receptor has been shown to interact with the ATI receptor. While apelin does not bind ATI and angiotensin II does not bind APJ, it has been postulated that certain physiological actions of apelin are mediated, at least in part, via functional antagonism of the angiotensin II and ATI receptor pathway (Chun, A. J. et al., *J. Clin. Invest.*, 118(10):3343-3354 (2008)).

It is also desirable and preferable to find compounds with advantageous and improved characteristics compared with known HF treatment agents, in one or more of the following categories that are given as examples, and are not intended to be limiting: (a) pharmacokinetic properties, including oral bioavailability, half life, and clearance. (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions, (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an APJ agonist. Exemplary subjects include human beings of any age with risk factors for development of heart failure and the sequelae thereof, angina, ischemia, cardiac ischemia, myocardial infarction, reperfusion injury, angioplastic restenosis, hypertension, vascular complications of diabetes, obesity or endotoxemia, stroke, as well as atherosclerosis, coronary artery disease, acute coronary syndrome, and/or dyslipidemias.

As used herein, "treating" or "treatment" cover a treatment of a disease-state in a mammal, particularly in a human, and include: (a) inhibiting a disease-state, i.e., arresting it development; and/or (b) relieving a disease-state, i.e., causing regression of a disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate APJ and/or to prevent or treat the disorders listed herein. When applied to a combination, the term refers to combined amounts of the active ingredients that result in the preventive or therapeutic effect, whether administered in combination, serially, or simultaneously.

Assay Methods
Intracellular cAMP Accumulation Assay

HEK293 cells stably expressing human APJ receptor were used to assess the activity of compounds. Cultured cells were detached and resuspended in the cAMP Homogeneous Time-Resolved Fluorescence (HTRF) assay buffer (Cisbio cat; #62AM4PEJ). The assay was performed in 384-well assay plates (Perkin-Elmer; cat #6008289) according to assay protocol provided by the manufacturer. Serial dilutions of a compound together with assay buffer containing 0.2 nM IBMX and 2 µM forskolin were added to each well containing 5,000 cells and incubated for 30 minutes at room temperature. Subsequently, cAMP D2 reagent was added in the lysis buffer followed by the EuK antibody (Cisbio; cat #62AM4PEJ) and incubated for 60 min. The fluorescence emission ratio was measured using fluorometer. The intracellular cAMP concentrations (compound-stimulated inhibition of forskolin-mediated cAMP production) were calculated by extrapolation from a standard curve using known cAMP concentrations. The $EC_{50}$ values were obtained by fitting the data to a sigmoidal concentration-response curve with variable slope. The maximal achievable inhibition of forskolin-induced cAMP levels ($Y_{max}$) for each compound was expressed as relative percentage of inhibition attained using pyroglutamated apelin-13 ((Pyr1)apelin-13) peptide, which was set to 100%.

The examples disclosed below were tested in the APJ in vitro assays described above and were found having human APJ cyclic AMP (hcAMP) activity. The $EC_{50}$ value of each compound is presented at the end of the example description.

The compounds of the present invention possess activity as agonists of APJ receptor, and, therefore, may be used in the treatment of diseases associated with APJ activity. Accordingly, the compounds of the present invention can be administered to mammals, preferably humans, for the treatment of a variety of conditions and disorders, including, but not limited to, treating, preventing, or slowing the progression of heart failure, coronary artery disease, peripheral vascular disease, atherosclerosis, diabetes, metabolic syndrome and the sequelae of thereof, hypertension, pulmonary hypertension, cerebrovascular disorders, atrial fibrillation, angina, ischemia, stroke, myocardial infarction, acute coronary syndrome, reperfusion injury, angioplastic restenosis, vascular complications of diabetes and obesity.

The biological activity of the exemplified compounds of this invention determined by the assay described above is shown at the end of each example. The APJ cAMP $EC_{50}$ potency ranges are as follows: A=0.01-10 nM; B=10.01-100 nM; C=100.01-300 nM.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated, the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example. Allen. Jr., L. V. et al.,

*Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., agents used in treatment of heart failure or other pharmaceutically active material.

The compounds of the present invention may be employed in combination with other APJ agonists or one or more other suitable therapeutic agents useful in the treatment of the aforementioned disorders including: agents for treating heart failure, anti-hypertensive agents, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, and agents for treating peripheral arterial disease.

The compounds of the present invention may be employed in combination with additional therapeutic agent(s) selected from one or more, preferably one to three, of the following therapeutic agents in treating heart failure and coronary artery disease: ACE inhibitors, β-blockers, diuretics, mineralocorticoid receptor antagonists, renin inhibitors, calcium channel blockers, angiotensin II receptor antagonists, nitrates, digitalis compounds, inotropic agents and β-receptor agonists, anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol), low density lipoprotein receptor inducers, clofibrate, fenofibrate, benzofibrate, cipofibrate, gemfibrizol, vitamin $B_6$, vitamin $B_{12}$, anti-oxidant vitamins, anti-diabetes agents, platelet aggregation inhibitors, fibrinogen receptor antagonists, aspirin and fibric acid derivatives.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, $DHEA-SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating heart failure and atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenergic receptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients but also to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the APJ receptor and apelin activity. Such compounds may be provided in a commercial kit, for example, for use in pharmaceutical research involving APJ and apelin or anti-heart failure activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving APJ and apelin.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof, and, (c) a package insert stating that the pharmaceutical composition can be used for the treatment and/or prophylaxis of multiple diseases or disorders associated with APJ and apelin (as defined previously). In another embodiment, the package insert states that the pharmaceutical composition can be used in combination (as defined previously) with a second therapeutic agent for the treatment and/or prophylaxis of multiple diseases or disorders associated with APJ and apelin. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As a person of ordinary skill in the art would be able to understand that a pyridone in a molecule may tautomerize to its keto and enol forms as shown in the following equation, wherein $R^1$, $R^2$, $R^3$ and $R^4$ are as defined above, this disclosure is intended to cover all possible tautomers even when a structure depicts only one of them.

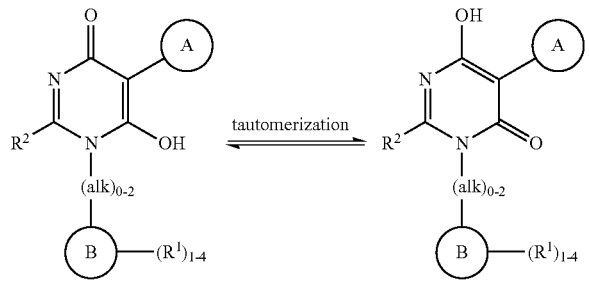

AcOH or HOAc acetic acid
ACN acetonitrile
Alk Alkyl
$AlMe_3$ Trimethylaluminum
$BBr_3$ boron tribromide
Bn benzyl
Boc tert-butyloxycarbonyl
BOP reagent benzotriazol-1-yloxytris(dimethylamino)phosphonium hexafluorophosphate
Bu butyl
i-Bu isobutyl
t-Bu tert-butyl
t-BuOH tert-butanol
Cbz carbobenzyloxy
$CDCl_3$ deutero-chloroform
$CD_3OD$ deutero-methanol
$CH_2Cl_2$ dichloromethane
$CH_3CN$ acetonitrile
$CHCl_3$ chloroform
DCM dichloromethane
DIEA, DIPEA or diisopropylethylamine Hunig's base
DMF dimethyl formamide
DMSO dimethyl sulfoxide
Et ethyl
$Et_3N$ or TEA triethylamine
$Et_2O$ diethyl ether
EtOAc ethyl acetate
EtOH ethanol
HCl hydrochloric acid
HPLC high-performance liquid chromatography
$K_2CO_3$ potassium carbonate
$K_2HPO_4$ potassium hydrogenphosphate
LCMS liquid chromatography mass spectrometry
LiHMDS lithium bis(trimethylsilyl)amide
LG leaving group
Me methyl
MeOH methanol
$MgSO_4$ magnesium sulfate
MsOH or MSA methylsulfonic acid
NaCl sodium chloride
$Na_2CO_3$ sodium carbonate
$NaHCO_3$ sodium bicarbonate
NaOH sodium hydroxide
$Na_2SO_4$ sodium sulfate
$NH_3$ ammonia
$NH_4Cl$ ammonium chloride
$NH_4OAc$ ammonium acetate
$Pd(OAc)_2$ palladium(II) acetate
$Pd(dppf)Cl_2$ [1,1'-Bis(diphenylphosphino)ferrocene]palladium(II) dichloride
$Pd(PPh_3)_4$ tetrakis(triphenylphosphine)palladium(0)
PG protecting group
Ph phenyl
Pr propyl
i-Pr isopropyl
i-PrOH or IPA isopropanol
Rt retention time
$SiO_2$ silica oxide
SFC supercritical fluid chromatography
TBAI Tetrabutylammonium iodide
TEA triethylamine
TFA trifluoroacetic acid
TFAA Trifluoroacetic anhydride
THF tetrahydrofuran
$TiCl_4$ titanium tetrachloride
T3P 1-propanephosphonic acid cyclic anhydride
Description of Analytical LCMS Methods:

Method A: Column: Waters Acquity UPLC BEH C18, 2.1×50 mm, 1.7 μm particles; Mobile Phase A: 5:95 ACN:water with 10 mM $NH_4OAc$; Mobile Phase B: 95:5 ACN:water with 10 mM $NH_4OAc$; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 μm particles; Mobile Phase A: 5:95 ACN:water with 0.1% TFA; Mobile Phase B: 95:5 ACN:water with 0.1% TFA; Temperature: 50° C.; Gradient: 0-100% B over 3 minutes, then a 0.75 minute hold at 100% B; Flow: 1.11 mL/min; Detection: UV at 220 nm.

Method C: Column: PHENOMENEX® Luna 3 μm C18 (2.0×30 mm): Mobile Phase A: 10:90 MeOH:water with 0.1% TFA; Mobile Phase B: 90:10 MeOH:water with 0.1% TFA; Gradient: 0-100% B over 2 minutes, then a 1 minute hold at 100% B: Flow: 1 mL/min; Detection: UV at 220 nm.

Method D: Waters Acquity UPLC BEH C18, 2.1×50 mm, 1.7 μm particles; Mobile Phase A: water with 0.1% TFA; Mobile Phase B: ACN with 0.1% TFA; Gradient: 2-98% B over 1 minute, then a 0.5 minute hold at 98% B; Flow: 0.8 mL/min; Detection: UV at 220 nm.

Example 1

5-(5-(benzo[d]isoxazol-3-ylmethyl)-1,3,4-oxadiazol-2-yl)-2-butyl-1-(2,6-dimethoxyphenyl)-6-hydroxypyrimidin-4(1H)-one

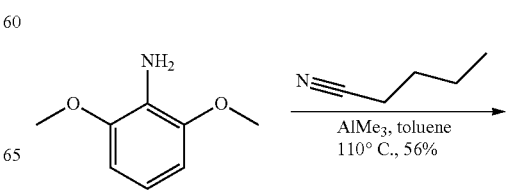

63

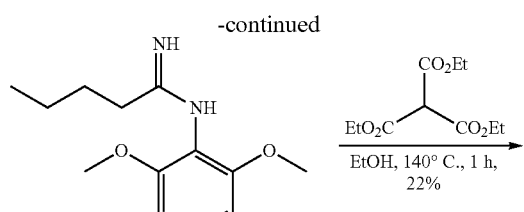

Compound 1a

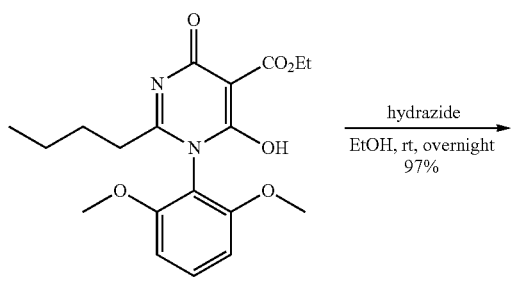

Compound 1b

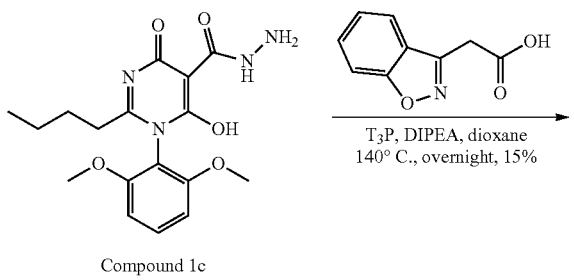

Compound 1c

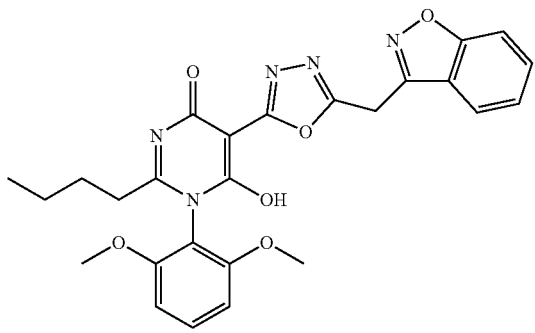

Example 1

Compound 1a. Ethyl 2-(2,6-dimethoxyphenyl)acetate

To a solution of pentanenitrile (310 mg, 3.7 mmol) and 2-methoxy-6-methylaniline (518 mg, 3.40 mmol) in toluene (13 mL) at RT was added a solution of trimethylaluminum in toluene (1.7 mL, 3.4 mmol) at 0° C. The reaction mixture was heated at 110° C. for 1 h. The cooled reaction mixture was quenched with saturated solution of Rochelle's salt (5 mL) and stirred at RT for 30 min. The reaction mixture was extracted with EtOAc (3×20 mL). The combined organic layer was washed with brine, dried over MgSO$_4$, filtered and concentrated under reduced pressure. The residue was purified by silica gel chromatography eluting with 20-100% EtOAc/hexanes with 0.5% Et$_3$N to give Compound 1a (450 mg, 56%) as a brown oil. LCMS (Method D) retention time=0.65 min, m/z=237.1 (M+H). $^1$H NMR (500 MHz, CHLOROFORM-d) δ 6.88 (t, J=8.4 Hz, 1H), 6.51 (d, J=8.3 Hz, 2H), 4.68-3.89 (m, 2H), 3.71 (s, 6H), 2.33 (br. s., 2H), 1.84-1.52 (m, 2H), 1.49-1.24 (m, 2H), 0.89 (br. s., 3H).

Compound 1b. Ethyl 2-butyl-1-(2,6-dimethoxyphenyl)-6-hydroxy-4-oxo-1,4-dihydropyrimidine-5-carboxylate A mixture of 1a (500 mg, 2.1 mmol) and triethyl methanetricarboxylate (590 mg, 2.5 mmol) in toluene (12 mL) was heated at 140° C. for 1 h in a microwave reactor. The reaction mixture was concentrated under reduced pressure and the residue was purified by silica gel chromatography eluting with 0-100% EtOAc/DCM to give compound 1b (170 mg, 22%) as a brown solid. LCMS (Method D) retention time=0.87 min, m/z=377.3 (M+H). $^1$H NMR (400 MHz, CHLOROFORM-d) δ 7.39 (t, J=8.5 Hz, 1H), 6.65 (d, J=8.6 Hz, 2H), 4.40 (q, J=7.2 Hz, 2H), 3.78 (s, 6H), 2.49-2.18 (m, 2H), 1.70-1.53 (m, 2H), 1.39 (t, J=7.2 Hz, 3H), 1.29-1.12 (m, 2H), 0.79 (t, J=7.3 Hz, 3H).

Compound 1c. 2-Butyl-1-(2,6-dimethoxyphenyl)-6-hydroxy-4-oxo-1,4-dihydropyrimidine-5-carbohydrazide Hydrazine (1.37 ml, 43.6 mmol) was added to a solution of compound 1b (1.64 g, 4.36 mmol) in EtOH (15 ml) at room temperature and the mixture was stirred for 16 h.

The reaction mixture was concentrated and dried under reduced pressure to give compound 1c (1.67 g, 100%) as a white solid which was used without further purification. LCMS (Method D) retention time=0.80 min, m=363.1 (M+H).

Example 1. 5-(5-(Benzo[d]isoxazol-3-ylmethyl)-1,3,4-oxadiazol-2-yl)-2-butyl-1-(2,6-dimethoxyphenyl)-6-hydroxypyrimidin-4(1H)-one To a mixture of compound 1c (600 mg, 1.66 mmol) and 2-(benzo[d]isoxazol-3-yl)acetic acid (350 mg, 2.00 mmol) in dioxane (12 mL) was added a 50% solution of 1-propanephosphonic acid cyclic anhydride in ethyl acetate (3.00 mL, 5.00 mmol). The reaction mixture was heated at 140° C. for 14 h. The reaction mixture was allowed to cool and purified by reverse phase preparative HPLC (Axia Luna, 5μ, C18 column, 30×100 mm, 10 min gradient from 15-100% B. A=H$_2$O/ACN/TFA 90/10/0.1. B=ACN/H$_2$O/TFA 90/10/0.1) to give example 1 (130 mg, 15%). LCMS (Method D) retention time=0.84 min, m/z=504.0 (M+H). $^1$H NMR (400 MHz, CHLOROFORM-d) δ 7.73 (d, J=7.9 Hz, 1H), 7.62-7.49 (m, 2H), 7.43 (t, J=8.5 Hz, 1H), 7.32-7.27 (m, 1H), 6.69 (d, J=8.4 Hz, 2H), 4.66 (s, 2H), 3.78 (s, 6H), 2.40 (t, J=7.7 Hz, 2H), 1.62 (q, J=7.6 Hz, 2H), 1.25 (sxt, J=7.4 Hz, 2H), 0.79 (t, J=7.4 Hz, 3H). Human APJ cAMP Potency Range: A.

Example 2 to Example 22 in Table 1 were prepared as described by the general procedure given for Example 1.

Example 23

5-(5-(Benzo[d]isoxazol-3-ylmethyl)-1,3,4-oxadiazol-2-yl)-2-butyl-1-(2,6-diethoxyphenyl)-6-hydroxypyrimidin-4(1H)-one

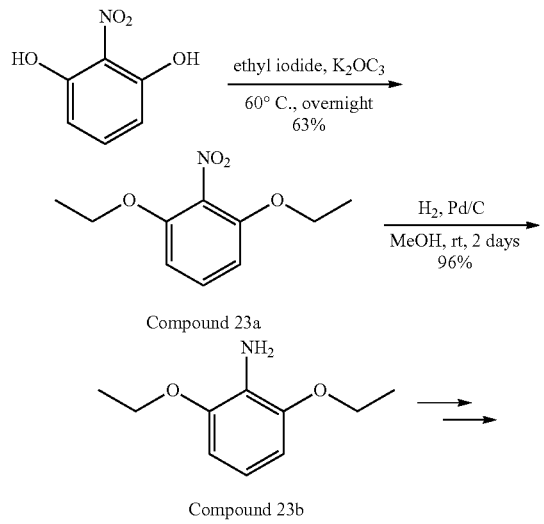

Example 23

Example 23a. 1,3-Diethoxy-2-nitrobenzene

A mixture of iodoethane (5.0 g, 32 mmol), 2-nitrobenzene-1,3-diol (1.0 g, 6.5 mmol) and potassium carbonate (3.6 g, 26 mmol) in DMF (21 ml) was heated at 60° C. for 14 h. The reaction mixture was diluted with EtOAc and washed with water and brine. The organic layer was dried over sodium sulfate, filtered and concentrated. The residue was purified by silica gel chromatography eluting with 0-100% EtOAc/DCM to give compound 23a (0.86 g, 63% yield). $^1$H NMR (400 MHz, CHLOROFORM-d) δ 7.40-7.16 (m, 1H), 6.58 (d, J=8.6 Hz, 2H), 4.11 (q, J=6.9 Hz, 4H), 1.39 (t, J=7.0 Hz, 6H).

Example 23b. 2,6-Diethoxyaniline

A solution of compound 23a (0.85 g, 4.0 mmol) and 10% Pd/C (200 mg, 0.19 mmol) in methanol (20 mL) was stirred under hydrogen atmosphere for 2 days. The reaction mixture was flushed with nitrogen and filtered through a pad of celite. The filtrate was concentrated under reduced pressure to give compound 23b (700 mg, 96%) as a brown solid. The residue was used directly in the next step without further purification. LCMS (Method D) retention time=0.61 min, m/z=182.2 (M+H).

Example 23. 5-(5-(Benzo[d]isoxazol-3-ylmethyl)-1,3,4-oxadiazol-2-yl)-2-butyl-1-(2,6-diethoxyphenyl)-6-hydroxypyrimidin-4(1H)-one Example 23 was prepared from compound 23b following a similar procedure as described for example 1 (21 mg, 6%) as a colorless film. LCMS (Method D) retention time=0.93 min, m/z=532.0 (M+H). $^1$H NMR (400 MHz, CHLOROFORM-d) δ 7.76 (d, J=8.4 Hz, 1H), 7.60-7.50 (m, 2H), 7.38 (t, J=8.5 Hz, 1H), 7.27-7.24 (m, 3H), 6.64 (d, J=8.4 Hz, 2H), 4.68 (s, 2H), 4.13-3.83 (m, 4H), 2.63-2.22 (m, 2H), 1.64 (t, J=7.7 Hz, 2H), 1.26 (t, J=7.0 Hz, 6H), 0.79 (t, J=7.4 Hz, 3H). Human APJ cAMP Potency Range: A.

Example 24 to Example 26 in Table 1 were prepared as described in the general procedure given for Example 23.

Example 27

5-(5-(Benzo[d]isoxazol-3-ylmethyl)-1,3,4-oxadiazol-2-yl)-2-butyl-1-(2,6-dicyclopropylphenyl)-6-hydroxypyrimidin-4(1H)-one

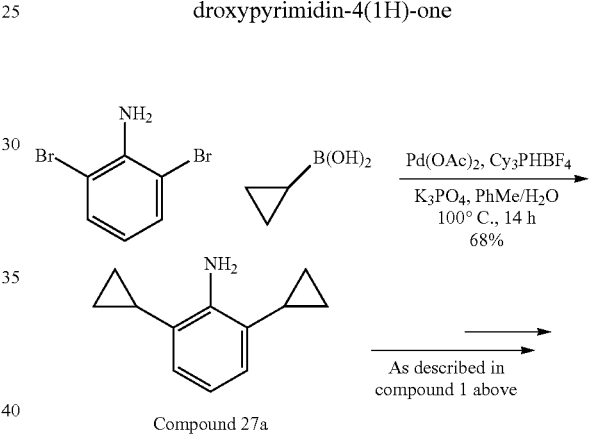

Compound 27a

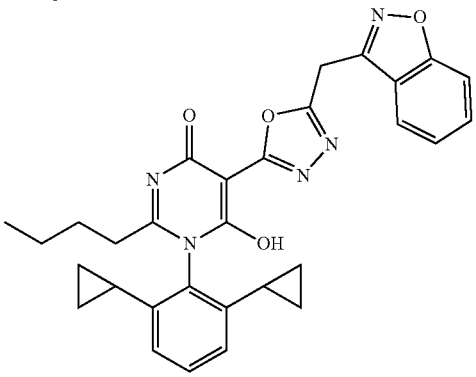

Example 27

Example 27a. 2,6-Dicyclopropylaniline

A mixture of 2,6-dibromoaniline (0.50 g, 2.0 mmol), cyclopropylboronic acid (0.70 g, 8.0 mmol), potassium phosphate (1.7 g, 8.0 mmol) and tricyclohexylphosphine (0.11 g, 0.40 mmol) in toluene (5 mL) and water (2 ml) was degassed with nitrogen then palladium acetate (0.12 g, 0.52 mmol) was added. The reaction mixture was heated at 100°

C. for 14 h. The reaction mixture was allowed to cool and ethyl acetate was added and the resulting mixture was washed with water, brine, dried over sodium sulfate and concentrated under reduced pressure. The residue was purified on silica gel chromatography eluting with 0-50% EtOAc/hexane to give compound 27a (240 mg, 68%) as a yellow oil. LCMS (Method D) retention time=0.80 min, m/z=174.2 (M+H). $^1$H NMR (400 MHz, DMSO-d$_6$) δ 6.84 (d, J=7.7 Hz, 2H), 6.71-6.62 (m, 1H), 1.82 (tt, J=8.3, 5.4 Hz, 2H), 0.99-0.91 (m, 4H), 0.64-0.53 (m, 4H).

Example 27. 5-(5-(Benzo[d]isoxazol-3-ylmethyl)-1,34-oxadiazol-2-yl)-2-butyl-1-(2,6-dicyclopropylphenyl)-6-hydroxypyrimidin-4(1H)-one Example 27 was prepared from compound 27a following a similar procedure as described for compound 1 (12 mg, 20%) as a clear oil. LCMS (Method D) retention time=1.01 min, m/z=524.1 (M+H). $^1$H NMR (500 MHz, DMSO-d$_6$) δ 7.88 (d, J=7.9 Hz, 1H), 7.78 (d, J=8.2 Hz, 1H), 7.69 (t, J=7.6 Hz, 1l), 7.41 (t, J=7.5 Hz, 1H), 7.34 (t, J=7.8 Hz, 1H), 6.86 (d, J=7.9 Hz, 2H), 4.83 (s, 2H), 2.41-2.31 (m, 2H), 1.70-1.44 (m, 4H), 1.30-1.12 (m, 2H), 1.00-0.77 (m, 6H), 0.72 (t, J=7.3 Hz, 3H), 0.64-0.41 (m, 2H). Human APJ cAMP Potency Range: A.

Example 28

2-(5-(5-(Benzo[d]isoxazol-3-ylmethyl)-1,3,4-oxadiazol-2-yl)-2-butyl-6-hydroxy-4-oxopyrimidin-1(4H)-yl)isophthalonitrile

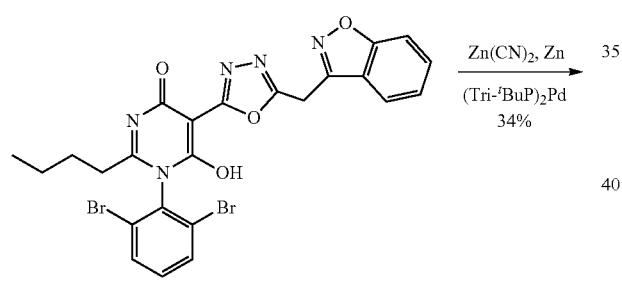

Example 15

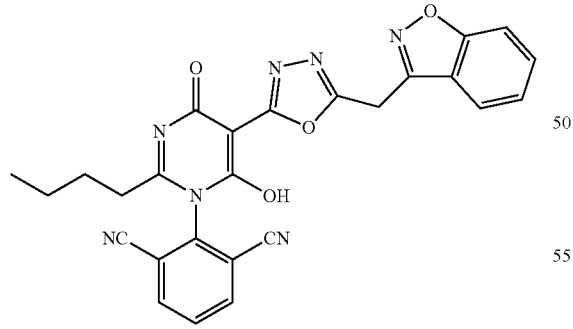

Example 28

A mixture of example 15 (30 mg, 0.05 mmol), zinc cyanide (35 mg, 0.30 mmol) and zinc (3 mg, 0.05 mmol) in DMF (1.0 mL) was degassed with argon and treated with bis(tri-t-butylphosphine)palladium (8 mg, 0.02 mmol). The reaction mixture was heated at 85° C. for 14 h. The reaction mixture was filtered and purified by reverse phase preparative HPLC (Axia Luna, 5μ, C18 column, 30×100 mm, 10 min gradient from 20-100% B. A=H$_2$O/ACN/TFA 90/10/0.1. B=ACN/H$_2$O/TFA 90/10/0.1) to give example 28 (9.0 mg, 34% yield). LCMS (Method D) retention time=0.89 min, m/z=493.9 (M+H). $^1$H NMR (400 MHz, DMSO-d$_6$) δ 8.51 (d, J=7.9 Hz, 2H), 8.02 (t, d=7.9 Hz, 1H), 7.88 (d. J=7.9 Hz, 1H), 7.82-7.76 (m, 1H), 7.73-7.65 (m, 1H), 7.41 (t, J=7.5 Hz, 1H), 4.85 (s, 2H), 2.45-2.24 (m, 2H), 1.61 (q, J=7.4 Hz, 2H), 1.35-1.16 (m, 2H), 0.80 (t, J=7.3 Hz, 3H). Human APJ cAMP Potency Range: B.

Example 29

2-butyl-5-(5-(4-chlorobenzyl)-1,3,4-oxadiazol-2-yl)-1-(2,6-dicyclopropoxyphenyl)-6-hydroxypyrimidin-4(1H)-one

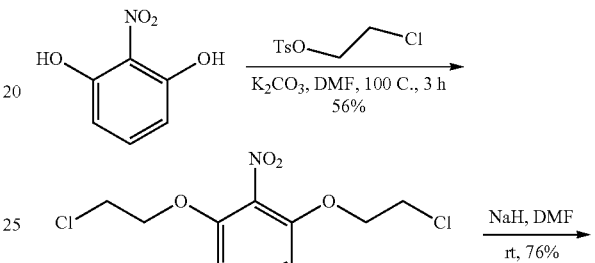

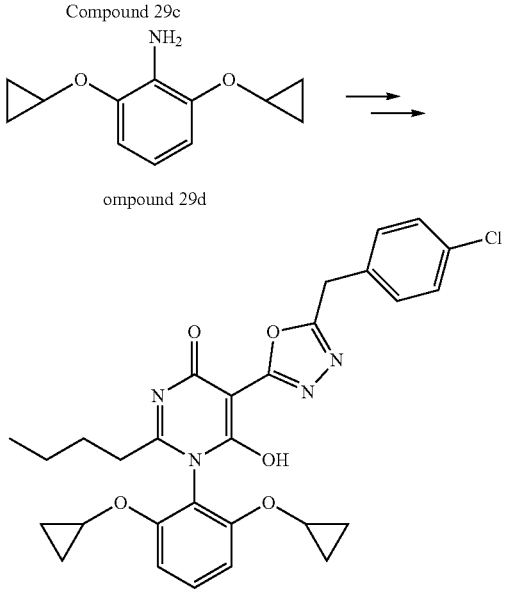

Example 29

Compound 29a.
1,3-Bis(2-chloroethoxy)-2-nitrobenzene

A mixture of 2-nitrobenzene-1,3-diol (1.0 g, 6.4 mmol), potassium carbonate (5.4 g, 39 mmol) and 2-chloroethyl 4-methylbenzenesulfonate (3.3 g, 14 mmol) in DMF (10 mL) was heated at 100° C. for 3 hours. The reaction mixture was allowed to cool to room temperature and diluted with EtOAc. The resulting mixture was washed with water and brine, dried over sodium sulfate, filtered and concentrated under reduced pressure. The residue was purified by silica gel chromatography eluting with 0-100% EtOAc/hexane to give compound 29a (1.0 g, 58%). $^1$H NMR (400 MHz, CHLOROFORM-d) δ 7.34 (t, J=-8.6 Hz, 1H), 6.67 (d, J=8.6 Hz, 2H), 4.30 (t, J=6.2 Hz, 4H), 3.77 (t, J=6.2 Hz, 4H).

Compound 29b. 2-Nitro-1,3-bis(vinyloxy)benzene

To a solution of compound 29a (200 mg, 0.71 mmol) in DMF (3 mL) was added NaH (123 mg, 3.10 mmol). The resulting mixture was stirred at room temperature for 14 h. The reaction mixture was carefully quenched by the addition of MeOH and then brine. The resulting mixture was extracted with EtOAc. The organic layer was separated and washed with brine, dried over sodium sulfate, filtered and concentrated under reduced pressure. The residue was purified by silica gel chromatography eluting with 0-100% EtOAc/hexane to give compound 29b (110 mg, 76%) as a white solid. $^1$H NMR (400 MHz, CHLOROFORM-d) δ 7.38 (t, J=8.5 Hz, 1H), 6.85 (d, J=8.4 Hz, 2H), 6.62 (d, J=5.9 Hz, 1H), 6.58 (d, J=6.2 Hz, 1H), 4.93 (dd, J=13.5, 2.3 Hz, 2H), 4.64 (dd, J=5.9, 2.2 Hz, 2H).

Compound 29c. 1,3-Dicyclopropoxy-2-nitrobenzene

To a solution of diethylzinc (11.6 mL, 12.7 mmol) in DCM (11 mL) at −10° C. was slowly added trifluoroacetic acid (1.0 mL, 13 mmol) while keeping reaction temperature below 0° C. The reaction mixture was stirred at 0° C. for 10 min and then diiodomethane (1.0 mL, 13 mmol) was added while keeping reaction temperature below 0° C. The reaction mixture was stirred at this temperature for 15 min and a solution of compound 29b (440 mg, 2.1 mmol) in DCM (12 mL) was added dropwise. The reaction mixture was allowed to warm to RT and stirred for 14 h. The reaction mixture was carefully quenched with the addition of 1N HCl and stirred at RT for 15 min. The organic layer was separated. The aqueous phase was extracted with DCM (500 mL). The combined organic extracts were washed with brine, dried over sodium sulfate and concentrated under reduced pressure. The residue was purified on silica gel chromatography eluting with 0-100% EtOAc/hexane to give compound 29c (330 mg, 66%) as a yellow oil. $^1$H NMR (400 MHz, CHLOROFORM-d) δ 7.34 (t, J=8.6 Hz, 1H), 6.97 (d, J=8.6 Hz, 2H), 3.84 (tt, J=5.9, 3.0 Hz, 2H), 0.87-0.70 (m, 8H).

Compound 29d. 2,6-Dicyclopropoxyaniline

To a solution of compound 29c (300 mg, 1.3 mmol) in MeOH (12 mL) was added ammonium chloride (410 mg, 7.6 mmol) and zinc (668 mg, 10.2 mmol). The reaction mixture was stirred at 60° C. for 14 h. The reaction mixture was diluted with a 1:1 mixture of DCM:MeOH and filtered through celite. The filtrate was concentrated under reduced pressure. The residue was purified on silica gel chromatography eluting with 0-100% EtOAc/hexane to give compound 29d (100 mg, 38%/o) as a yellow solid. LCMS (Method D) retention time=0.70 min, m/z=206.1 (M+H). $^1$H NMR (400 MHz, CHLOROFORM-d) δ 6.87 (d, J=8.4 Hz, 2H), 6.70 (dd, J=8.6, 7.9 Hz, 1H), 3.87-3.73 (m, 2H), 3.69 (br. s., 2H), 0.88-0.70 (m, 8H).

Compound 29. 2-(5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)-N,N-diethylacetamide Compound 29 was prepared from compound 29d following a similar procedure as described for compound 1 (21 mg, 33%) as a white solid. LCMS (Method D) retention time=1.02 min, m/z=549.0 (M+H). $^1$H NMR (400 MHz, CHLOROFORM-d) δ 7.46 (t, J=8.5 Hz, 1H), 7.31 (s, 4H), 7.05 (d, J=8.6 Hz, 2H), 4.24 (s, 2H), 3.82-3.72 (m, 2H), 2.38 (t, J=7.6 Hz, 2H), 1.58 (quin, J=7.5 Hz, 2H), 1.37-1.11 (m, 2H), 0.86-0.69 (m, 9H), 0.66-0.50 (m, 2H). Human APJ cAMP Potency Range: B.

Example 30 in Table 1 was prepared as described in the general procedure given for Example 29

Example 31

5-(1-benzyl-1H-pyrazol-4-yl)-2-butyl-3-(2,6-dimethoxyphenyl)-6-hydroxypyrimidin-4(3H)-one

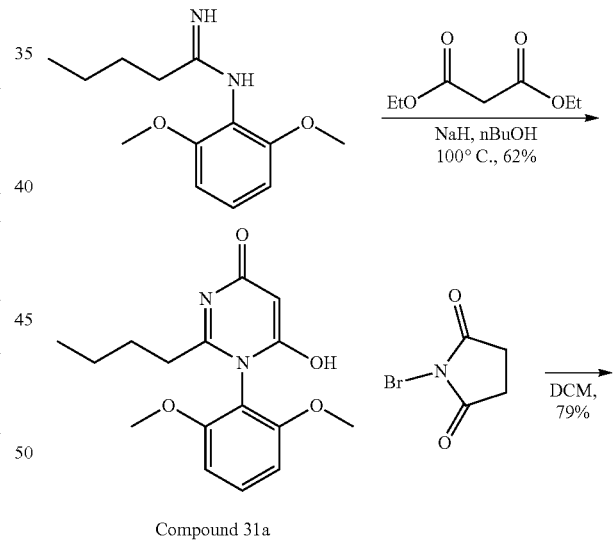

Compound 31a

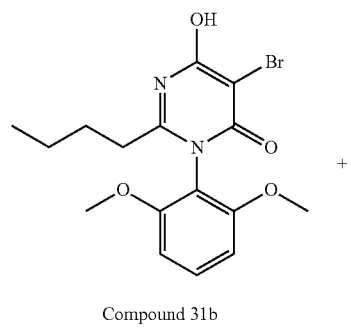

Compound 31b

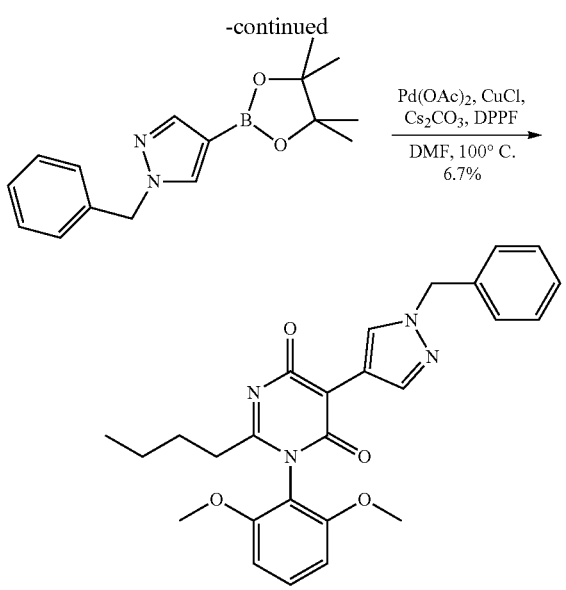

Example 31

Compound 31a. 2-Butyl-1-(2,6-dimethoxyphenyl)-6-hydroxypyrimidin-4(1H)-one

To a solution of N-(2,6-dimethoxyphenyl)pentanimidamide (2.00 g, 8.46 mmol) and diethyl malonate (6.42 mL, 42.3 mmol) in n-BuOH (15 mL) was added NaH (1.69 g, 42.3 mmol) portion wise. The resulting mixture, after bubbling ceased was stirred at 100° C. for 4 h. The reaction mixture was allowed to cool to RT and the solvent was evaporated in vacuo to remove n-BuOH. The residue was diluted with EtOAc and water. The organic layer was separated and washed with 1M HCl. The organic layer containing some solid was concentrated in vacuo. The residue was triturated with EtOAc and filtered to afford compound 31a (1.6 g, 62%) as an off white solid. MS m/z=305.1 (M+H), 1H NMR (500 MHz, CD$_3$OD) δ 7.47 (t, J=8.6 Hz, 1H), 6.82 (d, J=8.6 Hz, 2H), 5.41 (s, 1H), 3.81 (s, 6H), 2.31 (t, J=7.9 Hz, 2H), 1.44-1.56 (m, 2H), 116-1.26 (m, 2H), 0.77 (t, J=7.3 Hz, 3H).

Compound 31b. 5-Bromo-2-butyl-3-(2,6-dimethoxyphenyl)-6-hydroxypyrimidin-4(3H)-one To a stirred solution of compound 31a (100 mg, 0.33 mmol) in DCM (5 mL) was added 1-bromopyrrolidine-2,5-dione (58.5 mg, 0.330 mmol). The reaction mixture was kept at RT for 3 h. The reaction mixture was concentrated in vacuo. The residue was added to a silica gel (12 g) column and eluted with 0-30% MeOH in DCM. Fractions containing compound 31b were collected, combined and concentrated to give a white solid (100 mg, 79%). MS m/z=385.0 (M+H), 1H NMR (500 MHz, CDCl$_3$) δ 7.43 (t, J=8.5 Hz, 1H), 6.68 (d, J=8.5 Hz, 2H), 3.81 (s, 6H), 2.50 (t, J=8.0 Hz, 2H), 1.52-1.58 (m, 2H), 123-1.32 (m, 2H), 0.81 (t, J=8.0 Hz, 3H).

Example 31. 5-(1-Benzyl-1H-pyrazol-4-yl)-2-butyl-3-(2,6-dimethoxyphenyl)-6-hydroxypyrimidin-4(3H)-one To a mixture of compound 31b (15 mg, 0.039 mmol), 1-benzyl-4-(4,4,5,5-tetramethyl-1,3,2-dioxaborolan-2-yl)- 1H-pyrazole (22 mg, 0.078 mmol), Pd(OAc)$_2$ (0.44 mg, 2.0 μmol), copper (I) chloride (3.87 mg, 0.0390 mmol), Cs$_2$CO$_3$ (51.0 mg, 0.157 mmol) and DPPF (2.17 mg, 3.91 μmol) was added DMF (1 mL). The reaction mixture was degassed and heated at 100° C. for 10 h. The reaction mixture was concentrated in vacuo. The residue was purified via preparative HPLC (Column: XBridge C18, 19×200 mm, 5-μm particles. Mobile Phase A: 5:95 acetonitrile: water with 10-mM ammonium acetate, Mobile Phase B: 95:5 acetonitrile: water with 10-mM ammonium acetate; Gradient: 15-55% B over 20 minutes, then a 5-minute hold at 100% B; Flow: 20 mL/min). Fractions containing Example 31 were combined and dried via centrifugal evaporation, to give (1.2 mg, 6.7%) a white solid. MS m/z=461.3 (M+H), 1H NMR (500 MHz, DMSO-d6) 8.31 (s, 1H), 8.13 (s, 1H), 7.47 (t, J=7.9 Hz, 1H), 7.18-7.39 (m, 5H), 6.85 (d, J=8.5 Hz, 2H), 5.33 (s, 2H), 3.75 (s, 6H), 2.24 (br s, 2H), 1.46 (br s, 2H), 1.12-1.22 (m, 2H), 0.68-0.78 (m, 3H). Human APJ cAMP Potency Range: A.

Example 32 in Table 1 was prepared as described in the general procedure given for Example 31

Example 33

5-(5-(benzo[d]isoxazol-3-ylmethyl)-1,3,4-oxadiazol-2-yl)-1-(2,6-dimethoxyphenyl)-6-hydroxy-2-(ethoxymethyl)pyrimidin-4(1H)-one Compound 33a Compound 33b Compound 33c Example 33

Compound 33a. 2-Ethoxyacetamide

To a stirred solution of 2-ethoxyacetic acid (1.5 g, 14 mmol) in DCM (20 mL) at 0° C. was added oxalyl chloride (8.65 mL, 17.3 mmol), followed by DMF (2 drops). The cooling bath was removed and the reaction mixture was stirred at RT for 3 h. The reaction mixture was concentrated under reduced pressure and dissolved in DCM (20 mL). Ammonia (20.6 mL, 144 mmol) (7 M in MeOH) was added carefully and the reaction mixture stirred for 16 h. The reaction mixture was concentrated under reduced pressure, dissolved in DCM, filtered and washed with DCM. The filtrate was concentrated under reduced pressure to give Compound 33a (1.0 g, 67%) as a white solid. $^1$H NMR (500 MHz. CDCl$_3$) δ 6.51 (br s, 1H), 5.46 (br s, 1H), 3.94 (s, 2H), 3.59 (q, J=6.8 Hz, 2H), 1.25 (t, J=7.2 Hz, 3H).

Compound 33b. 2-Ethoxyacetonitrile

To a stirred solution of Compound 33a (1.0 g, 9.7 mmol) in THF (10 mL) at 0° C. was added pyridine (1.57 mL, 19.4 mmol) followed by TFAA (6.85 mL, 48.5 mmol). The reaction mixture was stirred at RT for 1 h. Aqueous NaHCO$_3$ solution was added carefully to the reaction mixture until pH=8 was attained. The reaction mixture was extracted with CH$_2$C$_2$ (2×). The combined organic layers were washed with 1N HCl, dried over MgSO$_4$, filtered and concentrated in vacuo to give Compound 33b (0.80 g, 97%) as a yellow liquid. $^1$H NMR (500 MHz, CDCl$_3$) δ 4.24 (s, 2H), 3.66 (q, J=6.9 Hz, 2H), 1.27 (t, J=6.9 Hz, 3H).

Compound 33c. N-(2,6-Dimethoxyphenyl)-2-ethoxyacetimidamide

Trimethylaluminum (2.0 M in toluene, 4.7 mL, 9.4 mmol) was added dropwise to a solution of 2,6-dimethoxyaniline (1.2 g, 7.8 mmol) and Compound 33b (0.80 g, 9.4 mmol) in toluene (10 mL) while cooling in an ice bath. After addition was complete, the reaction mixture was heated to 110° C., and was stirred at this temperature for 14 h. The reaction mixture was allowed to cool and was partitioned between a saturated solution of Rochelle's salt and EtOAc. The organic phase was separated, dried over MgSO$_4$, filtered and concentrated under reduced pressure. The residue was added to a silica gel (120 g) column and was eluted with 0-20% of 20% MeOH/DCM in 0.5% TEA/DCM to give Compound 33c (1.1 g, 57%) as a brown liquid. MS m/z=239.0 (M+H), 1H NMR (500 MHz, CDCl$_3$) δ 7.01 (t, J=8.3 Hz, 1H), 6.62 (d, J=7.7 Hz, 2H), 5.32 (s, 2H), 4.88 (br s, 2H), 4.31 (s, 2H), 3.82 (s, 6H), 3.62-3.73 (m, 2H), 1.19-1.33 (m, 3H).

Example 33 was prepared from compound 33c following a similar procedure as described for example 1 (1.2 mg, 1%) as a colorless film. LCMS (Method A) retention time=1.15 min, m/z=505.9 (M+H). $^1$H NMR (500 MHz, DMSO-d6) δ 7.87 (d, J=7.9 Hz, 1H), 7.78 (d, J=8.5 Hz, 1H), 7.69 (t, J=7.6 Hz, 1H), 7.43 (t, J=7.9 Hz, 1H), 7.42 (t, J=7.0 Hz, 1H), 6.81 (d, J=8.5 Hz, 2H), 4.80 (s, 2H), 3.95 (s, 2H), 3.76 (s, 6H), 3.33 (q, J=6.7 Hz, 2H), 1.01 (t, J=6.7 Hz, 3H). Human APJ cAMP Potency Range: A.

Example 34 to Example 41 in Table 1 were prepared as described in the general procedure given for Example 33.

Example 42

5-(5-(benzo[d]isoxazol-3-ylmethyl)-1,3,4-oxadiazol-2-yl)-2-(2-cyclopropylethyl)-1-(2,6-dimethoxyphenyl)-6-hydroxypyrimidin-4(1H)-one

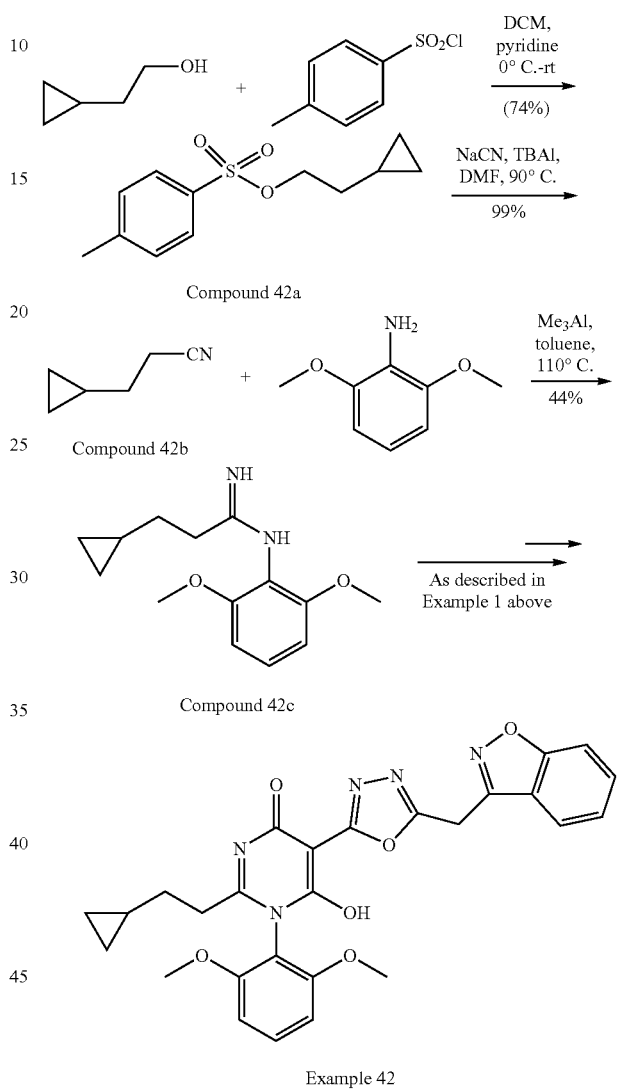

Example 42

Compound 42a. 2-Cyclopropylethyl 4-methylbenzenesulfonate

To 2-cyclopropylethanol at 0° C. (0.98 g, 11 mmol) and pyridine (2.4 mL, 30 mmol) in DCM (15 mL) was added 4-methylbenzene-1-sulfonyl chloride (22 g, 11 mmol). The cold bath was removed and the mixture allowed to warm to room temperature for 14 h. The reaction mixture was diluted with water and Et$_2$O and the phases were separated. The organic phase was washed sequentially with water, 10% aqueous HCl and brine, dried (MgSO$_4$) filtered and concentrated under reduced pressure to give Compound 41a (2.0 g, 74%) as a clear colorless oil. Compound 42a was used in the next step without further purification. MS m/z=241.4 (M+H). $^1$H NMR (400 MHz, CHLOROFORM-d) δ 7.77 (d, J=8.1 Hz, 2H), 7.32 (d, J=8.4 Hz, 2H), 4.06 (t, J=6.7 Hz, 2H), 2.42 (s, 3H), 1.56-1.45 (m, 2H), 0.70-0.57 (m, 1H), 0.44-0.32 (m, 2H), 0.04-0.10 (m, 2H).

Compound 42b. 3-Cyclopropylpropanenitrile

To a solution of Compound 42a (1.0 g, 4.2 mmol) in DMF (5 mL) was added NaCN (0.60 g, 13 mmol) and TBAI (0.06 g, 0.2 mmol) and the reaction mixture was stirred at 90° C. for 14 h. The reaction mixture was allowed to cool to room temperature, diluted with Et$_2$O and brine and the phases were separated. The organic phase was washed with 10% aqueous LiCl, dried over MgSO$_4$, filtered and concentrated under reduced pressure to give Compound 42b (0.39 g, 99%) as a clear colorless oil, which was used in the next step without further purification. $^1$H NMR (CHLOROFORM-d) δ 2.27 (t, J=7.2 Hz, 2H), 1.34-1.46 (m, 2H), 0.62-0.74 (m, 1H), 0.34-0.45 (m, 2H), −0.05-0.04 (m, 2H).

Compound 42c. 3-Cyclopropyl-N-(2,6-dimethoxyphenyl)propanimidamide

To a mixture of Compound 42b (0.37 g, 3.9 mmol) and 2,6-dimethoxyaniline (0.5 g, 3 mmol) in toluene (5 mL), at 0° C., was added a 2M solution of trimethylaluminum in hexane (2 ml, 4 mmol) dropwise. The reaction mixture was allowed to warm to room temperature and heated at 110° C. overnight. The reaction mixture was allowed to cool to RT and quenched with saturated aqueous Rochelle's salt and EtOAc. The phases were separated, the aqueous phase was extracted with EtOAc. The organic phases were combined and washed with brine, dried over MgSO$_4$, filtered and concentrated under reduced pressure. The residue was purified by silica gel chromatography eluting with 0 to 30% MeOH/0.5% TEA in DCM to give Compound 42c (0.35 g, 44% yield) as an orange oil. MS min=249.4 (M+H). $^1$H NMR (METHANOL-d$_4$) δ 7.01 (t, J=8.3 Hz, 1H), 6.64 (d, J=8.3 Hz, 2H), 2.29-2.48 (m, 2H), 1.50-1.67 (m, 2H), 0.78-0.93 (m, 1H), 0.44 (s, 2H), 0.02-0.16 (m, 2H).

Example 42 was prepared from compound 42c following a similar procedure as described for example 1 (6 mg, 7%) as a colorless film. LCMS (Method A) retention time=1.34 min, m/z=516.0 (M+H). $^1$H NMR (500 MHz, DMSO-d6) δ 8.03 (d, J=7.9 Hz, 1H), 7.95 (d. J=8.5 Hz, 1H), 7.82-7.88 (m, 1H), 7.67 (t, J=8.4 Hz, 1H), 7.58 (t, J=7.5 Hz, 1H), 7.03 (d, J=8.5 Hz, 2H), 4.98 (s, 2H), 3.94 (s, 6H), 2.61 (t, J=7.5 Hz, 2H), 1.47-1.55 (m, 2H), 0.72-0.84 (m, 1H), 0.43-0.53 (m, 2H), −0.03-0.04 (m, 2H). Human APJ cAMP Potency Range: A.

Example 43 to Example 47 in Table 1 were prepared as described in the general procedure given for Example 41.

Example 48

5-(5-(Benzo[d]isoxazol-3-ylmethyl)-1,3,4-oxadiazol-2-yl)-2-butyl-1-(2,6-di[$^2$H$_3$]methoxyphenyl)-6-hydroxypyrimidin-4(1H)-one

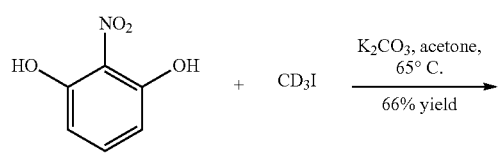

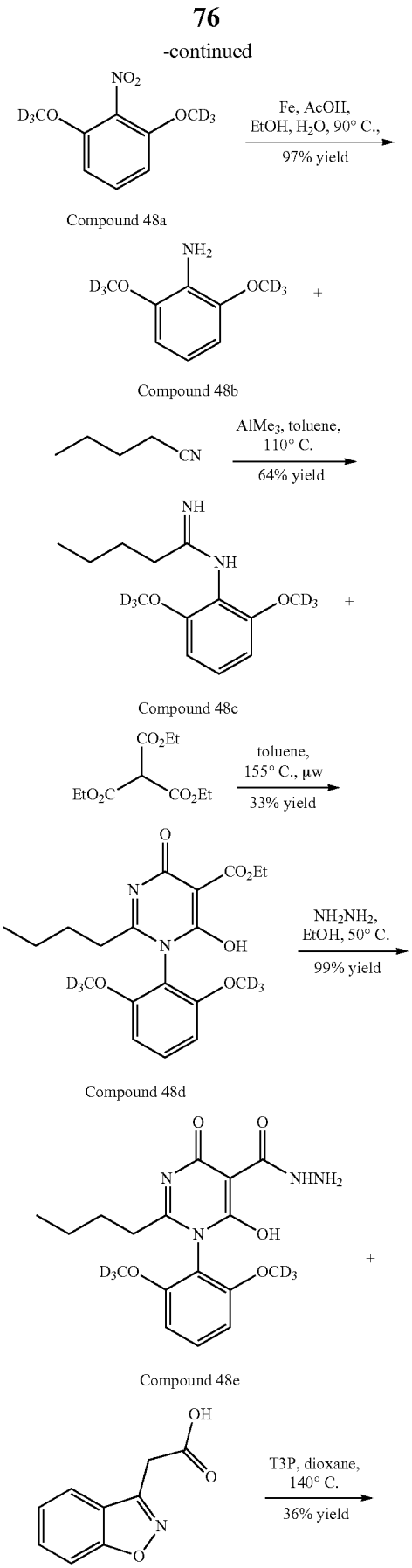

-continued

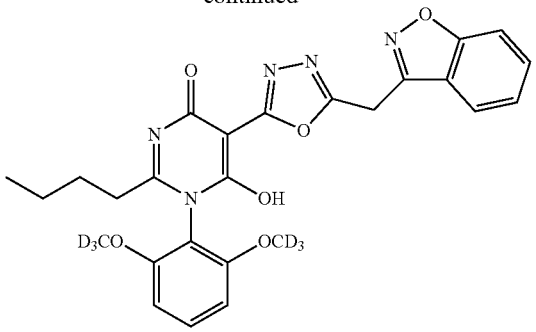

Example 48

Compound 48a. 1,3-Di[$^2$H$_3$]methoxy-2-nitrobenzene

To a solution of 2-nitrobenzene-1,3-diol (1.75, 11.0 mmol) in acetone (175 mL) was added methyl-d$_3$ iodide (4.9 g, 34 mmol) and K$_2$CO$_3$ (3.1 g, 23 mmol). The reaction mixture was stirred at 65° C. for 14 h. After allowing to cool to RT, the mixture was concentrated under reduced pressure. The residue was diluted with water and extracted with EtOAc (3×). The combined extracts were washed with brine, dried over MgSO$_4$, filtered and concentrated under reduced pressure. The residue was purified by silica gel chromatography eluting with 0 to 80% EtOAc/hexanes to give Compound 48a (1.4 g, 66%) as a light yellow foam. MS m/z=190.4 (M+H). $^1$H NMR (CHLOROFORM-d) δ 7.25 (t, J=8.5 Hz, 1H), 6.55 (d, J=8.4 Hz, 2H).

Compound 48b. 2,6-Di[$^2$H$_3$]methoxyaniline

To a solution of Compound 48a (1.4 g, 7.5 mmol) in a mixture of AcOH (40 mL), EtOH (40 mL) and H$_2$O (20 mL) was added iron (2.5 g, 45 mmol) potion wise and the reaction mixture was stirred at 90° C. for 14 h. The reaction mixture was allowed to cool to RT, poured onto ice, basified carefully with the addition of solid Na$_2$CO$_3$ and extracted with EtOAc (3×). The combined organic extracts were washed with brine, dried over MgSO$_4$, filtered and concentrated under reduced pressure to give compound 48b (1.2 g, 97%) as a dark solid. Compound 11a was used without further purification. MS m/z=160.4 (M+H).

Compound 48c. N-(2,6-di[$^2$H$_3$]methoxyphenyl)pentanimidamide

To a mixture of Compound 48b (1.2 g, 7.2 mmol) and pentanenitrile (0.72 g, 8.6 mmol) in toluene (11 mL) at 0° C. was added 2M trimethylaluminum in hexane (4.3 mL, 8.6 mmol) dropwise. The reaction mixture was allowed to warm to room temperature and was heated at 100° C. for 14 h. The reaction mixture was allowed to cool to RT and quenched with saturated aqueous Rochelle's salt and EtOAc. The phases were separated and the aqueous phase was extracted with EtOAc. The organic phases were combined and washed with brine, dried (MgSO$_4$), filtered and concentrated under reduced pressure. The residue was purified by silica gel chromatography eluting with 0 to 30% MeOH/0.5% TEA in DCM to give Compound 48c (1.1 g, 64%) as an orange oil. MS m/z=243.4 (M+H). $^1$H NMR (METHANOL-d$_4$) δ 7.01 (t, J=8.3 Hz, 1H), 6.64 (d, J=8.4 Hz, 2H), 2.22-2.34 (m, 2H), 1.60-1.72 (m, 2H), 1.40-1.53 (m, 2H), 0.96 (t, J=6.7 Hz, 3H).

Compound 48d. Ethyl 2-butyl-1-(2,6-di[$^2$H$_3$]methoxyphenyl)-6-hydroxy-4-oxo-1,4-dihydropyrimidine-5-carboxylate A solution of Compound 48c (0.35 g, 1.4 mmol) and triethyl methanetricarboxylate (0.50 g, 2.2 mmol) in toluene (10 ml) was heated at 155° C. in a microwave reactor for 15 min. The reaction mixture was concentrated under reduced pressure. The residue was purified by silica gel chromatography eluting with 0 to 100% EtOAc/hexanes to give Compound 48d (0.18 g, 33%) as a pale yellow solid. MS m/z=383.4 (M+H). $^1$H NMR (METHANOL-d$_4$) δ 7.88 (t, J=8.5 Hz, 1H), 7.22 (d. J=8.3 Hz, 2H), 4.73 (q, J=7.1 Hz, 2H), 2.75 (t, J=7.7 Hz, 2H), 1.88-1.97 (m, 2H), 1.72 (t, J=7.2 Hz, 3H), 1.56-1.65 (m, 2H), 1.16 (t, J=7.4 Hz, 3H)

Compound 48e. 6-2-Butyl-1-(2,6-di[$^2$H$_3$]methoxyphenyl)-6-hydroxy-4-oxo-1,4-dihydropyrimidine-5-carbohydrazide To a suspension of Compound 48d (105 mg, 0.280 mmol) in ethanol (5 mL) was added anhydrous hydrazine 0.086 mL, 2.8 mmol) and the reaction mixture was stirred for 2 h at 50° C. The reaction mixture was concentrated under reduced pressure to give Compound 47e (100 mg, 99%) as an off-white solid. MS m/z=369.4 (M+H).). $^1$H NMR (METHANOL-d$_4$) δ 7.88 (t, J=8.5 Hz, 1H), 7.22 (d, J=8.3 Hz, 2H), 2.71 (t, J=7.7 Hz, 2H), 1.88-1.97 (m, 2H), 1.56-1.65 (m, 2H), 1.16 (t, J=7.4 Hz, 3H)

Example 48. 5-(5-(Benzo[d]isoxazol-3-ylmethyl)-1,3,4-oxadiazol-2-yl)-2-butyl-1-(2,6-di[$^2$H$_3$]methoxyphenyl)-6-hydroxypyrimidin-4(1H)-one To a solution of Compound 48e (30 mg, 0.081 mmol) in dioxane (2.3 mL) was added 2-(benzo[d]isoxazol-3-yl)acetic acid (17 mg, 0.098 mmol) followed by a 50% solution of 1-propanephosphonic acid cyclic anhydride in ethyl acetate (0.145 mL, 0.244 mmol). The reaction mixture stirred at 140° C. for 14 h. Additional 50% solution of 1-propanephosphonic acid cyclic anhydride in ethyl acetate (0.145 mL, 0.244 mmol) was added and the reaction mixture was stirred at 140° C. for 5 h. The reaction mixture was concentrated under reduced pressure then purified by prep HPLC (conditions: Column: XBridge C18, 19×200 mm, 5-μm particles; Mobile Phase A: 5:95 acetonitrile: water with 10-mM ammonium acetate: Mobile Phase B: 95:5 acetonitrile: water with 10-mM ammonium acetate: Gradient: 10-50% B over 20 minutes, then a 5-minute hold at 100% B: Flow: 20 mL/min.) to give Example 48 (15 mg, 36%0). LCMS (Method A) Rt=1.34 min, m/z=510.1 (M+H), 1H NMR (DMSO-d6) δ 7.85 (d. J=7.9 Hz, 1H), 7.73-7.79 (m, 1H), 7.69 (t, J=7.6 Hz, 1H), 7.48 (t, J=8.5 Hz, 1H), 7.41 (t, J=7.5 Hz, 1H), 6.83 (d, J=8.5 Hz, 2H), 4.77 (s, 2H), 2.30 (t, J=7.5 Hz, 21-), 1.41 (s, 2H), 1.12-1.18 (m, 2H), 0.69 (t, J=7.3 Hz, 3H). Human APJ cAMP Potency Range: A.

Example 49 in Table 1 was prepared as described in the general procedure given for Example 48.

Example 50 to 51 in Table 1 were prepared from compound 48b and compound 33b following a similar procedure as described for example 48

Example 52

2-(5-(2-(2-Cyclopropylethyl)-1-(2,6-dimethoxyphenyl)-6-hydroxy-4-oxo-1,4-dihydropyrimidin-5-yl)-1,3,4-oxadiazol-2-yl)-N,N-diethylacetamide

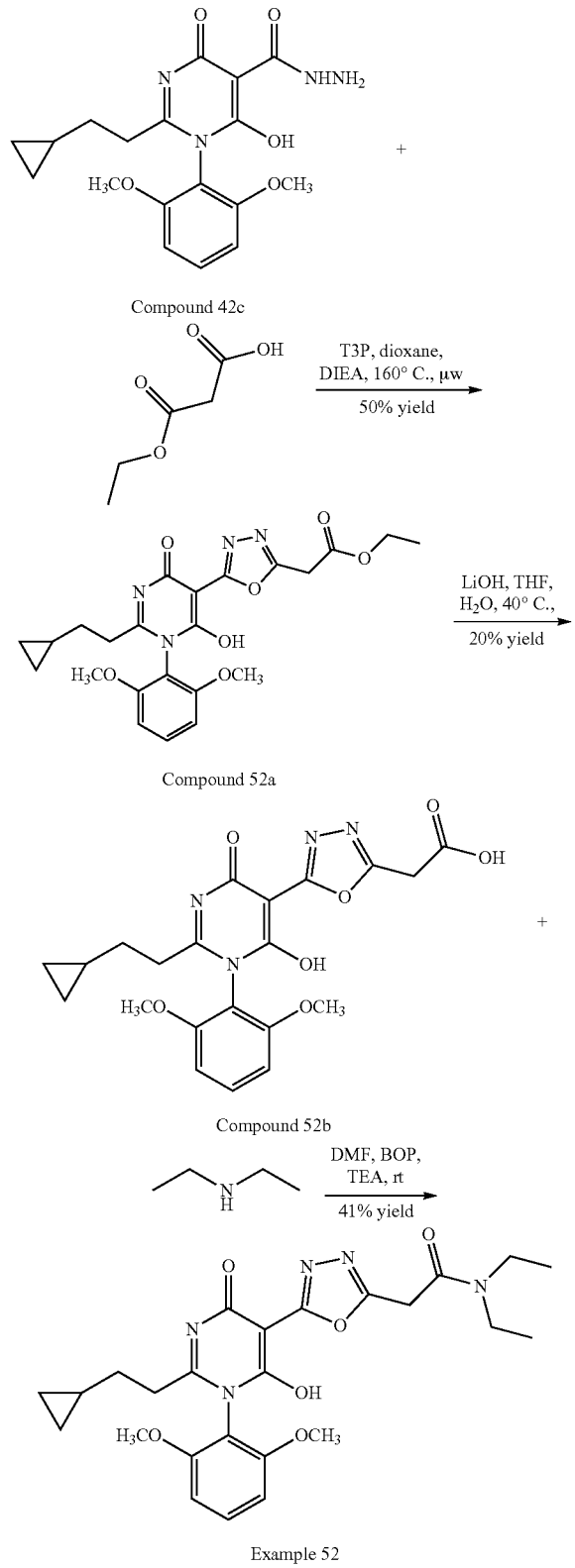

Compound 52a. Ethyl 2-(5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)acetate To a solution of Compound 42c (50 mg, 0.13 mol) in dioxane (2.0 mL) was added 3-ethoxy-3-oxopropanoic acid (21 mg, 0.16 mol) and DIEA (43 mg, 0.33 mol) followed by a 50% solution of I-propanephosphonic acid cyclic anhydride in ethyl acetate (0.40 mL, 0.67 mmol) and the reaction mixture heated by microwave irradiation at 160° C. for 1 h The reaction mixture was concentrated under reduced pressure and the residue was purified by silica gel chromatography eluting with 0 to 20% MeOH/DCM to give Compound 52a (32 mg, 50%) as a yellow oil, MS m/z=471.5 (M+H). 1H NMR (DMSO-d6, 500 MHz) δ 7.62 (t, J=8.2 Hz, 1H), 7.01 (d, J=8.5 Hz, 2H), 4.37 (s, 2H), 3.95 (s, 6H), 4.31 (q, J=6.5 Hz, 2H), 2.43 (t, J=7.2 Hz, 2H), 1.49-1.57 (m, 2H), 1.41 (t, J=6.9 Hz, 3H), 0.73-0.84 (m, 1H), 0.45-0.52 (m, 2H), −0.03-0.05 ppm (m, 2H)

Compound 52b. 2-(5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)acetic acid To a solution of Compound 52a (32 mg, 0.067 mmol) in a mixture of THF (1 mL) and H$_2$O (0.10 mL) was added lithium hydroxide monohydrate (9.6 mg, 0.30 mmol) and the mixture was stirred at 40° C. overnight. The reaction mixture was acidified to pH=2 with 1N HCl, concentrated under reduced pressure and the residue was purified by prep HPLC (conditions: Column: Phenomenex AXIA Luna C18, 20×200 mm, 5-μm particles; Mobile Phase A: 10/% acetonitrile/90% water/0.1% TFA; Mobile Phase B: 90% acetonitrile/10% water/0.1% TFA; Gradient: 0-100% B over 10 minutes, then a 3-minute hold at 100% B: Flow: 20 mL/min.) to give compound 52b (6 mg, 20%) as a white solid. MS m/z=443.4 (M+H). 1H NMR (DMSO-d6, 500 MHz) δ 7.62 (t, J=8.2 Hz, 1H), 7.01 (d, J=8.5 Hz, 2H), 4.37 (s, 2H), 3.95 (s, 6H), 2.43 (t, J=7.2 Hz, 2H), 1.49-1.57 (m, 2H), 0.73-0.84 (m, 1H), 0.45-0.52 (m, 2H), −0.03-0.05 ppm (m, 2H)

Example 52. 2-(5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)-N,N-diethylacetamide To a solution of Compound 52b (6 mg, 0.01 mmol) in DMF (0.5 mL) was added BOP (7.2, 0.016 mmol), diethylamine (2 mg, 0.03 mmol) and TEA (6.9 mg, 0.068 mmol) and the reaction mixture was stirred at room temperature for 2 h. The reaction mixture was purified by prep HPLC (conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B: Flow: 20 mL/min.) to give Example 52 (2.8 mg, 41% yield). LCMS (Method B) Rt=1.34 min, m/z=498.1 (M+H), 1H NMR (DMSO-d6, 500 MHz) δ 7.62 (t, J=8.2 Hz, 1H), 7.01 (d, J=8.5 Hz, 2H), 4.21 (s, 2H), 3.95 (s, 6H), 3.59 (q, J=6.7 Hz, 1H), 3.48 (q, J=6.5 Hz, 2H), 2.43 (t, J=7.2 Hz, 2H), 1.49-1.57 (m, 2H), 1.34 (t, J=6.9 Hz, 3H), 1.23 (t, J=6.9 Hz, 3H), 0.73-0.84 (m, 1H), 0.45-0.52 (m, 2H), −0.03-0.05 ppm (m, 2H). Human APJ cAMP EC$_{50}$ Potency range A.

Example 53

N-((5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)methyl)-N-methylpicolinamide

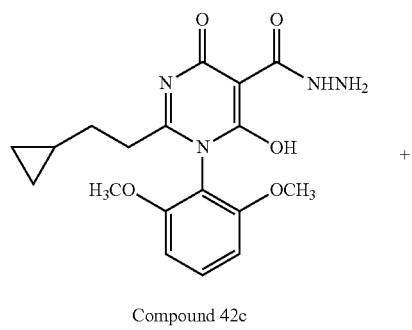

Compound 42c

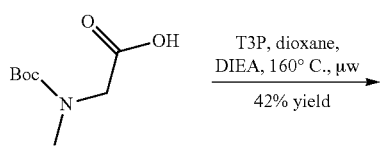

T3P, dioxane, DIEA, 160° C., μw

42% yield

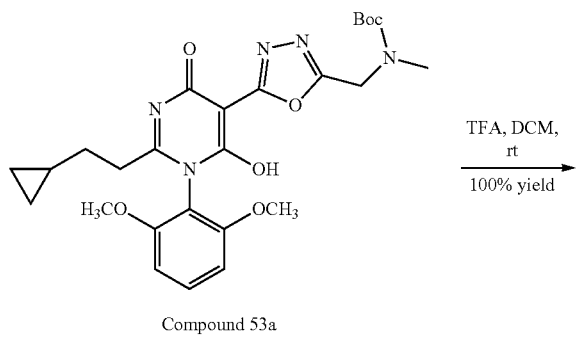

Compound 53a

TFA, DCM, rt

100% yield

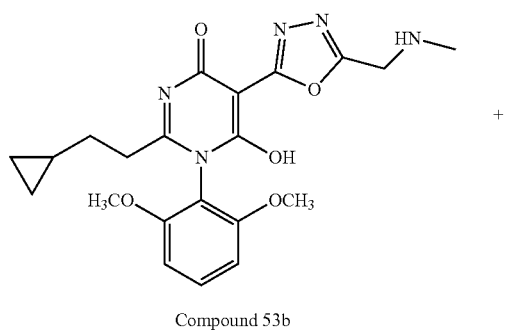

Compound 53b

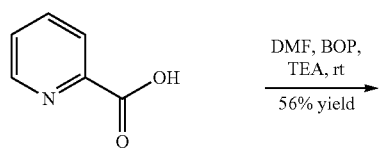

DMF, BOP, TEA, rt

56% yield

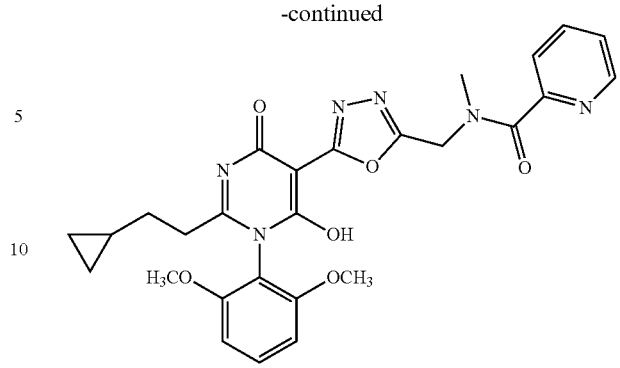

Example 53

Compound 53a. tert-Butyl ((5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)methyl)(methyl)carbamate To a solution of Compound 42c (60 mg, 0.16 mmol) in dioxane (2.0 mL) was added 2-((tert-butoxycarbonyl)(methyl)amino)acetic acid (36 mg, 0.19 mmol) and DIEA (52 mg, 0.40 mmol) followed by a 50% solution of 1-propanephosphonic acid cyclic anhydride in ethyl acetate (0.38 mL, 0.64 mmol) and the reaction mixture was heated by microwave irradiation at 160° C. for 30 min. The reaction mixture was concentrated under reduced pressure and the residue was purified by silica gel chromatography eluting with 0 to 100% EtOAc/hexane to give Compound 10a (36 mg, 42%) as a clear colorless oil, MS m/z=528.4 (M+H), 1H NMR ¹H NMR (CHLOROFORM-d) δ 7.53 (t, J=8.6 Hz, 1H), 6.74-6.84 (m, 2H), 4.73 (s, 2H), 3.88 (s, 6H), 2.57 (t, J=7.7 Hz, 2H), 2.14 (s, 3H), 1.60-1.69 (m, 2H), 1.52 (s, 9H), 0.63-0.79 (m, 1H), 0.38-0.51 (m, 2H), −0.05-0.02 (m, 2H)

Compound 53b. 2-(2-cyclopropylethyl)-1-(2,6-dimethoxyphenyl)-6-hydroxy-5-(5-((methylamino)methyl)-1,3,4-oxadiazol-2-yl)pyrimidin-4(1H)-one To a solution of Compound 53a (36 mg, 0.068 mmol) in DCM (0.5 mL) was added TFA (0.5 mL) and the reaction mixture was stirred at room temperature for 1 h. The reaction mixture was concentrated under reduced pressure to give compound 53b (29 mg, 100%) as a yellow solid that was used without further purification MS m/z=428.4 (M+H).

Example 53. N-((5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)methyl)-N-methylpicolinamide To a solution of Compound 53b (15 mg, 0.035 mmol) in DMF (0.5 mL) was added BOP (19 mg, 0.042 mmol), picolinic acid (4.2 mg, 0.035 mmol) and TEA (18 mg, 0.18 mmol) and the mixture was stirred at room temperature for 1 h. The reaction mixture was purified by prep HPLC (conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate: Gradient: 10-50% B over 20 minutes, then a 5-minute hold at 100% B; Flow: 20 mL/min.) to give Example 53 (11 mg, 56% yield). LCMS (Method B) Rt=1.32 min, m/z=533.1 (M+H), 1H NMR (DMSO-d6) Shift: 8.80 (d, J=3.7 Hz, 1H), 8.13 (t, J=7.6 Hz, 1H), 7.80 (d, J=7.6 Hz, 1H), 7.59-7.67 (m, 2H), 7.01 (d, J=7.9 Hz, 2H), 5.11 (s, 2H), 3.26 (s, 3H), 2.69 (s, 6H), 2.44-2.54 (m, 3H), 1.47-1.57 (m, 2H), 0.72-0.83 (m, 1H), 0.45-0.52 (m, 2H), −0.03-0.03 (m, 2H). Human APJ cAMP EC$_{50}$ Potency range A.

Example 54 in Table 1 was prepared as described in the general procedure given for Example 53.

TABLE 1

| Ex # | Structure | Name | $^1$H NMR | LC/MS Rt (min) Method M + H | hAPJ cAMP EC$_{50}$ Potency range |
|---|---|---|---|---|---|
| 2 | 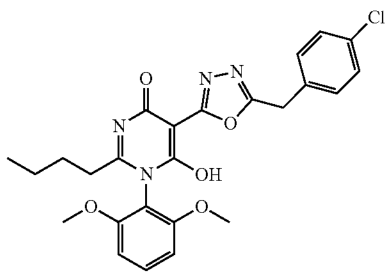 [SMILES: CCCCc1nc(=O)c(-c2nnc(Cc3ccc(Cl)cc3)o2)c(O)n1-c1c(OC)cccc1OC] | 2-butyl-5-{5-[(4-chlorophenyl)methyl]-1,3,4-oxadiazol-2-yl}-1-(2,6-dimethoxyphenyl)-6-hydroxy-1,4-dihydropyrimidin-4-one | $^1$H NMR (500 MHz, DMSO-d6) δ 7.50 (t, J = 8.4 Hz, 1H), 7.44-7.39 (m, 2H), 7.37-7.31 (m, 2H), 6.86 (m, 2H), 4.27 (s, 2H), 3.78 (s, 6H), 2.34 (t, J = 7.5 Hz, 2H), 1.43 (t, J = 7.5 Hz, 2H), 1.21-1.11 (m, 2H), 0.70 (t, J = 7.2 Hz, 3H) | 1.67 B 497.1 | A |
| 3 | 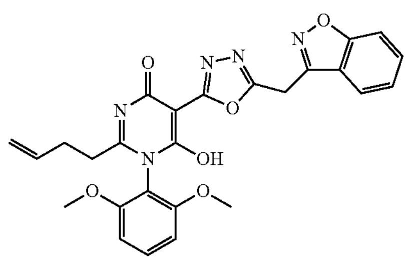 [SMILES: C=CCCc1nc(=O)c(-c2nnc(Cc3noc4ccccc34)o2)c(O)n1-c1c(OC)cccc1OC] | 5-[5-(1,2-benzoxazol-3-ylmethyl)-1,3,4-oxadiazol-2-yl]-2-(but-3-en-1-yl)-1-(2,6-dimethoxyphenyl)-6-hydroxy-1,4-dihydropyrimidin-4-one | $^1$H NMR (500 MHz, DMSO-d6) δ 7.86 (d, J = 7.9 Hz, 1H), 7.78 (d, J = 8.5 Hz, 1H), 7.70 (t, J = 7.9 Hz, 1H), 7.51 (t, J = 8.5 Hz, 1H), 7.42 (t, J = 7.6 Hz, 1H), 6.87 (d, J = 8.5 Hz, 2H), 5.66-5.73 (m, 1H), 4.98 (d, J = 10.7 Hz, 1H), 4.95 (d, J = 17.7 Hz, 1H), 4.82 (s, 2H), 3.80 (s, 6H), 2.45 (t, J = 7.6 Hz, 2H), 2.22-2.26 (m, 2H) | 1.22 A 503.2 | A |
| 4 | 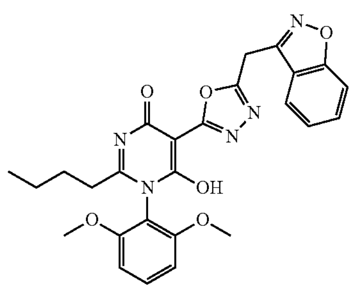 [SMILES: CCCCc1nc(=O)c(-c2nnc(Cc3noc4ccccc34)o2)c(O)n1-c1c(OC)cccc1OC] | 5-[5-(1,2-benzoxazol-3-ylmethyl)-1,3,4-oxadiazol-2-yl]-2-butyl-1-(2,6-diethylphenyl)-6-hydroxy-1,4-dihydropyrimidin-4-one | $^1$H NMR (500 MHz, DMSO-d6) δ 7.87 (d, J = 7.6 Hz, 1H), 7.77 (d, J = 8.5 Hz, 1H), 7.69 (t, J = 7.6 Hz, 1H), 7.46 (d, J = 7.6 Hz, 1H), 7.40 (s, 1H), 7.32 (d, J = 7.3 Hz, 2H), 2.43-2.34 (m, 2H), 2.31-2.20 (m, 4H), 1.52-1.37 (m, 2H), 1.20-1.01 (m, 10H), 0.69 (s, 3H) | 1.02 D 500.2 | A |
| 5 | 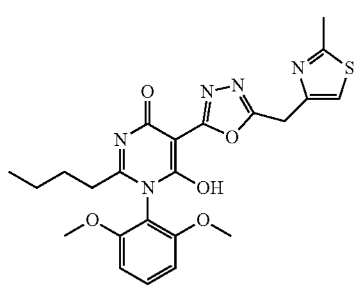 [SMILES: CCCCc1nc(=O)c(-c2nnc(Cc3csc(C)n3)o2)c(O)n1-c1c(OC)cccc1OC] | 2-butyl-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one | $^1$H NMR (400 MHz, DMSO-d6) δ 7.50 (t, J = 8.5 Hz, 1H), 7.37 (s, 1H), 6.87 (d, J = 8.4 Hz, 2H), 4.33 (s, 3H), 3.80 (s, 6H), 2.62 (s, 3H), 2.40-2.30 (m, 2H), 1.44 (quin, J = 7.5 Hz, 2H), 1.22-1.12 (m, 2H), 0.71 (t, J = 7.4 Hz, 3H). | 0.75 D 484.1 | A |
| 6 | 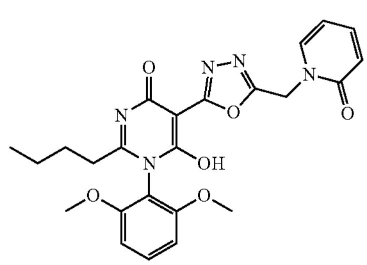 [SMILES: CCCCc1nc(=O)c(-c2nnc(Cn3ccccc3=O)o2)c(O)n1-c1c(OC)cccc1OC] | 2-butyl-1-(2,6-dimethoxyphenyl)-6-hydroxy-5-{5-[(2-oxo-1,2-dihydropyridin-1-yl)methyl]-1,3,4-oxadiazol-2-yl}-1,4-dihydropyrimidin-4-one | $^1$H NMR (500 MHz, DMSO-d6) δ 7.81 (d, J = 6.7 Hz, 1H), 7.58-7.44 (m, 2H), 6.88 (d, J = 8.5 Hz, 2H), 6.45 (d, J = 9.2 Hz, 1H), 6.35-6.25 (m, 1H), 5.37 (s, 2H), 3.80 (s, 6H), 2.40-2.16 (m, 2H), 1.55-1.37 (m, 2H), 1.22-1.12 (m, 2H), 0.71 (t, J = 7.2 Hz, 3H) | 0.71 D 479.9 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 7 | 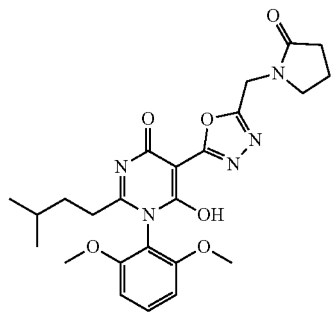 [SMILES: COc1cccc(OC)c1-n1c(CCC(C)C)nc(=O)c(-c2nnc(CN3CCCC3=O)o2)c1O] | 1-(2,6-dimethoxyphenyl)-6-hydroxy-2-(3-methylbutyl)-5-{5-[(2-oxopyrrolidin-1-yl)methyl]-1,3,4-oxadiazol-2-yl}-1,4-dihydropyrimidin-4-one | ¹H NMR (500 MHz, DMSO-d6) δ 7.52 (t, J = 8.2 Hz, 1H), 6.89 (d, J = 8.5 Hz, 2H), 4.66 (s, 2H), 3 81 (s, 6H), 3.43 (t, J = 7.0 Hz, 2H), 2.33-2.38 (m, 2H), 2.29 (t, J = 7.9 Hz, 2H), 1.95-2.01 (m, 2H), 1.37 (m, 3H), 0.68 (d, J = 4.0 Hz, 6H) | 1.25 A 484.0 | A |
| 8 | 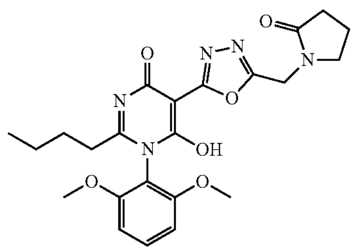 [SMILES: CCCCc1nc(=O)c(-c2nnc(CN3CCCC3=O)o2)c(O)n1-c1c(OC)cccc1OC] | 2-butyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one | ¹H NMR (500 MHz, DMSO-d6) δ 7.45 (s, 1H), 6.83 (d, J = 8.5 Hz, 2H), 4.62 (s, 2H), 3.78 (s, 6H), 2.56 (s, 2H), 2.39-2.15 (m, 4H), 2.05-1.94 (m, 2H), 1.50-1.34 (m, 2H), 1.26-1.01 (m, 2H), 0.72 (t, J = 7.3 Hz, 3H) | 0.71 D 470.0 | A |
| 9 | 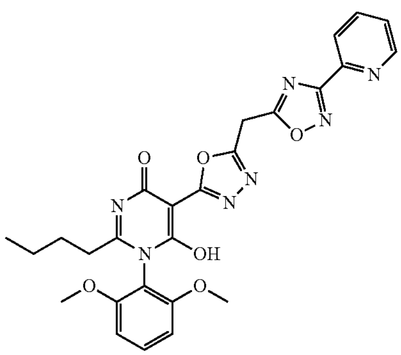 [SMILES: CCCCc1nc(=O)c(-c2nnc(Cc3nc(-c4ccccn4)no3)o2)c(O)n1-c1c(OC)cccc1OC] | 2-butyl-1-(2,6-dimethoxyphenyl)-6-hydroxy-5-(5-{[3-(pyridin-2-yl)-1,2,4-oxadiazol-5-yl]methyl}-1,3,4-oxadiazol-2-yl)-1,4-dihydropyrimidin-4-one | ¹H NMR (500 MHz, DMSO-d₆) δ 8.77 (br d, J = 4.3 Hz, 1H), 8.13-7.96 (m, 2H), 7.67-7.59 (m, 1H), 7.50 (t, J = 8.4 Hz, 1H), 6.86 (d, J = 8.5 Hz, 2H), 4.98 (s, 2H), 3.79 (s, 6H), 3.53-3.53 (m, 1H), 2.35 (m, 2H), 1.48-1.39 (m, 2H), 1.21-1.13 (m, 2H), 0.70 (t, J = 7.3 Hz, 3H) | 0.78 D 532.2 | A |
| 10 | 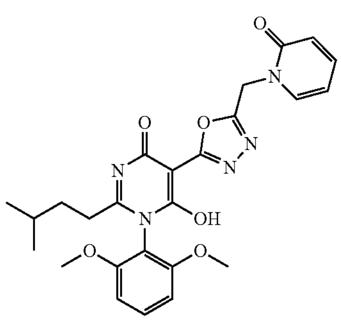 [SMILES: COc1cccc(OC)c1-n1c(CCC(C)C)nc(=O)c(-c2nnc(Cn3ccccc3=O)o2)c1O] | 1-(2,6-dimethoxyphenyl)-6-hydroxy-2-(3-methylbutyl)-5-{5-[(2-oxo-1,2-dihydropyridin-1-yl)methyl]-1,3,4-oxadiazol-2-yl}-1,4-dihydropyrimidin-4-one | ¹H NMR (500 MHz, DMSO-d6) δ 7.80 (d, J = 6.4 Hz, 1H), 7.49 (t, J = 7.6 Hz, 1H), 7.40 (t, J = 8.2 Hz, 1H), 6.79 (d, J = 8.2 Hz, 2H), 6.45 (d, J = 8.9 Hz, 1H), 6.31 (t, J = 6.7 Hz, 1H), 5.33 (s, 2H), 3.76 (s, 6H), 2.08 (t, J = 7.6 Hz, 2H), 1.28-1.39 (m, 3H), 0.68 (d, J = 5.8 Hz, 6H) | 1.25 A 494.0 | A |
| 11 | 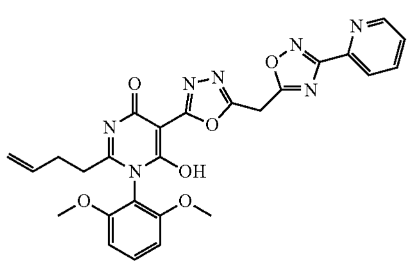 [SMILES: C=CCCc1nc(=O)c(-c2nnc(Cc3nc(-c4ccccn4)no3)o2)c(O)n1-c1c(OC)cccc1OC] | 2-(but-3-en-1-yl)-1-(2,6-dimethoxyphenyl)-6-hydroxy-5-(5-{(3-(pyridin-2-yl)-1,2,4-oxadiazol-5-yl]methyl}-1,3,4-oxadiazol-2-yl)-1,4-dihydropyrimidin-4-one | ¹H NMR (500 MHz, DMSO-d6) δ 8.77 (d, J = 4.3 Hz, 1H), 8.08 (d, J = 7.6 Hz, 1H), 8.03 (t, J = 7.3 Hz, 1H), 7.63 (t, J = 5.8 Hz, 1H), 7.49 (t, J = 8.5 Hz, 1H), 6.87 (d, J = 8.5 Hz, 2H), 5.66-5.74 (m, 1H), 4.98 (s, 2H), 4.97 (d, J = 10.7 Hz, 1H), 4.95 (d, J = 17.4 Hz, 1H), 3.79 (s, 6H), 2.42 (t, J = 6.4 Hz, 2H), 2.21-2.26 (m, 2H) | 1.11 A 530.2 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 12 | 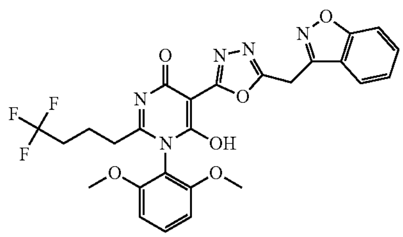 [SMILES: COc1cccc(OC)c1-n1c(CCCC(F)(F)F)nc(=O)c(-c2nnc(Cc3noc4ccccc34)o2)c1O] | 5-[5-(1,2-benzoxazol-3-ylmethyl)-1,3,4-oxadiazol-2-yl]-1-(2,6-dimethoxyphenyl)-6-hydroxy-2-(4,4,4-trifluorobutyl)-1,4-dihydropyrimidin-4-one | ¹H NMR (500 MHz, DMSO-d6) δ 7.86 (d, J = 7.9 Hz, 1H), 7.79 (d, J = 7.0 Hz, 1H), 7 70 (t, J = 7.9 Hz, 1H), 7.50 (t, J = 8.5 Hz, 1H), 7.43 (t, J = 7.3 Hz. 1H), 6.87 (d, J = 8.5 Hz, 2H), 4.84 (s, 2H), 3.78 (s, 6H), 2.43 (t, J = 7.3 Hz, 2H), 2.19-2.28 (m, 2H), 1.74-1.80 (m, 2H) | 1.36 A 558.2 | A |
| 13 | (Mixture of atropoisomers) | 5-[5-(1,2-benzoxazol-3-ylmethyl)-1,3,4-oxadiazol-2-yl]-2-butyl-6-hydroxy-1-(2-methoxy-6-methylphenyl)-1,4-dihydropyrimidin-4-one | ¹H NMR (500 MHz, DMSO-d6) δ 7.87 (d, J = 7.9 Hz, 1H), 7.78 (d, J = 8.5 Hz, 1H), 7.69 (t, J = 7.6 Hz, 1H), 7.43 (t, J = 7.3 Hz, 1H), 7.42 (t, J = 6.7 Hz, 1H), 7.02 (d, J = 7.3 Hz, 2H). 4.83 (s, 2H), 3.77 (s, 3H), 2.36-2.42 (m, 1H), 2.22-2.28 (m, 1H), 2.07 (s, 3H), 1.42-1.48 (m, 2H), 1.13-1.21 (m, 2H), 0.70 (t, J = 7.3 Hz, 3H) | 1.35 A 488.3 | A |
| 14 | 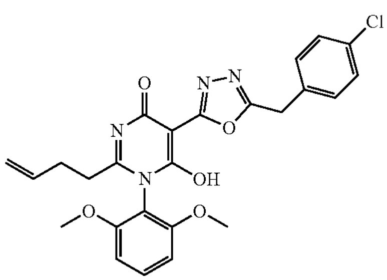 [SMILES: C=CCCc1nc(=O)c(-c2nnc(Cc3ccc(Cl)cc3)o2)c(O)n1-c1c(OC)cccc1OC] | 2-(but-3-en-1-yl)-5-{5-[(4-chlorophenyl)methyl]-1,3,4-oxadiazol-2-yl}-1-(2,6-dimethoxyphenyl)-6-hydroxy-1,4-dihydropyrimidin-4-one | ¹H NMR (500 MHz, DMSO-d6) δ 7.44 (t, J = 8.2 Hz, 1H), 7.42 (d, J = 8.2 Hz, 2H), 7.35 (d, J = 8.2 Hz, 2H), 6.82 (d, J = 8.5 Hz, 2H), 5.66-5.75 (m, 1H), 4.93 (d, J = 9.2 Hz, 1H), 4.92 (d, J = 18.3 Hz, 1H), 4.24 (s, 2H), 3.77 (s, 6H), 2.25-2.31 (m, 2H), 2.19-2.23 (m, 2H) | 1.33 A 517.2 | A |
| 15 | 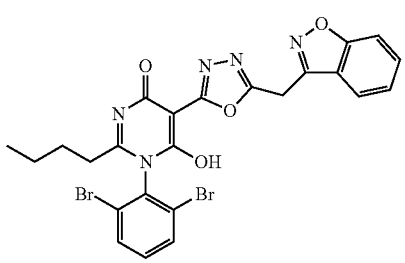 [SMILES: CCCCc1nc(=O)c(-c2nnc(Cc3noc4ccccc34)o2)c(O)n1-c1c(Br)cccc1Br] | 5-[5-(1,2-benzoxazol-3-ylmethyl)-1,3,4-oxadiazol-2-yl]-2-butyl-1-(2,6-dibromophenyl)-6-hydroxy-1,4-dihydropyrimidin-4-one | ¹H NMR (400 MHz, CHLOROFORM-d) δ 7.80 (d, J = 8.1 Hz, 1H), 7.75 (d, J = 8.1 Hz, 2H), 7.59-7.55 (m, 2H), 7.36-7.27 (m, 2H), 4.69 (s, 2H), 2.35 (t, J = 7.6 Hz, 2H), 1.79 (quin. J = 7.6 Hz, 2H), 1.37-1.27 (m, 2H), 0.87 (t, J = 7.4 Hz, 3H) | 0.99 D 601.8 | A |
| 16 | 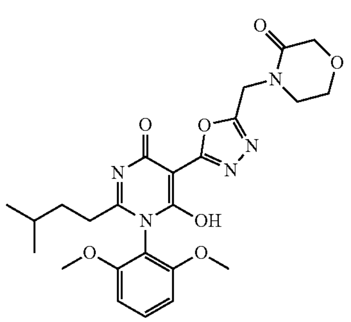 [SMILES: COc1cccc(OC)c1-n1c(CCC(C)C)nc(=O)c(-c2nnc(CN3CCOCC3=O)o2)c1O] | 4-({5-[1-(2,6-dimethoxyphenyl)-6-hydroxy-2-(3-methylbutyl)-4-oxo-1,4-dihydropyrimidin-5-yl]-1,3,4-oxadiazol-2-yl}methyl)morpholin-3-one | ¹H NMR (500 MHz, DMSO-d6) δ 7.43 (t, J = 8.5 Hz, 1H), 6.82 (d, J = 8.2 Hz, 2H), 4.79 (s, 2H), 4.13 (s, 2H), 3.88 (m, 2H), 3.77 (s, 6H), 3.49 (m, 2H), 2.12-2.19 (m, 2H), 1.30-1.40 (m, 3H), 0.69 (d, J = 5.8 Hz, 6H) | 1.22 A 500.0 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 17 | (mixture of atropoisomers) | 5-[5-(1,2-benzoxazol-3-ylmethyl)-1,3,4-oxadiazol-2-yl]-2-(but-3-en-1-yl)-6-hydroxy-1-(2-methoxy-6-methylphenyl)-1,4-dihydropyrimidin-4-one | $^1$H NMR (500 MHz, DMSO-d6) δ 7.87 (d, J = 7.9 Hz, 1H), 7.78 (d, J = 8.5 Hz, 1H), 7.70 (t, J = 7.6 Hz, 1H), 7.43 (t, J = 7.9 Hz, 1H), 7.42 (t, J = 7.6 Hz, 1H), 7.02 (d, J = 7.6 Hz, 2H), 5.66-5.74 (m, 1H), 4.96 (d, J = 9.5 Hz, 1H), 4.95 (d, J = 17.1 Hz, 1H), 4.83 (s, 2H), 3.78 (s, 3H), 2.43-2.50 (m, 1H), 2.32-2.38 (m, 1H), 2.25-2.29 (m, 2H), 2.07 (s, 3H) | 1.28 A 485.9 | A |
| 18 | 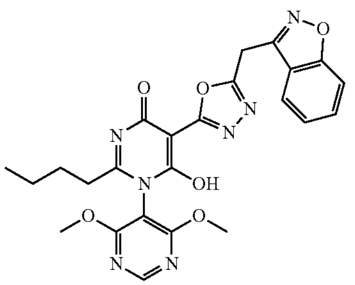 [SMILES: CCCCc1nc(=O)c(-c2nnc(Cc3noc4ccccc34)o2)c(O)n1-c1c(OC)ncnc1OC] | 5-[5-(1,2-benzoxazol-3-ylmethyl)-1,3,4-oxadiazol-2-yl]-2-butyl-1-(4,6-dimethoxypyrimidin-5-yl)-6-hydroxy-1,4-dihydropyrimidin-4-one | $^1$H NMR (400 MHz, METHANOL-d4) δ 8.61 (s, 1H), 7 88 (d, J = 7.9 Hz, 1H), 7.70-7.64 (m, 2H), 7.44-7.35 (m, 1H), 4.79 (s, 2H), 4.05 (s, 6H), 2.58-2.49 (m, 2H), 1.67-1.56 (m, 2H), 1.34 (dd, J = 14.9, 7.4 Hz, 2H), 0.86 (t, J = 7.3 Hz, 3H) | 1.85 C 506.1 | A |
| 19 | 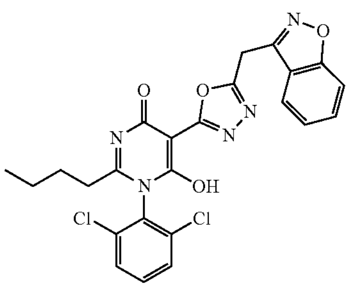 [SMILES: CCCCc1nc(=O)c(-c2nnc(Cc3noc4ccccc34)o2)c(O)n1-c1c(Cl)cccc1Cl] | 5-[5-(1,2-benzoxazol-3-ylmethyl)-1,3,4-oxadiazol-2-yl]-2-butyl-1-(2,6-dichlorophenyl)-6-hydroxy-1,4-dihydropyrimidin-4-one | $^1$H NMR (500 MHz, DMSO-d6) δ 7.85 (d, J = 7.6 Hz, 1H), 7.80-7.73 (m, 3H), 7.72-7.60 (m, 2H), 7.41 (t, J = 7.3 Hz, 1H), 4.82 (s, 2H), 2.34 (t, J = 7.6 Hz, 2H), 1.58 (dt, J = 14.9, 7.7 Hz, 2H), 1.30-1.14 (m, 2H), 0.75 (t, J = 7.3 Hz, 3H) | 0.98 D 512.0 | A |
| 20 | 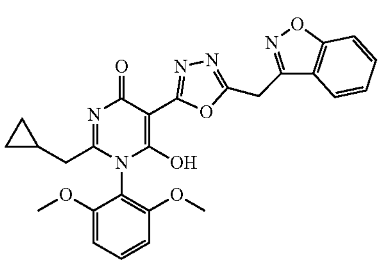 [SMILES: COc1cccc(OC)c1-n1c(CC2CC2)nc(=O)c(-c2nnc(Cc3noc4ccccc34)o2)c1O] | 5-[5-(1,2-benzoxazol-3-ylmethyl)-1,3,4-oxadiazol-2-yl]-2-(cyclopropylmethyl)-1-(2,6-dimethoxyphenyl)-6-hydroxy-1,4-dihydropyrimidin-4-one | $^1$H NMR (500 MHz, DMSO-d6) δ 7.86 (d, J = 7.9 Hz, 1H), 7.77 (d, J = 8.2 Hz, 1H), 7.68 (t, J = 7.9 Hz, 1H), 7.41 (t, J = 7.3 Hz, 1H), 7.40 (t, J = 7.3 Hz, 1H), 6.79 (d, J = 8.5 Hz, 2H), 4.75 (s, 2H), 3.74 (s, 6H), 2.11 (d, J = 5.2 Hz, 2H), 0.79 (br s, 1H), 0.38 (m, 2H), 0.01 (m, 2H) | 1.24 A 502.1 | A |
| 21 | 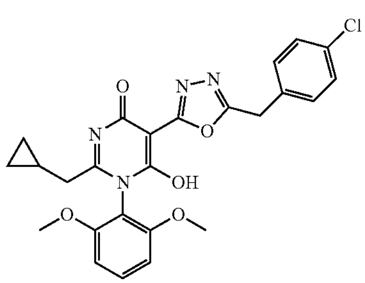 [SMILES: COc1cccc(OC)c1-n1c(CC2CC2)nc(=O)c(-c2nnc(Cc3ccc(Cl)cc3)o2)c1O] | 5-{5-[(4-chlorophenyl)methyl]-1,3,4-oxadiazol-2-yl}-2-(cyclopropylmethyl)-1-(2,6-dimethoxyphenyl)-6-hydroxy-1,4-dihydropyrimidin-4-one | $^1$H NMR (500 MHz, DMSO-d6) δ 7.41 (t, J = 8.2 Hz, 1H), 7.33 (d, J = 8.2 Hz, 2H), 7.26 (d, J = 8.5 Hz, 2H), 6.76 (d, J = 8.5 Hz, 2H), 4.18 (s, 2H), 3.69 (s, 6H), 2.19 (d, J = 7.0 Hz, 2H), 0.63-0.71 (m, 1H), 0.34 (d, J = 7.3 Hz, 2H), −0.02-0.03 (m, 2H) | 1.31 A 495.2 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 22 | 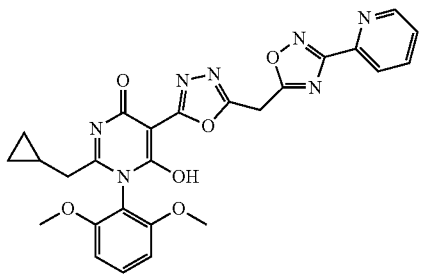 [SMILES: COc1cccc(OC)c1-n1c(CC2CC2)nc(=O)c(-c2nnc(Cc3nc(-c4ccccn4)no3)o2)c1O] | 2-(cyclopropylmethyl)-1-(2,6-dimethoxyphenyl)-6-hydroxy-5-(5-{[3-(pyridin-2-yl)-1,2,4-oxadiazol-5-yl]methyl}-1,3,4-oxadiazol-2-yl)-1,4-dihydropyrimidin-4-one | 1H NMR (500 MHz, DMSO-d6) δ 8.69 (d, J = 4.6 Hz, 1H), 8.00 (d, J = 7.6 Hz, 1H), 7.94 (t, J = 7.3 Hz, 1H), 7.54 (t, J = 5.5 Hz, 1H), 7.41 (t, J = 8.2 Hz, 1H), 6.77 (d, J = 8.2 Hz, 2H), 4.89 (s, 2H), 3.70 (s, 6H), 2.17 (d, J = 7.0 Hz, 2H), 0.68 (br s, 1H), 0.32-0.38 (m, 2H), 0.01 (m, 2H) | 1.01 A 530.1 | A |
| 24 | 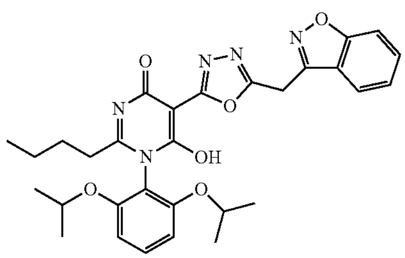 [SMILES: CCCCc1nc(=O)c(-c2nnc(Cc3noc4ccccc34)o2)c(O)n1-c1c(OC(C)C)cccc1OC(C)C] | 5-[5-(1,2-benzoxazol-3-ylmethyl)-1,3,4-oxadiazol-2-yl]-1-[2,6-bis(propan-2-yloxy)phenyl]-2-butyl-6-hydroxy-1,4-dihydropyrimidin-4-one | ¹H NMR (400 MHz, CHLOROFORM-d) δ 7.81 (d, J = 7.9 Hz, 1H), 7.64-7.49 (m, 2H), 7.35 (t, J = 8.5 Hz, 2H), 6.61 (d, J = 8.6 Hz, 2H), 4.68 (s, 2H), 4.55 (dt, J = 12.2, 6.0 Hz, 2H), 2.47-2.39 (m, 2H), 1.66 (quin, J = 7.6 Hz, 2H), 1.29-1.22 (m, 8H), 1.19 (d, J = 6.2 Hz, 6H), 0.80 (t, J = 7.4 Hz, 3H). | 0.98 D 560.1 | C |
| 25 | 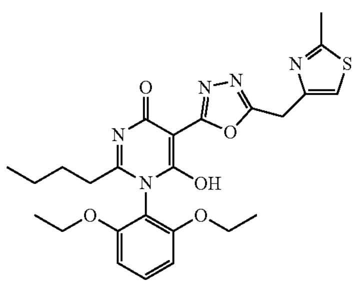 [SMILES: CCCCc1nc(=O)c(-c2nnc(Cc3csc(C)n3)o2)c(O)n1-c1c(OCC)cccc1OCC] | 2-butyl-1-(2,6-diethoxyphenyl)-6-hydroxy-5-{5-[(2-methyl-1,3-thiazol-4-yl)methyl]-1,3,4-oxadiazol-2-yl}-1,4-dihydropyrimidin-4-one | ¹H NMR (500 MHz, DMSO-d6) δ 7.50-7.40 (m, 1H), 7.39-7.34 (m, 1H), 6.81 (d, J = 8.5 Hz, 2H), 4.32 (s, 2H), 4.08 (q, J = 6.7 Hz, 4H), 2.63 (s, 3H), 2.33 (t, J = 7.5 Hz, 2H), 1.53-1.39 (m, 2H), 1.23 (s, 8H), 0.72 (t, J = 7.3 Hz, 3H) | 0.85 D 512.0 | A |
| 26 | 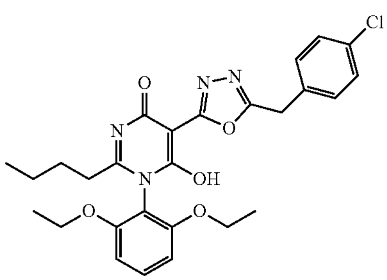 [SMILES: CCCCc1nc(=O)c(-c2nnc(Cc3ccc(Cl)cc3)o2)c(O)n1-c1c(OCC)cccc1OCC] | 2-butyl-5-{5-[(4-chlorophenyl)methyl]-1,3,4-oxadiazol-2-yl}-1-(2,6-diethoxyphenyl)-6-hydroxy-1,4-dihydropyrimidin-4-one | ¹H NMR (500 MHz, DMSO-d6) δ 7.46-7.40 (m, 3H), 7.37 (s, 2H), 6.85-6.75 (m, 2H), 4.27 (s, 2H), 4.07 (q, J = 6.8 Hz, 4H), 2.32 (t, J = 7.5 Hz, 2H), 1.50-1.39 (m, 2H), 1.31-1.12 (m, 8H), 0.72 (t, J = 7.3 Hz, 3H) | 1.00 D 525.0 | A |
| 30 | 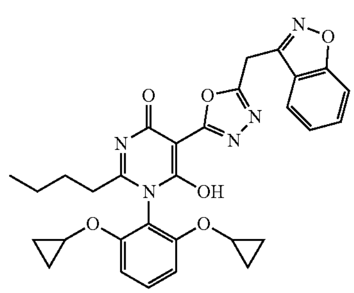 [SMILES: CCCCc1nc(=O)c(-c2nnc(Cc3noc4ccccc34)o2)c(O)n1-c1c(OC2CC2)cccc1OC1CC1] | 5-[5-(1,2-benzoxazol-3-ylmethyl)-1,3,4-oxadiazol-2-yl]-2-butyl-1-(2,6-dicyclopropoxyphenyl)-6-hydroxy-1,4-dihydropyrimidin-4-one | ¹H NMR (400 MHz, CHLOROFORM-d) δ 7.77 (d, J = 7.9 Hz, 1H), 7.56 (d, J = 5.3 Hz, 2H), 7.44 (t, J = 8.5 Hz, 1H), 7.26 (s, 4H), 7.04 (d, J = 8.6 Hz, 2H), 3.82-3.54 (m, 2H), 2.41-2.29 (m, 2H), 1.67-1.46 (m, 2H), 1.32-1.13 (m, 2H), 0.84-0.68 (m, 8H), 0.63-0.55 (m, 2H) | 0.98 D 556.0 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 32 | 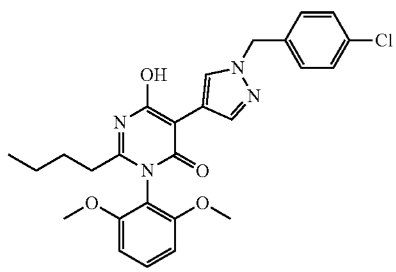 [SMILES: CCCCc1nc(O)c(-c2cnn(Cc3ccc(Cl)cc3)c2)c(=O)n1-c1c(OC)cccc1OC] | 2-butyl-5-{1-[(4-chlorophenyl)methyl]-1H-pyrazol-4-yl}-3-(2,6-dimethoxyphenyl)-6-hydroxy-3,4-dihydropyrimidin-4-one | ¹H NMR (500 MHz, DMSO-d6) δ 8.33 (s, 1H), 8.14 (s, 1H), 7.47 (t, J = 7.9 Hz, 1H), 7.40 (d, J = 7.6 Hz, 2H), 7.24 (d, J = 7.6 Hz, 2H), 6.85 (d, J = 8.2 Hz, 2H), 5.33 (s, 2H), 3.75 (s, 6H), 2.23 (br s, 2H), 1.46 (br s, 2H), 1.12-1.21 (m, 2H), 0.73 (t, J = 6.4 Hz, 3H) | 1.73 A 494.9 | A |
| 34 | 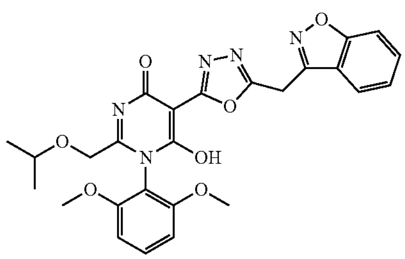 [SMILES: COc1cccc(OC)c1-n1c(COC(C)C)nc(=O)c(-c2nnc(Cc3noc4ccccc34)o2)c1O] | 5-[5-(1,2-benzoxazol-3-ylmethyl)-1,3,4-oxadiazol-2-yl]-1-(2,6-dimethoxyphenyl)-6-hydroxy-2-[(propan-2-yloxy)methyl]-1,4-dihydropyrimidin-4-one | ¹H NMR (500 MHz, DMSO-d6) δ 7.87 (d, J = 7.9 Hz, 1H), 7.77 (d, J = 6.7 Hz, 1H), 7.69 (t, J = 6.7 Hz, 1H), 7.38-7.48 (m, 2H), 6.82 (d, J = 8.5 Hz, 2H), 4.81 (s, 2H), 3.90 (s, 2H), 3.74 (s, 6H), 3.72 (m, 1H), 0.91 (t, J = 6.1 Hz, 6H) | 1.26 A 520.1 | A |
| 35 | 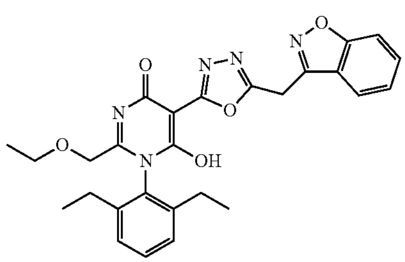 [SMILES: CCOCc1nc(=O)c(-c2nnc(Cc3noc4ccccc34)o2)c(O)n1-c1c(CC)cccc1CC] | 5-[5-(1,2-benzoxazol-3-ylmethyl)-1,3,4-oxadiazol-2-yl]-1-(2,6-diethylphenyl)-2-(ethoxymethyl)-6-hydroxy-1,4-dihydropyrimidin-4-one | ¹H NMR (500 MHz, DMSO-d6) δ 7.92-7.83 (m, 1H), 7.81-7.74 (m, 2H), 7.72-7.66 (m, 2H), 7.47 (d, J = 7.6 Hz, 1H), 7.43-7.38 (m, 1H), 7.33-7.30 (m, 2H), 3.52 (br. s., 2H), 3.30 (q, J = 6.9 Hz, 2H), 2.45-2.38 (m, 2H), 2.24 (dq, J = 15.1, 7.5 Hz, 2H), 1.13-1.07 (m, 6H), 0.99 (s, 3H) | D 0.89 502.2 | A |
| 36 | 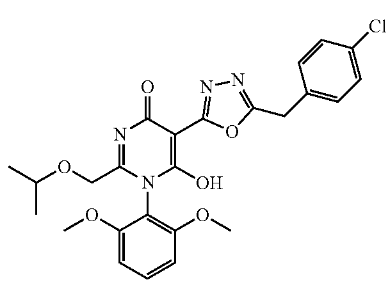 [SMILES: COc1cccc(OC)c1-n1c(COC(C)C)nc(=O)c(-c2nnc(Cc3ccc(Cl)cc3)o2)c1O] | 5-{5-[(4-chlorophenyl)methyl]-1,3,4-oxadiazol-2-yl}-1-(2,6-dimethoxyphenyl)-6-hydroxy-2-[(propan-2-yloxy)methyl]-1,4-dihydropyrimidin-4-one | ¹H NMR (500 MHz, DMSO-d6) δ 7.31-7.47 (m, 4H), 7.14-7.30 (m, 1H), 6.80 (d, J = 7.6 Hz, 2H), 4.29 (s, 2H), 3.85 (s, 2H), 3.73-3.78 (m, 1H), 3.73 (s, 6H), 0.90 (d, J = 5.8 Hz, 2H) | 1.34 A 513.1 | A |
| 37 | 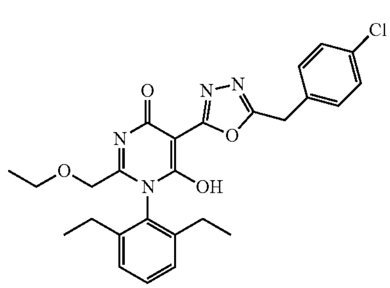 [SMILES: CCOCc1nc(=O)c(-c2nnc(Cc3ccc(Cl)cc3)o2)c(O)n1-c1c(CC)cccc1CC] | 5-{5-[(4-chlorophenyl)methyl]-1,3,4-oxadiazol-2-yl}-1-(2,6-diethylphenyl)-2-(ethoxymethyl)-6-hydroxy-1,4-dihydropyrimidin-4-one | ¹H NMR (500 MHz, DMSO-d6) δ 7.49-7.34 (m, 5H), 7.24 (d, J = 7.6 Hz, 2H), 4.24 (s, 2H), 3.74 (s, 2H), 3.22 (q, J = 7.0 Hz, 2H), 2.46-2.19 (m, 4H), 1.11 (t, J = 7.5 Hz, 6H), 0.96 (t, J = 6.9 Hz, 3H) | 1.00 D 495.0 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 38 | 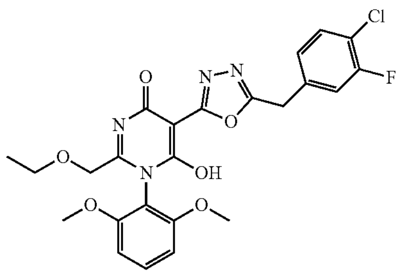 [SMILES: CCOCc1nc(=O)c(-c2nnc(Cc3ccc(Cl)c(F)c3)o2)c(O)n1-c1c(OC)cccc1OC] | 5-{5-[(4-chloro-3-fluorophenyl)methyl]-1,3,4-oxadiazol-2-yl}-1-(2,6-dimethoxyphenyl)-2-(ethoxymethyl)-6-hydroxy-1,4-dihydropyrimidin-4-one | ¹H NMR (500 MHz, DMSO-d6) δ 7.58 (t, J = 7.9 Hz, 1H), 7.42 (t, J = 10.4 Hz, 1H), 7.38 (t, J = 8.5 Hz, 1H), 7.22 (d, J = 8.2 Hz, 1H), 6.77 (d, J = 8.2 Hz, 2H), 4.28 (s, 2H), 3.84 (s, 2H), 3.75 (s, 6H), 3.29 (q, J = 7.0 Hz, 2H), 0.98 (t, J = 7.0 Hz, 3H) | 1.35 A 517.2 | A |
| 39 | 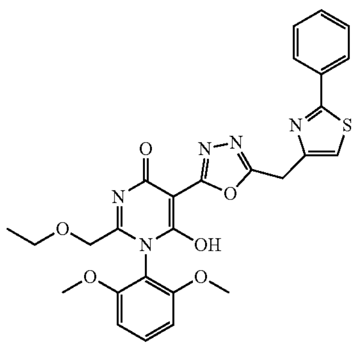 [SMILES: CCOCc1nc(=O)c(-c2nnc(Cc3csc(-c4ccccc4)n3)o2)c(O)n1-c1c(OC)cccc1OC] | 1-(2,6-dimethoxyphenyl)-2-(ethoxymethyl)-6-hydroxy-5-{5-[(2-phenyl-1,3-thiazol-4-yl)methyl]-1,3,4-oxadiazol-2-yl}-1,4-dihydropyrimidin-4-one | ¹H NMR (500 MHz, DMSO-d6) δ 7.61 (s, 1H), 7.47-7.54 (m, 5H), 7.35 (t, J = 8.5 Hz, 1H), 6.74 (d, J = 8.2 Hz, 2H), 4.40 (s, 2H), 3.78 (s, 2H), 3.74 (s, 6H), 3.26 (q, J = 7.0 Hz, 2H), 0.97 (t, J = 6.7 Hz, 3H) | 1.32 A 548.0 | B |
| 40 | 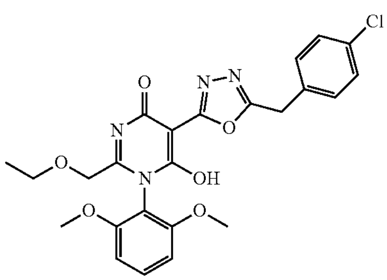 [SMILES: CCOCc1nc(=O)c(-c2nnc(Cc3ccc(Cl)cc3)o2)c(O)n1-c1c(OC)cccc1OC] | 5-{5-[(4-chlorophenyl)methyl]-1,3,4-oxadiazol-2-yl}-1-(2,6-dimethoxyphenyl)-2-(ethoxymethyl)-6-hydroxy-1,4-dihydropyrimidin-4-one | ¹H NMR (500 MHz, DMSO-d6) δ 7.41 (d, J = 8.2 Hz, 2H), 7.36 (t, J = 7.9 Hz, 1H), 7.35 (d, J = 8.2 Hz, 2H), 6.75 (d, J = 8.5 Hz, 2H), 4.21 (s, 2H), 3.80 (s, 2H), 3.74 (s, 6H), 3.27 (q, J = 7.0 Hz, 2H), 0.97 (t, J = 6.7 Hz, 3H) | 1.27 A 499.2 | A |
| 41 | 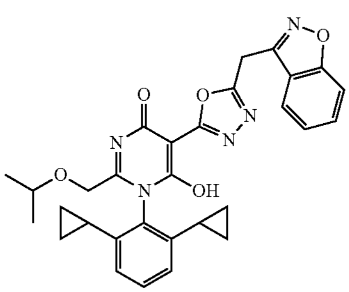 [SMILES: CC(C)OCc1nc(=O)c(-c2nnc(Cc3noc4ccccc34)o2)c(O)n1-c1c(C2CC2)cccc1C1CC1] | 5-[5-(1,2-benzoxazol-3-ylmethyl)-1,3,4-oxadiazol-2-yl]-1-(2,6-dicyclopropylphenyl)-6-hydroxy-2-[(propan-2-yloxy)methyl]-1,4-dihydropyrimidin-4-one | ¹H NMR (400 MHz, CHLOROFORM-d) d 7.87-7.80 (m, 1H), 7.57 (s, 2H), 7.39-7.30 (m, 2H), 6.86 (d, J = 7.7 Hz, 2H), 4.70 (s, 2H), 4.13 (s, 2H), 3.62-3.53 (m, 2H), 1.57-1.44 (m, 2H), 1.11 (d, J = 6.2 Hz, 6H). 0.96-0.78 (m, 6H), 0.61 (dt, J = 9.2, 4.5 Hz, 2H) | 0.89 D 540.2 | A |
| 43 | 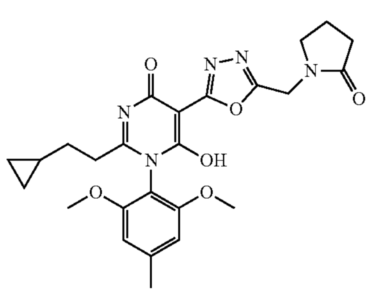 [SMILES: COc1cc(C)cc(OC)c1-n1c(CCC2CC2)nc(=O)c(-c2nnc(CN3CCCC3=O)o2)c1O] | 2-(2-cyclopropylethyl)-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one | ¹H NMR (DMSO-d6) δ 7.62 (t, J = 8.5 Hz, 1H), 7.01 (d, J = 8.2 Hz, 2H), 4 80 (s, 2H), 3.95 (s, 6H), 2.39-2.51 (m, 4H), 2.12-2.21 (m, 2H), 1.48-1.56 (m, 2H), 0.72-0.85 (m, 1H), 0 43-0.53 (m, 2H), −0.04-0.05 (m, 2H) | 1.13 A 481.9 | A |

TABLE 1-continued

| Ex # | Structure | Name | $^1$H NMR | LC/MS Rt (min) Method M + H | hAPJ cAMP EC$_{50}$ Potency range |
|---|---|---|---|---|---|
| 44 | 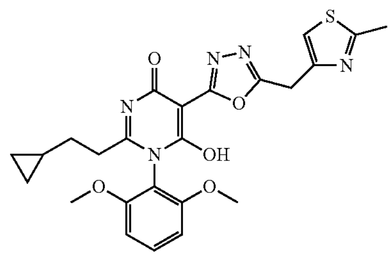 [SMILES: COc1cccc(OC)c1-n1c(CCC2CC2)nc(=O)c(-c2nnc(Cc3csc(C)n3)o2)c1O] | 2-(2-cyclopropylethyl)-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one | $^1$H NMR (DMSO-d6) δ 7.67 (t, J = 8.5 Hz, 1H), 7.53 (s, 1H), 7.03 (d, J = 8.5 Hz, 2H), 4.49 (s, 2H), 3.95 (s, 6H), 2.78 (s, 3H), 2.61 (t, J = 7.0 Hz, 2H), 1.46-1.57 (m, 2H), 0.73-0.83 (m, 1H), 0.44-0.53 (m, 2H), −0.04-0.04 (m, 2H) | 1.25 A 496.3 | A |
| 45 | 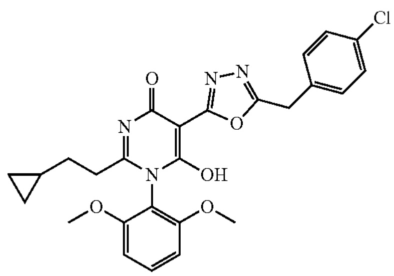 | 5-{5-[(4-chlorophenyl)methyl]-1,3,4-oxadiazol-2-yl}-2-(2-cyclopropylethyl)-1-(2,6-dimethoxyphenyl)-6-hydroxy-1,4-dihydropyrimidin-4-one | $^1$H NMR (DMSO-d6) δ 7.65 (t, J = 8.4 Hz, 1H), 7.57-7.61 (m, 2H), 7.50-7.55 (m, 2H), 7.02 (d, J = 8.5 Hz, 2H), 4.43 (s, 2H), 3.94 (s, 6H), 2.53 (t, J = 7.6 Hz, 2H), 1.46-1.58 (m, 2H), 0.79 (m, 1H), 0.49 (m, 2H), 0.00 (m, 2H) | 1.51 A 508.9 | A |
| 46 | 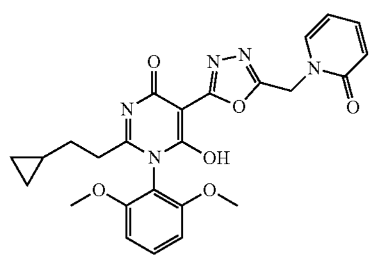 [SMILES: COc1cccc(OC)c1-n1c(CCC2CC2)nc(=O)c(-c2nnc(Cn3ccccc3=O)o2)c1O] | 2-(2-cyclopropylethyl)-1-(2,6-dimethoxyphenyl)-6-hydroxy-5-{5-[(2-oxo-1,2-dihydropyridin-1-yl)methyl]-1,3,4-oxadiazol-2-yl}-1,4-dihydropyrimidin-4-one | $^1$H NMR (DMSO-d6) δ 7.99 (t, J = 6.7 Hz, 1H), 7 69 (br. t, J = 7.8 Hz, 1H), 7.61 (t, J = 8.2 Hz, 1H), 7.00 (d, J = 8.5 Hz, 2H), 6.64 (d, J = 9.2 Hz, 1H), 6.51 (t, J = 6.6 Hz, 1H), 5.52 (s, 2H), 3.95 (s, 6H), 2.39 (t, J = 7.5 Hz, 2H), 1.46-1.57 (m, 2H), 0.74-0.84 (m, 1H), 0.44-0.52 (m, 2H), −0.03-0.04 (m, 2H) | 1.16 A 492.1 | A |
| 47 | 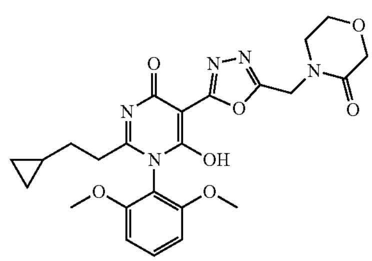 [SMILES: COc1cccc(OC)c1-n1c(CCC2CC2)nc(=O)c(-c2nnc(CN3CCOCC3=O)o2)c1O] | 4-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)morpholin-3-one | $^1$H NMR (DMSO-d6, 500 MHz) δ 7.67 (t, J = 8.4 Hz, 1H), 7.04 (d, J = 8.2 Hz, 2H), 4.98 (s, 2H), 4.28 (s, 2H), 4.03 (t, J = 4.2 Hz, 2H), 3.95 (s, 6H), 3.64 (t, J = 4.2 Hz, 2H), 2.61 (t, J = 7.2 Hz, 2H), 1.43-1.59 (m, 2H), 0.70-0.82 (m, 1H), 0.30-0.64 (m, 2H), −0.19-0.16 ppm (m, 2H) | 1.19 B 498.0 | A |
| 49 | 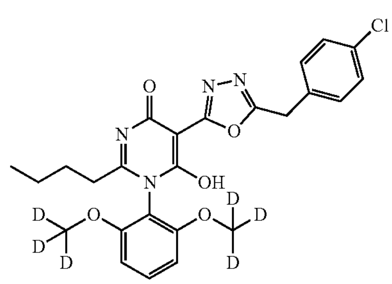 [SMILES: [2H]C([2H])([2H])Oc1cccc(OC([2H])([2H])[2H])c1-n1c(CCCC)nc(=O)c(-c2nnc(Cc3ccc(Cl)cc3)o2)c1O] | 1-[2,6-bis($^2$H$_3$)methoxyphenyl]-2-butyl-5-{5-[(4-chlorophenyl)methyl]-1,3,4-oxadiazol-2-yl}-6-hydroxy-1,4-dihydropyrimidin-4-one | $^1$H NMR (DMSO-d6) δ 7.47 (t, J = 8.4 Hz, 1H), 7.37-7.42 (m, 2H), 7.31-7.36 (m, 2H), 6.83 (d, J = 8.5 Hz, 2H), 4.23 (s, 2H), 2.29 (t, J = 7.3 Hz, 2H), 1.40 (t, J = 7.3 Hz, 2H), 1.14 (q, J = 7.3 Hz, 2H), 0.68 (t, J = 7.3 Hz, 3H) | 1.45 A 503.1 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 50 | 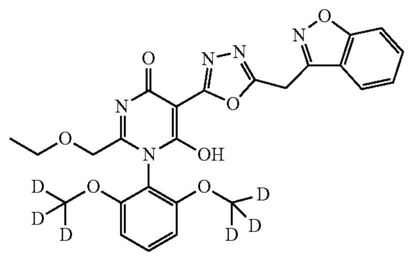 [SMILES: [2H]C([2H])([2H])Oc1cccc(OC([2H])([2H])[2H])c1-n1c(COCC)nc(=O)c(-c2nnc(Cc3noc4ccccc34)o2)c1O] | 5-[5-(1,2-benzoxazol-3-ylmethyl)-1,3,4-oxadiazol-2-yl]-1-[2,6-bis(²H₃)methoxyphenyl]-2-(ethoxymethyl)-6-hydroxy-1,4-dihydropyrimidin-4-one | ¹H NMR (DMSO-d6, 500 MHz): δ 7.88 (d, J = 7.9 Hz, 1H), 7.77 (d, J = 8.2 Hz, 1H), 7.68 (t, J = 7.8 Hz, 1H), 7.41 (t, J = 7.5 Hz, 1H), 7.34 (t, J = 8.4 Hz, 1H), 6.73 (d, J = 8.5 Hz, 2H), 4.72 (s, 2H), 3.77 (s, 2H), 3.25 (q, J = 7.0 Hz, 2H), 0.96 ppm (t, J = 7.0 Hz, 3H) | 1.37 B 512.1 | A |
| 51 | 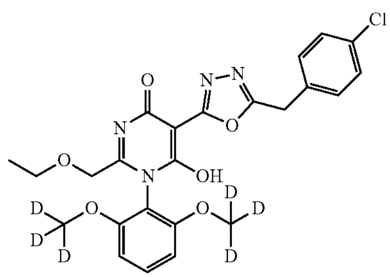 | 1-[2,6-bis(²H₃)methoxyphenyl]-5-{5-[(4-chlorophenyl)methyl]-1,3,4-oxadiazol-2-yl}-2-(ethoxymethyl)-6-hydroxy-1,4-dihydropyrimidin-4-one | ¹H NMR (DMSO-d6) δ 7.33-7.44 (m, 5H), 6.76 (d, J = 8.5 Hz, 2H), 4.23 (s, 2H), 3.84 (s, 2H), 3.27 (q, J = 7.0 Hz, 2H), 0.98 (t, J = 7.0 Hz, 3H) | 1.54 B 505.2 | A |
| 54 | 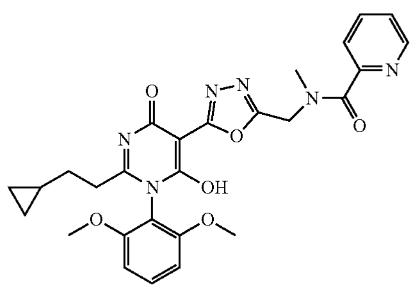 [SMILES: COc1cccc(OC)c1-n1c(CCC2CC2)nc(=O)c(-c2nnc(CN(C)C(=O)c3ccccn3)o2)c1O] | N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)-N-methylpyridine-2-carboxamide | ¹H NMR (DMSO-d6) δ 8.80 (d, J = 3.7 Hz, 1H), 8.13 (t, J = 7.6 Hz, 1H), 7.80 (d, J = 7.6 Hz, 1H), 7.59-7.67 (m, 2H), 7.01 (d, J = 7.9 Hz, 2H), 5.11 (s, 2H), 3.26 (s, 3H), 2.69 (s, 6H), 2.44-2.54 (m, 3H), 1.47-1.57 (m, 2H), 0.72-0.83 (m, 1H), 0.45-0.52 (m, 2H), −0.03-0.03 (m, 2H) | 1.32 B 533.1 | A |
| 55 | 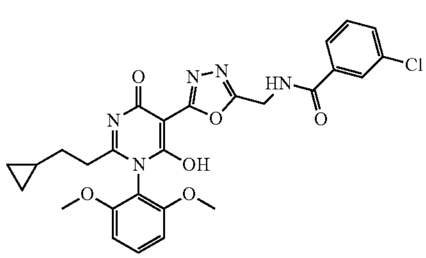 [SMILES: COc1cccc(OC)c1-n1c(CCC2CC2)nc(=O)c(-c2nnc(CNC(=O)c3cccc(Cl)c3)o2)c1O] | 3-chloro-N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)benzamide | ¹H NMR (DMSO-d6) δ 9.58 (br t, J = 5.5 Hz, 1H), 8.13 (s, 1H), 8.06 (br d, J = 7.6 Hz, 1H), 7.84 (br d, J = 7.6 Hz, 1H), 7.73 (t, J = 7.9 Hz, 1H), 7.63 (t, J = 8.4 Hz, 1H), 7.01 (d, J = 8.5 Hz, 2H), 4.87 (d, J = 5.8 Hz, 2H), 3.95 (s, 6H), 2.46 (br s, 2H), 1.53 (q, J = 7.3 Hz, 2H), 0.75-0.83 (m, 1H), 0.49 (br d, J = 7.0 Hz, 2H), 0.01 (br d, J = 4.3 Hz, 2H) | 2.08 A 552.1 | A |
| 56 | 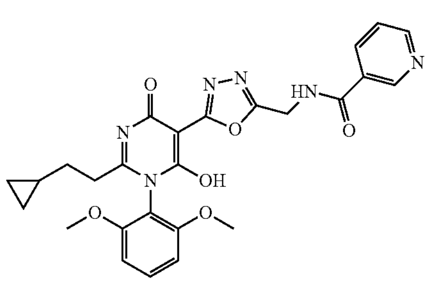 [SMILES: COc1cccc(OC)c1-n1c(CCC2CC2)nc(=O)c(-c2nnc(CNC(=O)c3cccnc3)o2)c1O] | N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)pyridine-3-carboxamide | ¹H NMR (DMSO-d6) δ 9.63-9.68 (m, 1H), 8.41 (br d, J = 7.9 Hz, 1H), 7.64-7.74 (m, 2H), 7.45 (s, 1H), 7.34 (s, 1H), 7.04 (d, J = 8.5 Hz, 2H), 4.90 (br d, J = 5.5 Hz, 2H), 3.95 (s, 6H), 2.62 (br t, J = 7.5 Hz, 2H), 1.45-1.58 (m, 2H), 0.74-0.90 (m, 1H), 0.49 (br d, J = 7.3 Hz, 2H), 0.01 (br d, J = 4.6 Hz, 2H) | 1.21 B 519.1 | A |

TABLE 1-continued

| Ex # | Structure | Name | ¹H NMR | LC/MS Rt (min) Method M + H | hAPJ cAMP EC$_{50}$ Potency range |
|---|---|---|---|---|---|
| 57 | 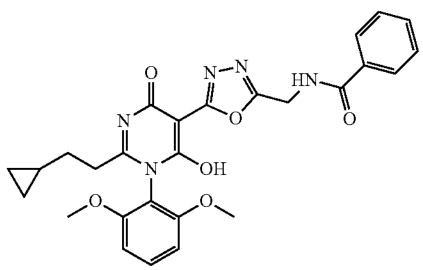 [SMILES: COc1cccc(OC)c1-n1c(CCC2CC2)nc(=O)c(-c2nnc(CNC(=O)c3ccccc3)o2)c1O] | N-({5-(2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)benzamide | ¹H NMR (DMSO-d6) δ 9.43 (br s, 1H), 8.03-8.11 (m, 1H), 7.53-7.82 (m, 5H), 7.03 (br d, J = 7.6 Hz., 2H), 4.86 (br s, 2H), 3.95 (br s, 6H), 2.52-2.64 (m, 2H), 1.46-1.69 (m, 2H), 0.67-0.88 (m, 1H), 0.37-0.55 (m, 2H), −0.15-0.06 (m, 2H) | 1.40 A 518.1 | A |
| 58 | 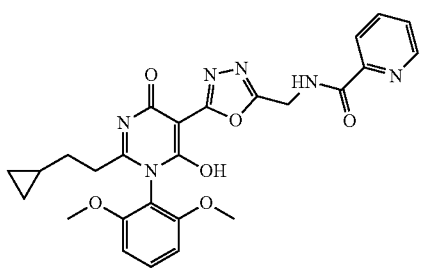 [SMILES: COc1cccc(OC)c1-n1c(CCC2CC2)nc(=O)c(-c2nnc(CNC(=O)c3ccccn3)o2)c1O] | N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)pyridine-2-carboxamide | ¹H NMR (DMSO-d6) δ 9.62 (t, J = 5.8 Hz, 1H), 8.88 (br d, J = 4.3 Hz, 1H), 8.18-8.31 (m, 2H), 7.84 (t, J = 6.3 Hz, 1H), 7.63 (br t, J = 8.4 Hz, 1H), 7.01 (br d, J = 8.5 Hz, 2H), 4.89 (br d, J = 5.8 Hz, 2H), 3.95 (s, 6H), 2.34-2.55 (m, 2H), 1.48-1.69 (m, 2H), 0.72-0.84 (m, 1H), 0.49 (br d, J = 7.0 Hz, 2H), 0.00 (br d, J = 4.0 Hz, 2H) | 1.30 A 519.1 | A |
| 59 | 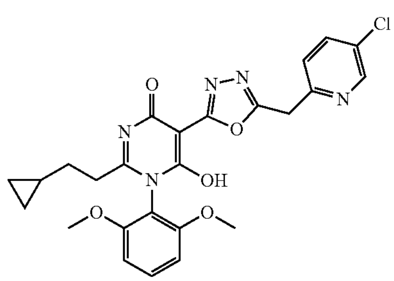 [SMILES: COc1cccc(OC)c1-n1c(CCC2CC2)nc(=O)c(-c2nnc(Cc3ccc(Cl)cn3)o2)c1O] | 5-{5-[(5-chloropyridin-2-yl)methyl]-1,3,4-oxadiazol-2-yl}-2-(2-cyclopropylethyl)-1-(2,6-dimethoxyphenyl)-6-hydroxy-1,4-dihydropyrimidin-4-one | ¹H NMR (DMSO-d6) δ 8.73 (s, 1H), 8.12 (br d, J = 8.5 Hz, 1H), 7.60-7.75 (m, 2H), 7.04 (br d, J = 8.5 Hz, 2H), 4.61 (s, 2H), 3.95 (s, 6H), 2.55-2.65 (m, 2H), 1.47-1.60 (m, 2H), 0.69-0.87 (m, 1H), 0.49 (br d, J = 7.6 Hz, 2H), 0.00 (br d, J = 4.0 Hz, 2H) | 1.48 B 510.1 | A |
| 60 | 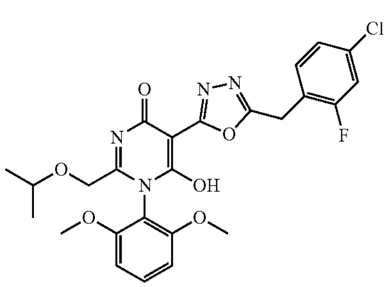 [SMILES: COc1cccc(OC)c1-n1c(COC(C)C)nc(=O)c(-c2nnc(Cc3ccc(Cl)cc3F)o2)c1O] | 5-{5-[(4-chloro-2-fluorophenyl)methyl]-1,3,4-oxadiazol-2-yl}-1-(2,6-dimethoxyphenyl)-6-hydroxy-2-[(propan-2-yloxy)methyl]-1,4-dihydropyrimidin-4-one | ¹H NMR (DMSO-d6) δ 7.41-7.51 (m, 2H), 7.35 (t, J = 8.2 Hz, 1H), 7.30 (d, J = 8.0 Hz, 1H), 6.74 (br d, J = 8.2 Hz, 2H), 4.22 (s, 2H), 3.78 (s, 2H), 3.73 (s, 6H), 3.24-3.37 (m, 1H), 0.88 (br d, J = 6.1 Hz, 6H) | 1.33 A 531.3 | A |
| 61 | 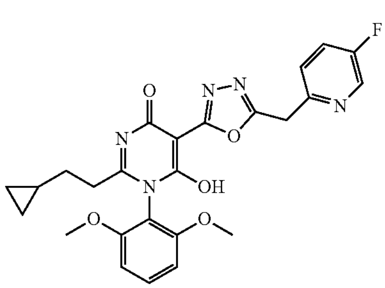 [SMILES: COc1cccc(OC)c1-n1c(CCC2CC2)nc(=O)c(-c2nnc(Cc3ccc(F)cn3)o2)c1O] | 2-(2-cyclopropylethyl)-1-(2,6-dimethoxyphenyl)-5-{5-[(5-fluoropyridin-2-yl)methyl]-1,3,4-oxadiazol-2-yl}-6-hydroxy-1,4-dihydropyrimidin-4-one | ¹H NMR (DMSO-d6) δ 8.68-8.75 (m, 1H), 7.95 (t, J = 8.5 Hz, 1H), 7.73 (dd, J = 8.5, 4.4 Hz, 1H), 7.62 (t, J = 8.4 Hz, 1H), 7.00 (d, J = 8.5 Hz, 2H), 4.59 (s, 2H), 3.95 (s, 6H), 2.30-2.43 (m, 2H), 1.53 (q, J = 7.2 Hz, 2H), 0.79 (br s, 1H), 0.49 (br d, J = 7.5 Hz, 2H), 0.00 (br d, J = 4.3 Hz, 2H) | 1.12 A 493.9 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 62 | 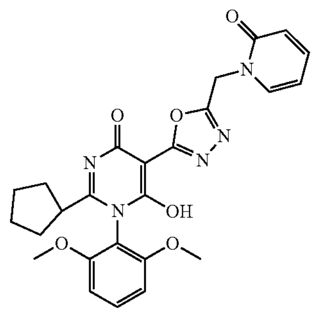 [SMILES: COc1cccc(OC)c1-n1c(C2CCCC2)nc(=O)c(-c2nnc(Cn3ccccc3=O)o2)c1O] | 2-cyclopentyl-1-(2,6-dimethoxyphenyl)-6-hydroxy-5-{5-[(2-oxo-1,2-dihydropyridin-1-yl)methyl]-1,3,4-oxadiazol-2-yl}-1,4-dihydropyrimidin-4-one | ¹H NMR (500 MHz, DMSO-d6) δ 7.83 (dd, J = 6.7, 1.5 Hz, 1H), 7.60-7.42 (m, 2H), 6 86 (d, J = 8.5 Hz, 2H), 6.45 (d, J = 9.2 Hz, 1H), 6.37-6.28 (m, 1H), 5.39 (s, 2H), 3.79 (s, 6H), 2.69-2.58 (m, 1H), 1.95-1.79 (m, 2H), 1.77-1.59 (m, 4H), 1.54-1.37 (m, 2H) | 1.23 A 492.1 | A |
| 63 | 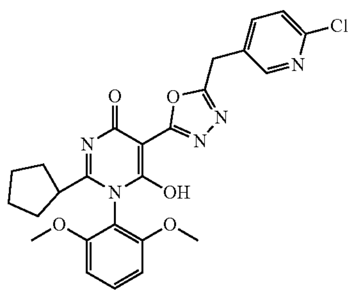 [SMILES: COc1cccc(OC)c1-n1c(C2CCCC2)nc(=O)c(-c2nnc(Cc3ccc(Cl)nc3)o2)c1O] | 5-{5-[(6-chloropyridin-3-yl)methyl]-1,3,4-oxadiazol-2-yl}-2-cyclopentyl-1-(2,6-dimethoxyphenyl)-6-hydroxy-1,4-dihydropyrimidin-4-one | ¹H NMR (500 MHz, DMSO-d6) δ 8.42 (d, J = 1.8 Hz, 1H), 7.84 (dd, J = 8.1, 2.0 Hz, 1H), 7.52 (d, J = 8.2 Hz, 1H), 7.34 (t, J = 8.4 Hz, 1H), 6.74 (d, J = 8.5 Hz, 2H), 4.26 (s, 2H), 3.73 (s, 6H), 2.39 (quin, J = 8.1 Hz, 1H), 1.84-1.70 (m, 2H), 1.61 (br s, 2H), 1.47 (br d, J = 7.9 Hz, 2H), 1.39-1.25 (m, 2H) | 1.36 A 510.3 | A |
| 64 | 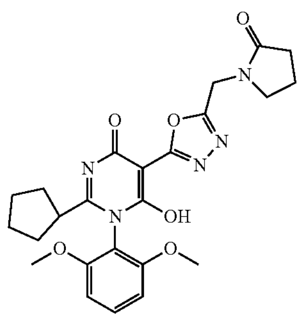 [SMILES: COc1cccc(OC)c1-n1c(C2CCCC2)nc(=O)c(-c2nnc(CN3CCCC3=O)o2)c1O] | 2-cyclopentyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one | ¹H NMR (500 MHz, DMSO-d6) δ 7.49 (t, J = 8.5 Hz, 1H), 6.86 (d, J = 8.2 Hz, 2H), 4.68 (s, 2H), 3.79 (s, 6H), 2.62 (quin, J = 8.1 Hz, 1H), 2.54-2.42 (m, 2H), 2.34-2.22 (m, 2H), 1.98 (quin, J = 7.5 Hz, 2H), 1 91-1.78 (m, 2H), 1.77-1.60 (m, 4H), 1.54-1.36 (m, 2H) | 1.22 A 482.1 | A |
| 65 | 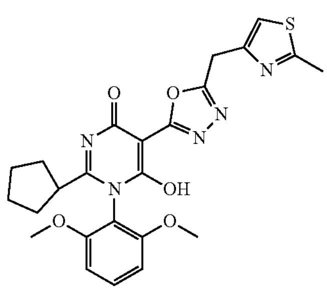 [SMILES: COc1cccc(OC)c1-n1c(C2CCCC2)nc(=O)c(-c2nnc(Cc3csc(C)n3)o2)c1O] | 2-cyclopentyl-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one | ¹H NMR (500 MHz, DMSO-d6) δ 7.48 (t, J = 8.4 Hz, 1H), 7.38 (s, 1H), 6.85 (d, J = 8.5 Hz, 2H), 4.36 (s, 2H), 3.78 (s, 6H), 2.69-2.58 (m, 4H), 1.94-1.78 (m, 2H), 1.77-1.59 (m, 4H), 1.55-1.35 (m, 2H) | 1.31 A 496.3 | A |
| 66 | 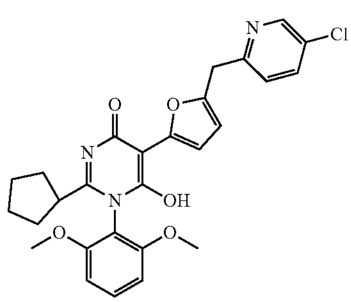 [SMILES: COc1cccc(OC)c1-n1c(C2CCCC2)nc(=O)c(-c2ccc(Cc3ccc(Cl)cn3)o2)c1O] | 5-{5-[(5-chloropyridin-2-yl)methyl]-1,3,4-oxadiazol-2-yl}-2-cyclopentyl-1-(2,6-dimethoxyphenyl)-6-hydroxy-1,4-dihydropyrimidin-4-one | ¹H NMR (500 MHz, DMSO-d6) δ 8.56 (d, J = 1.8 Hz, 1H), 7.94 (dd, J = 8.4, 2.3 Hz, 1H), 7.48 (d, J = 8.5 Hz, 1H), 7.34 (t, J = 8.4 Hz, 1H), 6.74 (d, J = 8.5 Hz, 2H), 4.36 (s, 2H), 3.73 (s, 6H), 2.39 (quin, J = 8.1 Hz, 1H), 1.83-1.68 (m, 2H), 1.61 (br s, 2H), 1.46 (br d, J = 7.6 Hz, 2H), 1.38-1.25 (m, 2H) | 1.40 A 510.0 | A |

TABLE 1-continued

| Ex # | Structure | Name | ¹H NMR | LC/MS Rt (min) Method M + H | hAPJ cAMP EC₅₀ Potency range |
|---|---|---|---|---|---|
| 67 | 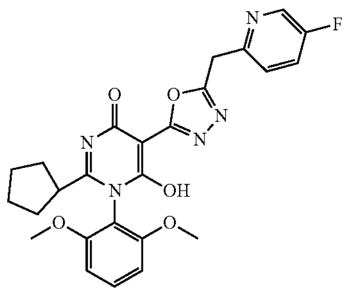 [SMILES: COc1cccc(OC)c1-n1c(C2CCCC2)nc(=O)c(-c2nnc(Cc3ccc(F)cn3)o2)c1O] | 2-cyclopentyl-1-(2,6-dimethoxyphenyl)-5-{5-[(5-fluoropyridin-2-yl)methyl]-1,3,4-oxadiazol-2-yl}-6-hydroxy-1,4-dihydropyrimidin-4-one | ¹H NMR (500 MHz, DMSO-d6) δ 8.50 (br d, J = 2.1 Hz, 1H), 7.74 (td, J = 8.6, 2.6 Hz, 1H), 7.52 (dd, J = 8.5, 4.3 Hz, 1H), 7.39 (t, J = 8.4 Hz, 1H), 6.77 (d, J = 8.5 Hz, 2H), 4.39 (s, 2H), 3.74 (s, 6H), 2.46 (quin, J = 8.3 Hz, 1H), 1.87-1.72 (m, 2H), 1.64 (br s, 2H), 1.59-1.46 (m, 2H), 1.45-1.24 (m, 2H) | 1.37 A 494.0 | A |
| 68 | 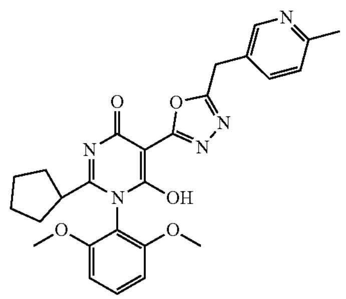 [SMILES: COc1cccc(OC)c1-n1c(C2CCCC2)nc(=O)c(-c2nnc(Cc3ccc(C)nc3)o2)c1O] | 2-cyclopentyl-1-(2,6-dimethoxyphenyl)-6-hydroxy-5-{5-[(6-methylpyridin-3-yl)methyl]-1,3,4-oxadiazol-2-yl}-1,4-dihydropyrimidin-4-one | ¹H NMR (500 MHz, DMSO-d6) δ 8.41 (s, 1H), 7.62 (br d, J = 6.4 Hz, 1H), 7.35 (t, J = 8.4 Hz, 1H), 7.23 (d, J = 7.9 Hz, 1H), 6.75 (d, J = 8.2 Hz, 2H), 4.18 (s, 2H), 3.73 (s, 6H), 2.45 (s, 3H), 2.43-2.36 (m, 1H), 1.84-1.70 (m, 2H), 1.62 (br s, 2H), 1.47 (br s, 2H), 1.34 (br d, J = 5.5 Hz, 2H) | 1.35 A 490.0 | A |
| 69 | 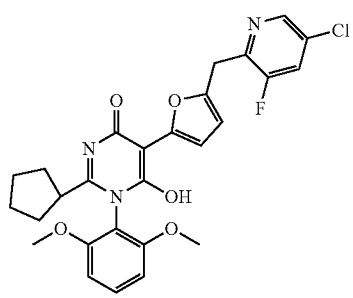 [SMILES: COc1cccc(OC)c1-n1c(C2CCCC2)nc(=O)c(-c2ccc(Cc3ncc(Cl)cc3F)o2)c1O] | 5-{5-[(5-chloro-3-fluoropyridin-2-yl)methyl)-1,3,4-oxadiazol-2-yl}-2-cyclopentyl-1-(2,6-dimethoxyphenyl)-6-hydroxy-1,4-dihydropyrimidin-4-one | ¹H NMR (500 MHz, DMSO-d6) δ 8.48 (s, 1H), 8.12 (br d, J = 9.2 Hz, 1H), 7.36 (t, J = 8.4 Hz, 1H), 6.75 (d, J = 8.5 Hz, 2H), 4.40 (d, J = 1.5 Hz, 2H), 3.73 (s, 6H), 2.41 (quin, J = 8.2 Hz, 1H), 1.82-1.70 (m, 2H), 1.62 (br s, 2H), 1.48 (br s, 2H), 1.34 (br d, J = 5.2 Hz, 2H) | 1.33 A 528.4 | A |
| 70 | 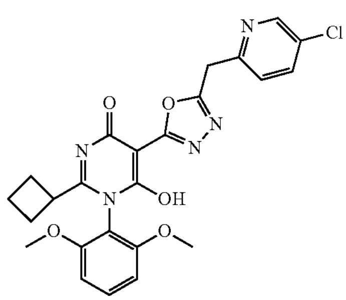 [SMILES: COc1cccc(OC)c1-n1c(C2CCC2)nc(=O)c(-c2nnc(Cc3ccc(Cl)cn3)o2)c1O] | 5-{5-[(5-chloropyridin-2-yl)methyl]-1,3,4-oxadiazol-2-yl}-2-cyclobutyl-1-(2,6-dimethoxyphenyl)-6-hydroxy-1,4-dihydropyrimidin-4-one | ¹H NMR (500 MHz, DMSO-d6) δ 8.54 (br s, 1H), 7.98-7.86 (m, 1H), 7.47 (br d, J = 8.3 Hz, 1H), 7.42-7.30 (m, 1H), 6.72 (br d, J = 8.4 Hz, 2H), 4.35 (s, 2H), 3.69 (s, 6H), 2.83 (br t, J = 8.4 Hz, 1H), 2.36-2.11 (m, 4H), 1.56 (br s, 2H) | 1.10 A 496.2 | A |
| 71 | 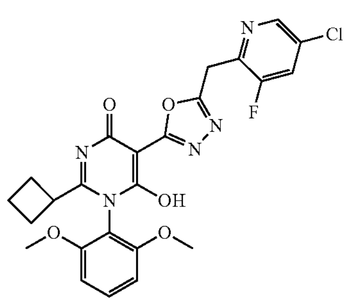 [SMILES: COc1cccc(OC)c1-n1c(C2CCC2)nc(=O)c(-c2nnc(Cc3ncc(Cl)cc3F)o2)c1O] | 5-{5-[(5-chloro-3-fluoropyridin-2-yl)methyl]-1,3,4-oxadiazol-2-yl}-2-cyclobutyl-1-(2,6-dimethoxyphenyl)-6-hydroxy-1,4-dihydropyrimidin-4-one | ¹H NMR (500 MHz, DMSO-d6) δ 8.43 (br s, 1H), 8.04 (br d, J = 9.1 Hz, 1H), 7.39 (br t, J = 8.2 Hz, 1H), 6.75 (br d, J = 8.5 Hz, 2H), 4.43 (s, 2H), 3.69 (s, 6H), 3.04-2.83 (m, 1H), 2.33-2.12 (m, 4H), 1.75-1.45 (m, 2H) | 1.14 A 514.0 | A |

TABLE 1-continued

| Ex # | Structure | Name | ¹H NMR | LC/MS Rt (min) Method M + H | hAPJ cAMP EC$_{50}$ Potency range |
|---|---|---|---|---|---|
| 72 | 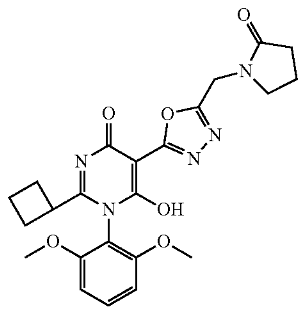 [SMILES: COc1cccc(OC)c1-n1c(C2CCC2)nc(=O)c(-c2nnc(CN3CCCC3=O)o2)c1O] | 2-cyclobutyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one | ¹H NMR (500 MHz, DMSO-d6) δ 7.36 (br t, J = 8.3 Hz, 1H), 6.73 (br d, J = 8.3 Hz, 2H), 4.58 (s, 2H), 3.79-3.54 (m, 6H), 3.41 (br t, J = 6.8 Hz, 2H), 3.03-2.79 (m, 3H), 2.36-2.16 (m, 4H), 2.03-1.93 (m, 2H), 1.72-1.49 (m, 2H) | 0.93 A 468.3 | A |
| 73 | 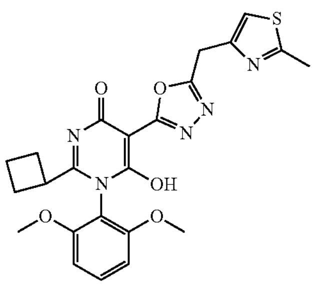 [SMILES: COc1cccc(OC)c1-n1c(C2CCC2)nc(=O)c(-c2nnc(Cc3csc(C)n3)o2)c1O] | 2-cyclobutyl-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one | ¹H NMR (500 MHz, DMSO-d6) δ 7.46 (br t, J = 8.4 Hz, 1H), 7.34 (s, 1H), 6.81 (br d, J = 8.5 Hz, 2H), 4.32 (s, 2H), 3.81-3.63 (m, 6H), 3.08 (br t, J = 8.4 Hz, 1H), 2.59 (s, 3H), 2.37-2.21 (m, 2H), 1.85-1.56 (m, 4H) | 1.03 A 482.1 | A |

Example 55-58 in Table 1 was prepared as described in the general procedure given for Example 53.

Example 59-73 in Table 1 was prepared as described in the general procedure given for Example 1.

Example 74

(S)-5-(5-(Benzo[d]isoxazol-3-ylmethyl)-1,3,4-oxadiazol-2-yl)-2-butyl-6-hydroxy-3-(1-phenylpropyl)pyrimidin-4(3H)-one

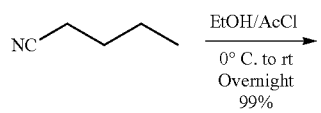

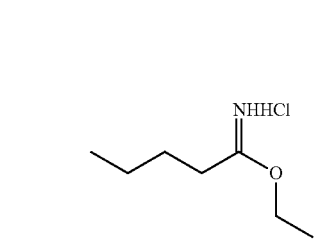

Compound 74a

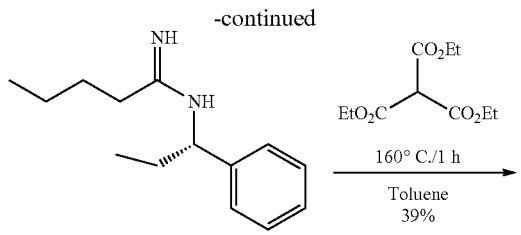

Compound 74b

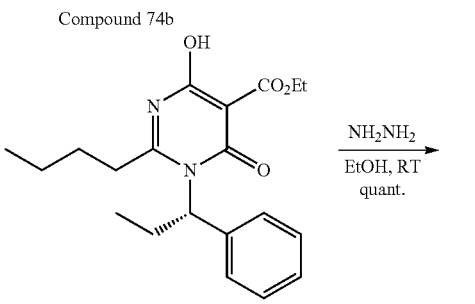

Compound 74c

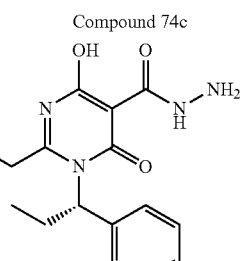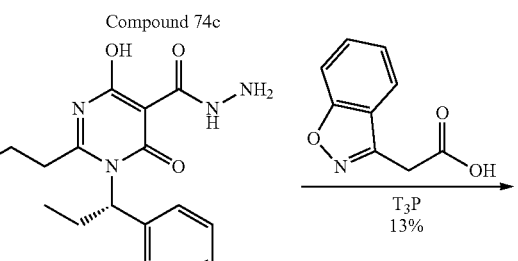

Compound 74d

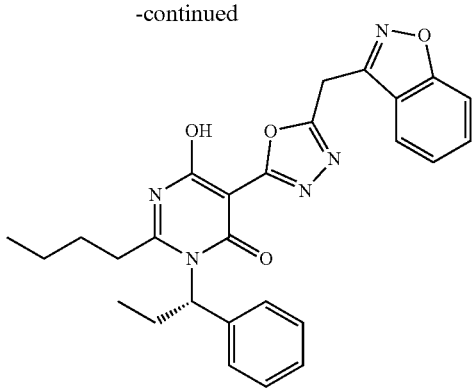

Example 74

Compound 74a. Ethyl Pentanimidate Hydrochloride

Pentanenitrile (9 mL, 86 mmol) in EtOH (59.9 mL, 1.03 mol) was cooled to 0° C. by ice bath. AcCl (48.64 mL, 685 mmol) was added dropwise over 3 hours. After complete addition, the reaction mixture was stirred at room temperature. After 16 h, the solution was concentrated under reduced pressure. The residue was washed with $Et_2O$ two times to remove trace HCl, then the solid was suspended in 200 ml of $Et_2O$ and stored in refrigerator for 14 h. Compound 20a (14 g, 99% yield) was obtained by filtration as a white solid. $^1$H NMR (400 MHz, CHLOROFORM-d) δ 4.64 (d, J=6.6 Hz, 2H), 2.74 (t, J=7.5 Hz, 2H), 1.87-1.64 (m, 2H), 1.49 (t, J=6.2 Hz, 3H), 1.45-1.38 (m, 2H), 0.95 (t, J=7.3 Hz, 3H).

Compound 20b. (S)—N-(1-Phenylpropyl)pentanimidamide

To a solution of compound 74a (1.35 g, 8.15 mmol) in ethanol (15 mL) was added (S)-1-phenylpropan-1-amine (0.918 g, 6.79 mmol) at 0° C. The reaction mixture was stirred from 0° C. to room temperature over 14 h, followed by addition of ammonia in MeOH (14.6 mL, 102 mmol) and stirred at room temperature for 2 hours. The reaction mixture was concentrated and the residue was dissolved in MeOH and purified by prep HPLC. The fractions containing Compound 20b were collected and concentrated under reduced pressure. The residue was dissolved in DCM and washed with 1N NaOH (2×). The combined organic layer was washed with brine and concentrated under reduced pressure to afford compound 74b (710 mg, 48% yield) as a colorless oil. MS m/z=219 [M+H]$^+$. $^1$H NMR (400 MHz, CHLOROFORM-d) δ 7.29-7.05 (m, 5H), 4.41 (br. s., 1H), 2.23-2.05 (m, 2H), 1.91-1.62 (m, 2H), 1.55-1.38 (m, 2H), 1.27 (sxt, J=7.4 Hz, 2H), 0.83 (td, J=7.4, 2.0 Hz, 6H).

Compound 74c. (S)-ethyl 2-butyl-4-hydroxy-6-oxo-1-(1-phenylpropyl)-1,6-dihydropyrimidine-5-carboxylate A mixture of 74b (710 mg, 3.25 mmol), triethyl methanetricarboxylate (1.24 mL, 5.85 mmol) and toluene (15 mL) was heated at 160° C. for 1 hour in a microwave reactor. The reaction mixture was allowed to cool to room temperature and loaded onto a 40 g ISCO column eluted with 0-70% EtOAc/DCM for 30 min. The fractions containing Compound 74c were collected and concentrated under reduced pressure to give 74c (580 mg, 39% yield). MS m/z=359.3 [M+H]$^+$. $^1$H NMR (400 MHz, METHANOL-d4 at 333K) δ 7.43-7.35 (m, 2H), 7.33-7.26 (m, 3H), 6.26 (br. s., 1H), 4.43-4.30 (m, 2H), 2.75-2.51 (m, 3H), 2.47-2.24 (m, 1H), 1.67-1.51 (m, 1H), 1.40-1.28 (m, 4H), 1.26-1.13 (m, 2H), 1.04 (t, J=7.4 Hz, 3H), 0.79 (t, J=7.4 Hz, 3H). $^{13}$C NMR (101 MHz, METHANOL-$d_4$ at 333K) δ 171.0, 169.5, 162.5, 140.7, 130.1, 128.7, 127.7, 93.0, 62.9, 60.3, 36.1, 30.4, 30.3, 25.7, 23.3, 14.6, 13.9, 11.5.

Compound 74d. (S)-2-Butyl-4-hydroxy-6-oxo-1-(1-phenylpropyl)-1,6-dihydropyrimidine-5-carbohydrazide To a solution of compound 74c (210 mg, 0.586 mmol) in EtOH (2 ml) was added hydrazine (0.368 ml, 11.7 mmol). The reaction mixture was stirred at room temperature for 14 h. The solvent was removed under vacuum to give 74d (202 mg, 0.586 mmol, 100% yield) which was used in the next step without further purification. MS m/z=345 [M+H]$^+$.

Example 74

A solution of 74d (55 mg, 0.16 mmol) and 2-(benzo[d]isoxazol-3-yl)acetic acid (33.9 mg, 0.192 mmol) in dioxane (1 mL) was added 2,4,6-tripropyl-1,3,5,2,4,6-trioxatriphosphinane 2,4,6-trioxide (T3P) (0.190 mL, 0.320 mmol). The reaction mixture was heated at 160° C. for 24 hours. The reaction mixture was allowed to cool to room temperature then quenched by the addition of MeOH. The residue was purified via preparative LC/MS (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 30-70% B over 20 minutes, then a 5-minute hold at 100% B; Flow: 20 mL/min. Fractions containing the Compound 74 were combined and dried via centrifugal evaporation) to yield 9.9 mg, 13%. $^1$H NMR (500 MHz, DMSO-d6) δ 7.88 (br d, J=7.3 Hz, 1H), 7.78 (br d, J=8.5 Hz, 1H), 7.70 (br t, J=7.6 Hz, 1H), 7.46-7.35 (m, 3H), 7.32 (br d, J=7.3 Hz, 3H), 4.81 (br s, 2H), 2.40 (m, 2H), 1.87 (m, 4H), 1.05-0.73 (m, 6H). LC-MS (Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50 OC; Gradient: 0-100%/o B over 3 minutes, then a 0.75-minute hold at 100% B; Flow: 1.11 mL/min; Detection: UV at 220 nm) RT=1.82 min, MS (ESI) m/z: 486.1 (M+H)$^+$. Human APJ cAMP Potency Range: A.

Example 75 to 124 in Table 2 was prepared as described in the general procedure given for Example 73.

TABLE 2

| Ex # | Structure | Name | ¹H NMR | LC/MS Rt (min) Method M + H | hAPJ cAMP EC$_{50}$ Potency range |
|---|---|---|---|---|---|
| 75 | 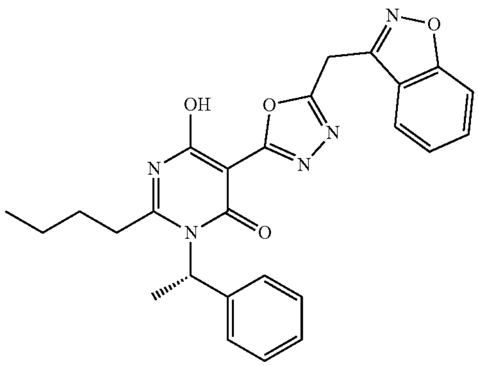 [SMILES: CCCCc1nc(O)c(-c2nnc(Cc3noc4ccccc34)o2)c(=O)n1[C@@H](C)c1ccccc1] | 5-{5-[(1,2-benzoxazol-3-yl)methyl]-1,3,4-oxadiazol-2-yl}-2-butyl-6-hydroxy-3-[(1S)-1-phenylethyl]-3,4-dihydro-pyrimidin-4-one | ¹H NMR (500 MHz, DMSO-d$_6$) δ 7.89 (br d, J = 7.6 Hz, 1H), 7.78 (d, J = 8.5 Hz, 1H), 7.69 (br t, J = 7.8 Hz, 1H), 7.47-7.32 (m, 3H), 7.30-7.14 (m, 3H), 4.75 (s, 2H), 2.56 (s, 3H), 1.60-1.04 (m, 4H), 0.74 (br s, 3H). | 1.74 A 472.0 | B |
| 76 | 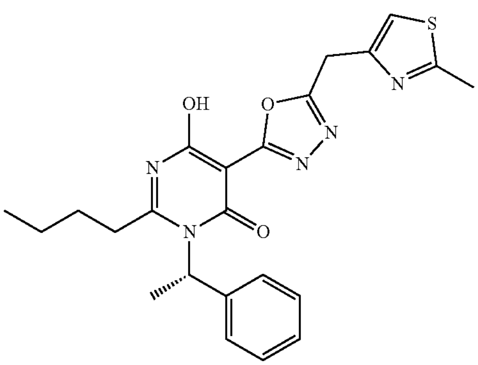 [SMILES: CCCCc1nc(O)c(-c2nnc(Cc3csc(C)n3)o2)c(=O)n1[C@@H](C)c1ccccc1] | 2-butyl-6-hydroxy-5-{5-[(2-methyl-1,3-thiazol-4-yl)-methyl]-1,3,4-oxadiazol-2-yl}-3-[(1S)-1-phenylethyl]-3,4-dihydro-pyrimidin-4-one | ¹H NMR (500 MHz, DMSO-d$_6$) δ 7.41-7.33 (m, 3H), 7.29-7.18 (m, 3H), 4.28 (s, 2H), 2.63 (s, 3H), 2.52 (br s, 3H), 1.62-1.07 (m, 4H), 0.74 (br s, 3H) | 1.47 A 452.3 | A |
| 77 | 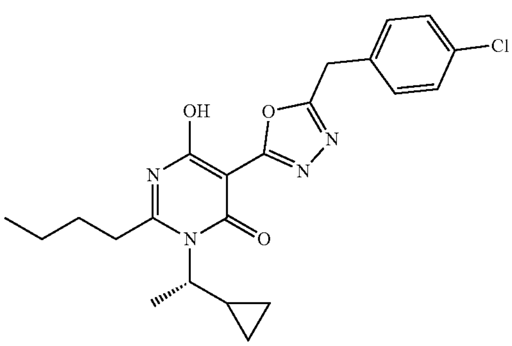 [SMILES: CCCCc1nc(O)c(-c2nnc(Cc3ccc(Cl)cc3)o2)c(=O)n1[C@@H](C)C1CC1] | 2-butyl-5-{5-[(4-chlorophenyl)-methyl]-1,3,4-oxadiazol-2-yl}-3-[(1S)-1-cyclo-propylethyl]-6-hydroxy-3,4-dihydro-pyrimidin-4-one | ¹H NMR (500 MHz, DMSO-d$_6$) δ 7.24-7.19 (m, 2H), 7.15 (br d, J = 8.2 Hz, 2H), 4.06 (s, 2H), 2.33 (s, 3H), 1.47-1.10 (m, 5H), 0.69 (br t, J = 7.0 Hz, 3H), 0.35 (br s, 1H), 0.23 (br d, J = 5.8 Hz, 2H), 0.00 (br d, J = 5.5 Hz, 1H) | 1.66 A 429.2 | C |
| 78 | 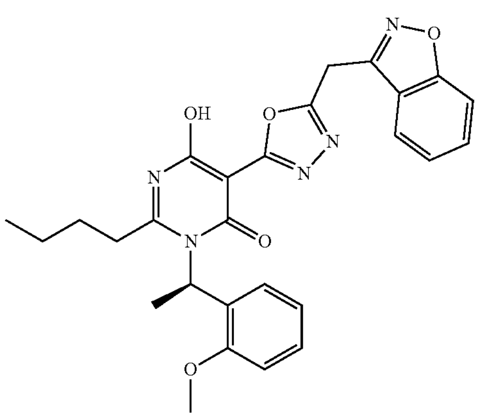 [SMILES: CCCCc1nc(O)c(-c2nnc(Cc3noc4ccccc34)o2)c(=O)n1[C@H](C)c1ccccc1OC] | 5-{5-[{1,2-benzoxazol-3-yl)methyl]-1,3,4-oxadiazol-2-yl}-2-butyl-6-hydroxy-3-[(1R)-1-(2-methoxy-phenyl)ethyl]-3,4-dihydro-pyrimidin-4-one | ¹H NMR (500 MHz, DMSO-d$_6$) δ 7.88 (br d, J = 7.6 Hz, 1H), 7.78 (d, J = 8.5 Hz, 1H), 7.73-7.64 (m, 1H), 7.52 (br d, J = 7.6 Hz, 1H), 7.41 (br t, J = 7.5 Hz, 1H), 7.33-7.24 (m, 1H), 6.99 (br d, J = 7.9 Hz, 2H), 4.78 (s, 2H), 3.70 (s, 3H), 2.56 (s, 3H), 1.70-1.23 (m, 4H), 0.95-0.77 (m, 3H) | 1.69 A 502.0 | B |

TABLE 2-continued

| Ex # | Structure | Name | ¹H NMR | LC/MS Rt (min) Method M + H | hAPJ cAMP EC$_{50}$ Potency range |
|---|---|---|---|---|---|
| 79 | 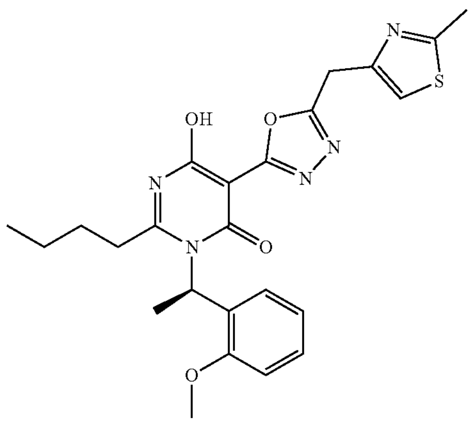 [SMILES: CCCCc1nc(O)c(-c2nnc(Cc3csc(C)n3)o2)c(=O)n1[C@H](C)c1ccccc1OC] | 2-butyl-6-hydroxy-3-[(1R)-1-(2-methoxyphenyl)-ethyl]-5-{5-[(2-methyl-1,3-thiazol-4-yl)-methyl]-1,3,4-oxadiazol-2-yl}-3,4-dihydro-pyrimidin-4-one | ¹H NMR (500 MHz, DMSO-d$_6$) δ 7.50 (br d, J = 7.3 Hz, 1H), 7.37 (s, 1H), 7.27 (br t, J = 7.8 Hz, 1H), 7.02-6.86 (m, 2H), 6.19-5.53 (m, 1H), 4.27 (s, 2H), 3.71 (s, 3H), 2.63 (s, 3H), 2.56 (br s, 3H), 1.67-1.19 (m, 4H), 0.85 (br s, 3H) | 1.55 A 482.1 | A |
| 80 | 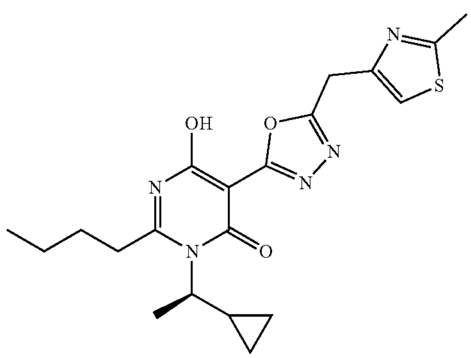 [SMILES: CCCCc1nc(O)c(-c2nnc(Cc3csc(C)n3)o2)c(=O)n1[C@H](C)C1CC1] | 2-butyl-3-[(1R)-1-cyclopropylethyl]-6-hydroxy-5-{5-[(2-methyl-1,3-thiazol-4-yl)-methyl]-1,3,4-oxadiazol-2-yl}-3,4-dihydro-pyrimidin-4-one | ¹H NMR (500 MHz, DMSO-d$_6$) δ 7.22 (s, 1H), 4.13 (s, 2H), 2.47 (s, 3H), 2.39 (s, 3H), 1.50-1.15 (m, 5H), 0.75 (br t, J = 7.2 Hz, 3H), 0.38 (br s, 1H), 0.30-0.16 (m, 2H), 0.00 (br s, 1H) | 1.42 A 416.1 | C |
| 81 | 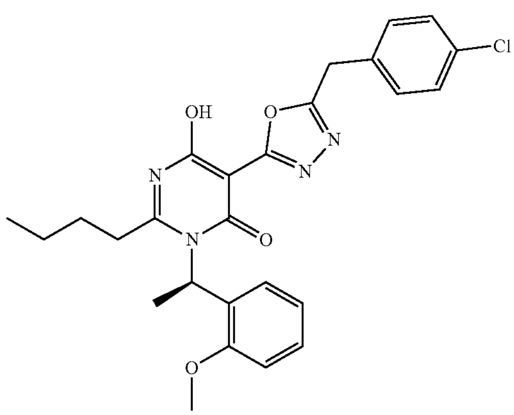 [SMILES: CCCCc1nc(O)c(-c2nnc(Cc3ccc(Cl)cc3)o2)c(=O)n1[C@H](C)c1ccccc1OC] | 2-butyl-5-{5-[(4-chlorophenyl)-methyl]-1,3,4-oxadiazol-2-yl}-6-hydroxy-3-[(1R)-1-(2-methoxyphenyl)-ethyl]-3,4-dihydropyrimidin-4-one | ¹H NMR (500 MHz, DMSO-d$_6$) δ 7.49 (d, J = 7.9 Hz, 1H), 7.40 (d, J = 7.9 Hz, 2H), 7.34-7.26 (m, 3H), 6.99 (br. s, 2H), 4.23 (s, 2H), 2.54 (s, 3H), 1.82 (d, J = 4.9 Hz, 3H), 1.63-0.98 (m, 4H), 0.90-0.73 (m, 3H) | 1.91 B 495.0 | B |

TABLE 2-continued

| Ex # | Structure | Name | ¹H NMR | LC/MS Rt (min) Method M + H | hAPJ cAMP EC₅₀ Potency range |
|---|---|---|---|---|---|
| 82 | 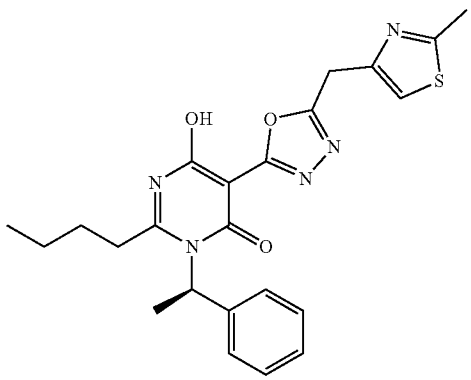 [SMILES: CCCCc1nc(O)c(-c2nnc(Cc3csc(C)n3)o2)c(=O)n1[C@H](C)c1ccccc1] | 2-butyl-6-hydroxy-5-{5-[(2-methyl-1,3-thiazol-4-yl)methyl]-1,3,4-oxadiazol-2-yl}-3-[(1R)-1-phenylethyl]-3,4-dihydro-pyrimidin-4-one | ¹H NMR (500 MHz, DMSO-d₆) δ 7.51-7.31 (m, 3H), 7.26-7.08 (m, 3H), 4.26 (s, 2H), 2.61 (s, 3H), 1.78 (d, J = 5.8 Hz, 3H), 1.56-1.00 (m, 4H), 0.71 (br s., 3H) | 1.50 A 452.0 | B |
| 83 | 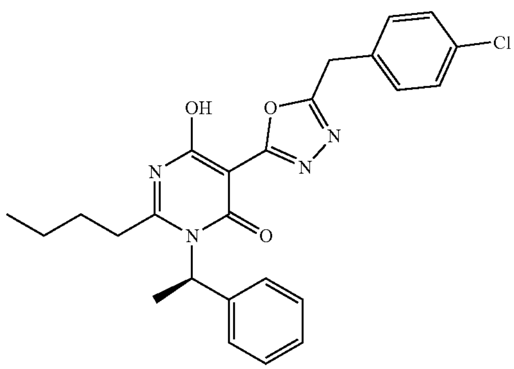 [SMILES: CCCCc1nc(O)c(-c2nnc(Cc3ccc(Cl)cc3)o2)c(=O)n1[C@H](C)c1ccccc1] | 2-butyl-5-{5-[(4-chlorophenyl)-methyl]-1,3,4-oxadiazol-2-yl}-6-hydroxy-3-[(1R)-1-phenyl-ethyl]-3,4-di-hydropyrimidin-4-one | ¹H NMR (500 MHz, DMSO-d₆) δ 7.47-7.38 (m, 2H), 7.35-7.17 (m, 7H), 4.20 (s, 2H), 1.77 (d, J = 5.8 Hz, 3H), 1.51-1.05 (m, 4H), 0.71 (br, s., 3H). | 1.77 A 465.0 | B |
| 84 | 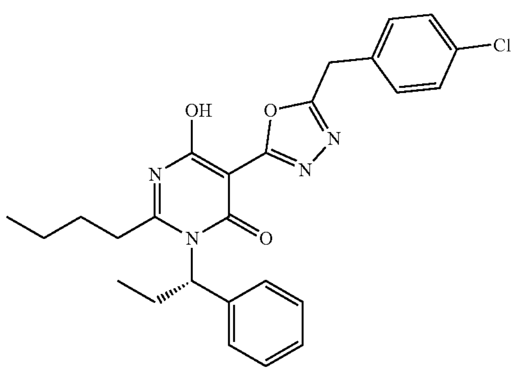 [SMILES: CCCCc1nc(O)c(-c2nnc(Cc3ccc(Cl)cc3)o2)c(=O)n1[C@@H](CC)c1ccccc1] | 2-butyl-5-{5-[(4-chlorophenyl)-methyl]-1,3,4-oxadiazol-2-yl}-6-hydroxy-3-[(1S)-1-phenyl-propyl]-3,4-di-hydropyrimidin-4-one | ¹H NMR (500 MHz, DMSO-d₆) δ 7.46-7.40 (m, 2H), 7.37 (br d, J = 7.6 Hz, 4H), 7.29 (br d, J = 7.3 Hz, 3H), 4.26 (br s, 2H), 2.49-2.32 (m, 3H), 1.83-1.09 (m, 4H), 0.94 (br t, J = 7.3 Hz, 3H), 0.86-0.51 (m, 3H) | 1.80 A 479.1 | B |
| 85 | 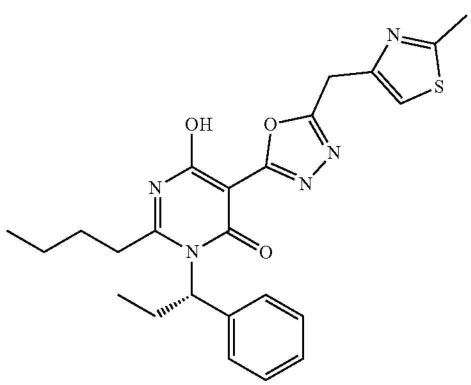 [SMILES: CCCCc1nc(O)c(-c2nnc(Cc3csc(C)n3)o2)c(=O)n1[C@@H](CC)c1ccccc1] | 2-butyl-6-hydroxy-5-{5-[(2-methyl-1,3-thiazol-4-yl)methyl]-1,3,4-oxadiazol-2-yl}-3-[(1S)-1-phenyl-propyl]-3,4-di-hydropyrimidin-4-one | ¹H NMR (500 MHz, DMSO-d₆) δ 7.38 (br s, 3H), 7.32 (br d, J = 7.6 Hz, 3H), 4.33 (br s, 2H), 2.63 (s, 3H), 2.46-2.14 (m, 2H), 1.96-1.07 (m, 4H), 0.96 (br t, J = 7.3 Hz, 3H), 0.88-0.60 (m, 3H) | 1.54 A 466.3 | A |

TABLE 2-continued

| Ex # | Structure | Name | ¹H NMR | LC/MS Rt (min) Method M + H | hAPJ cAMP EC₅₀ Potency range |
|---|---|---|---|---|---|
| 86 | 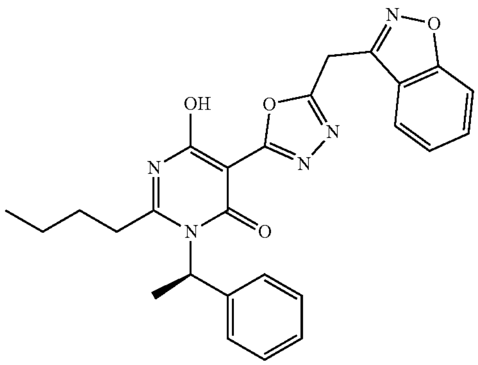 [SMILES: CCCCc1nc(O)c(-c2nnc(Cc3noc4ccccc34)o2)c(=O)n1[C@H](C)c1ccccc1] | 5-{5-[(1,2-benzoxazol-3-yl)methyl]-1,3,4-oxadiazol-2-yl}-2-butyl-6-hydroxy-3-[(1R)-1-phenyl-ethyl]-3,4-di-hydropyrimidin-4-one | ¹H NMR (500 MHz, DMSO-d₆) δ 7.89 (br d, J = 7.9 Hz, 1H), 7.78 (d, J = 8.2 Hz, 1H), 7.69 (br t, J = 7.6 Hz, 1H), 7.49-7.32 (m, 3H), 7.29-7.15 (m, 3H), 4.75 (s, 2H), 1.79 (br d, J = 5.5 Hz, 3H), 1.56-1.07 (m, 4H), 0.73 (br s, 3H) | 1.15 A 472.1 | A |
| 87 | 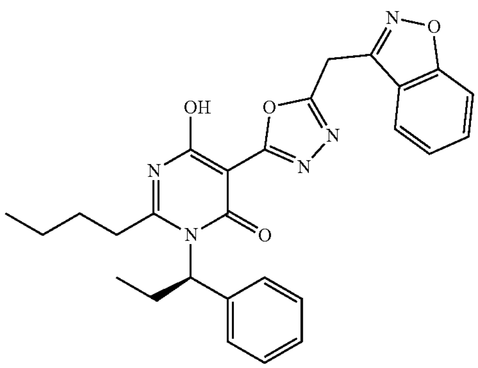 [SMILES: CCCCc1nc(O)c(-c2nnc(Cc3noc4ccccc34)o2)c(=O)n1[C@H](CC)c1ccccc1] | 5-{5-[(1,2-benzoxazol-3-yl)methyl]-1,3,4-oxadiazol-2-yl}-2-butyl-6-hydroxy-3-[(1R)-1-phenyl-propyl]-3,4-di-hydropyrimidin-4-one | ¹H NMR (500 MHz, DMSO-d₆) δ 7.89 (br d, J = 7.9 Hz, 1H), 7.78 (d, J = 8.2 Hz, 1H), 7.69 (t, J = 7.8 Hz, 1H), 7.46-7.33 (m, 3H), 7.28 (br d, J = 6.7 Hz, 3H), 4.77 (s, 2H), 2.53-2.40 (m, 2H), 1.77-1.02 (m, 4H), 0.99-0.64 (m, 6H) | 1.80 B 486.2 | A |
| 88 | 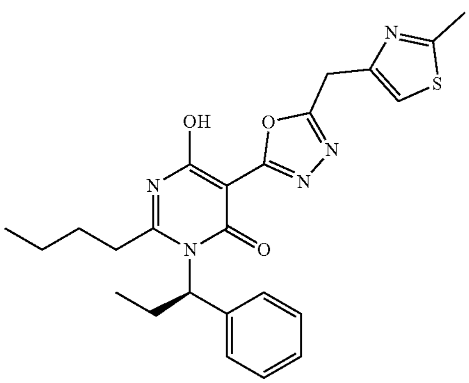 [SMILES: CCCCc1nc(O)c(-c2nnc(Cc3csc(C)n3)o2)c(=O)n1[C@H](CC)c1ccccc1] | 2-butyl-6-hydroxy-5-{5-[(2-methyl-1,3-thiazol-4-yl)-methyl]-1,3,4-oxadiazol-2-yl}-3-[(1R)-1-phenylpropyl]-3,4-dihydro-pyrimidin-4-one | ¹H NMR (500 MHz, DMSO-d₆) δ 7.38 (br s, 3H), 7.32 (br d, J = 7.3 Hz, 3H), 4.33 (br s, 2H), 2.63 (s, 3H), 2.50-2.29 (m, 2H), 1.97-1.09 (m, 4H), 1.04-0.53 (m, 6H) | 1.45 A 466.2 | A |
| 89 | 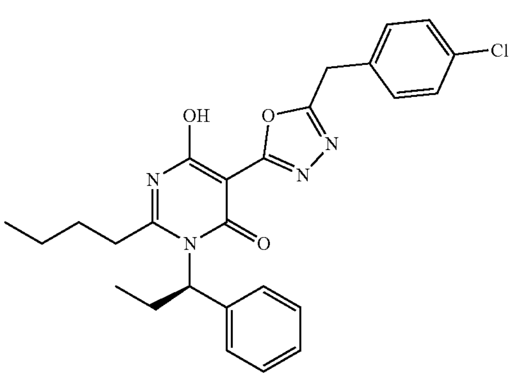 [SMILES: CCCCc1nc(O)c(-c2nnc(Cc3ccc(Cl)cc3)o2)c(=O)n1[C@H](CC)c1ccccc1] | 2-butyl-5-{5-[(4-chlorophenyl)-methyl]-1,3,4-oxadiazol-2-yl}-6-hydroxy-3-[(1R)-1-phenyl-propyl]-3,4-di-hydropyrimidin-4-one | ¹H NMR (500 MHz, DMSO-d₆) δ 7.48-7.41 (m, 2H), 7.37 (br d, J = 7.0 Hz, 4H), 7.29 (br d, J = 7.0 Hz, 3H), 4.26 (br s, 2H), 2.50-2.25 (m, 2H), 1.99-1.03 (m, 4H), 0.96-0.53 (m, 6H) | 1.95 B 479.9 | B |

TABLE 2-continued

| Ex # | Structure | Name | ¹H NMR | LC/MS Rt (min) Method M + H | hAPJ cAMP EC₅₀ Potency range |
|---|---|---|---|---|---|
| 90 | 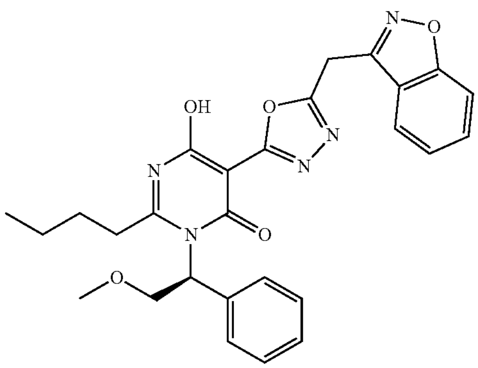 | 5-{5-[(1,2-benzoxazol-3-yl)methyl]-1,3,4-oxadiazol-2-yl}-2-butyl-6-hydroxy-3-[(1S)-2-methoxy-1-phenylethyl]-3,4-dihydro-pyrimidin-4-one | ¹H NMR (500 MHz, DMSO-d₆) δ 7.95-7.84 (m, 1H), 7.80-7.71 (m, 1H), 7.71-7.62 (m, 1H), 7.40-7.32 (m, 3H), 7.25 (br d, J = 7.3 Hz, 3H), 5.69-5.25 (m, 1H), 4.76 (br s, 2H), 4.44-4.05 (m, 2H), 3.35 (s, 3H), 1.87-1.06 (m, 4H), 0.85 (br d, J = 6.0 Hz, 3H) | 1.45 A 502.1 | C |
| 91 | 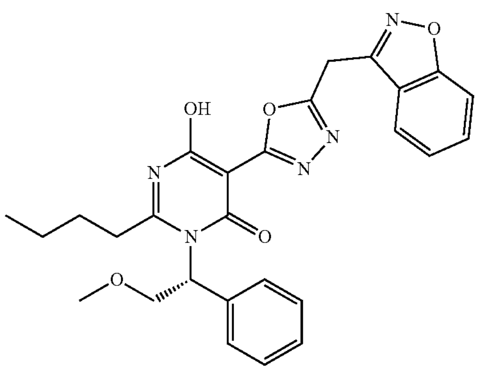 [SMILES: CCCCc1nc(O)c(-c2nnc(Cc3noc4ccccc34)o2)c(=O)n1[C@@H](COC)c1ccccc1] | 5-{5-[(1,2-benzoxazol-3-yl)methyl]-1,3,4-oxadiazol-2-yl}-2-butyl-6-hydroxy-3-[(1R)-2-methoxy-1-phenylethyl]-3,4-dihydro-pyrimidin-4-one | ¹H NMR (500 MHz, DMSO-d₆) δ 7.85 (br d, J = 7.4 Hz, 1H), 7.75 (br d, J = 8.1 Hz, 1H), 7.72-7.64 (m, 1H), 7.47-7.30 (m, 3H), 7.29-7.17 (m, 3H), 5.59-5.26 (m, 1H), 4.73 (br s, 2H), 4.28 (br dd, J = 9.1, 6.3 Hz, 1H), 3.62 (br d, J = 11.6 Hz, 1H), 3.34 (s, 3H), 3.06-2.61 (m, 2H), 1.72-1.09 (m, 4H), 0.98-0.60 (m, 3H) | 1.44 A 502.3 | B |
| 92 | 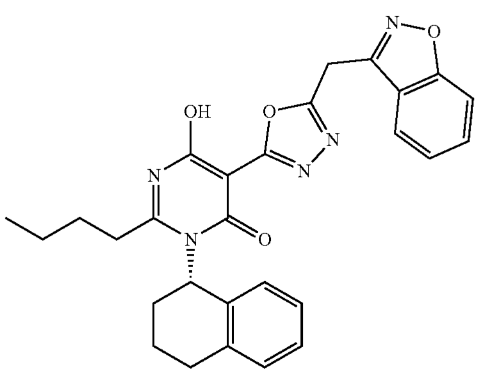 [SMILES: CCCCc1nc(O)c(-c2nnc(Cc3noc4ccccc34)o2)c(=O)n1[C@H]1CCCc2ccccc21] | 5-{5-[(1,2-benzoxazol-3-yl)methyl]-1,3,4-oxadiazol-2-yl}-2-butyl-6-hydroxy-3-[(1S)-1,2,3,4-tetrahydro-naphthalen-1-yl]-3,4-dihydro-pyrimidin-4-one | ¹H NMR (500 MHz, DMSO-d₆) δ 7.91-7.62 (m, 3H), 7.48-7.25 (m, 1H), 7.18-7.02 (m, 3H), 6.91-6.70 (m, 1H), 6.56 and 5.32 (br s, 1H), 4.73 (br s, 1H), 4.67 (br s, 1H), 2.99-2.62 (m, 2H), 2.29-1.95 (m, 2H), 1.81-1.61 (m, 2H), 1.49-1.20 (m, 2H), 1.18-0.98 (m, 2H), 0.96-0.70 (m, 3H), 0.54 (br t, J = 6.9 Hz, 2H) | 1.58 A 498.3 | C |
| 93 | 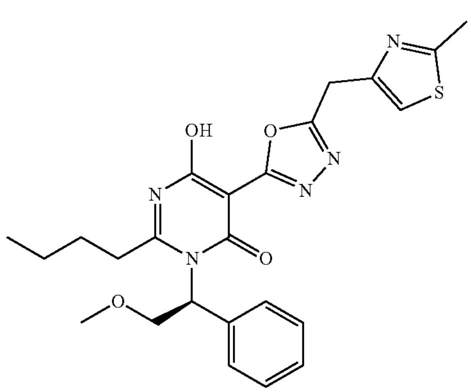 [SMILES: CCCCc1nc(O)c(-c2nnc(Cc3csc(C)n3)o2)c(=O)n1[C@H](COC)c1ccccc1] | 2-butyl-6-hydroxy-3-[(1S)-2-methoxy-1-phenylethyl]-5-{5-[(2-methyl-1,3-thiazol-4-yl)methyl]-1,3,4-oxadiazol-2-yl}-3,4-dihydro-pyrimidin-4-one | ¹H NMR (500 MHz, DMSO-d₆) δ 7.33 (br s, 3H), 7.25 (br d, J = 5.6 Hz, 1H), 7.20 (br s, 2H), 4.25 (br s, 2H), 3.81-3.68 (m, 3H), 3.33 (s, 3H), 3.16 (s, 1H), 3.06-2.63 (m, 1H), 1.83-0.94 (m, 4H), 0.99-0.47 (m, 3H) | 1.27 A 482.1 | C |

TABLE 2-continued

| Ex # | Structure | Name | ¹H NMR | LC/MS Rt (min) Method M + H | hAPJ cAMP EC₅₀ Potency range |
|---|---|---|---|---|---|
| 94 | 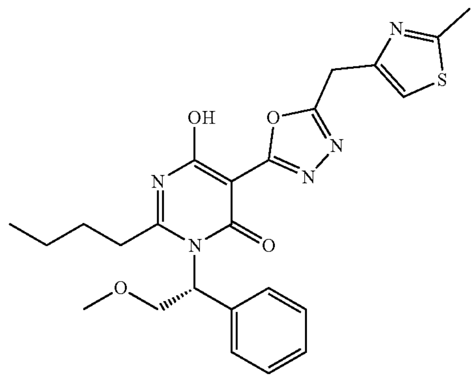 [SMILES: CCCCc1nc(O)c(-c2nnc(Cc3csc(C)n3)o2)c(=O)n1[C@@H](COC)c1ccccc1] | 2-butyl-6-hydroxy-3-[(1R)-2-methoxy-1-phenylethyl]-5-{5-[(2-methyl-1,3-thiazol-4-yl)methyl]-1,3,4-oxadiazol-2-yl}-3,4-dihydro-pyrimidin-4-one | ¹H NMR (500 MHz, DMSO-$d_6$) δ 7.34 (br s, 3H), 7.31-7.18 (m, 3H), 4.28 (br s, 2H), 3.70-3.52 (m, 3H), 3.35 (s, 3H), 2.91 (br d, J = 5.5 Hz, 2H), 1.86-1.18 (m, 4H), 0.85 (br s, 3H) | 1.27 A 482.1 | A |
| 95 | 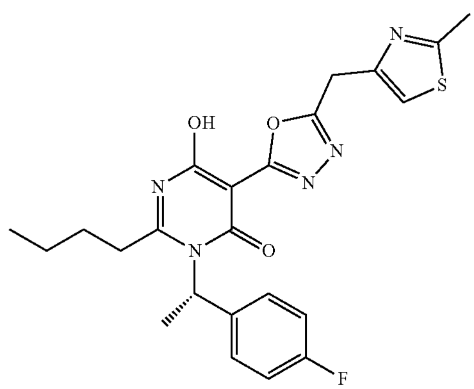 [SMILES: CCCCc1nc(O)c(-c2nnc(Cc3csc(C)n3)o2)c(=O)n1[C@@H](C)c1ccc(F)cc1] | 2-butyl-3-[(1S)-1-(4-fluoro-phenyl)ethyl]-6-hydroxy-5-{5-[(2-methyl-1,3-thiazol-4-yl)-methyl]-1,3,4-oxadiazol-2-yl}-3,4-dihydro-pyrimidin-4-one | ¹H NMR (500 MHz, DMSO-$d_6$) δ 7.35 (s, 1H), 7.32-7.24 (m, 2H), 7.16 (br s, 2H), 4.26 (br s, 2H), 2.60 (s, 3H), 1.81 (br s, 3H), 1.63-1.04 (m, 4H), 0.78 (br s, 3H) | 1.42 A 470.2 | B |
| 96 | 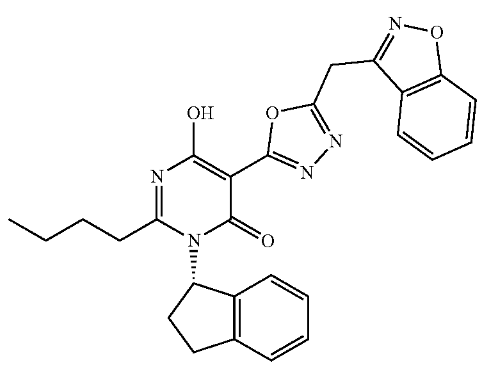 [SMILES: CCCCc1nc(O)c(-c2nnc(Cc3noc4ccccc34)o2)c(=O)n1[C@H]1CCc2ccccc21] | 5-{5-[(1,2-benzoxazol-3-yl)methyl]-1,3,4-oxadiazol-2-yl}-2-butyl-3-[(1S)-2,3-dihydro-1H-inden-1-yl]-6-hydroxy-3,4-dihydro-pyrimidin-4-one | ¹H NMR (500 MHz, DMSO-$d_6$) δ 7.90-7.72 (m, 2H), 7.67 (br d, J = 7.3 Hz, 1H), 7.36 (br t, J = 7.6 Hz, 1H), 7.27-7.10 (m, 4H), 5.95-5.80 (m, 1H) 4.73 (s, 2H), 3.25-2.86 (m, 4H), 1.84-1.60 (m, 2H), 1.51-1.22 (m, 2H), 0.92 (br t, J = 7.0 Hz, 3H) | 1.58 A 484.2 | B |
| 97 | 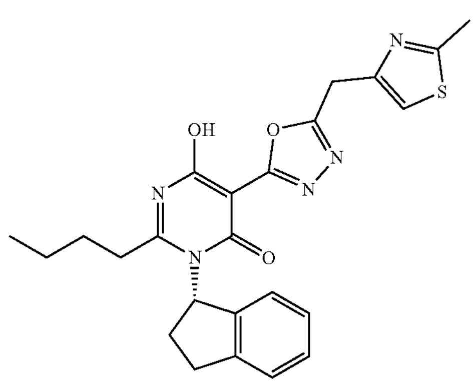 [SMILES: CCCCc1nc(O)c(-c2nnc(Cc3csc(C)n3)o2)c(=O)n1[C@H]1CCc2ccccc21] | 2-butyl-3-[(1S)-2,3-dihydro-1H-inden-1-yl]-6-hydroxy-5-{5-[(2-methyl-1,3-thiazol-4-yl)methyl]-1,3,4-oxadiazol-2-yl}-3,4-dihydro-pyrimidin-4-one | ¹H NMR (500 MHz, DMSO-$d_6$) δ 7.33 (s, 1H), 7.26-7.13 (m, 3H), 7.04 (s, 1H), 5.89 (br t, J = 7.2 Hz, 1H), 4.24 (s, 2H), 3.29-2.83 (m, 4H), 2.59 (s, 3H), 1.72 (br dd, J = 14.5, 7.0 Hz, 2H), 1.44 (br d, J = 7.3 Hz, 2H), 0.93 (br t, J = 7.2 Hz, 3H) | 1.45 A 464.0 | A |

TABLE 2-continued

| Ex # | Structure | Name | ¹H NMR | LC/MS Rt (min) Method M + H | hAPJ cAMP EC$_{50}$ Potency range |
|---|---|---|---|---|---|
| 98 | 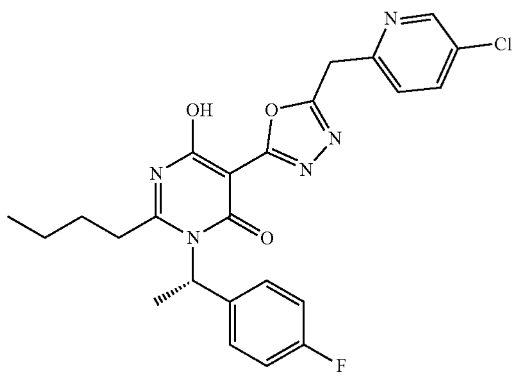 [SMILES: CCCCc1nc(O)c(-c2nnc(Cc3ccc(Cl)cn3)o2)c(=O)n1[C@@H](C)c1ccc(F)cc1] | 2-butyl-5-{5-[(5-chloro-pyridin-2-yl)-methyl]-1,3,4-oxadiazol-2-yl}-3-[(1S)-1-(4-fluorophenyl)-ethyl]-6-hydroxy-3,4-di-hydropyrimidin-4-one | ¹H NMR (500 MHz, DMSO-d$_6$) δ 8.54 (br s, 1H), 7.93 (br d, J = 7.9 Hz, 1H), 7.47 (br d, J = 8.3 Hz, 1H), 7.32 (br s, 2H), 7.16 (br s, 2H), 4.41 (br s, 2H), 3.00-2.67 (m, 2H), 1.85 (br d, J = 4.8 Hz, 3H), 1.70-1.11 (m, 4H), 0.81 (br d, J = 6.4 Hz, 3H) | 1.48 A 484.2 | A |
| 99 | 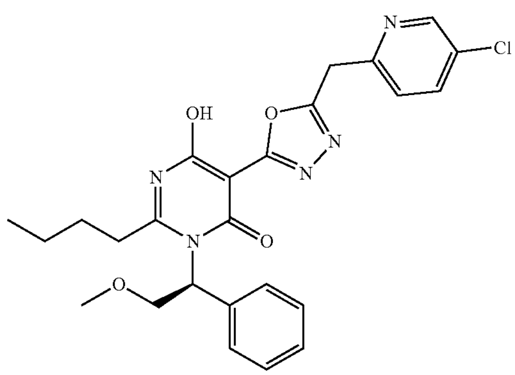 [SMILES: CCCCc1nc(O)c(-c2nnc(Cc3ccc(Cl)cn3)o2)c(=O)n1[C@H](COC)c1ccccc1] | 2-butyl-5-{5-[(5-chloropyridin-2-yl)methyl]-1,3,4-oxadiazol-2-yl}-6-hydroxy-3-[(1S)-2-methoxy-1-phenylethyl]-3,4-dihydro-pyrimidin-4-one | ¹H NMR (500 MHz, DMSO-d$_6$) δ 8.55 (br s, 1H), 7.93 (br d, J = 7.8 Hz, 1H), 7.48 (br d, J = 8.2 Hz, 1H), 7.33 (br s, 2H), 7.27-7.10 (m, 3H), 4.38 (br s, 2H), 4.30-4.13 (m, 1H), 3.35 (s, 3H), 3.02-2.62 (m, 1H), 1.81-1.10 (m, 4H), 1.00-0.67 (m, 3H) | 1.38 A 496.3 | B |
| 100 | 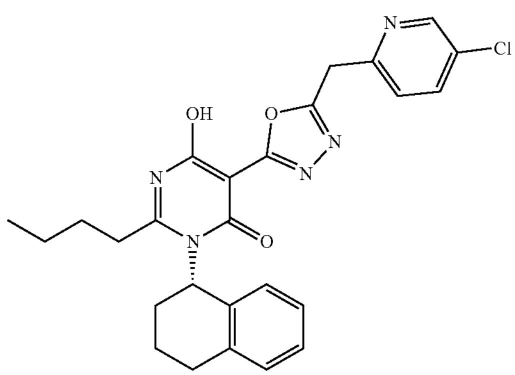 [SMILES: CCCCc1nc(O)c(-c2nnc(Cc3ccc(Cl)cn3)o2)c(=O)n1[C@H]1CCCc2ccccc21] | 2-butyl-5-{5-[(5-chloropyridin-2-yl)methyl]-1,3,4-oxadiazol-2-yl}-6-hydroxy-3-[(1S)-1,2,3,4-tetrahydro-naphthalen-1-yl]-3,4-dihydro-pyrimidin-4-one | ¹H NMR (500 MHz, DMSO-d6) δ 8.62-8.50 (m, 1H), 7.98-7.86 (m, 2H), 7.55-7.41 (m, 2H), 6.92-6.73 (m, 2H), 6.68-6.54 (m, 1H), 5.37 (br s, 1H), 4.41 (s, 2H), 2.83 (br s, 4H), 2.13-1.96 (m, 4H), 1.86-1.62 (m, 2H), 1.49-1.40 (m, 2H), 0.92 (br t, J = 7.3 Hz, 3H). | 1.56 A 492.2 | A |
| 101 | 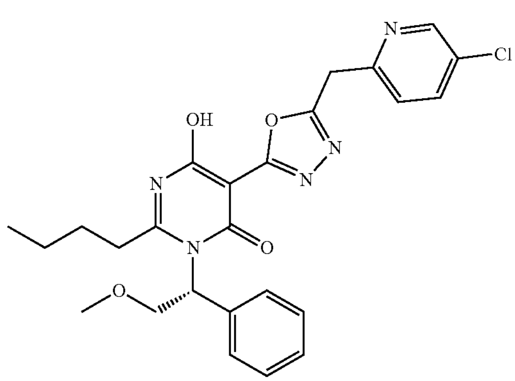 | 2-butyl-5-{5-[(5-chloro-pyridin-2-yl)-methyl]-1,3,4-oxadiazol-2-yl}-6-hydroxy-3-[(1R)-2-methoxy-1-phenylethyl]-3,4-dihydro-pyrimidin-4-one | ¹H NMR (500 MHz, DMSO-d$_6$) δ 8.51(br s, 1H), 7.91 (br d, J = 7.1 Hz, 1H), 7.46 (br d, J = 7.7 Hz, 1H), 7.34 (br s, 2H), 7.27 (br s, 1H), 7.23 (br d, J = 7.7 Hz, 2H), 4.38 (br s, 2H), 4.30-4.14 (m, 2H), 3.34 (s, 3H), 3.00-2.78 (m, 2H), 1.84-1.18 (m, 4H), 0.83 (br s, 3H) | 1.38 A 496.1 | A |

TABLE 2-continued

| Ex # | Structure | Name | ¹H NMR | LC/MS Rt (min) Method M + H | hAPJ cAMP EC$_{50}$ Potency range |
|---|---|---|---|---|---|
| 102 | 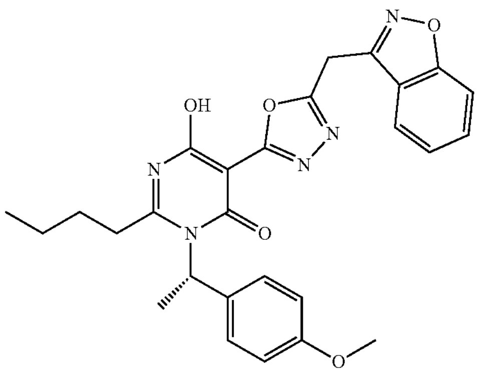 [SMILES: CCCCc1nc(O)c(-c2nnc(Cc3noc4ccccc34)o2)c(=O)n1[C@@H](C)c1ccc(OC)cc1] | 5-{5-[(1,2-benzoxazol-3-yl)methyl]-1,3,4-oxadiazol-2-yl}-2-butyl-6-hydroxy-3-[(1S)-1-(4-methoxy-phenyl)ethyl]-3,4-dihydro-pyrimidin-4-one | ¹H NMR (500 MHz, DMSO-d$_6$) δ 7.85 (br d, J = 7.7 Hz, 1H), 7.77 (br d, J = 8.4 Hz, 1H), 7.73-7.64 (m, 1H), 7.40 (br t, J = 7.4 Hz, 1H), 7.21 (br d, J = 8.5 Hz, 2H), 6.91 (br d, J = 7.5 Hz, 2H), 4.78 (br s, 2H), 3.73 (s, 2H), 1.83 (br s, 3H), 1.65-0.94 (m, 4H), 0.98-0.60 (m, 3H) | 1.46 A 502.2 | C |
| 103 | 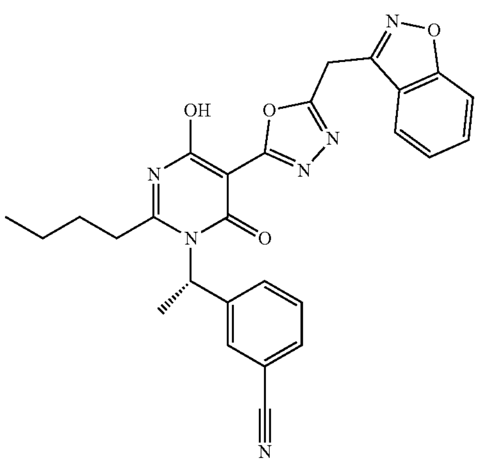 [SMILES: CCCCc1nc(O)c(-c2nnc(Cc3noc4ccccc34)o2)c(=O)n1[C@@H](C)c1cccc(C#N)c1] | 3-[(1S)-1-(5-{5-[(1,2-benzoxazol-3-yl)methyl]-1,3,4-oxadiazol-2-yl}-2-butyl-4-hydroxy-6-oxo-1,6-dihydro-pyrimidin-1-yl)-ethyl]benzonitrile | ¹H NMR (500 MHz, DMSO-d$_6$) δ 7.84 (br d, J = 7.0 Hz, 1H), 7.79-7.58 (m, 5H), 7.54 (br s, 2H), 7.42-7.31 (m, 1H), 4.70 (br s, 2H), 3.02-2.62 (m, 2H), 1.83 (br s, 3H), 1.66-1.06 (m, 4H), 0.99-0.53 (m, 3H) | 1.37 A 497.2 | B |
| 104 | 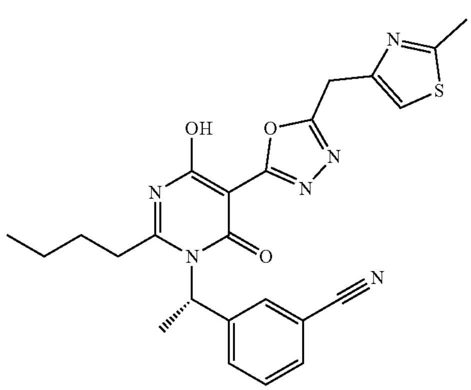 [SMILES: CCCCc1nc(O)c(-c2nnc(Cc3csc(C)n3)o2)c(=O)n1[C@@H](C)c1cccc(C#N)c1] | 3-[(1S)-1-(2-butyl-4-hydroxy-5-{5-[(2-methyl-1,3-thiazol-4-yl)-methyl]-1,3,4-oxadiazol-2-yl}-6-oxo-1,6-dihydro-pyrimidin-1-yl)-ethyl]benzonitrile | ¹H NMR (500 MHz, DMSO-d$_6$) δ 7.68 (br s, 3H), 7.53 (br s, 2H), 7.33 (br s, 1H), 5.66-5.27 (m, 1H), 4.23 (br s, 2H), 2.98-2.60 (m, 2H), 2.59 (s, 3H), 1.82 (br s, 3H), 1.67-1.19 (m, 4H), 0.95-0.70 (m, 3H) | 1.18 A 477.3 | B |

TABLE 2-continued

| Ex # | Structure | Name | ¹H NMR | LC/MS Rt (min) Method M + H | hAPJ cAMP EC₅₀ Potency range |
|---|---|---|---|---|---|
| 105 | 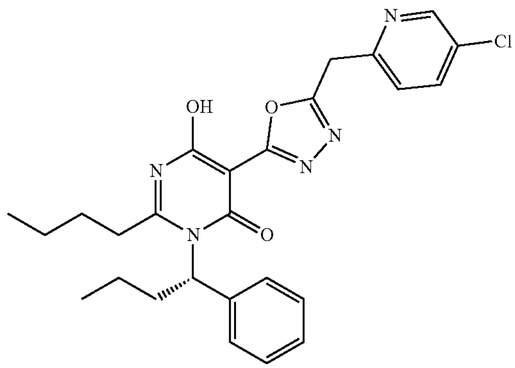 [SMILES: CCCCc1nc(O)c(-c2nnc(Cc3ccc(Cl)cn3)o2)c(=O)n1[C@@H](CCC)c1ccccc1] | 2-butyl-5-{5-[(5-chloropyridin-2-yl)methyl]-1,3,4-oxadiazol-2-yl}-6-hydroxy-3-[(1S)-1-phenyl-butyl]-3,4-di-hydropyrimidin-4-one | ¹H NMR (500 MHz, DMSO-d₆) δ 8.54 (br s, 1H), 7.93 (br d, J = 7.7 Hz, 1H), 7.49 (br d, J = 7.7 Hz, 1H), 7.34 (br s, 2H), 7.24 (br s, 3H), 6.79-6.37 (m, 1H), 4.39 (br s, 2H), 2.41-2.02 (m, 2H), 1.68-1.05 (m, 6H), 0.94 (br t, J = 7.1 Hz, 3H), 0.78-0.36 (m, 3H) | 1.72 A 494.3 | A |
| 106 | 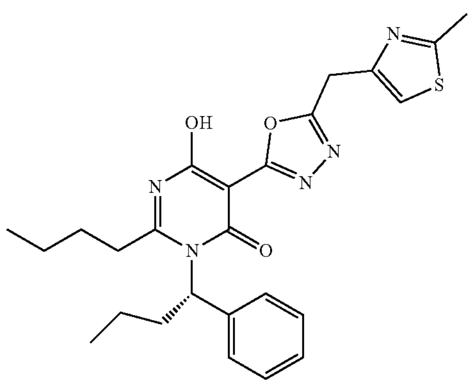 [SMILES: CCCCc1nc(O)c(-c2nnc(Cc3csc(C)n3)o2)c(=O)n1[C@@H](CCC)c1ccccc1] | 2-butyl-6-hydroxy-5-{5-[(2-methyl-1,3-thiazol-4-yl)-methyl]-1,3,4-oxadiazol-2-yl}-3-[(1S)-1-phenyl-butyl]-3,4-di-hydropyrimidin-4-one | ¹H NMR (500 MHz, DMSO-d₆) δ 7.36 (br d, J = 11.5 Hz, 3H), 7.25 (br s, 3H), 4.28 (br s, 2H), 2.62 (s, 3H), 2.44-2.17 (m, 2H), 1.62-1.16 (m, 4H), 0.95 (br t, J = 7.2 Hz, 5H), 0.62 (br s, 3H) | 1.52 A 480.3 | B |
| 107 | 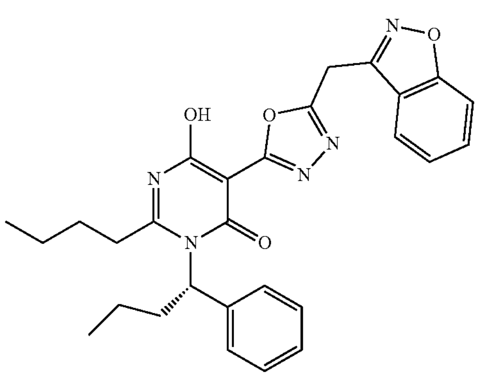 [SMILES: CCCCc1nc(O)c(-c2nnc(Cc3noc4ccccc34)o2)c(=O)n1[C@@H](CCC)c1ccccc1] | 5-{5-[(1,2-benzoxazol-3-yl)methyl]-1,3,4-oxadiazol-2-yl}-2-butyl-6-hydroxy-3-[(1S)-1-phenyl-butyl]-3,4-di-hydropyrimidin-4-one | ¹H NMR (500 MHz, DMSO-d₆) δ 7.87 (br d, J = 6.5 Hz, 1H), 7.78 (br d, J = 8.4 Hz, 1H), 7.69 (br t, J = 7.7 Hz, 1H), 7.39 (br d, J = 15.3 Hz, 3H), 7.30 (br d, J = 7.3 Hz, 3H), 4.81 (br s, 2H), 2.46 (br d, J = 13.0 Hz, 2H), 1.49-1.22 (m, 4H), 1.16 (br t, J = 6.6 Hz, 2H), 0.96 (br t, J = 7.2 Hz, 3H), 0.87-0.54 (m, 3H) | 1.99 B 500.1 | B |

TABLE 2-continued

| Ex # | Structure | Name | ¹H NMR | LC/MS Rt (min) Method M + H | hAPJ cAMP EC₅₀ Potency range |
|---|---|---|---|---|---|
| 108 | 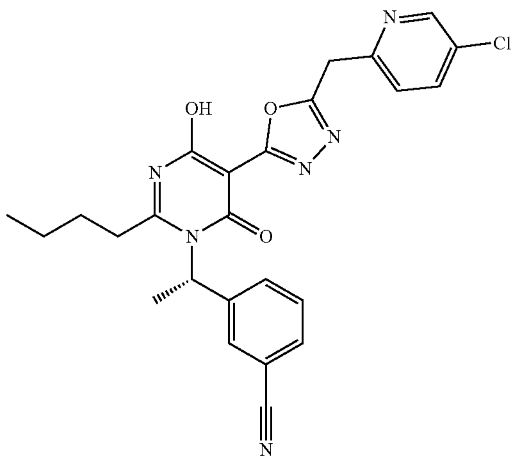 [SMILES: CCCCc1nc(O)c(-c2nnc(Cc3ccc(Cl)cn3)o2)c(=O)n1[C@@H](C)c1cccc(C#N)c1] | 3-[(1S)-1-(2-butyl-5-{5-[(5-chloropyridin-2-yl)methyl]-1,3,4-oxadiazol-2-yl}-4-hydroxy-6-oxo-1,6-dihydropyrimidin-1-yl)ethyl]-benzonitrile | $^1$H NMR (500 MHz, DMSO-d$_6$) δ 8.53 (br s, 1H), 7.92 (br d, J = 8.2 Hz, 1H), 7.82 (br s, 1H), 7.71 (br s, 1H), 7.62 (br d, J = 6.8 Hz, 1H), 7.55 (br d, J = 7.3 Hz, 1H), 7.46 (br d, J = 8.2 Hz, 1H), 5.72-5.45 (m, 1H), 4.39 (br s, 2H), 1.87 (br d, J = 4.9 Hz, 3H), 1.71-1.24 (m, 4H), 0.87 (br d, J = 2.4 Hz, 3H) | 1.27 A 491.3 | A |
| 109 | (Racemate) | 2-butyl-5-{5-[(5-chloropyridin-2-yl)methyl]-1,3,4-oxadiazol-2-yl}-6-hydroxy-3-[1-(pyridin-4-yl)-ethyl]-3,4-dihydropyrimidin-4-one | $^1$H NMR (500 MHz, DMSO-d$_6$) δ 8.54 (br s, 1H), 8.48 (br s, 2H), 7.92 (br d, J = 8.2 Hz, 1H), 7.47 (br d, J = 8.6 Hz, 1H), 7.19 (br d, J = 5.0 Hz, 2H), 4.36 (s, 2H), 1.85-1.71 (m, 3H), 1.63-1.26 (m, 4H), 0.95-0.76 (m, 3H) | 1.01 A 467.2 | A |
| 110 | (Racemate) | 5-{5-[(1,2-benzoxazol-3-yl)methyl]-1,3,4-oxadiazol-2-yl}-2-butyl-6-hydroxy-3-[1-(pyridin-4-yl)-ethyl]-3,4-dihydropyrimidin-4-one | $^1$H NMR (500 MHz, DMSO-d$_6$) δ 8.48 (br s, 2H), 7.87 (br d, J = 7.7 Hz, 1H), 7.76 (br d, J = 8.4 Hz, 1H), 7.68 (br d, J = 7.4 Hz, 1H), 7.38 (br t, J = 7.3 Hz, 1H), 7.17 (br d, J = 5.0 Hz, 2H), 4.70 (br s, 2H), 1.78 (br s, 3H), 1.64-1.14 (m, 4H), 1.00-0.69 (m, 3H) | 0.94 B 472.9 | B |

TABLE 2-continued

| Ex # | Structure | Name | ¹H NMR | LC/MS Rt (min) Method M + H | hAPJ cAMP EC₅₀ Potency range |
|---|---|---|---|---|---|
| 111 | 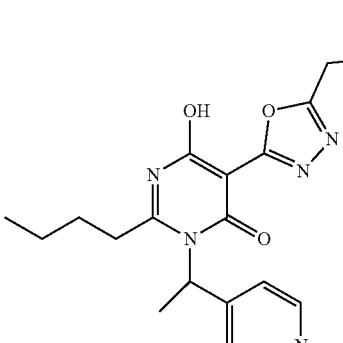<br>(Racemate) | 2-butyl-5-{5-[(5-chloropyridin-2-yl)methyl]-1,3,4-oxadiazol-2-yl}-6-hydroxy-3-[1-(pyridin-4-yl)ethyl]-3,4-dihydropyrimidin-4-one | ¹H NMR (500 MHz, DMSO-d₆) δ 8.54 (br s, 1H), 8.51 (br s, 2H), 7.93 (br d, J = 8.2 Hz, 1H), 7.47 (br d, J = 8.2 Hz, 1H), 7.28 (br d, J = 4.9 Hz, 2H), 5.75-5.43 (m, 1H), 4.40 (br s, 2H), 1.86 (br d, J = 6.3 Hz, 3H), 1.70-1.08 (m, 4H), 1.01-0.73 (m, 3H) | 1.01 A 467.2 | A |
| 112 | 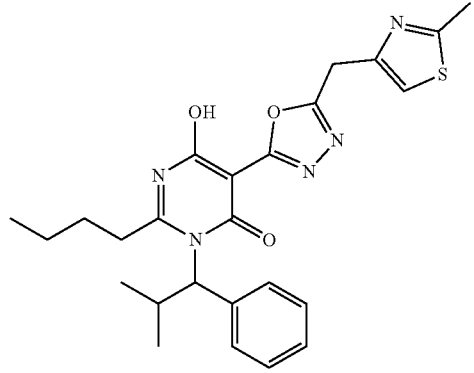<br>(Racemate) | 2-butyl-6-hydroxy-5-{5-[(2-methyl-1,3-thiazol-4-yl)methyl]-1,3,4-oxadiazol-2-yl}-3-(2-methyl-1-phenylpropyl)-3,4-dihydropyrimidin-4-one | ¹H NMR (500 MHz, DMSO-d₆) δ 7.55 (br d, J = 2.7 Hz, 1H), 7.45-7.19 (m, 6H), 6.32 (m, 1H), 4.29 (br s, 2H), 2.60 (br s, 3H), 2.44-2.17 (m, 1H), 1.81-1.03 (m, 4H), 0.99-0.70 (m, 7H), 0.57 (br s, 3H) | 1.60 B 480.1 | B |
| 113 | 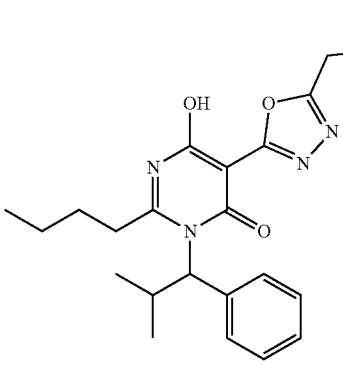<br>(Racemate) | 2-butyl-5-{5-[(5-chloropyridin-2-yl)methyl]-1,3,4-oxadiazol-2-yl}-6-hydroxy-3-(2-methyl-1-phenylpropyl)-3,4-dihydropyrimidin-4-one | ¹H NMR (500 MHz, DMSO-d₆) δ 8.29 (br s, 1H), 7.67 (br s, 1H), 7.41-7.19 (m, 2H), 7.10 (br d, J = 19.8 Hz, 4H), 6.24-5.94 and 4.52 (m, 1H), 4.18 (br s, 2H), 2.18 (br d, J = 3.1 Hz, 1H), 1.67-1.03 (m, 2H), 0.87 (br s, 2H), 0.74-0.50 (m, 6H), 0.43-0.14 (m, 3H) | 1.58 A 494.3 | A |

TABLE 2-continued

| Ex # | Structure | Name | ¹H NMR | LC/MS Rt (min) Method M + H | hAPJ cAMP EC₅₀ Potency range |
|---|---|---|---|---|---|
| 114 | 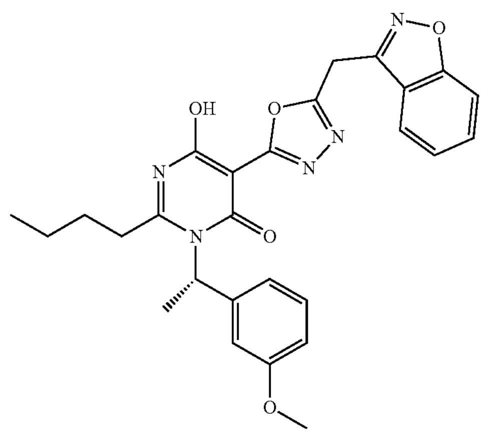 [SMILES: CCCCc1nc(O)c(-c2nnc(Cc3noc4ccccc34)o2)c(=O)n1[C@@H](C)c1cccc(OC)c1] | 5-{5-[(1,2-benzoxazol-3-yl)methyl]-1,3,4-oxadiazol-2-yl}-2-butyl-6-hydroxy-3-[(1S)-1-(3-methoxyphenyl)ethyl]-3,4-dihydropyrimidin-4-one | ¹H NMR (500 MHz, DMSO-d₆) δ 7.84 (br d, J = 7.4 Hz, 1H), 7.74 (br d, J = 8.4 Hz, 1H), 7.70-7.61 (m, 1H), 7.38 (br t, J = 6.9 Hz, 1H), 7.26 (br t, J = 7.6 Hz, 1H), 6.83 (br d, J = 6.9 Hz, 1H), 6.76 (br d, J = 7.3 Hz, 1H), 6.72 (br s, 1H), 4.72 (br s, 2H), 3.76 (br s, 3H), 1.77 (br s, 3H), 1.59-0.91 (m, 4H), 0.72 (br s, 3H) | 1.46 A 502.3 | B |
| 115 | (Racemate) | 5-{5-[(1,2-benzoxazol-3-yl)methyl]-1,3,4-oxadiazol-2-yl}-2-butyl-6-hydroxy-3-(2-methyl-1-phenylpropyl)-3,4-dihydropyrimidin-4-one | ¹H NMR (500 MHz, DMSO-d₆) δ 7.72-7.56 (m, 1H), 7.55-7.48 (m, 1H), 7.48-7.39 (m, 1H), 7.31 (br s, 1H), 7.21-6.96 (m, 4H), 4.53 (br s, 2H), 2.23-2.10 (m, 1H), 1.58-1.01 (m, 2H), 0.88 (br s, 2H), 0.75-0.45 (m, 6H), 0.40-0.12 (m, 3H) | 1.65 A 500.3 | B |
| 116 | 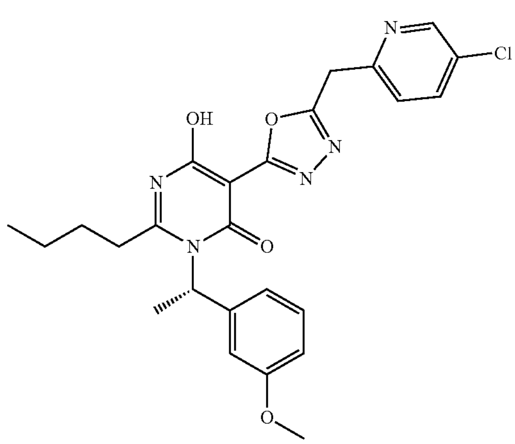 [SMILES: CCCCc1nc(O)c(-c2nnc(Cc3ccc(Cl)cn3)o2)c(=O)n1[C@@H](C)c1cccc(OC)c1] | 2-butyl-5-{5-[(5-chloropyridin-2-yl)methyl]-1,3,4-oxadiazol-2-yl}-6-hydroxy-3-[(1S)-1-(3-methoxyphenyl)ethyl]-3,4-dihydropyrimidin-4-one | ¹H NMR (500 MHz, DMSO-d₆) δ 8.53 (br s, 1H), 7.92 (br d, J = 7.7 Hz, 1H), 7.47 (br d, J = 8.1 Hz, 1H), 7.27 (br s, 1H), 6.86 (br s, 1H), 6.81-6.66 (m, 2H), 4.40 (br s, 2H), 3.81-3.52 (m, 3H), 1.82 (br d, J = 3.2 Hz, 3H), 1.62-1.04 (m, 4H), 0.78 (br s, 3H) | 1.39 A 496.3 | A |

TABLE 2-continued

| Ex # | Structure | Name | ¹H NMR | LC/MS Rt (min) Method M + H | hAPJ cAMP EC₅₀ Potency range |
|---|---|---|---|---|---|
| 117 | 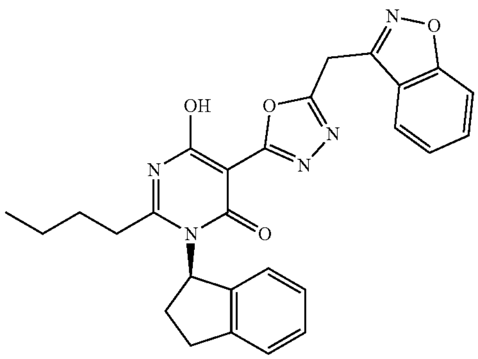 [SMILES: CCCCc1nc(O)c(-c2nnc(Cc3noc4ccccc34)o2)c(=O)n1[C@@H]1CCc2ccccc21] | 5-{5-[(1,2-benzoxazol-3-yl)methyl]-1,3,4-oxadiazol-2-yl}-2-butyl-3-[(1R)-2,3-dihydro-1H-inden-1-yl]-6-hydroxy-3,4-dihydropyrimidin-4-one | ¹H NMR (500 MHz, DMSO-d₆) δ 7.93-7.59 (m, 3H), 7.59-6.91 (m, 5H), 5.79 (br s, 1H), 4.75 and 4.68 (s, 2H), 3.00-2.77 (m, 4H), 2.43-2.00 (m, 2H), 1.69 (br d, J = 7.5 Hz, 2H), 1.41 (br d, J = 6.8 Hz, 2H), 0.98-0.27 (m, 3H) | 1.48 A 484.2 | C |
| 118 | 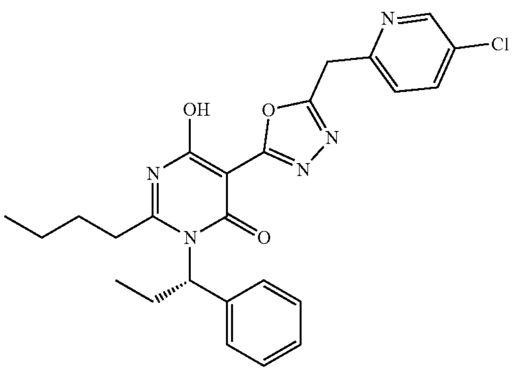 [SMILES: CCCCc1nc(O)c(-c2nnc(Cc3ccc(Cl)cn3)o2)c(=O)n1[C@@H](CC)c1ccccc1] | 2-butyl-5-{5-[(5-chloropyridin-2-yl)methyl]-1,3,4-oxadiazol-2-yl}-6-hydroxy-3-[(1S)-1-phenylpropyl]-3,4-dihydropyrimidin-4-one | ¹H NMR (500 MHz, DMSO-d₆) δ 8.55 (br s, 1H), 7.94 (br d, J = 6.6 Hz, 1H), 7.49 (br d, J = 7.7 Hz, 1H), 7.37 (br s, 2H), 7.30 (br d, J = 7.5 Hz, 3H), 4.43 (br s, 2H), 2.42-2.02 (m, 2H), 1.90-1.01 (m, 4H), 0.97-0.57 (m, 6H) | 1.49 A 480.3 | A |
| 119 | 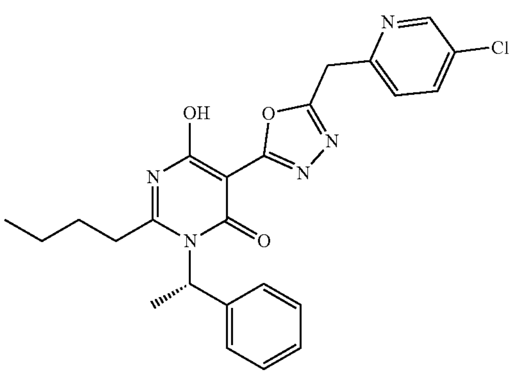 [SMILES: CCCCc1nc(O)c(-c2nnc(Cc3ccc(Cl)cn3)o2)c(=O)n1[C@@H](C)c1ccccc1] | 2-butyl-5-{5-[(5-chloropyridin-2-yl)methyl]-1,3,4-oxadiazol-2-yl}-6-hydroxy-3-[(1S)-1-phenylethyl]-3,4-dihydropyrimidin-4-one | ¹H NMR (500 MHz, DMSO-d₆) δ 8.54 (br s, 1H), 7.93 (br d, J = 8.2 Hz, 1H), 7.48 (br d, J = 8.3 Hz, 1H), 7.42-7.31 (m, 2H), 7.28-7.18 (m, 3H), 4.38 (s, 2H), 1.79 (br s, 3H), 1.58-0.98 (m, 4H), 0.72 (br s, 3H) | 1.40 A 466.3 | A |
| 120 | 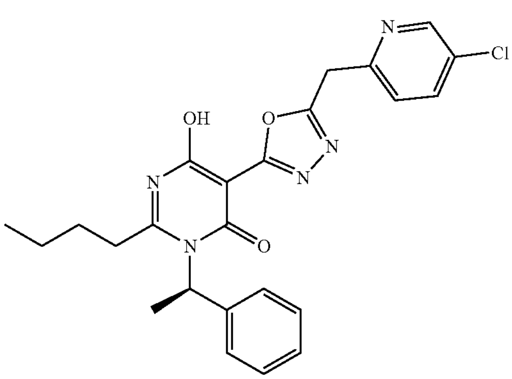 [SMILES: CCCCc1nc(O)c(-c2nnc(Cc3ccc(Cl)cn3)o2)c(=O)n1[C@H](C)c1ccccc1] | 2-butyl-5-{5-[(5-chloropyridin-2-yl)methyl]-1,3,4-oxadiazol-2-yl}-6-hydroxy-3-[(1R)-1-phenylethyl]-3,4-dihydropyrimidin-4-one | ¹H NMR (500 MHz, DMSO-d₆) δ 8.53 (br s, 1H), 7.92 (br d, J = 8.0 Hz, 1H), 7.47 (br d, J = 1.9 Hz, 1H), 7.34 (br d, J = 7.0 Hz, 2H), 7.24 (br d, J = 7.2 Hz, 3H), 4.39 (br s, 2H), 1.83 (br d, J = 4.3 Hz, 3H), 1.66-1.12 (m, 4H), 0.75 (br s, 3H) | 1.36 A 466.2 | A |

TABLE 2-continued

| Ex # | Structure | Name | ¹H NMR | LC/MS Rt (min) Method M + H | hAPJ cAMP EC$_{50}$ Potency range |
|---|---|---|---|---|---|
| 121 | 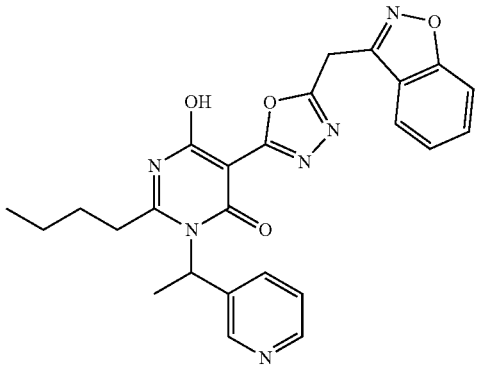 (Racemate) | 5-{5-[(1,2-benzoxazol-3-yl)methyl]-1,3,4-oxadiazol-2-yl}-2-butyl-6-hydroxy-3-[1-(pyridin-3-yl)ethyl]-3,4-dihydropyrimidin-4-one | ¹H NMR (500 MHz, DMSO-d$_6$) δ 8.56-8.31 (m, 2H), 7.85 (br d, J = 7.8 Hz, 1H), 7.75 (br d, J = 8.4 Hz, 1H), 7.70-7.59 (m, 2H), 7.44-7.11 (m, 2H), 4.71 (s, 2H), 1.84 (br d, J = 3.7 Hz, 3H), 1.67-1.04 (m, 4H), 0.81 (br s, 3H) | 1.11 A 473.3 | C |
| 122 | 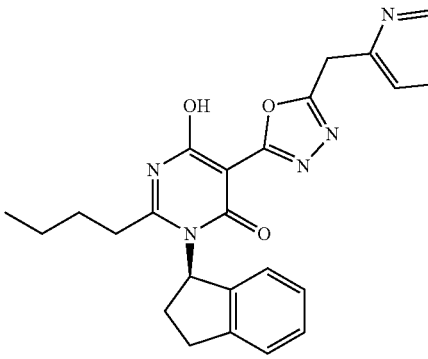 | 2-butyl-5-{5-[(5-chloropyridin-2-yl)methyl]-1,3,4-oxadiazol-2-yl}-3-[(1R)-2,3-dihydro-1H-inden-1-yl]-6-hydroxy-3,4-dihydropyrimidin-4-one | ¹H NMR (500 MHz, DMSO-d$_6$) δ 8.52 (s, 1H), 7.96-7.75 (m, 1H), 7.45 (d, J = 8.3 Hz, 1H), 7.25 (s, 1H), 7.23-7.20 (m, 1H), 7.20-7.09 (m, 2H), 7.05 (s, 1H), 5.89 (br t, J = 7.4 Hz, 1H), 4.37 (s, 2H), 3.21-2.86 (m, 4H), 1.81-1.63 (m, 2H), 1.55-1.35 (m, 2H), 0.92 (br t, J = 7.3 Hz, 3H) | 1.59 B 478.2 | B |
| 123 | 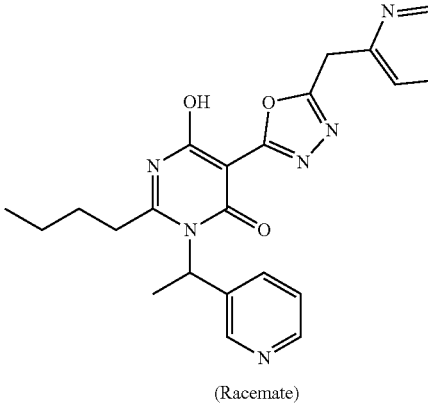 (Racemate) | 2-butyl-5-{5-[(5-chloropyridin-2-yl)methyl]-1,3,4-oxadiazol-2-yl}-6-hydroxy-3-[1-(pyridin-3-yl)ethyl]-3,4-dihydropyrimidin-4-one | ¹H NMR (500 MHz, DMSO-d$_6$) δ 8.53 (br s, 1H), 8.46-8.34 (m, 2H), 7.92 (br d, J = 7.9 Hz, 1H), 7.62 (br d, J = 7.4 Hz, 1H), 7.47 (br d, J = 8.2 Hz, 1H), 7.38-7.30 (m, 1H), 4.36 (s, 2H), 1.83 (br d, J = 3.6 Hz, 3H), 1.64-1.05 (m, 4H), 0.94-0.51 (m, 3H) | 0.88 B 467.1 | B |

TABLE 2-continued

| Ex # | Structure | Name | ¹H NMR | LC/MS Rt (min) Method M + H | hAPJ cAMP EC$_{50}$ Potency range |
|---|---|---|---|---|---|
| 124 | 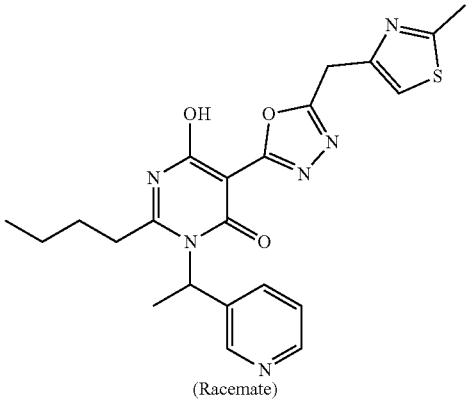<br>(Racemate) | 2-butyl-6-hydroxy-5-{5-[(2-methyl-1,3-thiazol-4-yl)-methyl]-1,3,4-oxadiazol-2-yl}-3-[1-(pyridin-3-yl)ethyl]-3,4-dihydropyrimidin-4-one | ¹H NMR (500 MHz, DMSO-d$_6$) δ 8.44 (br d, J = 13.8 Hz, 2H), 7.64 (br d, J = 7.3 Hz, 1H), 7.46-7.09 (m, 2H), 4.24 (br s, 2H), 2.60 (s, 3H), 1.85 (br d, J = 3.7 Hz, 3H), 1.72-1.04 (m, 4H), 1.02-0.71 (m, 3H) | 0.95<br>A<br>453.3 | C |

What is claimed is:

1. A compound of Formula (I):

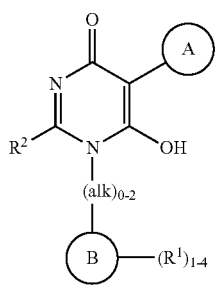

or a stereoisomer, an enantiomer, a diastereoisomer, a tautomer, or a pharmaceutically acceptable salt thereof, wherein:

alk is $C_{1-6}$ alkyl substituted with 1-5 $R^7$;

ring A is 5- to 6-membered heteroaryl;

ring B is independently selected from $C_{3-6}$ cycloalkyl, $C_{3-6}$ cycloalkenyl, aryl, bicyclic carbocyclyl, and 6-membered heteroaryl;

$R^1$ is independently selected from H, halogen, NO$_2$, —(CH$_2$)$_n$OR$^b$, —(CH$_2$)$_n$S(O)$_p$R$^c$, —(CH$_2$)$_n$C(=O)R$^b$, —(CH$_2$)$_n$NR$^a$R$^a$, —(CH$_2$)$_n$CN, —(CH$_2$)$_n$C(=O)NR$^a$R$^a$, —(CH$_2$)$_n$NR$^a$C(=O)R$^b$, —(CH$_2$)$_n$NR$^a$C(=O)NR$^a$R$^a$, —(CH$_2$)$_n$NR$^a$C(=O)OR$^b$, —(CH$_2$)$_n$OC(=O)NR$^a$R$^a$, —(CH$_2$)$_n$C(=O)OR$^b$, —(CH$_2$)$_n$S(O)$_p$NR$^a$R$^a$, —(CH$_2$)$_n$NR$^a$S(O)$_p$NR$^a$R$^a$, —(CH$_2$)$_n$NR$^a$S(O)$_p$R$^c$, C$_{1-4}$ alkyl substituted with 0-3 R$^e$, —(CH$_2$)$_n$—C$_{3-6}$ carbocyclyl substituted with 0-3 R$^e$, and —(CH$_2$)$_n$-heterocyclyl substituted with 0-3 R$^e$;

$R^2$ is independently selected from $C_{1-5}$ alkyl substituted with 0-3 R$^e$; $C_{2-5}$ alkenyl substituted with 0-3 R$^e$, aryl substituted with 0-3 R$^e$, heterocyclyl substituted with 0-3 R$^e$, and $C_{3-6}$ cycloalkyl substituted with 0-3 R$^e$; provided when $R^2$ is $C_{1-5}$ alkyl, the carbon atom and the groups attached thereto except the one attached to the pyrimidine ring may be replaced by O, N, and S;

$R^7$ is independently selected from H, $C_{1-5}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;

$R^a$, at each occurrence, is independently selected from H, $C_{1-6}$ alkyl substituted with 0-5 R$^e$, $C_{2-6}$ alkenyl substituted with 0-5 R$^e$, $C_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$; or R$^a$ and R$^a$ together with the nitrogen atom to which they are both attached form a heterocyclic ring substituted with 0-5 R$^e$;

$R^b$, at each occurrence, is independently selected from H, $C_{1-6}$ alkyl substituted with 0-5 R$^e$, $C_{2-6}$ alkenyl substituted with 0-5 R$^e$, $C_{2-6}$ alkynyl substituted with 0-5 R$^e$, —(CH$_2$)$_n$—C$_{3-10}$carbocyclyl substituted with 0-5 R$^e$, and —(CH$_2$)$_n$-heterocyclyl substituted with 0-5 R$^e$;

$R^c$, at each occurrence, is independently selected from $C_{1-6}$ alkyl substituted with 0-5 R$^e$, $C_{2-6}$alkenyl substituted with 0-5 R$^e$, $C_{2-6}$alkynyl substituted with 0-5 R$^e$, $C_{3-6}$carbocyclyl, and heterocyclyl;

$R^e$, at each occurrence, is independently selected from $C_{1-6}$ alkyl (optionally substituted with halogen, OH, and CN), $C_{2-6}$ alkenyl, $C_{2-6}$ alkynyl, —(CH$_2$)$_n$—C$_{3-6}$ cycloalkyl, —(CH$_2$)$_n$—C$_{4-6}$ heterocyclyl, —(CH$_2$)$_n$-aryl, —(CH$_2$)$_n$-heteroaryl, F, Cl, Br, CN, NO$_2$, =O, CO$_2$H, —(CH$_2$)$_n$OR$_f$, S(O)$_p$R$^f$, C(=O)NR$^f$R$^f$, NR$^f$C(=O)R$^f$, S(O)$_p$NR$^f$R$^f$, NR$^f$S(O)$_p$R$^f$, NR$^f$C(=O)OR$^f$, OC(=O)NR$^f$R$^f$ and —(CH$_2$)$_n$NR$^f$R$^f$;

$R^f$, at each occurrence, is independently selected from H, $C_{1-5}$alkyl (optionally substituted with halogen and OH), $C_{3-6}$ cycloalkyl, and phenyl, or R$^f$ and R$^f$ together with the nitrogen atom to which they are both attached form a heterocyclic ring optionally substituted with $C_{1-4}$alkyl;

n is independently selected from zero, 1, 2, and 3;

r is independently selected from 1 and 2; and p, at each occurrence, is independently selected from zero, 1, and 2.

2. The compound according to claim 1, or a stereoisomer, an enantiomer, a diastereomer, a tautomer, or a pharmaceutically acceptable salt thereof, wherein:

ring A is independently selected from

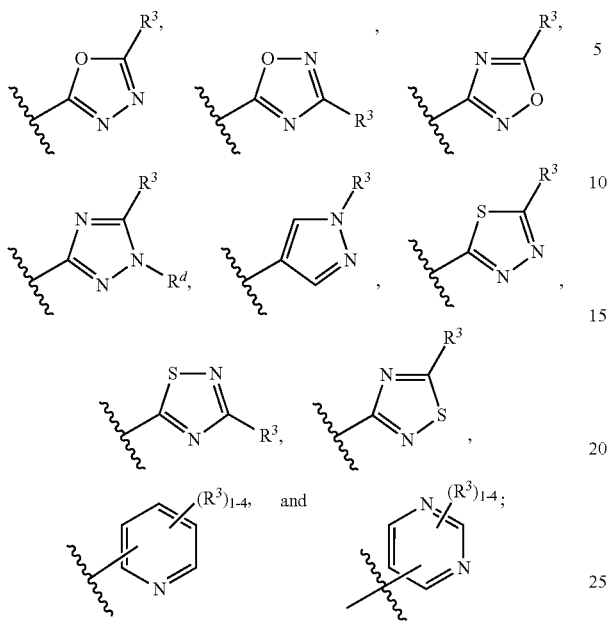

R$^3$ is independently selected from
(1) —(CR$^4$R$^4$)$_r$C(=O)OC$_{1-4}$ alkyl substituted with 0-5 R$^e$,
(2) —(CR$^4$R$^4$)$_r$NR$^8$R$^8$,
(3) —(CR$^4$R$^4$)$_r$C(=O)NR$^8$R$^8$,
(4) —(CR$^4$R$^4$)$_r$NR$^a$C(=O) C$_{1-4}$alkyl substituted with 0-5 R$^e$,
(5) —(CR$^4$R$^4$)$_r$NR$^a$C(=O)(CR$^4$R$^4$)$_n$OC$_{1-4}$alkyl substituted with 0-5 R$^e$,
(6) —(CR$^4$R$^4$)$_r$—R$^5$,
(7) —(CR$^4$R$^4$)$_r$—OR$^5$, and
(8) —(CR$^4$R$^4$)$_r$NR$^a$C(=O)(CR$^4$R$^4$)$_n$R$^5$;

R$^4$ is independently selected from H, halogen, NR$^a$R$^a$, OC$_{1-4}$ alkyl, and C$_{1-4}$ alkyl; or R$^4$ and R$^4$ together with the carbon atom to which they are both attached form C$_{3-6}$ cycloalkyl substituted with 0-5 R$^e$;

R$^5$ is independently selected from —(CH$_2$)$_n$—C$_{3-10}$ carbocycle and —(CH$_2$)$_n$-heterocycle comprising carbon atoms and 1-3 heteroatoms selected from N, NR$^{6a}$, O, and S, each substituted with 0-5 R$^6$;

R$^6$ is independently selected from H, halogen, =O, —(CH$_2$)$_n$OR$^b$, (CH$_2$)$_n$S(O)$_p$R$^c$, —(CH$_2$)$_n$C(=O)R$^b$, —(CH$_2$)$_n$NR$^a$R$^a$, —(CH$_2$)$_n$CN, —(CH$_2$)$_n$C(=O)NR$^a$R$^a$, —(CH$_2$)$_n$NR$^a$C(=O)R$^b$, —(CH$_2$)$_n$NR$^a$C(=O)NR$^a$R$^a$, —(CH$_2$)$_n$NR$^a$C(=O)OR$^b$, —(CH$_2$)$_n$OC(=O)NR$^a$R$^a$, —(CH$_2$)$_n$C(=O)OR$^b$, —(CH$_2$)$_n$S(O)$_p$NR$^a$R$^a$, —(CH$_2$)$_n$NR$^a$S(O)$_p$NR$^a$R$^a$, —(CH$_2$)$_n$NR$^a$S(O)$_p$R$^c$, C$_{1-5}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$;

R$^{6a}$ is independently selected from H, —S(O)$_p$R$^c$, —C(=O)R$^b$, —C(=O)NR$^a$R$^a$, —C(=O)OR$^b$, —S(O)$_p$NR$^a$R$^a$, C$_{1-5}$ alkyl substituted with 0-3 R$^e$, (CH$_2$)$_n$—C$_{3-6}$ carbocyclyl substituted with 0-3 R$^e$, and —(CH$_2$)$_n$-heterocyclyl substituted with 0-3 R$^e$; and R$^8$ and R$^8$ together with the nitrogen atom to which they are both attached form a heterocyclic ring comprising carbon atoms and 0-3 additional heteroatoms selected from N, NR$^{6a}$, O, and S, and substituted with 0-5 R$^6$.

3. The compound according to claim 2 having Formula (II):

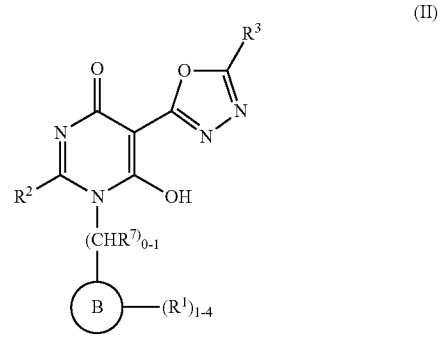

or a stereoisomer, an enantiomer, a diastereoisomer, a tautomer, or a pharmaceutically acceptable salt thereof, wherein:

ring B is independently selected from

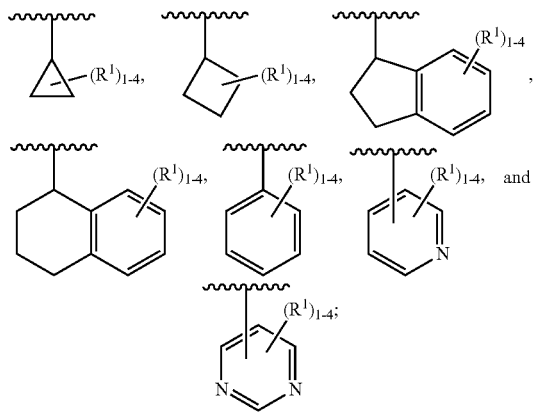

R$^1$ is independently selected from H, F, Cl, Br, NO$_2$, —(CH$_2$)$_n$OR$^b$, —(CH$_2$)$_n$C(=O)R$^b$, —(CH$_2$)$_n$NR$^a$R$^a$, —(CH$_2$)$_n$CN, —(CH$_2$)$_n$C(=O)NR$^a$R$^a$, —(CH$_2$)$_n$NR$^a$C(=O)R$^b$, C$_{1-4}$ alkyl substituted with 0-3 R$^e$ and C$_{3-6}$ cycloalkyl substituted with 0-3 R$^e$;

R$^2$ is independently selected from C$_{1-5}$ alkyl substituted with 0-3 R$^e$; C$_{2-5}$ alkenyl, aryl substituted with 0-3 R$^e$, heterocyclyl substituted with 0-3 R$^e$, and C$_{3-6}$ cycloalkyl; provided when R$^2$ is C$_{1-5}$ alkyl, the carbon atom and the groups attached thereto except the one attached to the pyrimidine ring may be replaced by O, N, and S;

R$^3$ is independently selected from
(1) —(CR$^4$R$^4$)$_r$C(=O)OC$_{1-4}$ alkyl substituted with 0-5 R$^e$,
(2) —(CR$^4$R$^4$)$_r$NR$^8$R$^8$,
(3) —(CR$^4$R$^4$)$_r$C(=O)NR$^8$R$^8$,
(4) —(CR$^4$R$^4$)$_r$NR$^a$C(=O)C$_{1-4}$alkyl substituted with 0-5 R$^e$,
(5) —(CR$^4$R$^4$)$_r$NR$^a$C(=O)(CR$^4$R$^4$)$_n$OC$_{1-4}$alkyl substituted with 0-5 R$^e$,
(6) —(CR$^4$R$^4$)$_r$—R$^5$,
(7) —(CR$^4$R$^4$)$_r$—OR$^5$, and
(8) —(CR$^4$R$^4$)$_r$NR$^a$C(=O)(CR$^4$R$^4$)$_n$R$^5$;

R$^4$ is independently selected from H, F, Cl, NR$^a$R$^a$, OC$_{1-4}$ alkyl, and C$_{1-4}$ alkyl; or R$^4$ and R$^4$ together with the carbon atom to which they are both attached form $C_{3-6}$ cycloalkyl substituted with 0-5 $R^e$;

$R^5$ is independently selected from —$(CH_2)_n$-aryl, —$(CH_2)_n$—$C_{3-6}$ cycloalkyl and —$(CH_2)_n$-heterocycle, each substituted with 0-3 $R^6$;

$R^6$ is independently selected from H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^{6a}$ is independently selected from H, —$S(O)_pR^c$, —$C(=O)R^b$, —$C(=O)NR^aR^a$, —$C(=O)OR^b$, —$S(O)_pNR^aR^a$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^8$ and $R^8$ together with the nitrogen atom to which they are both attached form a heterocyclic ring comprising carbon atoms and 0-3 additional heteroatoms selected from N, $NR^{6a}$, O, and S, and substituted with 0-5 $R^6$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with halogen, OH, and CN), $C_{2-6}$ alkenyl, $C_{2-6}$ alkynyl, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$, —$(CH_2)_nOR^f$, $S(O)_pR^f$, $C(=O)NR^fR^f$, $NR^fC(=O)R^f$, $S(O)_pNR^fR^f$, $NR^fS(O)_pR^f$, $NR^fC(=O)OR^f$, $OC(=O)NR^fR^f$ and —$(CH_2)_nNR^fR^f$;

$R^f$, at each occurrence, is independently selected from H, $C_{1-5}$alkyl (optionally substituted with halogen and OH), $C_{3-6}$ cycloalkyl, and phenyl;

n is independently selected from zero, 1, 2, and 3;
r is independently selected from 1 and 2; and
p, at each occurrence, is independently selected from zero, 1, and 2.

4. The compound according to claim 3 having Formula (III):

or a stereoisomer, a tautomer, or a pharmaceutically acceptable salt thereof, wherein:

$R^1$ is independently selected from H, F, Cl, Br, $OR^b$, CN, $C_{1-4}$ alkyl, and $C_{3-6}$cycloalkyl;

$R^{1a}$ is independently selected from F, Cl, and $C_{1-2}$ alkyl;

$R^2$ is independently selected from $C_{1-5}$ alkyl optionally substituted with halogen and $C_{3-6}$cycloalkyl, $C_{2-5}$ alkenyl, phenyl substituted with 0-3 $R^e$, 6-membered heteroaryl substituted with 0-3 $R^e$, $C_{3-6}$ cycloalkyl, —$(CH_2)_{1-4}OC_{1-3}$alkyl, and —$(CH_2)_{1-3}$O-cycloalkyl;

$R^3$ is independently selected from
(1) —$(CR^4R^4)_rC(=O)OC_{1-4}$ alkyl substituted with 0-5 $R^e$,
(2) —$(CR^4R^4)_rNR^8R^8$,
(3) —$(CR^4R^4)_rC(=O)NR^8R^8$,
(4) —$(CR^4R^4)_rNR^aC(=O)C_{1-4}$alkyl substituted with 0-5 $R^e$,
(5) —$(CR^4R^4)_rNR^aC(=O)(CR^4R^4)_nOC_{1-4}$alkyl substituted with 0-5 $R^e$,
(6) —$(CR^4R^4)_r$—$R^5$,
(7) —$(CR^4R^4)_r$—$OR^5$, and
(8) —$(CR^4R^4)_rNR^aC(=O)(CR^4R^4)_nR^5$;

$R^4$ is independently selected from H, F, Cl, $NR^aR^a$, $OC_{1-4}$ alkyl, and $C_{1-4}$ alkyl; or $R^4$ and $R^4$ together with the carbon atom to which they are both attached form $C_{3-6}$ cycloalkyl substituted with 0-5 $R^e$;

$R^5$ is independently selected from —$(CH_2)_n$-aryl, —$(CH_2)_n$—$C_{3-6}$ cycloalkyl and —$(CH_2)_n$-heterocycle, each substituted with 0-3 $R^6$;

$R^6$ is independently selected from H, F, Cl, Br, —$OR^b$, =O, —$(CH_2)_nC(=O)R^b$, —$(CH_2)_nC(=O)OR^b$, —$(CH_2)_nNR^aR^a$, CN, —$(CH_2)_nC(=O)NR^aR^a$, $C_{1-4}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^{6a}$ is independently selected from H, —$S(O)_pR^c$, —$C(=O)R^b$, —$C(=O)NR^aR^a$, —$C(=O)OR^b$, —$S(O)_pNR^aR^a$, $C_{1-5}$ alkyl substituted with 0-3 $R^e$, $(CH_2)_n$—$C_{3-6}$ carbocyclyl substituted with 0-3 $R^e$, and —$(CH_2)_n$-heterocyclyl substituted with 0-3 $R^e$;

$R^8$ and $R^8$ together with the nitrogen atom to which they are both attached form a heterocyclic ring comprising carbon atoms and 0-3 additional heteroatoms selected from N, $NR^{6a}$, O, and S, and substituted with 0-5 $R^6$;

$R^a$, at each occurrence, is independently selected from H, $C_{1-6}$ alkyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, and —$(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, $CO_2H$;

r is independently selected from 1 and 2; and
n is independently selected from zero, 1, 2, and 3.

5. The compound according to claim 4, or a stereoisomer, an enantiomer, a diastereomer, a tautomer, or a pharmaceutically acceptable salt thereof, wherein:

$R^1$ is independently selected from F, Cl, Br, OH, $OC_{1-4}$ alkyl, $OC_{3-6}$cycloalkyl, CN, $C_{1-4}$ alkyl, and $C_{3-6}$cycloalkyl;

$R^2$ is independently selected from —$CH_2CH_2CH_2CH_3$, —$CH_2CH_2CH(CH_3)_2$, $CH_2CH_2CH_2CF_3$, —$CH_2$-cyclopropyl, —CH₂CH₂-cyclopropyl, CH₂CH₂CH=CH₂, phenyl (optionally substituted with F), pyridyl (optionally substituted with $C_{1-2}$alkyl), $C_{3-5}$ cycloalkyl, CH₂O(CH₂)$_{1-3}$CH₃, CH₂OCH(CH₃)₂, and CH₂O-cyclopropyl;

$R^3$ is independently selected from
(1) —CR⁴R⁴—R⁵ and
(2) —CR⁴R⁴—NR$^a$C(=O)(CR⁴R⁴)$_n$R⁵;

$R^4$ is independently selected from H, F, Cl, N(CH₃)₂, OCH₃, and CH₃; or $R^4$ and $R^4$ together with the carbon atom to which they are both attached form cyclopropyl;

$R^5$ is independently selected from

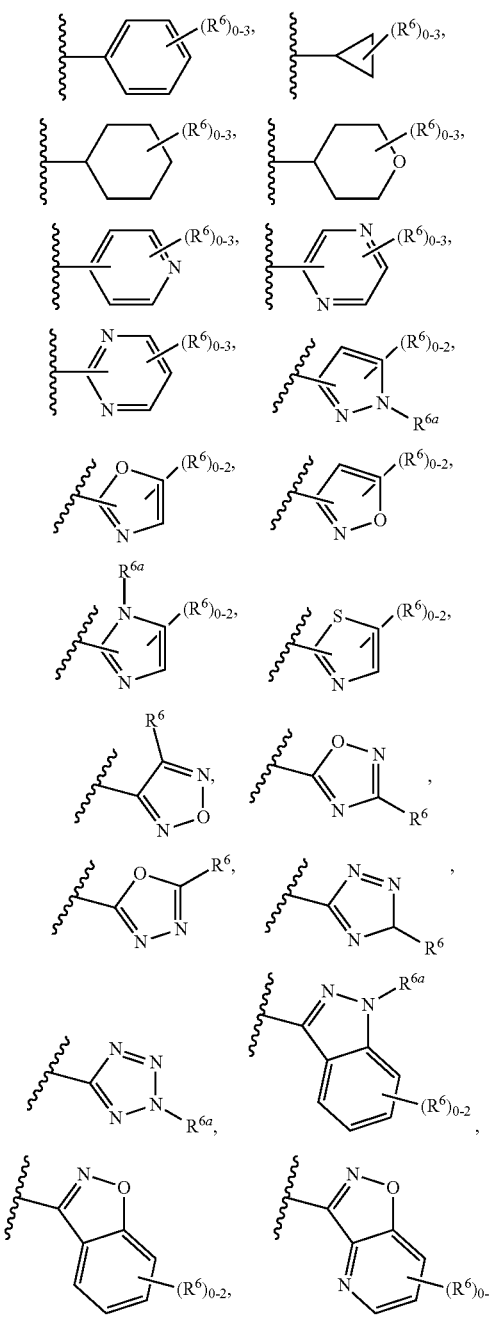

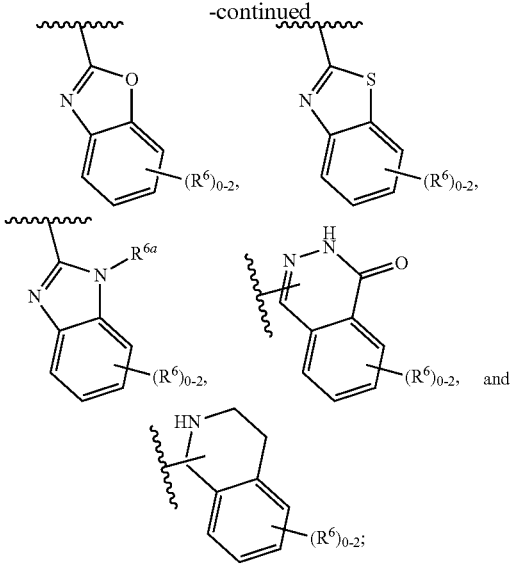

$R^6$ is independently selected from H, F, Cl, Br, —OCH₃, —OCF₃, =O, CN, CH₃, CF₃—(CH₂)$_n$-aryl, —(CH₂)$_n$—$C_{3-6}$ cycloalkyl substituted with 0-3 R$^e$, and —(CH₂)$_n$-heterocyclyl substituted with 0-3 R$^e$;

$R^{6a}$ is independently selected from H, CH₃, aryl substituted with 0-3 R$^e$, and heterocyclyl substituted with 0-3 R$^e$;

$R^a$, at each occurrence, is independently selected from H, $C_{1-6}$ alkyl substituted with 0-5 R$^e$, —(CH₂)$_n$—$C_{3-10}$carbocyclyl substituted with 0-5 R$^e$, and —(CH₂)$_n$-heterocyclyl substituted with 0-5 R$^e$;

$R^e$, at each occurrence, is independently selected from $C_{1-6}$ alkyl (optionally substituted with F and Cl), OH, OCH₃, OCF₃, —(CH₂)$_n$—$C_{3-6}$ cycloalkyl, —(CH₂)$_n$—$C_{4-6}$ heterocyclyl, —(CH₂)$_n$-aryl, —(CH₂)$_n$-heteroaryl, F, Cl, Br, CN, NO₂, =O, CO₂H; and n is independently selected from zero, 1, 2, and 3.

6. The compound according to claim 5, or a stereoisomer, an enantiomer, a diastereomer, a tautomer, or a pharmaceutically acceptable salt thereof, wherein:

$R^1$ is independently selected from F, Cl, Br, OH, OCH₃, OCD₃, OCH₂CH₃, OCH(CH₃)₂, O-cyclopropyl, CN, and cyclopropyl;

$R^2$ is independently selected from —CH₂CH₂CH₂CH₃, —CH₂CH₂CH(CH₃)₂, CH₂CH₂CH₂CF₃, —CH₂-cyclopropyl, —CH₂CH₂-cyclopropyl, CH₂CH₂CH=CH₂, phenyl (optionally substituted with F), pyridyl (optionally substituted with $C_{1-2}$alkyl), cyclobutyl, cyclopentyl, CH₂O(CH₂)$_{1-3}$CH₃, CH₂OCH(CH₃)₂, and CH₂O-cyclopropyl;

$R^3$ is independently selected from
(1) —CH₂—R⁵ and
(2) —CH₂—NR$^a$C(=O)R⁵;

$R^5$ is independently selected from

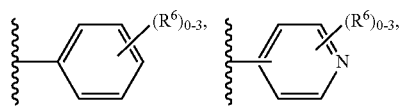

-continued

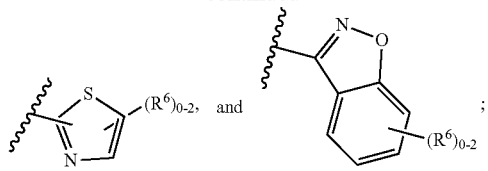

R⁶ is independently selected from H, F, Cl, Br, —OCH₃, —OCF₃, CN, CH₃, CF₃—(CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ;

Rᵃ, at each occurrence, is independently selected from H, C₁₋₆ alkyl substituted with 0-5 Rᵉ, —(CH₂)ₙ—C₃₋₁₀carbocyclyl substituted with 0-5 Rᵉ, and —(CH₂)ₙ-heterocyclyl substituted with 0-5 Rᵉ;

Rᵉ, at each occurrence, is independently selected from C₁₋₆ alkyl (optionally substituted with F and Cl), OH, OCH₃, OCF₃, —(CH₂)ₙ—C₃₋₆ cycloalkyl, —(CH₂)ₙ—C₄₋₆ heterocyclyl, —(CH₂)ₙ-aryl, —(CH₂)ₙ-heteroaryl, F, Cl, Br, CN, NO₂, =O, CO₂H; and n is independently selected from zero, 1, 2, and 3.

7. The compound according to claim 6, having Formula (IIIa):

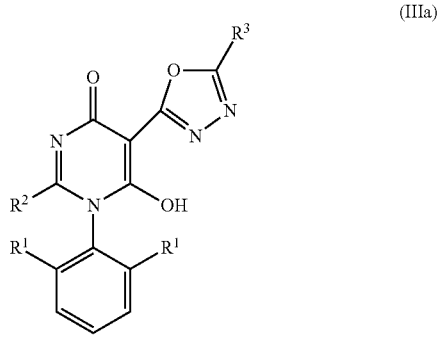

or a stereoisomer, an enantiomer, a diastereomer, a tautomer, or a pharmaceutically acceptable salt thereof, wherein:

R¹ is independently selected from OCH₃ and OCD₃;

R² is independently selected from —CH₂CH₂CH₂CH₃, —CH₂CH₂CH(CH₃)₂, CH₂CH₂CH₂CF₃, —CH₂-cyclopropyl, —CH₂CH₂-cyclopropyl, cyclobutyl, cyclopentyl, CH₂O(CH₂)₁₋₃CH₃, and CH₂OCH(CH₃)₂;

R³ is independently selected from
(1) —CH₂—R⁵ and
(2) —CH₂—NHC(=O)R⁵;

R⁵ is independently selected from

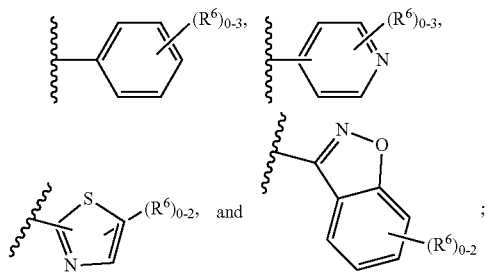

and

R⁶ is independently selected from H, F, Cl, Br, —OCH₃, —OCF₃, CN, CH₃, and CF₃.

8. The compound according to claim 4, or a stereoisomer, an enantiomer, a diastereomer, a tautomer, or a pharmaceutically acceptable salt thereof, wherein:

R¹ is independently selected from F, Cl, Br, OH, OC₁₋₄ alkyl, OC₃₋₆cycloalkyl, CN, C₁₋₄ alkyl, and C₃₋₆cycloalkyl;

R² is independently selected from —CH₂CH₂CH₂CH₃, —CH₂CH₂CH(CH₃)₂, CH₂CH₂CH₂CF₃, —CH₂-cyclopropyl, —CH₂CH₂-cyclopropyl, CH₂CH₂CH=CH₂, phenyl (optionally substituted with F), pyridyl (optionally substituted with C₁₋₂alkyl), C₃₋₅ cycloalkyl, CH₂O(CH₂)₁₋₃CH₃, CH₂OCH(CH₃)₂, and CH₂O-cyclopropyl;

R³ is independently selected from
(1) —(CR⁴R⁴)ᵣNR⁸R⁸ and
(2) —(CR⁴R⁴)ᵣC(=O)NR⁸R⁸;

R⁴ is independently selected from H, F, Cl, N(CH₃)₂, OCH₃, and CH₃; or R⁴ and R⁴ together with the carbon atom to which they are both attached form C₃₋₆ cycloalkyl substituted with 0-5 Rᵉ;

R⁶ is independently selected from H, F, Cl, Br, —OCH₃, —OCF₃, =O, CN, CH₃, CF₃—(CH₂)ₙ-aryl, —(CH₂)ₙ—C₃₋₆ cycloalkyl substituted with 0-3 Rᵉ, and —(CH₂)ₙ-heterocyclyl substituted with 0-3 Rᵉ;

R⁶ᵃ is independently selected from H, CH₃, aryl substituted with 0-3 Rᵉ, and heterocyclyl substituted with 0-3 Rᵉ;

R⁸ and R⁸ together with the nitrogen atom to which they are both attached form a heterocyclic ring selected from

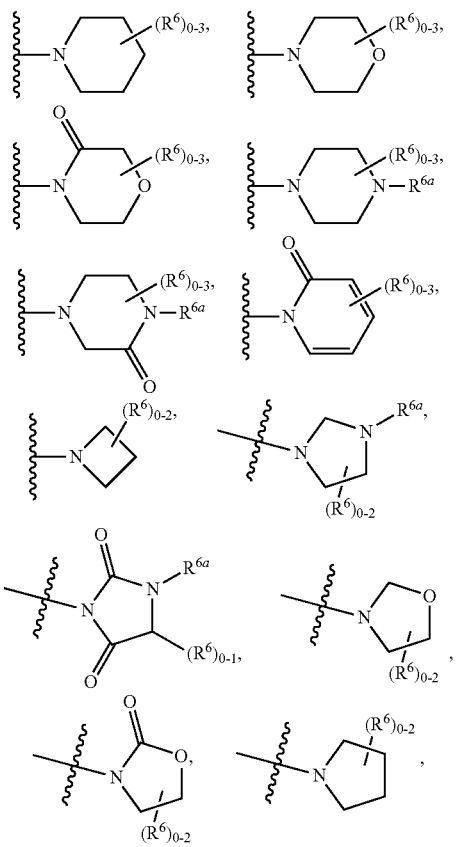

149

-continued

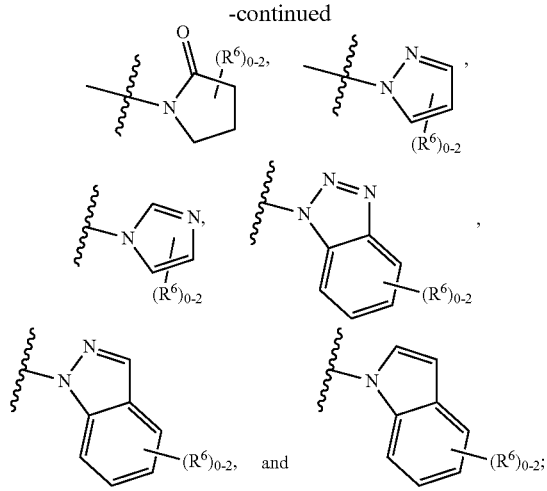

$R^e$, at each occurrence, is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, =O, $CO_2H$;

r is independently selected from 1 and 2; and n is independently selected from zero, 1, 2, and 3.

9. The compound according to claim 8, or a stereoisomer, an enantiomer, a diastereomer, a tautomer, or a pharmaceutically acceptable salt thereof, wherein:

$R^1$ is independently selected from $OCH_3$ and $OCD_3$;

$R^2$ is independently selected from $-CH_2CH_2CH_2CH_3$, $-CH_2CH_2CH(CH_3)_2$, $CH_2CH_2CH_2CF_3$, $-CH_2$-cyclopropyl, $-CH_2CH_2$-cyclopropyl, $CH_2CH_2CH=CH_2$, phenyl (optionally substituted with F), pyridyl (optionally substituted with $C_{1-2}$alkyl), cyclopentyl, $CH_2O(CH_2)_{1-3}CH_3$, $CH_2OCH(CH_3)_2$, and $CH_2O$-cyclopropyl;

$R^3$ is independently selected from
(1) $-CH_2-NR^8R^8$ and
(2) $-CH_2-C(=O)NR^8R^8$;

$R^6$ is independently selected from H, F, Cl, Br, $-OCH_3$, $-OCF_3$, CN, $CH_3$, $CF_3-(CH_2)_n$-aryl, $-(CH_2)_n-C_{3-6}$ cycloalkyl substituted with 0-3 $R^e$, and $-(CH_2)_n$-heterocyclyl substituted with 0-3 $R^e$;

$R^8$ and $R^8$ together with the nitrogen atom to which they are both attached form a heterocyclic ring selected from

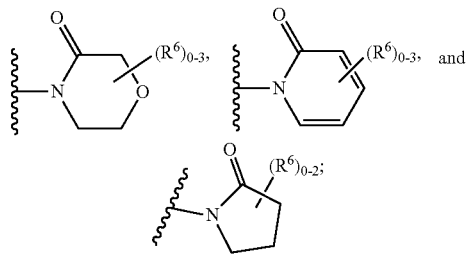

$R^e$, at each occurrence, is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, =O, $CO_2H$; and n is independently selected from zero, 1, 2, and 3.

150

10. The compound according to claim 2 having Formula (IV):

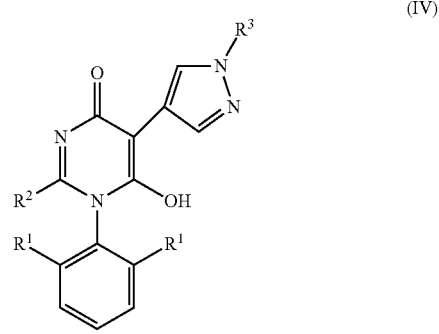

or a stereoisomer, an enantiomer, a diastereomer, a tautomer, or a pharmaceutically acceptable salt thereof, wherein:

$R^1$ is independently selected from F, Cl, Br, $OR^b$, CN, $C_{1-4}$ alkyl, and $C_{3-6}$cycloalkyl;

$R^2$ is independently selected from $C_{1-5}$ alkyl, optionally substituted with halogen and $C_{3-6}$cycloalkyl, $C_{2-5}$ alkenyl, phenyl substituted with 0-3 $R^e$, 6-membered heteroaryl substituted with 0-3 $R^e$, $C_{3-6}$ cycloalkyl, $CH_2OC_{1-3}$alkyl, and $CH_2O$-cycloalkyl;

$R^3$ is independently selected from
(1) $-CH_2-R^5$,
(2) $-CH_2-OR^5$, and
(3) $-CH_2-NR^aC(=O)R^5$;

$R^4$ is independently selected from H, F, Cl, $NR^aR^a$, $OC_{1-4}$ alkyl, and $C_{1-4}$ alkyl;

$R^5$ is independently selected from aryl, $C_{3-6}$ cycloalkyl and heterocycle, each substituted with 0-3 $R^6$;

$R^6$ is independently selected from H, F, Cl, Br, $-OR^b$, =O, $-(CH_2)_nC(=O)R^b$, $-(CH_2)_nC(=O)OR^b$, $-(CH_2)_nNR^aR^a$, CN, $-(CH_2)_nC(=O)NR^aR^a$, $C_{1-4}$ alkyl substituted with 0-3 $R^e$, $(CH_2)_n-C_{3-6}$ carbocyclyl substituted with 0-3 $R^e$, and $-(CH_2)_n$-heterocyclyl substituted with 0-3 $R^e$;

$R^a$, at each occurrence, is independently selected from H, $C_{1-6}$ alkyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$; or $R^a$ and $R^a$ together with the nitrogen atom to which they are both attached form a heterocyclic ring substituted with 0-5 $R^e$;

$R^b$, at each occurrence, is independently selected from H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $-(CH_2)_n-C_{3-10}$carbocyclyl substituted with 0-5 $R^e$, and $-(CH_2)_n$-heterocyclyl substituted with 0-5 $R^e$;

$R^e$, at each occurrence, is independently selected from $C_{1-6}$ alkyl (optionally substituted with F and Cl), OH, $OCH_3$, $OCF_3$, $-(CH_2)_n-C_{3-6}$ cycloalkyl, $-(CH_2)_n-C_{4-6}$ heterocyclyl, $-(CH_2)_n$-aryl, $-(CH_2)_n$-heteroaryl, F, Cl, Br, CN, $NO_2$, =O, $CO_2H$; and n is independently selected from zero, 1, 2, and 3.

11. The compound according to claim 3 having Formula (V):

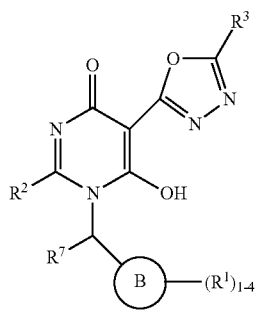

(V)

or a stereoisomer, an enantiomer, a diastereomer, a tautomer, or a pharmaceutically acceptable salt thereof, wherein:

ring B is independently selected from

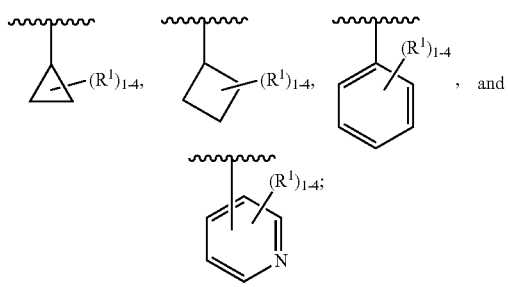

$R^1$ is independently selected from H, F, Cl, Br, $OC_{1-4}$ alkyl, CN, and $C_{1-4}$ alkyl;

$R^2$ is independently selected from —$CH_2CH_2CH_2CH_3$, —$CH_2CH_2CH(CH_3)_2$, $CH_2CH_2CH_2CF_3$, —$CH_2$-cyclopropyl, —$CH_2CH_2$-cyclopropyl, $CH_2CH_2CH=CH_2$, phenyl (optionally substituted with F), pyridyl (optionally substituted with $C_{1-2}$alkyl), $C_{3-5}$ cycloalkyl, $CH_2O(CH_2)_{1-3}CH_3$, $CH_2OCH(CH_3)_2$, and $CH_2O$-cyclopropyl;

$R^3$ is independently selected from
(1) —$CH_2R^5$ and
(2) —$CH_2OR^5$;

$R^5$ is independently selected from

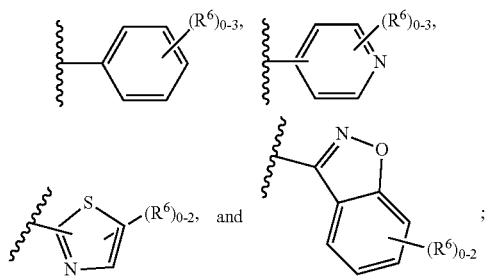

$R^6$ is independently selected from H, F, Cl, Br, —$OCH_3$, —$OCF_3$, =O, CN, $CH_3$, $CF_3$—$(CH_2)_n$-aryl, —$(CH_2)_n$—$C_{3-6}$ cycloalkyl substituted with 0-3 $R^e$, and —$(CH_2)_n$-heterocyclyl substituted with 0-3 $R^e$;

$R^7$ is independently selected from $CH_3$, $CH_2CH_3$, $CH_2CH_2CH_3$, $CH(CH_3)_2$, and $CH_2OCH_3$;

$R^e$, at each occurrence, is independently selected from $C_{1-6}$ alkyl (optionally substituted with halogen, OH, and CN), $C_{2-6}$ alkylene, —$(CH_2)_n$—$C_{3-6}$ cycloalkyl, —$(CH_2)_n$—$C_{4-6}$ heterocyclyl, —$(CH_2)_n$-aryl, —$(CH_2)_n$-heteroaryl, F, Cl, Br, CN, $NO_2$, =O, and $CO_2H$; and n is independently selected from zero, 1, 2, and 3.

12. The compound according to claim 11, or a stereoisomer, an enantiomer, a diastereomer, a tautomer, or a pharmaceutically acceptable salt thereof, wherein:

ring B is independently selected from

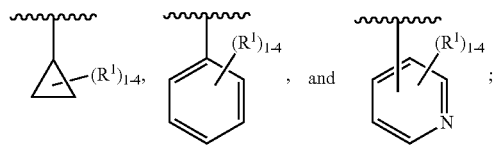

$R^1$ is independently selected from H, F, Cl, Br, $OC_{1-4}$ alkyl, CN, and $C_{1-4}$ alkyl;

$R^2$ is independently selected from —$CH_2CH_2CH_2CH_3$, —$CH_2CH_2CH(CH_3)_2$, $CH_2CH_2CH_2CF_3$, —$CH_2CH_2CH=CH_2$, $CH_2O(CH_2)_{1-3}CH_3$, and $CH_2OCH(CH_3)_2$;

$R^3$ is independently selected from
(1) —$CH_2R^5$ and
(2) —$CH_2OR^5$;

$R^5$ is independently selected from

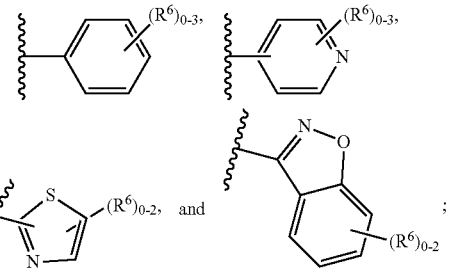

$R^6$ is independently selected from H, F, Cl, Br, —$OCH_3$, —$OCF_3$, =O, CN, $CH_3$, and $CF_3$;

$R^7$ is independently selected from $CH_3$, $CH_2CH_3$, $CH_2CH_2CH_3$, $CH(CH_3)_2$, and $CH_2OCH_3$; and n is independently selected from zero, 1, 2, and 3.

13. The compound according to claim 3 having Formula (VI):

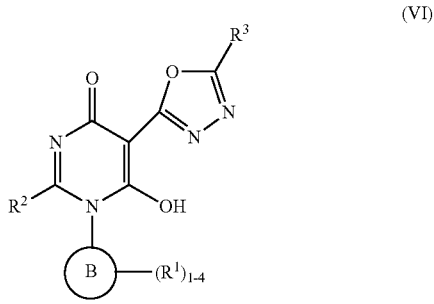

(VI)

or a stereoisomer, an enantiomer, a diastereomer, a tautomer, or a pharmaceutically acceptable salt thereof, wherein:

ring B is independently selected from

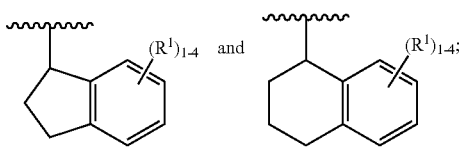

R¹ is independently selected from H, F, Cl, Br, OC$_{1-4}$ alkyl, CN, and C$_{1-4}$ alkyl;
R² is independently selected from —CH$_2$CH$_2$CH$_2$CH$_3$, —CH$_2$CH$_2$CH(CH$_3$)$_2$, CH$_2$CH$_2$CH$_2$CF$_3$, —CH$_2$-cyclopropyl, —CH$_2$CH$_2$-cyclopropyl, cyclobutyl, cyclopentyl, CH$_2$O(CH$_2$)$_{1-3}$CH$_3$, and CH$_2$OCH(CH$_3$)$_2$;
R³ is independently selected from
(1) —CH$_2$—R⁵ and
(2) —CH$_2$—NHC(=O)R⁵;
R⁵ is independently selected from

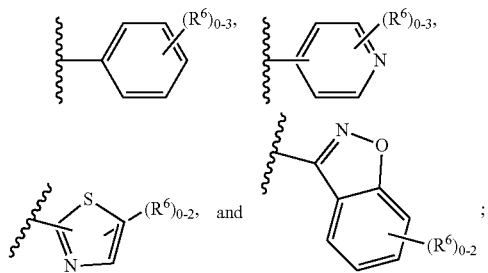

and
R⁶ is independently selected from H, F, Cl, Br, —OCH$_3$, —OCF$_3$, CN, CH$_3$, and CF$_3$.

14. A pharmaceutical composition, comprising a pharmaceutically acceptable carrier and a compound according to claim 1, or a stereoisomer, a tautomer, or a pharmaceutically acceptable salt thereof.

15. A method of treating cardiovascular diseases, comprising administering to a patient in need thereof a therapeutically effective amount of the pharmaceutical composition according to claim 14.

16. The method according to claim 15, wherein said cardiovascular diseases are coronary heart disease, stroke, heart failure, systolic heart failure, diastolic heart failure, diabetic heart failure, heart failure with preserved ejection fraction, cardiomyopathy, myocardial infarction, left ventricular dysfunction, left ventricular dysfunction after myocardial infarction, cardiac hypertrophy, myocardial remodeling, myocardial remodeling after infarction or after cardiac surgery and valvular heart diseases.

17. A compound selected from:
5-(5-(benzo[d]isoxazol-3-ylmethyl)-1,3,4-oxadiazol-2-yl)-2-butyl-1-(2,6-dimethoxyphenyl)-6-hydroxypyrimidin-4(1H)-one (1),
2-butyl-5-{5-[(4-chlorophenyl)methyl]-1,3,4-oxadiazol-2-yl}-1-(2,6-dimethoxyphenyl)-6-hydroxy-1,4-dihydropyrimidin-4-one (2),
5-[5-(1,2-benzoxazol-3-ylmethyl)-1,3,4-oxadiazol-2-yl]-2-(but-3-en-1-yl)-1-(2,6-dimethoxyphenyl)-6-hydroxy-1,4-dihydropyrimidin-4-one (3),
5-[5-(1,2-benzoxazol-3-ylmethyl)-1,3,4-oxadiazol-2-yl]-2-butyl-1-(2,6-diethylphenyl)-6-hydroxy-1,4-dihydropyrimidin-4-one (4),
2-butyl-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one (5),
2-butyl-1-(2,6-dimethoxyphenyl)-6-hydroxy-5-{5-[(2-oxo-1,2-dihydropyridin-1-yl)methyl]-1,3,4-oxadiazol-2-yl}-1,4-dihydropyrimidin-4-one (6),
1-(2,6-dimethoxyphenyl)-6-hydroxy-2-(3-methylbutyl)-5-{5-[(2-oxopyrrolidin-1-yl)methyl]-1,3,4-oxadiazol-2-yl}-1,4-dihydropyrimidin-4-one (7),
2-butyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one (8),
2-butyl-1-(2,6-dimethoxyphenyl)-6-hydroxy-5-(5-{[3-(pyridin-2-yl)-1,2,4-oxadiazol-5-yl]methyl}-1,3,4-oxadiazol-2-yl)-1,4-dihydropyrimidin-4-one (9),
1-(2,6-dimethoxyphenyl)-6-hydroxy-2-(3-methylbutyl)-5-{5-[(2-oxo-1,2-dihydropyridin-1-yl)methyl]-1,3,4-oxadiazol-2-yl}-1,4-dihydropyrimidin-4-one (10),
2-(but-3-en-1-yl)-1-(2,6-dimethoxyphenyl)-6-hydroxy-5-(5-{[3-(pyridin-2-yl)-1,2,4-oxadiazol-5-yl]methyl}-1,3,4-oxadiazol-2-yl)-1,4-dihydropyrimidin-4-one (11),
5-[5-(1,2-benzoxazol-3-ylmethyl)-1,3,4-oxadiazol-2-yl]-1-(2,6-dimethoxyphenyl)-6-hydroxy-2-(4,4,4-trifluorobutyl)-1,4-dihydropyrimidin-4-one (12),
5-[5-(1,2-benzoxazol-3-ylmethyl)-1,3,4-oxadiazol-2-yl]-2-butyl-6-hydroxy-1-(2-methoxy-6-methylphenyl)-1,4-dihydropyrimidin-4-one (13),
2-(but-3-en-1-yl)-5-{5-[(4-chlorophenyl)methyl]-1,3,4-oxadiazol-2-yl}-1-(2,6-dimethoxyphenyl)-6-hydroxy-1,4-dihydropyrimidin-4-one (14),
5-[5-(1,2-benzoxazol-3-ylmethyl)-1,3,4-oxadiazol-2-yl]-2-butyl-1-(2,6-dibromophenyl)-6-hydroxy-1,4-dihydropyrimidin-4-one (15),
4-({5-[1-(2,6-dimethoxyphenyl)-6-hydroxy-2-(3-methylbutyl)-4-oxo-1,4-dihydropyrimidin-5-yl]-1,3,4-oxadiazol-2-yl}methyl)morpholin-3-one (16),
5-[5-(1,2-benzoxazol-3-ylmethyl)-1,3,4-oxadiazol-2-yl]-2-(but-3-en-1-yl)-6-hydroxy-1-(2-methoxy-6-methylphenyl)-1,4-dihydropyrimidin-4-one (17),
5-[5-(1,2-benzoxazol-3-ylmethyl)-1,3,4-oxadiazol-2-yl]-2-butyl-1-(4,6-dimethoxypyrimidin-5-yl)-6-hydroxy-1,4-dihydropyrimidin-4-one (18),
5-[5-(1,2-benzoxazol-3-ylmethyl)-1,3,4-oxadiazol-2-yl]-2-butyl-1-(2,6-dichlorophenyl)-6-hydroxy-1,4-dihydropyrimidin-4-one (19),
5-[5-(1,2-benzoxazol-3-ylmethyl)-1,3,4-oxadiazol-2-yl]-2-(cyclopropylmethyl)-1-(2,6-dimethoxyphenyl)-6-hydroxy-1,4-dihydropyrimidin-4-one (20),
5-{5-[(4-chlorophenyl)methyl]-1,3,4-oxadiazol-2-yl}-2-(cyclopropylmethyl)-1-(2,6-dimethoxyphenyl)-6-hydroxy-1,4-dihydropyrimidin-4-one (21),
2-(cyclopropylmethyl)-1-(2,6-dimethoxyphenyl)-6-hydroxy-5-(5-{[3-(pyridin-2-yl)-1,2,4-oxadiazol-5-yl]methyl}-1,3,4-oxadiazol-2-yl)-1,4-dihydropyrimidin-4-one (22),
5-(5-(Benzo[d]isoxazol-3-ylmethyl)-1,3,4-oxadiazol-2-yl)-2-butyl-1-(2,6-diethoxyphenyl)-6-hydroxypyrimidin-4(1H)-one (23),
5-[5-(1,2-benzoxazol-3-ylmethyl)-1,3,4-oxadiazol-2-yl]-1-[2,6-bis(propan-2-yloxy)phenyl]-2-butyl-6-hydroxy-1,4-dihydropyrimidin-4-one (24),
2-butyl-1-(2,6-diethoxyphenyl)-6-hydroxy-5-{5-[(2-methyl-1,3-thiazol-4-yl)methyl]-1,3,4-oxadiazol-2-yl}-1,4-dihydropyrimidin-4-one (25),
2-butyl-5-{5-[(4-chlorophenyl)methyl]-1,3,4-oxadiazol-2-yl}-1-(2,6-diethoxyphenyl)-6-hydroxy-1,4-dihydropyrimidin-4-one (26), 5-(5-(Benzo[d]isoxazol-3-ylmethyl)-1,3,4-oxadiazol-2-yl)-2-butyl-1-(2,6-dicyclopropylphenyl)-6-hydroxypyrimidin-4(1H)-one Example 27a, 2,6-Dicyclopropylaniline (27)

2-(5-(5-(Benzo[d]isoxazol-3-ylmethyl)-1,3,4-oxadiazol-2-yl)-2-butyl-6-hydroxy-4-oxopyrimidin-1 (4H)-yl) isophthalonitrile (28)

2-butyl-5-(5-(4-chlorobenzyl)-1,3,4-oxadiazol-2-yl)-1-(2,6-dicyclopropoxyphenyl)-6-hydroxypyrimidin-4 (1H)-one (29), 5-[5-(1,2-benzoxazol-3-ylmethyl)-1,3,4-oxadiazol-2-yl]-2-butyl-1-(2,6-dicyclopropoxyphenyl)-6-hydroxy-1,4-dihydropyrimidin-4-one (30), 5-(1-benzyl-1H-pyrazol-4-yl)-2-butyl-3-(2,6-dimethoxyphenyl)-6-hydroxypyrimidin-4(3H)-one (31), 2-butyl-5-{1-[(4-chlorophenyl)methyl]-1H-pyrazol-4-yl}-3-(2,6-dimethoxyphenyl)-6-hydroxy-3,4-dihydropyrimidin-4-one (32), 5-(5-(benzo[d]isoxazol-3-ylmethyl)-1,3,4-oxadiazol-2-yl)-1-(2,6-dimethoxyphenyl)-6-hydroxy-2-(ethoxymethyl)pyrimidin-4(1H)-one (33)

5-[5-(1,2-benzoxazol-3-ylmethyl)-1,3,4-oxadiazol-2-yl]-1-(2,6-dimethoxyphenyl)-6-hydroxy-2-[(propan-2-yloxy)methyl]-1,4-dihydropyrimidin-4-one (34), 5-[5-(1,2-benzoxazol-3-ylmethyl)-1,3,4-oxadiazol-2-yl]-1-(2,6-diethylphenyl)-2-(ethoxymethyl)-6-hydroxy-1,4-dihydropyrimidin-4-one (35), 5-{5-[(4-chlorophenyl)methyl]-1,3,4-oxadiazol-2-yl)}-1-(2,6-dimethoxyphenyl)-6-hydroxy-2-[(propan-2-yloxy)methyl]-1,4-dihydropyrimidin-4-one (36), 5-{5-[(4-chlorophenyl)methyl]-1,3,4-oxadiazol-2-yl}-1-(2,6-diethylphenyl)-2-(ethoxymethyl)-6-hydroxy-1,4-dihydropyrimidin-4-one (37), 5-{5-[(4-chloro-3-fluorophenyl)methyl]-1,3,4-oxadiazol-2-yl}-1-(2,6-dimethoxyphenyl)-2-(ethoxymethyl)-6-hydroxy-1,4-dihydropyrimidin-4-one (38), 1-(2,6-dimethoxyphenyl)-2-(ethoxymethyl)-6-hydroxy-5-{5-[(2-phenyl-1,3-thiazol-4-yl)methyl]-1,3,4-oxadiazol-2-yl}-1,4-dihydropyrimidin-4-one (39), 5-{5-[(4-chlorophenyl)methyl]-1,3,4-oxadiazol-2-yl}-1-(2,6-dimethoxyphenyl)-2-(ethoxymethyl)-6-hydroxy-1,4-dihydropyrimidin-4-one (40), 5-[5-(1,2-benzoxazol-3-ylmethyl)-1,3,4-oxadiazol-2-yl]-1-(2,6-dicyclopropylphenyl)-6-hydroxy-2-[(propan-2-yloxy)methyl]-1,4-dihydropyrimidin-4-one (41), 5-(5-(benzo[d]isoxazol-3-ylmethyl)-1,3,4-oxadiazol-2-yl)-2-(2-cyclopropylethyl)-1-(2,6-dimethoxyphenyl)-6-hydroxypyrimidin-4(1H)-one (42), 2-(2-cyclopropylethyl)-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one (43), 2-(2-cyclopropylethyl)-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one (44), 5-{5-[(4-chlorophenyl)methyl]-1,3,4-oxadiazol-2-yl}-2-(2-cyclopropylethyl)-1-(2,6-dimethoxyphenyl)-6-hydroxy-1,4-dihydropyrimidin-4-one (45), 2-(2-cyclopropylethyl)-1-(2,6-dimethoxyphenyl)-6-hydroxy-5-{5-[(2-oxo-1,2-dihydropyridin-1l-yl)methyl]-1,3,4-oxadiazol-2-yl}-1,4-dihydropyrimidin-4-one (46), 4-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)morpholin-3-one (47), 5-(5-(Benzo[d]isoxazol-3-ylmethyl)-1,3,4-oxadiazol-2-yl)-2-butyl-1-(2,6-di[$^2$H$_3$]methoxyphenyl)-6-hydroxypyrimidin-4(1H)-one (48), 1-[2,6-bis($^2$H3)methoxyphenyl]-2-butyl-5-{5-[(4-chlorophenyl)methyl]-1,3,4-oxadiazol-2-yl}-6-hydroxy-1,4-dihydropyrimidin-4-one (49), 5-[5-(1,2-benzoxazol-3-ylmethyl)-1,3,4-oxadiazol-2-yl]-1-[2,6-bis($^2$H3)methoxyphenyl]-2-(ethoxymethyl)-6-hydroxy-1,4-dihydropyrimidin-4-one (50), 1-[2,6-bis($^2$H3)methoxyphenyl]-5-{5-[(4-chlorophenyl)methyl]-1,3,4-oxadiazol-2-yl}-2-(ethoxymethyl)-6-hydroxy-1,4-dihydropyrimidin-4-one (51), 2-(5-(2-(2-Cyclopropylethyl)-1-(2,6-dimethoxyphenyl)-6-hydroxy-4-oxo-1,4-dihydropyrimidin-5-yl)-1,3,4-oxadiazol-2-yl)-N,N-diethyl acetamide (52), N-((5-(2-(2-cyclopropylethyl)-1-(2,6-dimethoxyphenyl)-6-hydroxy-4-oxo-1,4-dihydropyrimidin-5-yl)-1,3,4-oxadiazol-2-yl)methyl)-N-methylpicolinamide (53), N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)-N-methylpyridine-2-carboxamide (54), 3-chloro-N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)benzamide (55), N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)pyridine-3-carboxamide (56), N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)benzamide (57), N-({5-[2-(2-cyclopropylethyl)-1-(2,6-dimethoxyphenyl)-6-hydroxy-4-oxo-1,4-dihydropyrimidin-5-yl]-1,3,4-oxadiazol-2-yl}methyl)pyridine-2-carboxamide (58), 5-{5-[(5-chloropyridin-2-yl)methyl]-1,3,4-oxadiazol-2-yl}-2-(2-cyclopropylethyl)-1-(2,6-dimethoxyphenyl)-6-hydroxy-1,4-dihydropyrimidin-4-one (59), 5-{5-[(4-chloro-2-fluorophenyl)methyl]-1,3,4-oxadiazol-2-yl}-1-(2,6-dimethoxyphenyl)-6-hydroxy-2-[(propan-2-yloxy)methyl]-1,4-dihydropyrimidin-4-one (60), 2-(2-cyclopropylethyl)-1-(2,6-dimethoxyphenyl)-5-{5-[(5-fluoropyridin-2-yl)methyl]-1,3,4-oxadiazol-2-yl}-6-hydroxy-1,4-dihydropyrimidin-4-one (61), 2-cyclopentyl-1-(2,6-dimethoxyphenyl)-6-hydroxy-5-{5-[(2-oxo-1,2-dihydropyridin-1-yl)methyl]-1,3,4-oxadiazol-2-yl}-1,4-dihydropyrimidin-4-one (62), 5-{5-[(6-chloropyridin-3-yl)methyl]-1,3,4-oxadiazol-2-yl}-2-cyclopentyl-1-(2,6-dimethoxyphenyl)-6-hydroxy-1,4-dihydropyrimidin-4-one (63), 2-cyclopentyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one (64), 2-cyclopentyl-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one (65), 5-{5-[(5-chloropyridin-2-yl)methyl]-1,3,4-oxadiazol-2-yl}-2-cyclopentyl-1-(2,6-dimethoxyphenyl)-6-hydroxy-1,4-dihydropyrimidin-4-one (66), 2-cyclopentyl-1-(2,6-dimethoxyphenyl)-5-{5-[(5-fluoropyridin-2-yl)methyl]-1,3,4-oxadiazol-2-yl}-6-hydroxy-1,4-dihydropyrimidin-4-one (67), 2-cyclopentyl-1-(2,6-dimethoxyphenyl)-6-hydroxy-5-{5-[(6-methylpyridin-3-yl)methyl]-1,3,4-oxadiazol-2-yl}-1,4-dihydropyrimidin-4-one (68), 5-{5-[(5-chloro-3-fluoropyridin-2-yl)methyl]-1,3,4-oxadiazol-2-yl}-2-cyclopentyl-1-(2,6-dimethoxyphenyl)-6-hydroxy-1,4-dihydropyrimidin-4-one (69), 5-{5-[(5-chloropyridin-2-yl)methyl]-1,3,4-oxadiazol-2-yl}-2-cyclobutyl-1-(2,6-dimethoxyphenyl)-6-hydroxy-1,4-dihydropyrimidin-4-one (70), 5-{5-[(5-chloro-3-fluoropyridin-2-yl)methyl]-1,3,4-oxadiazol-2-yl}-2-cyclobutyl-1-(2,6-dimethoxyphenyl)-6-hydroxy-1,4-dihydropyrimidin-4-one (71), 2-cyclobutyl-1-(2,6-dimethoxyphenyl)-6-hydroxy-5-{5-[(2-oxopyrrolidin-1-yl)methyl]-1,3,4-oxadiazol-2-yl}-1,4-dihydropyrimidin-4-one (72), 2-cyclobutyl-1-(2,6-dimethoxyphenyl)-6-hydroxy-5-{5-[(2-methyl-1,3-thiazol-4-yl)methyl]-1,3,4-oxadiazol-2-yl}-1,4-dihydropyrimidin-4-one (73), (S)-5-(5-(Benzo[d]isoxazol-3-ylmethyl)-1,3,4-oxadiazol-2-yl)-2-butyl-6-hydroxy-3-(1-phenylpropyl)pyrimidin-4(3H)-one (74), 5-{5-[(1,2-benzoxazol-3-yl)methyl]-1,3,4-oxadiazol-2-yl}-2-butyl-6-hydroxy-3-[(1S)-1-phenylethyl]-3,4-dihydropyrimidin-4-one (75), 2-butyl-6-hydroxy-5-{5-[(2-methyl-1,3-thiazol-4-yl)methyl]-1,3,4-oxadiazol-2-yl}-3-[(1S)-1-phenylethyl]-3,4-dihydropyrimidin-4-one (76), 2-butyl-5-{5-[(4-chlorophenyl)methyl]-1,3,4-oxadiazol-2-yl}-3-[(1S)-1-cyclopropylethyl]-6-hydroxy-3,4-dihydropyrimidin-4-one (77), 5-{5-[(1,2-benzoxazol-3-yl)methyl]-1,3,4-oxadiazol-2-yl}-2-butyl-6-hydroxy-3-[(1R)-1-(2-methoxyphenyl)ethyl]-3,4-dihydropyrimidin-4-one (78), 2-butyl-6-hydroxy-3-[(1R)-1-(2-methoxyphenyl)ethyl]-5-{5-[(2-methyl-1,3-thiazol-4-yl)methyl]-1,3,4-oxadiazol-2-yl})-3,4-dihydropyrimidin-4-one (79), 2-butyl-3-[(1R)-1-cyclopropylethyl]-6-hydroxy-5-{5-[(2-methyl-1,3-thiazol-4-yl)methyl]-1,3,4-oxadiazol-2-yl)}-3,4-dihydropyrimidin-4-one (80), 2-butyl-5-{5-[(4-chlorophenyl)methyl]-1,3,4-oxadiazol-2-yl}-6-hydroxy-3-[(1R)-1-(2-methoxyphenyl)ethyl]-3,4-dihydropyrimidin-4-one (81), 2-butyl-6-hydroxy-5-{5-[(2-methyl-1,3-thiazol-4-yl)methyl]-1,3,4-oxadiazol-2-yl}-3-[(1R)-1-phenylethyl]-3,4-dihydropyrimidin-4-one (82), 2-butyl-5-{5-[(4-chlorophenyl)methyl]-1,3,4-oxadiazol-2-yl}-6-hydroxy-3-[(1R)-1-phenylethyl]-3,4-dihydropyrimidin-4-one (83), 2-butyl-5-{5-[(4-chlorophenyl)methyl]-1,3,4-oxadiazol-2-yl}-6-hydroxy-3-[(1S)-1-phenylpropyl]-3,4-dihydropyrimidin-4-one (84), 2-butyl-6-hydroxy-5-{5-[(2-methyl-1,3-thiazol-4-yl)methyl]-1,3,4-oxadiazol-2-yl}-3-[(1S)-1-phenylpropyl]-3,4-dihydropyrimidin-4-one (85), 5-{5-[(1,2-benzoxazol-3-yl)methyl]-1,3,4-oxadiazol-2-yl}-2-butyl-6-hydroxy-3-[(1R)-1-phenylethyl]-3,4-dihydropyrimidin-4-one (86), 5-{5-[(1,2-benzoxazol-3-yl)methyl]-1,3,4-oxadiazol-2-yl}-2-butyl-6-hydroxy-3-[(1R)-1-phenylpropyl]-3,4-dihydropyrimidin-4-one (87), 2-butyl-6-hydroxy-5-{5-[(2-methyl-1,3-thiazol-4-yl)methyl]-1,3,4-oxadiazol-2-yl}-3-[(1R)-1-phenylpropyl]-3,4-dihydropyrimidin-4-one (88), 2-butyl-5-{5-[(4-chlorophenyl)methyl]-1,3,4-oxadiazol-2-yl}-6-hydroxy-3-[(1R)-1-phenylpropyl]-3,4-dihydropyrimidin-4-one (89), 5-{5-[(1,2-benzoxazol-3-yl)methyl]-1,3,4-oxadiazol-2-yl}-2-butyl-6-hydroxy-3-[(1S)-2-methoxy-1-phenylethyl]-3,4-dihydropyrimidin-4-one (90), 5-{5-[(1,2-benzoxazol-3-yl)methyl]-1,3,4-oxadiazol-2-yl}-2-butyl-6-hydroxy-3-[(1R)-2-methoxy-1-phenylethyl]-3,4-dihydropyrimidin-4-one (91), 5-{5-[(1,2-benzoxazol-3-yl)methyl]-1,3,4-oxadiazol-2-yl}-2-butyl-6-hydroxy-3-[(1S)-1,2,3,4-tetrahydronaphthalen-1-yl]-3,4-dihydropyrimidin-4-one (92), 2-butyl-6-hydroxy-3-[(1S)-2-methoxy-1-phenylethyl]-5-{5-[(2-methyl-1,3-thiazol-4-yl)methyl]-1,3,4-oxadiazol-2-yl}-3,4-dihydropyrimidin-4-one (93), 2-butyl-6-hydroxy-3-[(1R)-2-methoxy-1-phenylethyl]-5-{5-[(2-methyl-1,3-thiazol-4-yl)methyl]-1,3,4-oxadiazol-2-yl})-3,4-dihydropyrimidin-4-one (94), 2-butyl-3-[(1S)-1-(4-fluorophenyl)ethyl]-6-hydroxy-5-{5-[(2-methyl-1,3-thiazol-4-yl)methyl]-1,3,4-oxadiazol-2-yl}-3,4-dihydropyrimidin-4-one (95), 5-{5-[(1,2-benzoxazol-3-yl)methyl]-1,3,4-oxadiazol-2-yl}-2-butyl-3-[(1S)-2,3-dihydro-1H-inden-1-yl]-6-hydroxy-3,4-dihydropyrimidin-4-one (96), 2-butyl-3-[(1S)-2,3-dihydro-1H-inden-1-yl]-6-hydroxy-5-{5-[(2-methyl-1,3-thiazol-4-yl)methyl]-1,3,4-oxadiazol-2-yl})-3,4-dihydropyrimidin-4-one (97), 2-butyl-5-{5-[(5-chloropyridin-2-yl)methyl]-1,3,4-oxadiazol-2-yl}-3-[(1S)-1-(4-fluorophenyl)ethyl]-6-hydroxy-3,4-dihydropyrimidin-4-one (98), 2-butyl-5-{5-[(5-chloropyridin-2-yl)methyl]-1,3,4-oxadiazol-2-yl}-6-hydroxy-3-[(1S)-2-methoxy-1-phenylethyl]-3,4-dihydropyrimidin-4-one (99), 2-butyl-5-{5-[(5-chloropyridin-2-yl)methyl]-1,3,4-oxadiazol-2-yl}-6-hydroxy-3-[(1S)-1,2,3,4-tetrahydronaphthalen-1-yl]-3,4-dihydropyrimidin-4-one (100), 2-butyl-5-{5-[(5-chloropyridin-2-yl)methyl]-1,3,4-oxadiazol-2-yl}-6-hydroxy-3-[(1R)-2-methoxy-1-phenylethyl]-3,4-dihydropyrimidin-4-one (101), 5-{5-[(1,2-benzoxazol-3-yl)methyl]-1,3,4-oxadiazol-2-yl}-2-butyl-6-hydroxy-3-[(1S)-1-(4-methoxyphenyl)ethyl]-3,4-dihydropyrimidin-4-one (102), 3-[(1S)-1-(5-{5-[(1,2-benzoxazol-3-yl)methyl]-1,3,4-oxadiazol-2-yl}-2-butyl-4-hydroxy-6-oxo-1,6-dihydropyrimidin-1-yl)ethyl]benzonitrile (103), 3-[(1S)-1-(2-butyl-4-hydroxy-5-{5-[(2-methyl-1,3-thiazol-4-yl)methyl]-1,3,4-oxadiazol-2-yl}-6-oxo-1,6-dihydropyrimidin-1-yl)ethyl]benzonitrile (104), 2-butyl-5-{5-[(5-chloropyridin-2-yl)methyl]-1,3,4-oxadiazol-2-yl}-6-hydroxy-3-[(1S)-1-phenylbutyl]-3,4-dihydropyrimidin-4-one (105), 2-butyl-6-hydroxy-5-{5-[(2-methyl-1,3-thiazol-4-yl)methyl]-1,3,4-oxadiazol-2-yl}-3-[(1S)-1-phenylbutyl]-3,4-dihydropyrimidin-4-one (106), 5-{5-[(1,2-benzoxazol-3-yl)methyl]-1,3,4-oxadiazol-2-yl}-2-butyl-6-hydroxy-3-[(1S)-1-phenylbutyl]-3,4-dihydropyrimidin-4-one (107), 3-[(1S)-1-(2-butyl-5-{5-[(5-chloropyridin-2-yl)methyl]-1,3,4-oxadiazol-2-yl}-4-hydroxy-6-oxo-1,6-dihydropyrimidin-1-yl)ethyl]benzonitrile (108), 2-butyl-5-{5-[(5-chloropyridin-2-yl)methyl]-1,3,4-oxadiazol-2-yl}-6-hydroxy-3-[1-(pyridin-4-yl)ethyl]-3,4-dihydropyrimidin-4-one (109), 5-{5-[(1,2-benzoxazol-3-yl)methyl]-1,3,4-oxadiazol-2-yl}-2-butyl-6-hydroxy-3-[1-(pyridin-4-yl)ethyl]-3,4-dihydropyrimidin-4-one (110), 2-butyl-5-{5-[(5-chloropyridin-2-yl)methyl]-1,3,4-oxadiazol-2-yl}-6-hydroxy-3-[1-(pyridin-4-yl)ethyl]-3,4-dihydropyrimidin-4-one (111), 2-butyl-6-hydroxy-5-{5-[(2-methyl-1,3-thiazol-4-yl)methyl]-1,3,4-oxadiazol-2-yl}-3-(2-methyl-1-phenylpropyl)-3,4-dihydropyrimidin-4-one (112), 2-butyl-5-{5-[(5-chloropyridin-2-yl)methyl]-1,3,4-oxadiazol-2-yl}-6-hydroxy-3-(2-methyl-1-phenylpropyl)-3,4-dihydropyrimidin-4-one (113), 5-{5-[(1,2-benzoxazol-3-yl)methyl]-1,3,4-oxadiazol-2-yl}-2-butyl-6-hydroxy-3-[(1S)-1-(3-methoxyphenyl)ethyl]-3,4-dihydropyrimidin-4-one (114), 5-{5-[(1,2-benzoxazol-3-yl)methyl]-1,3,4-oxadiazol-2-yl}-2-butyl-6-hydroxy-3-(2-methyl-1-phenylpropyl)-3,4-dihydropyrimidin-4-one (115), 2-butyl-5-{5-[(5-chloropyridin-2-yl)methyl]-1,3,4-oxadiazol-2-yl}-6-hydroxy-3-[(1S)-1-(3-methoxyphenyl)ethyl]-3,4-dihydropyrimidin-4-one (116), 5-{5-[(1,2-benzoxazol-3-yl)methyl]-1,3,4-oxadiazol-2-yl}-2-butyl-3-[(1R)-2,3-dihydro-1H-inden-1-yl]-6-hydroxy-3,4-dihydropyrimidin-4-one (117), 2-butyl-5-{5-[(5-chloropyridin-2-yl)methyl]-1,3,4-oxadiazol-2-yl}-6-hydroxy-3-[(1S)-1-phenylpropyl]-3,4-dihydropyrimidin-4-one (118), 2-butyl-5-{5-[(5-chloropyridin-2-yl)methyl]-1,3,4-oxadiazol-2-yl}-6-hydroxy-3-[(1S)-1-phenylethyl]-3,4-dihydropyrimidin-4-one (119), 2-butyl-5-{5-[(5-chloropyridin-2-yl)methyl]-1,3,4-oxadiazol-2-yl}-6-hydroxy-3-[(1R)-1-phenylethyl]-3,4-dihydropyrimidin-4-one (120), 5-{5-[(1,2-benzoxazol-3-yl)methyl]-1,3,4-oxadiazol-2-yl}-2-butyl-6-hydroxy-3-[1-(pyridin-3-yl)ethyl]-3,4-dihydropyrimidin-4-one (121), 2-butyl-5-{5-[(5-chloropyridin-2-yl)methyl]-1,3,4-oxadiazol-2-yl}-3-[(1R)-2,3-dihydro-1H-inden-1-yl]-6-hydroxy-3,4-dihydropyrimidin-4-one (122), 2-butyl-5-{5-[(5-chloropyridin-2-yl)methyl]-1,3,4-oxadiazol-2-yl}-6-hydroxy-3-[1-(pyridin-3-yl)ethyl]-3,4-dihydropyrimidin-4-one (123), and 2-butyl-6-hydroxy-5-{5-[(2-methyl-1,3-thiazol-4-yl)methyl]-1,3,4-oxadiazol-2-yl}-3-[1-(pyridin-3-yl)ethyl]-3,4-dihydropyrimidin-4-one (124), or a stereoisomer, an enantiomer, a diastereomer, a tautomer, or a pharmaceutically acceptable salt thereof.

* * * * *